(12) United States Patent
Williams et al.

(10) Patent No.: US 10,428,156 B2
(45) Date of Patent: Oct. 1, 2019

(54) ANTI-MFI2 ANTIBODIES AND METHODS OF USE

(71) Applicant: ABBVIE STEMCENTRX LLC, North Chicago, IL (US)

(72) Inventors: Samuel Williams, San Mateo, CA (US); Laura Saunders, San Francisco, CA (US); Holger Karsunky, Redwood City, CA (US); Mandy Boontanrart, San Francisco, CA (US)

(73) Assignee: Abbvie Stemcentrx LLC, North Chicago, IL (US)

(*) Notice: Subject to any disclaimer, the term of this patent is extended or adjusted under 35 U.S.C. 154(b) by 276 days.

(21) Appl. No.: 15/508,836

(22) PCT Filed: Sep. 4, 2015

(86) PCT No.: PCT/US2015/048659
§ 371 (c)(1),
(2) Date: Mar. 3, 2017

(87) PCT Pub. No.: WO2016/037119
PCT Pub. Date: Mar. 10, 2016

(65) Prior Publication Data
US 2017/0320960 A1  Nov. 9, 2017

Related U.S. Application Data

(60) Provisional application No. 62/203,836, filed on Aug. 11, 2015, provisional application No. 62/046,610, filed on Sep. 5, 2014.

(51) Int. Cl.
| | | |
|---|---|---|
| C07K 16/30 | (2006.01) | |
| C07K 16/28 | (2006.01) | |
| A61K 47/68 | (2017.01) | |
| A61K 45/06 | (2006.01) | |
| A61K 39/395 | (2006.01) | |
| A61K 49/00 | (2006.01) | |
| C12Q 1/6886 | (2018.01) | |
| G01N 33/574 | (2006.01) | |
| A61K 39/00 | (2006.01) | |

(52) U.S. Cl.
CPC ...... *C07K 16/2896* (2013.01); *A61K 39/3955* (2013.01); *A61K 45/06* (2013.01); *A61K 47/6803* (2017.08); *A61K 47/6809* (2017.08); *A61K 47/6849* (2017.08); *A61K 49/0004* (2013.01); *C07K 16/30* (2013.01); *C12Q 1/6886* (2013.01); *G01N 33/57492* (2013.01); *A61K 2039/505* (2013.01); *C07K 2317/24* (2013.01); *C07K 2317/33* (2013.01); *C07K 2317/34* (2013.01); *C07K 2317/53* (2013.01); *C07K 2317/56* (2013.01); *C07K 2317/565* (2013.01); *C07K 2317/73* (2013.01); *C07K 2317/77* (2013.01); *C07K 2317/92* (2013.01); *C12Q 2600/158* (2013.01); *G01N 33/5743* (2013.01); *G01N 33/57415* (2013.01); *G01N 33/57419* (2013.01); *G01N 33/57423* (2013.01); *G01N 2333/70596* (2013.01)

(58) Field of Classification Search
CPC combination set(s) only.
See application file for complete search history.

(56) References Cited

U.S. PATENT DOCUMENTS

| | | |
|---|---|---|
| 4,816,567 A | 3/1989 | Cabilly et al. |
| 5,191,066 A | 3/1993 | Bieniarz et al. |
| 5,648,237 A | 7/1997 | Carter |
| 5,693,762 A | 12/1997 | Queen et al. |
| 5,714,350 A | 2/1998 | Co et al. |
| 5,851,795 A | 12/1998 | Linsley et al. |
| 5,981,194 A | 11/1999 | Jefferies et al. |
| 6,180,370 B1 | 1/2001 | Queen et al. |
| 6,329,179 B1 | 12/2001 | Kopreski |
| 6,350,861 B1 | 2/2002 | Co et al. |
| 6,362,331 B1 | 3/2002 | Kamal et al. |
| 6,376,217 B1 | 4/2002 | Better et al. |
| RE38,008 E | 2/2003 | Abrams et al. |
| 6,737,056 B1 | 5/2004 | Presta |
| 6,753,165 B1 | 6/2004 | Cox et al. |
| 6,916,634 B2 | 7/2005 | Kopreski |
| 6,982,321 B2 | 1/2006 | Winter |
| 7,049,311 B1 | 5/2006 | Thurston et al. |
| 7,087,409 B2 | 8/2006 | Barbas, III et al. |
| 7,189,710 B2 | 3/2007 | Kamal et al. |
| 7,407,951 B2 | 8/2008 | Thurston et al. |

(Continued)

FOREIGN PATENT DOCUMENTS

| | | |
|---|---|---|
| EP | 1120651 | 8/2001 |
| KR | 2002/0007432 | 1/2002 |

(Continued)

OTHER PUBLICATIONS

Almagro, J.C., et al., "Antibody engineering: Humanization, affinity, maturation, and selection techniques," Therapeutic Monoclonal Antibodies: From Bench to Clinic, Oct. 1, 2009, pp. 311-334 (XP055311028).

(Continued)

*Primary Examiner* — Meera Natarajan
(74) *Attorney, Agent, or Firm* — Womble Bond Dickinson (US) LLP

(57) ABSTRACT

Provided are novel anti-MFI2 antibodies and antibody drug conjugates, and methods of using such anti-MFI2 antibodies and antibody drug conjugates to treat cancer.

32 Claims, 46 Drawing Sheets
Specification includes a Sequence Listing.

(56) References Cited

U.S. PATENT DOCUMENTS

| | | | |
|---|---|---|---|
| 7,429,658 B2 | 9/2008 | Howard et al. | |
| 7,557,099 B2 | 7/2009 | Howard et al. | |
| 7,608,429 B2 | 10/2009 | Reilly et al. | |
| 7,619,068 B2 | 11/2009 | Pilkington et al. | |
| 7,632,678 B2 | 12/2009 | Hansford et al. | |
| 7,723,485 B2 | 5/2010 | Junutula et al. | |
| 7,741,319 B2 | 6/2010 | Howard et al. | |
| 7,837,980 B2 | 11/2010 | Alley et al. | |
| 7,855,275 B2 | 12/2010 | Eigenbrot et al. | |
| 7,919,103 B2 | 4/2011 | Béliveau et al. | |
| 8,003,774 B2 | 8/2011 | Stavenhagen et al. | |
| 8,008,443 B2 | 8/2011 | Dall'Acqua et al. | |
| 8,030,031 B2 | 10/2011 | Kopreski | |
| 8,034,808 B2 | 10/2011 | Delavault et al. | |
| 8,053,562 B2 | 11/2011 | Humphreys | |
| 8,163,736 B2 | 4/2012 | Gauzy et al. | |
| 8,226,945 B2 | 7/2012 | Ebens, Jr. et al. | |
| 8,507,654 B2 | 8/2013 | Baker et al. | |
| 8,722,019 B2 | 5/2014 | Jefferies et al. | |
| 8,735,553 B1 | 5/2014 | Li et al. | |
| 8,865,875 B2 | 10/2014 | Liu | |
| 9,150,846 B2 | 10/2015 | Jefferies et al. | |
| 2003/0008840 A1 | 1/2003 | Vicari et al. | |
| 2003/0138413 A1 | 7/2003 | Vicari et al. | |
| 2003/0190311 A1 | 10/2003 | Dall'Acqua et al. | |
| 2004/0055022 A1 | 3/2004 | Cheng et al. | |
| 2005/0152894 A1 | 7/2005 | Krummen et al. | |
| 2006/0120959 A1 | 6/2006 | De Haen et al. | |
| 2007/0292414 A1 | 12/2007 | Duntsch et al. | |
| 2008/0138313 A1 | 6/2008 | Frankel | |
| 2008/0175870 A1 | 7/2008 | Mather et al. | |
| 2008/0220448 A1 | 9/2008 | Blincko et al. | |
| 2008/0305044 A1 | 12/2008 | McDonagh et al. | |
| 2009/0010945 A1 | 1/2009 | Alley et al. | |
| 2009/0130105 A1 | 5/2009 | Glaser et al. | |
| 2009/0155255 A1 | 6/2009 | Glaser et al. | |
| 2009/0232822 A1 | 9/2009 | Joseloff et al. | |
| 2010/0162416 A1 | 6/2010 | Krtolica et al. | |
| 2010/0275280 A1 | 10/2010 | Clevers et al. | |
| 2011/0020221 A1 | 1/2011 | Berman et al. | |
| 2011/0033378 A1 | 2/2011 | Dimasi et al. | |
| 2011/0219464 A1 | 9/2011 | Domon et al. | |
| 2011/0243952 A1 | 10/2011 | Beliveau et al. | |
| 2011/0256157 A1 | 10/2011 | Howard et al. | |
| 2011/0301334 A1 | 12/2011 | Bhakta et al. | |
| 2012/0071634 A1 | 3/2012 | Igawa et al. | |
| 2013/0040362 A1 | 2/2013 | Vogel et al. | |
| 2013/0058873 A1 | 3/2013 | Jefferies et al. | |
| 2013/0061340 A1 | 3/2013 | Dylla et al. | |
| 2013/0061342 A1 | 3/2013 | Dylla et al. | |
| 2013/0101581 A1 | 4/2013 | Kuramochi et al. | |
| 2013/0144041 A1 | 6/2013 | Dillon et al. | |
| 2013/0183368 A1* | 7/2013 | Hutchison | C07K 16/32 424/450 |
| 2013/0259806 A1 | 10/2013 | Light et al. | |
| 2013/0260385 A1 | 10/2013 | Dylla et al. | |
| 2013/0266579 A1 | 10/2013 | Wei et al. | |
| 2013/0288272 A1 | 10/2013 | Narimatsu et al. | |
| 2013/0330350 A1 | 12/2013 | Dimasi | |
| 2014/0010861 A1 | 1/2014 | Bancel et al. | |
| 2014/0120581 A1 | 5/2014 | Niwa et al. | |
| 2014/0322132 A1 | 10/2014 | Vitalis et al. | |
| 2014/0348839 A1 | 11/2014 | Chowdhury et al. | |
| 2015/0005477 A1 | 1/2015 | Lowman et al. | |
| 2015/0030636 A1 | 1/2015 | Dylla et al. | |
| 2015/0056218 A1 | 2/2015 | Jeffries et al. | |
| 2015/0079109 A1 | 3/2015 | Li et al. | |
| 2015/0086550 A1 | 3/2015 | Heiss et al. | |
| 2015/0093399 A1 | 4/2015 | Jefferies | |
| 2015/0320879 A1 | 11/2015 | Lyon et al. | |

FOREIGN PATENT DOCUMENTS

| | | |
|---|---|---|
| WO | WO 94/04690 | 3/1994 |
| WO | WO 96/27011 | 9/1996 |
| WO | WO 97/34631 | 9/1997 |
| WO | WO 99/37779 | 1/1999 |
| WO | WO 2000/042072 | 7/2000 |
| WO | WO 2004/029207 | 4/2004 |
| WO | WO 2005/003171 A2 | 7/2004 |
| WO | WO 2006/034488 A2 | 9/2005 |
| WO | WO 2011/128650 | 10/2011 |
| WO | WO 2011/130613 | 10/2011 |
| WO | WO 2011/130616 | 10/2011 |
| WO | WO 2012/064733 A2 | 11/2011 |
| WO | WO 2012/031280 | 3/2012 |
| WO | WO 2012/117002 | 9/2012 |
| WO | WO 2013/006706 | 1/2013 |
| WO | WO 2013/022738 | 2/2013 |
| WO | WO 2013/056372 | 4/2013 |
| WO | WO 2013/093809 | 6/2013 |
| WO | WO 2013/119964 | 8/2013 |
| WO | WO 2013/126810 A1 | 8/2013 |
| WO | WO 2013/151665 A2 | 10/2013 |
| WO | WO 2013/177481 | 11/2013 |
| WO | WO 2014/057073 | 4/2014 |
| WO | WO 2014/057074 | 4/2014 |
| WO | WO 2014/124316 A2 | 7/2014 |
| WO | WO 2014/130879 | 8/2014 |
| WO | WO 2014/160438 | 10/2014 |
| WO | WO 2014/201021 | 12/2014 |
| WO | WO 2015/013579 | 1/2015 |
| WO | WO 2015/013581 | 1/2015 |
| WO | WO 2015/123265 | 2/2015 |
| WO | WO 2015/031673 | 3/2015 |
| WO | WO 2015/031698 | 3/2015 |
| WO | WO 2015/035606 | 3/2015 |
| WO | WO 2015/127407 | 8/2015 |
| WO | WO 2016/064749 | 4/2016 |

OTHER PUBLICATIONS

Brown J P, et al., "Structural Characterization of Human Melanoma-Associated Antigen p-97 with Monoclonal Antibodies," The Journal of Immunology, The American Association of Immunologists (Jan. 1, 1981), vol. 127, No. 2, pp. 539-546 (XP002167880).

Casellas, P., et al., "Human melanoma cells can be killed in vitro by an immunotoxin specific for melanoma-associated antigen p97" International Journal of Cancer (Oct. 15, 1982), pp. 437-443 (XP055449493) Denmark.

Garrigues, H.J. et al., "Detection of a Human Melanoma-Associated Antigen, p97, in Histological Sections of Primary Human Melanomas" International Journal of Cancer (May 15, 1982), vol. 29, No. 5, pp. 511-515 (XP055449224).

Hellström I, et al., "Monoclonal antibodies to two determinants of melanoma-antigen p97 act synergistically in complement-dependent cytotoxicity", The Journal of Immunology, Jul. 1, 1981, p. 157-160 (XP055195523).

Junutula, J.R., et al., "Site-specific conjugation of a cytotoxic drug to an antibody improves the therapeutic index", Nature Biotechnology (Advance Online Publication), Gale Group Inc (Aug. 1, 2008) vol. 26, No. 8, pp. 925-932 (XP002499771).

Lazar et al., "A molecular immunology approach to antibody humanization and functional optimization," Molecular Immunology, Dec. 1, 2006, 44(8):1986-1998 (XP005792736).

Rolland, Y., et al., "Inhibition of melanoma brain metastasis by targeting melanotransferrin at the cell surface," Pigment Cell Melanoma Res. (Feb. 1, 2009) vol. 22, No. 1, pp. 86-98 (XP055449695).

Smith, L. M., et al., "Effective inhibition of melanoma cell proliferation using an antibody drug conjugate targeting melanotransferrin/p97.", Proc. Amer. Assoc. Cancer Res. (Apr. 1, 2005) vol. 46, pp. 162 (XP055202518) * abstract *.

Official action dated Aug. 20, 2018, issued in Chilean application (No. 0506-2017).

Official action dated Aug. 14, 2018, issued in Colombian application (No. NC2017/0003005).

(56) References Cited

OTHER PUBLICATIONS

Official action dated Jan. 10, 2019, issued in Colombian application (No. NC2017/0003005).
Official action dated Oct. 3, 2018, issued in Eurasian application (No. 201790529).
Official action dated Mar. 13, 2018, issued in European application (No. 15837897.6 ).
Extended European Search Report dated Jul. 6, 2018, issued in European application (No. 15837897.6).
Biolegend, "Purified anti-human CD228 (MFI2, MTF1) Antibody," BioLegend Inc. (Aug. 21, 2014), Version 1.
Boswell, C. A., et al., "An Integrated Approach to Identify Normal Tissue Expression of Targets for Antibody-drug Conjugates: Case Study of TENB2," British Journal of Pharmacology 2013, vol. 168, pp. 445-457.
Chothia et al., "Canonical Structures for the Hypervariable Regions of Immunoglobulins," J. Mol. Biol. (Aug. 20, 1987) 196(4):901-917, PMID: 3681981.
Chothia et al., "Conformations of immunoglobulin hypervariable regions," Nature (Dec. 21-28, 1989), 342(6252):877-83, PMID: 2687698.
Chothia, D., et al., "Structural repertoire of the human VH segments," J. Mol. Biol. (1992) 227(3):799-817 Abstract.
Cook, G. P., et al., "The human immunoglobulin VH repertoire," Immunol. Today (May 1995) 16(5):237-242 Abstract.
Dylla et al., "Colorectal Cancer Stem Cells Are Enriched in Xenogeneic Tumors Following Chemotherapy," PLoS One (Jun. 2008) vol. 3, Issue 6, PMID: PMC2413402.
Fazekas et al., "The evaluation of limiting dilution assays," J. Immunol Methods (Mar. 1982) 49(2):R11-23, PMID: 7040548.
Hoey et al., "DLL4 Blockade Inhibits Tumor Growth and Reduces Tumor-Initiating Cell Frequency," Cell Stem Cell (Aug. 7, 2009) 5(2):168-77, PMID: 19664991.
Kabat et al. (1991) Sequences of Proteins of Immunological Interest (5th Ed.), US Dept. of Health and Human Services, PHS, NIH, NIH Publication No. 91-3242.
MacCallum et al., "Antibody-antigen Interactions: Contact Analysis and Binding Site Topography," J. Mol. Biol. (Oct. 11, 1996) 262(5):732-745, PMID: 8876650.
Miller et al., "Epitope binning of murine monoclonal antibodies by a multiplexed pairing assay," J. Immunol Methods (Feb. 28, 2011) 365(1-2):118-25, PMID: 21223970.
Morrison et al., "Chimeric human antibody molecules: Mouse antigen-binding domains with human constant region domains," Proc. Natl. Acad. Sci. USA (Nov. 1984) 81:6851-6855, PMID: 6436822.
NM_005929.5—*Homo sapiens* melanotransferrin (MELTF), transcript variant 1, mRNA.
NM_033316.3—*Homo sapiens* melanotransferrin (MELTF), transcript variant 2, mRNA.
NP_001099342.1—melanotransferring precursor [Rattus norvegicus].
NP_005920.2—melanotransferrin isoform 1 preproprotein [*Homo sapiens*].
NP_038928.1—melanotransferrin precursor [Mus musculus].
Panowski, S., et al., "Site-specific Antibody Drug Conjugates for Cancer Therapy," MAbs Jan.-Feb. 2014, vol. 6, Issue 1, pp. 34-35.
Rahmanto et al., "The melanoma tumor antigen, melanotransferrin (p97): a 25-year hallmark—from iron metabolism to tumorigenesis," Oncogene (2007) 26(42):6113-24, PMID: 17452986.
Rahmanto et al., "Melanotransferrin: Search for a function," Biochim Biophys Acta (2012) 1820(3):237-43, PMID: 21933697.
Ravetch et al., "Fc Receptors," Annu. Rev. Immunol (1991) 9:457-92.
Retter et al., "VBASE2, an integrative V gene database," Nucl. Acids Res. (2005) 33 (Database issue): D671-D674.
Rodrigues, M. L., et al., "Engineering Fab' Fragments for Efficient F(ab)2 Formation in *Escherichia coli* and for Improved In Vivo Stability," The Journal of Immunology, Dec. 15, 1993, vol. 151, No. 12, pp. 6954-6961.
Rosenblum et al. "Pharmacokinetics of 111In-labeled anti-p97 monoclonal antibody in patients with metastatic malignant melanoma." *Cancer Res.* May 1985;45(5):2382-6.
Schulenburg et al., "Neoplastic stem cells: Current concepts and clinical perspectives," Crit. Rev. Oncol. Hematol (2010) 76(2):79-98, PMID: 20185329.
Shields et al., "High Resolution Mapping of the Binding Site on Human IgG1 for FcγRI, FcγRII, FcγRIII, and FcRn and Design of IgG1 Variants with Improved Binding to the Fc_R," J. Biol. Chem. (2001) 9(2):6591-6604.
Shields, R. L., et al., "Lack of Fucose on Human IgG1 N-Linked Oligosaccharide Improves Binding to Human FcγRIII and Antibody-dependent Cellular Toxicity," J. Biol. Chem. (2002) 277:26733-26740.
Smith et al., "Potent cytotoxicity of an auristatin-containing antibody-drug conjugate targeting melanoma cells expressing melanotransferrin/p97," Mol Cancer Ther (Jun. 2006) 5:1474.
Strop, P., et al., "Location Matters: Site of Conjugation Modulates Stability and Pharmacokinetics of Antibody Drug Conjugates," Chemistry & Biology 20, Feb. 21, 2013, pp. 161-167.
Sun, M., et al., "Reduction-Alkylation Strategies for the Modification of Specific Monoclonal Antibody Disulfides," Bioconug. Chem. 2005, vol. 16, No. 5, pp. 1282-1290.
Suresh et al., "Bispecific Monoclonal Antibodies from Hybrid Hybridomas," Methods in Enzymology (1986) 121:210-228.
Sussman, D., et al., "Abstract 4634: Engineered Cysteine Drug Conjugates Show Potency and Improved Safety," Cancer Research, Apr. 15, 2012, vol. 72, Issue 8, Supp. 1.
Tomlinson et al., "The structural repertoire of the human VK domain," EMBO J (1995) 14(18):4628-4638.
Tomlinson, I. A., et al., "The repertoire of human germline VH sequences reveals about fifty groups of VH segments with different hypervariable loops," J Mol Biol. (Oct. 5, 1992) 227(3):776-798 Abstract.
Umetsu, M., et al., "How Additives Influence the Refolding of Immunoglobulin-folded Proteins in a Stepwise Dialysis System: Spectroscopic Evidence for Highly Efficient Refolding of a Single-chain FV Fragment," J. Biol. Chem., Mar. 14, 2003, vol. 278, No. 11, pp. 8979-8987.
Visvader et al., "Cancer stem cells in solid tumours: accumulating evidence and unresolved questions," Nature Reviews Cancer (Oct. 2008) 8:755-768, PMID: 18784658.
Official action dated May 8, 2017, issued in Colombian application (No. NC2017/0003005).
International Search Report dated Jan. 29, 2016, issued in International application (No. PCT/US2015/048659).
Written Opinion dated Jan. 29, 2016, issued in International application (No. PCT/US2015/048659).

\* cited by examiner

Anti-MFI2 Antibody Characteristics

| Antibody | Isotype | Rat MFI2 Binding (Forte Bio) | Bin | Binding Affinity (nM) | TLD1 (1) or TLD2 (2) Binding |
|---|---|---|---|---|---|
| SC57.1 | IgG1/K | - | X | | 1 |
| SC57.2 | IgG1/K | - | E | | 1 |
| SC57.3 | IgG1/K | - | X | | ND |
| SC57.4 | IgG1/K | + | D | 12.8 | 2 |
| SC57.5 | IgG1/K | + | B | 1.1 | 2 |
| SC57.6 | ND/K | - | X | | 2 |
| SC57.7 | IgG1/K | - | X | | 1 |
| SC57.8 | IgG2a/K | - | X | | ND |
| SC57.9 | IgG2a/K | - | F | | 2 |
| SC57.10 | IgG1/K | - | C | 1.6 | 2 |
| SC57.11 | IgG1/K | - | C | 3.2 | 2 |
| SC57.12 | IgG1/K | - | X | | ND |
| SC57.13 | ND/K | - | X | | ND |
| SC57.14 | IgG1/K | - | X | | ND |
| SC57.15 | IgG1/K | - | D | | ND |
| SC57.16 | IgG1/K | - | X | | ND |
| SC57.17 | IgG1/K | - | D | | 2 |
| SC57.18 | IgG1/K | + | X | | ND |
| SC57.19 | IgG2b/K | - | X | | ND |
| SC57.20 | IgG2b/K | - | X | | ND |
| SC57.21 | ND | - | X | | ND |
| SC57.22 | ND | - | X | | 2 |
| SC57.23 | ND | - | X | | ND |
| SC57.24 | ND | - | D | | 2 |
| SC57.25 | IgG1/K | - | X | | 2 |
| SC57.26 | ND | - | E | | ND |
| SC57.27 | IgG1/K | - | D | | 1 |
| SC57.28 | IgG1/K | - | C | | 2 |
| SC57.29 | IgG1/K | - | C | 1.9 | 2 |
| SC57.30 | IgG1/K | - | C | | 2 |

ND = Not Determined

FIG. 5

Anti-MFI2 Antibody Characteristics

| Antibody | Isotype | Rat MFI2 Binding (Forte Bio) | Bin | Binding Affinity (nM) | Transferrin-Like Domain Binding |
|---|---|---|---|---|---|
| SC57.31 | IgG1/K | - | A | | 2 |
| SC57.32 | IgG1/K | - | C | | 2 |
| SC57.33 | IgG1/K | + | B | | 2 |
| SC57.34 | IgG1/K | - | E | | 1 |
| SC57.35 | IgG1/K | - | C | 2.3 | 2 |
| SC57.36 | IgG1/K | + | C | | 2 |
| SC57.37 | IgG1/K | - | D | | 2 |
| SC57.38 | IgG1/K | - | C | | 2 |
| SC57.39 | IgG1/K | + | B | | 2 |
| SC57.40 | IgG1/K | - | C | | 2 |
| SC57.41 | IgG1/K | - | C | | 2 |
| SC57.42 | IgG1/K | - | E | | 1 |
| SC57.43 | IgG1/K | - | A | | 2 |
| SC57.44 | IgG1/K | - | E | | ND |
| SC57.45 | IgG1/K | - | C | | 2 |
| SC57.46 | IgG1/K | + | D | 4.5 | 2 |
| SC57.47 | IgG1/K | - | C | | 2 |
| SC57.48 | IgG1/K | - | ND | | 1 |
| SC57.49 | ND | - | ND | | 1 |
| SC57.50 | IgG2b/K | - | X | | ND |
| SC57.51 | IgG1/K | - | C | | 2 |
| SC57.52 | IgG1/K | - | X | | 2 |
| SC57.53 | IgG1/K | - | A | | 2 |
| SC57.54 | IgG1/K | - | C | | 2 |
| SC57.55 | IgG1/K | - | X | | 2 |
| SC57.56 | IgG1/K | - | C | | 2 |
| SC57.57 | IgG1/K | - | A | | 2 |
| SC57.58 | IgG1/K | + | B&C | | 2 |
| SC57.59 | IgG1/K | - | A | | ND |
| SC57.60 | IgG1/K | ND | E | | ND |
| hSC57.5 | hIgG1/K | ND | B | 4.4 | 2 |
| hSC57.32 | hIgG1/K | ND | C | 5.4 | 2 |
| hSC57.43 | hIgG1/K | ND | A | 44.9 | 2 |

FIG. 5 cont.

ND = Not Determined

Anti-MFI2 Murine Antibody Amino Acid Variable Region Light Chain Sequences

| Name | FR1 | CDRL1 | FR2 | CDRL2 | FR3 | CDRL3 | FR4 | SEQ ID NO |
|---|---|---|---|---|---|---|---|---|
| SC57.1 | QIVLTQSPAIMSASPGEKVTMTC | SASSSVSYMH | WYQQKSGTSPKRWIY | DTSKLAS | GVPVRFSGSGSGTSYSLTISSIEADDAATYYC | QQWSRTPPT | FGGGTKLEIK | 21 |
| SC57.3 | DIVLTQSPATLSVTPGDSVSLSC | RASQGISNNLH | WYQQKSHESPRLLIK | YASQSIS | GIPSRFSGSGSGTDFALSINSVETEDFGMFFC | QQSNSWPLT | FGAGTKLELK | 25 |
| SC57.4 | DVVMTQTPLSLPVSLGDQASISC | RSSQSLVHSNGNTYLH | WYLQKPGQSPKLLIY | RVSNRFS | GVPDRFSGSGSGTDFTLKISRVEAEDLGVYLC | SQSTHVPLT | FGAGTKLELK | 29 |
| SC57.5 | DIVMTQSHKFMSTSVGDRVSITC | KASQDVYAAVA | WYHQKPGQSPKLLIY | WASTRHA | GVPDRFTGSGSGTDYTLTISSVQAEDLALYYC | QQHYRTPWT | FGGGTKLEIK | 33 |
| SC57.6 | DIVMSQSPSSLAVSAGEKVTMSC | KSSQSLLHSRIRKNYLA | WYQQKPGQSPKLLIY | WASTRES | GVPDRFTGSGSGTDFLTISSVQAEDLAVYYC | KQSYNLFT | FGGGTKLEIK | 37 |
| SC57.8 | DIVMTQSHKFMSTSVGDRVNITC | KASQDVGTTVA | WYQQKPGQSPKLLIY | WASTRHT | GVPDRFTGSGSGTDFTLLISNVQSEDLADYFC | QQYSSYPLT | FGAGTKLELK | 41 |
| SC57.9 | QIVLTQSPAIMSASPGEKVTITC | SASSSVSYMH | WFQQKPGTSPKLWIY | TTSNLAS | GVPARFSGSGSGTSYSLTISRMEAEDAATYYC | QQRSSFPPT | FGSGTKLEIK | 45 |
| SC57.10 (SC57.32) | DIQMTQTTSSLSASLGDRVTISC | RASQDISNYLN | WYQQKPDGTVKLLIF | YTSRLHS | GVPSRFSGSGSGTDYSLTISNLEQEDFATYFC | QQGNTLPPT | FGGGTKLEIK | 49 |
| SC57.11 | DIQMTQTTSSLSASLGDRVTISC | RASQDISSYLN | WYQQKPDGTVKLLIY | YTSRLHS | GVPSRFSGSGSGTDYSLTINNLEQEDIATYFC | QQGNTLPPT | FGGGTKLEIK | 53 |
| SC57.12 | DIQMTQSPPSLSASVGETVTITC | RTSENIYSYLT | WYQQKQGKSPQLLVY | NAKTLAE | GVPSRFSGSGSGTQFSLKINSLQPEDFGSYYC | QHHYGTPLT | FGAGTKLELK | 57 |
| SC57.14 | DIVMSQSPSSLAVSAGEKVTMSC | KSSQSLLNSRTRKNYLA | WYQQKPGQSPKLLIY | WASTRES | GVPDRFTGSGSGTDFTLTISSVQAEDLAVYYC | KQSYNLWT | FGGGTKLEIK | 61 |
| SC57.15 | DIQMTQSPASLSASVGETVTITC | GASENIYGALN | WYQRKQGKSPQLLIY | GATNLAD | GMSSRFSGSGSGGQYSLKISGLHPADVATYYC | QNVLNTPWT | FGGGTKLEIK | 65 |

FIG. 6A

Anti-MFI2 Murine Antibody Amino Acid Variable Region Light Chain Sequences

| Name | FR1 | CDRL1 | FR2 | CDRL2 | FR3 | CDRL3 | FR4 | SEQ ID NO |
|---|---|---|---|---|---|---|---|---|
| SC57.17 | DIQMTQTTSSLSASLGDRVTISC | SASQDINNYLN | WYQQKPDGTVKLLIH | YTSSLHS | GVPSRFSGSGSGTDYSLTISNLEPEDIATYYC | QQYSKVPWT | FGGGTKLEIK | 69 |
| SC57.20 | DIVMTQSHKFMSTSVGDRVSITC | KASQDVGSAVA | WSQQKPGQSPKLLIY | WASSRHT | GVPDRFTGSGSGTDFTLTISNVQSEDLADYFC | QQYSNYPLT | FGAGTKLELK | 73 |
| SC57.27 | DIQMTQSPVSLSASVGETVTITC | RASEIIYSYLA | WYQQKQGKSPQLLVY | NAKTLAE | GVPSRFSGSGSGTQFSLKINSLQPEDFGTYYC | QHHYGVPVT | FGAGTKLELK | 77 |
| SC57.31 | DIVLTQSPATLSVTPGDSVSLSC | RASQSVGNSLH | WYQQKSHESPRLLIK | YASQSIS | GIPSRFSGSGSGTDFTLSINSVETEDFGMYFC | QQSDSWPLT | FGTGTKLELK | 81 |
| SC57.43 | DVVMTQTPLSLPVSLGDQASISC | RSSQSLVHSNGNTYLH | WYLQKPGQSPKLLIY | KVSNRFS | GVPDRFSGSGSGTDFTLKISRVEAEDLGVYFC | SQSTHVPLYT | FGGGTKLEIK | 85 |
| SC57.60 | DIQMTQSPASLSASVGETVTITC | RASENIYSYLA | WSQQKQGKSPHLLVY | NAKTLAE | GVPSRFSGSGSGTQFSLKINSLQPEDFGSYYC | QHHYGIPLT | FGAGTKLELK | 89 |

FIG. 6A Cont.

Anti-MFI2 Humanized Antibody Amino Acid Variable Region Light Chain Sequences

| Name | FR1 | CDRL1 | FR2 | CDRL2 | FR3 | CDRL3 | FR4 | SEQ ID NO |
|---|---|---|---|---|---|---|---|---|
| hSC57.5 | DIQMTQSPSSLSASVGDRVTITC | KASQDVYAAVA | WYQQKPGKAPKLLIY | WASTRHA | GVPSRFSGSGSGTDFTLTISSLQPEDFATYYC | QQHYRTPWT | FGQGTKVEIK | 93 |
| hSC57.32 | DIQMTQSPSSLSASVGDRVTITC | RASQDISNYLN | WYQQKPGKAPKLLIY | YTSRLHS | GVPSRFSGSGSGTDYTLTISSLQPEDFATYYC | QQGNTLPPT | FGGGTKVEIK | 99 |
| hSC57.43 | DIVMTQSPDSLAVSLGERATINC | RSSQSLVHSNGNTYLH | WYQQKPGQPPKLLIY | KVSNRFS | GVPDRFSGSGSGTDFTLTISSLQAEDVAVYYC | SQSTHVPLYT | FGGGTKVEIK | 105 |

FIG. 6A Cont.

Anti-MFI2 Murine Antibody Amino Acid Variable Region Heavy Chain Sequences

| Name | FR1 | CDRH1 | FR2 | CDRH2 | FR3 | CDRH3 | FR4 | SEQ ID NO |
|---|---|---|---|---|---|---|---|---|
| SC57.1 | QVQLKQSGPGLVQPSQSLSITCTVSGFSLT | DYGVH | WVRQSPGKGLDWLG | VIWSGGNTDYNAAFIS | RLSISKDNSKSQIFFEMNSLQDTDTAIYYCAR | QLHYYGPFAY | WGQGTLVTVSA | 23 |
| SC57.3 | QVQLKQSGPGLVQPSQSLSITCTVSGFSLS | SYGVH | WVRQSPGKGLEMLG | VIWSGGNTDYNAAFIS | RLSISKDNSKSQVFFKMNSLQADDTAIYYCAR | RNNSAWFAY | WGQGTLVTVSA | 27 |
| SC57.4 | EIQLQQSGPEMVKPGASVKVTCKASGYSFT | DFMMH | WMKQSHGKSLEWIG | YIDPYKGGISYNQKFKG | RATLTVDKSSSTAFMHLNSLTSDDSAVYYCAR | DYYGSRFPYYFDY | WGQGTTLTVSS | 31 |
| SC57.5 | EVQLQQSGPELVKPGASVKISCKASGYSFT | DYYLH | WVKQSHVKSLEWIG | RINPYNGATSYNQIFKD | KASLTVDKSSSTAYMDLHSLTSEDSAVYYCAR | GGDYDFPWY | WGQGTTLTVSP | 35 |
| SC57.6 | GVQVVESGGGVVQPGGSLKLSCAASGFTFS | SYAMS | WVRQTPEKRLEWVA | YLSRGGGSTYYLDTVKG | RFTISRDNAKNTLYLQMNSLKSEDTAMYYCAR | LDGYNWYFDV | WGAGTPVTVSS | 39 |
| SC57.8 | QVQLKQSGPGLVQPSQSLSISCTVSGFSLT | TYGVY | WVRQSPGKGLEWLG | VIWSGGSTDYNAAFIS | RLIISKDNSKSQVFFKMNSLQANDTAIYYCAR | ISYDYDGAY | WGQGTLVTVSA | 43 |
| SC57.9 | QVQLQQSGPELMKPGASVKISCKATGYTFS | SYWIE | WVKQRPGHGLEWIG | EILPGSGSTEYNEKFKG | KATFTADTSSNTAYMQLSSLTSEDSDVYYCAR | KRYGTMDY | WGQGTSVTVSS | 47 |
| SC57.10 (SC57.32) | QVQLQQSGAELMKPGASVKISCKATGYTFS | NYRIE | WIKQRPGHGLEWIG | EILPRGGNTNYNEKFKG | KATFTADTSSNTAYMQLTSLTSEDSAVYYCAR | DDGYYGRFAY | WGQGTLVTVSA | 51 |
| SC57.11 | QVQLQQSGAELMKPGASVKISCKATGYTFS | NYRIE | WMKQRPGHGLEWIG | EILPRTGNTNYNENFKG | KATFTADTSSNTAYIQLSSLTSEDSAVYYCAR | DDGYYGRFAY | WGQGTLVTVSA | 55 |
| SC57.12 | QVQLKESGPGLVAPSQSLSITCTVSGFSLT | SYGVH | WVRQPPGKGLEWLG | IIWAGGTTNYNSALMS | RLSIRKDNSKSQVFLKMNSLQTDDTAMYYCAR | DRGYDGYFDYAVDY | WGQGTSVTVSS | 59 |
| SC57.14 | DVQLQESGPGLVKPSQSLSLTCSVTGYSIT | SGYWN | WIRQFPGNKLEWMG | YISYDGVNMYDPSLKN | RISITRDTSKNQFFLKLNSVTTEDTATYYCAS | NYWYDAYFDY | WGQGTTLTVSS | 63 |
| SC57.15 | DVQLQESGPDLVKPSQSLSLTCAVTGYSIT | SAYTWH | WIRQFPGNKLEWMG | YMHYSGSTSYNPSLKS | RISITRDTSKNQFFLQLNSVTTEDTATYYCAN | SLLYYGYGLYWFDV | WGAGTVTVSS | 67 |

FIG. 6B

Anti-MFI2 Murine Antibody Amino Acid Variable Region Heavy Chain Sequences

| Name | FR1 | CDRH1 | FR2 | CDRH2 | FR3 | CDRH3 | FR4 | SEQ ID NO |
|---|---|---|---|---|---|---|---|---|
| SC57.17 | EVQLQQSGAELVKPGASVKLSCTASGFNIK | DTYMH | WVKQRPEQGLEWIG | RIDPANVNTSDDPKFQG | KATIAADTSSNTVYLQLSSLTSEDTAVYYCAR | DYRYDGYYYAMDY | WGQGTSVTVSS | 71 |
| SC57.20 | DVQLQESGPDLVKPSQSLSLTCTVTGYSIT | SGYSWH | WIRQFPGNKLEWMG | FIHYSGSSNYNPFLKS | RISITRDTSKNQFFLQMNSVNTEDTATYYCSR | KGSFYPMDY | WGQGTSVTVSS | 75 |
| SC57.27 | ELKLVESGGDLVKPGGSLKLSCAASGFSFN | NYAMS | WVRQTPEKRLEWVA | SISSGGTTFYPDSVKG | RFTMSRDHARNILYLQMNSLRSEDTAMYYCVR | GQWLSLYSMDY | WGQGTSVTVSS | 79 |
| SC57.31 | QVHLKESGPGLVAPSQSLSITCTVSGFSLT | TYGVH | WVRQPPGKGLEWLG | VIWAGGSTKYNSAFMS | RLSISKDNSKTQVLLKMNSLQTDDTAMYYCAR | VASHGSSSWFAY | WGQGTLVTVSA | 83 |
| SC57.43 | EVKLVESGGGLVQPGGSLKLSCAASGFTFG | SYTMS | WVRQTPEKRLEWVA | YISNGGVYTYPDTVKG | RFTISRDNAKNTLYLQMSSLKSEDTAMYYCAR | GYDWYFDV | WGAGTTVTVSS | 87 |
| SC57.60 | QVQLQQSGAELVRPGSSVKISCKASGYAFS | SYWMN | WVKQRPGQGLEWIG | QIYPGDGDTNYNGKFKG | KATLTADKSSSTAYMQLSSLTSEDSAVYFCAR | AYYGNLYVMDY | WGQGTSVTVSS | 91 |

FIG. 6B Cont.

Anti-MFI2 Humanized Antibody Amino Acid Variable Region Heavy Chain Sequence

| Name | FR1 | CDRH1 | FR2 | CDRH2 | FR3 | CDRH3 | FR4 | SEQ ID NO |
|---|---|---|---|---|---|---|---|---|
| hSC57.5 | EVQLVQSGAEVKKPGESLKISCKGSGYSFT | DYYLH | WVRQMPGKGLEWMG | RINPYNGATSYNQIFKD | QVTISADKSISTAYLQWSSLKASDTAMYYCAR | GGDYDFPWY | WGQGTTVTVSS | 95 |
| hSC57.5v1 | EVQLVQSGAEVKKPGESLKISCKGSGYSFT | DYYLH | WVRQMPGKGLEWMG | RINPYNAATSYNQIFKD | QVTISADKSISTAYLQWSSLKASDTAMYYCAR | GGDYDFPWY | WGQGTTVTVSS | 97 |
| hSC57.32 | QVQLVQSGAEVKKPGASVKVSCKASGYTFT | NYRIE | WVRQAPGQGLEWMG | EILPRGGNTNYNEKFKG | RVTFTADTSTSTAYMELRSLRSDDTAVYYCAR | DDGYYGRFAY | WGQGTLVTVSS | 101 |
| hSC57.32v1 | QVQLVQSGAEVKKPGASVKVSCKASGYTFT | NYRIE | WVRQAPGQGLEWMG | EILPRGGNTNYNEKFKG | RVTMTADTSTSTAYMELRSLRSDDTAVYYCAR | DDGYYGRFAY | WGQGTLVTVSS | 103 |
| hSC57.43 | QVQLVESGGGVVQPGRSLRLSCAASGFTFG | SYTMS | WVRQAPGKGLEWVA | YISNGGVTYYPDTVKG | RFTISRDNSKNTLYLQMNSLRAEDTAVYYCAR | GYDWYFDV | WGQGTTVTVSS | 107 |

FIG. 6B Cont.

Anti-MFI2 Murine Antibody Nucleotide Variable Region Sequences

| Name | Chain | Nucleic Acid Sequence | SEQ ID NO |
|------|-------|----------------------|-----------|
| SC57.1 | Light chain | CAAATTGTTCTCACCCAGTCTCCAGCAATCATGTCTGCATCTCCAGGGGAGAAAGGTCACCATGACCTGCAGTGCCAGTCAAGTGTAAGTTACATGCACTGGTACCAGCAGAAGTCAGGCACCTCCCCAAAAGATGGATTTATGACACATCCAAACTGGCTTCTGGAGTCCCAGTTCGCTTCAGTGGCAGTGGGTCTGGGACCTCTTACTCTCTCACAATCAGCAGCATTGAGGCTGACGATGCTGCCACTTATTACTGCCAGCAGTGGAGTAGAACCCCACCCACGTTCGGAGGGGGGACCAAGCTGGAAATAAAA | 20 |
| SC57.1 | Heavy chain | CAGGTGCAACTGAAGCAGTCAGGACCTGGCCTAGTGCAGCCCTCACAGAGCCTGTCCATCACCTGCACAGTCTCTGGTTTCTCATTAACTGACTATGGTGTACACTGGGTTCGCCAGTCTCCAGGAAAGGGTCTGGACTGGCTGGGAGTGATATGGAGTGGTGGAAACACAGACTATAATGCAGCTTTCATATCCAGACTGAGCATCAGCAAGGACAATCCAAGGACCAATTCCAAGAGCCAAATTTCTTTGAAATGAACAGTCTACAAGATACTGACACAGCCATATATTACTGTGCCAGACAACTTCATTACTACGGCCCCTTTGCTTACTGGGGCCAAGGGACTCTGGTCACTGTCTCTGCA | 22 |
| SC57.3 | Light chain | GATATTGTGCTAACTCAGTCTCCAGCCACCCTGTCTGTGACTCCAGGAGATAGCGTCAGTCTTTCCTGCAGGGCCAGCCAAGGTATTAGCAACAACCTACACTGGTATCAACAAAATCACATGAGTCTCCAAGGCTTCTCATCAAGTATGCTTCCCAGTCCATCTCTGGGATCCCCTCAGCGGCCAGTGGATCAGGGACACAGATTTCGCTCTCAGTATCAACAGTGTGGAGACTGAAGATTTTGGAATGTTTTCTGTCAACAGAGTAACAGCTGGCCGCTCACGTTCGGTGCTGGGACCAAGCTGGAGCTGAAA | 24 |
| SC57.3 | Heavy chain | CAGGTGCAGCTGAAGCAGTCAGGACCTGAAGCAGTCAGGACCTGGCCTAGTGCAGCCCTCACAGAGCCTGTCTCATCACCTGCACAGTCTCTGGTTTCTCATTAAGTAGTTATGGTGTACACTGGGTTCGCCAGTCTCCAGGAAAGGGTCTGGAATGGCTGGGAGTGATATGGAGTGGTGGAAACACAGACTATAATGCAGCTTTCATATCCAGACTGAGCATCAGCAAGGACAACTCCAAGAGCCAAGTTTTCTTTAAAATGAACAGTCTGCAAGCTGATGACACAGCCATATATTACTGTGCCAGAAGGAATAACTCGGCCTGGTTTGCTTACTGGGGCCAAGGGACTCTGGTCACTGTCTCTGCA | 26 |
| SC57.4 | Light chain | GATGTTGTGATGACCCAAACTCCACTCTCCCTGCCTGTCAGTCTTGGAGATCAAGCCTCCATCTCTTGCAGATCTAGTCAGAGTAGTACACAGTAATGGAAACACCTATTTACATTGGTACCTTCAGAAGCCAGGCCAGTCTCCAAAGCTCCTGATCTACAAAGTTTCCAATCGATTTTCTGGGGTCCCAGACAGGTTCAGTGGCAGTGGATCAGGGACAGATTTCACACTCAAGATCAGCAGAGTGGAGGCTGAGGATCTGGGAGTTTATCTCTGCTCTCAAAGTACACATGTTCCGCTCACGTTCGGTGCTGGGACCAAGCTGGAGCTGAAA | 28 |
| SC57.4 | Heavy chain | GAGATCCAGCTGCAGCAGTCTGGACCTGAGCTGGTGAAGCCTGGGGCTTCAGTGAAGATAGTCCTGTCAAGGCTTCTGGCTACTCATTCACTGACTTCAACATGCACTGGGTGAAGCAGAGCCATGGAAAGAGCCTTGAGTGGATTGGATATATTGATCCTTACAAAGGTGGTATTAGCTACAACCAGAAGTTCAAGGGCAGGGCCACATTGACTGTAGACAAGTCCTCCAGCACAGCCTATATGCATCTCAAAGAGCCTGACATCTGACGACTCTGCAGTCTATTACTGTGCAAGAGATTACGGTAGTAGATTACGGGATCCCCTTACTATTTTGATTACTGGGGCCAAGGCCCACCCACTCTCACAGTCTCCTCA | 30 |

FIG. 6C

Anti-MFI2 Murine Antibody Nucleotide Variable Region Sequences

| Name | Chain | Nucleic Acid Sequence | SEQ ID NO |
|---|---|---|---|
| SC57.5 | Light Chain | GACATTGTGATGACCCAGTCTCACAAATTCATGTCCACATCAGTAGGAGACAGGGTCAGCATCACCTGTAAGGCCAGTCAGGATGTGTATGCTGCTGGTATCATCAAAAACCAGGGCAATCTCCTAAACTACTGATTTACTGGGCATCCACCCGGCACGCTGGAGTCCCTGATCGCTTCACAGGCAGTGGATCTGGGACAGATTATCTCTCACCATCAGCAGTGTGCAGGCTGAAGACCTGGCACTTTATTACTGTCAGCAACATTATCGCACTCCGTGGACGTTCGGTGGAGGCACCAAGCTGGAAATCAAA | 32 |
| SC57.5 | Heavy Chain | GAGGTCCAGCTGCAACAGTCTGGACCTGAGCTGGTGAAGCCTGGGGCTTCAGTGAAGATATCCTGCAAGGCTTCTGGTTACTCATTCACTGACTACTACTTTGCACTGGGTGAAGCAAAGCCATGTAAAGAGCCTTGAGTGGATTGGAGATTACTTACAATGGTGCTACTAGTTACAACCAGATTTTCAAGGACAAGGCCAGCTTGACTGTAGATAAGTCCTCCAGCACAGCCTACATGGACCTCCACAGCCTGACATCTGAGGACTCTGCAGTCTATTACTGTGCAAGAGGGGGACTATGATTTTCCCCTGGTACTGGGGCCAAGGCACCACTCTCACAGTCTCCCA | 34 |
| SC57.6 | Light Chain | GACATTGTGATGTCCCAGTCTCCGTCTCCCTGGCTGTGTCAGCAGGGAGAAGGTCACTATGAGCTGCAAATCCAGTCAGAGTCTGCTCAACAGTAGAATCCGAAAGAACTACTTGGCTTGGTACCAGCAGAAACCAGGGCAGTCTCCTAAACTGCTGATCTACTGGGCATCCACTAGGGAATCTGGGGTCCCTGATCGCTTCACAGGCAGTGGATCTGGGACAGATTTCACTCTCACCATCAGCAGTGTGCAGGCTGAAGACCTGGCAGTTTATTACTGCCAGCAATATTATAGCTATCCGTACACGTTCGGAGGGGGGACCAAACTGGAAATAAAA | 36 |
| SC57.6 | Heavy Chain | GGAGTGCAGGTGGTGGAGTCTGGGGGAGGTAGTGCAGCCTGGAGGGTCCCTGAAACTCTCCTGTGCAGCCTCTGGATTCACTTTCAGTAGCTATGCCATGTCTTGGGTTCGCCAGACTCCAGAGAAGAGGCTGGAGTGGGTCGCATACATTAGTAGTGGTGGTAGCACCTATTACCCAGACACTGTAAAGGGCCGATTCACCATCTCCAGAGACAATGCCAAGAACACCCTGTACCTACAAATGAACAGTCTGAAGTCTGAAGACACGGCCATGTATTACTGTGCAAGACTGGATCTTACTTCGATGTCTGGGGCGCAGGGACCCCGGTCACCGTCCTCA | 38 |
| SC57.8 | Light Chain | GACATTGTGATGACCCAGTCTCACAAATTCATGTCCACATCAGTAGGAGACAGGGTCAGCATCACCTGCAAGGCCAGTCAGGATGTGGGTACGACTGTAGCCTGGTATCAACAGAAACCAGGGCAATCTCCTAAACTACTTATTTACTGGGCATCCACCCGGCACACTGGAGTCCCTGATCGCTTCACAGGCAGTGGATCTGGGACAGATTTCACTCTCATTATTAGCAATGTGCAGTCTGAAGACTTGGGAGCTGAAA | 40 |
| SC57.8 | Heavy Chain | CAGGTGCAGCTGAAGCAGTCAGGACCTGGCCTAGTGCAGCCCTCACAGAGCCTGTCCATCTCTGCACAGTCTCTGGTTTCTCATTAACTACCTATGGTGTATACTGGGTTCGCCAGTCTCCAGGAAAGGGTCTGGAGTGGCTGGGAGTGATATGGAGTGGAAGCACAGACTATAATGCAGCTTTCATATCCAGACTGATCATCAGCAAGGACAATTCCAAGAGCCAAGTTTTCTTTAAAATGAACAGTCTGCAAGCTAATGACACAGCCATATTATTACTGTGCCAGAATCTCCTATGATTACGACGGGGCTTACTGGGGCCAAGGGACTCTGGTCACTGTCTCTGCA | 42 |

FIG. 6C Cont.

Anti-MFI2 Murine Antibody Nucleotide Variable Region Sequences

| Name | Chain | Nucleic Acid Sequence | SEQ ID NO |
|---|---|---|---|
| SC57.9 | Light chain | CAAATTGTTCTCACCCAGTCTCCAGCAATCATGTCTGCATCTCCAGGGGAGAAGGTCACCATAACCTGCAGTGCCAGCTCAAGTGTAAGTTACATGCACTGGTTCCAGCAGAAGCCAGGCACTTCTCCCAAACTCTGGATTTATACCACATCCAACCTGGCTTCTGGAGTCCCTGCTCGCTTCAGTGGCAGTGGATCTGGAACCTCTTACTCTCTCACAATCAGCCGAATGGAGGCTGAAGATGCTGCCACTTATTACTGCCAGCAAAGGAGTAGTTTCCCACCCACGTTCGGCTCGGGGACAAAGTTGGAAATAAAA | 44 |
| SC57.9 | Heavy chain | CAGGTTCAGCTGCAGCAGTCTGGACCTGAGCTGGTGAAGCCTGGGGCTTCAGTGAAGATATCCTGCAAGGCTACTGGCTACACATTCACTGACTATAACATGAACTGGGTAAAGCAGAGGCCTGGACATGGCCTTGAGTGGATTGGAGAGATTTTACCTGAAGTGGTAGTACTGAGTAATGAGAAGTTCAAGGGCAAGGCCACATTCACTGCAGATAAATCTTCCAACAGCCTACATGCAACTCAGCAGCCTGACATCTGAGGACTCTGACGTCTATTACTGTGCAAGAAAGAGGTACGGGACTATGGACTACTGGGGTCAAGGAACCTCAGTCACCGTCTCCTCA | 46 |
| SC57.10 (SC57.32) | Light chain | GATATCCAGATGACACAGACTACATCCTCCCTGTCTGCCTCTGTAGGAGACAGAGTCACCATCAGTTGCAGGGCAAGTCAGGACATTAGCAATTATTAAACTGGTATCAGCAGAAACCAGATGGAACTGTTAAACTCCTGATCTTTTACACATCCAAGATTACACTCAGGAGTCCCATCCAGGTTCAGTGGTAGTGGGTCTGGAACAGATTATTCTCTCACCATTAGCAACCTGGAACAAGAAGATTTTGCCACTTACTTTTGCCAACAGGGTAATACGCTTCCTCCGACGTTCGGTGGAGGCACCAAGCTGGAAATCAAA | 48 |
| SC57.10 (SC57.32) | Heavy chain | CAGGTTCAGCTGCAGCAGTCTGGAGCTGAGCTGGTGATGAAGCCTGGGGCCTCAGTGAAGATATCCTGCAAGGCTACTGGCTACACATTCAGTAACTACATTCAGTGGGCAAGGGTCAAGGCTACATGGCTGGATGGCAAGGGTACAATAGCCTACATGCAACTCATCGACATCTCTGAGGACATCTGAGGCACTCTGCCGTCTATTACTGTGCAAGGGATGGTTGCTTACTGGGGCCAAGGGACTCTGGTCACTGTCTCTGCA | 50 |
| SC57.11 | Light chain | GATATCCAGATGACACAGACTACATCCTCCCTGTCTGCCTCTCTGGGAGACAGAGTCACCATCAGTTGCAGGGCAAGTCAGGACATTAGCAAGTATTATTAAACTGGTATCAGCAGAAACCAGATGGAACTGTTAAACTCCTGATCTATTACACATCAAGATTACACTCAGGAGTCCCATCAAGGTTCAGTGGCAGTGGGTCTGGAACAGATTATTCTCTCACCATTAACAACCTGGAGCAAGAAGATATTGCCACTTACTTTTGCCAACAGGGTAATACGCTTCCTCCGACGTTCGGTGGAGGCACCAAGCTGGAAATCAAA | 52 |
| SC57.11 | Heavy chain | CAGGTTCAGCTGCAGCAGTCTGGAGCTGAGCTGGTGAAGCCTGGGGCCTCAGTGAAGATATCCTGCAAGGCTACTGGCTACACATTCAGTAACTACAGGATAGAGTGGATGAAACAGAGGCCTGGACATGGCCTTGAGTGGATTGGAGAGATTTTACCTAGAACTGGTAATACTAGAATGGAGAACTTCAAGGGCAAGGCCACATTCACTGCAGATACATCCTCCAACACGCCTACATACAACTCACCTGACATCTGAGGACTCTGCCGTCTATTACTGTGCAAGGGATGATGGTTACTACGGGAGGTTTGCTTACTGGGGCCAAGGGACTCTGGTCACTGTCTCTGCA | 54 |

FIG. 6C Cont.

Anti-MFI2 Murine Antibody Nucleotide Variable Region Sequences

| Name | Chain | Nucleic Acid Sequence | SEQ ID NO |
|---|---|---|---|
| SC57.12 | Light chain | GACATCCAGATGACTCAGTCTCCACCCTCCCTATCTGCATCTGTGGGAGAAACTGTCACCATCACATGTCGAACAAGTGAGAATATTTACAGTTATTTAACATGGTATCAGCAGAAACAGGGAAA ATCTCCTCAGCTCCTGGTCTCTGGTCTATAATGCAAAAACCTTAGCAGAGGGTGTGCCATCAAGGTTCAGTGGCAGTGGATCAGGCACACAGTTTTCTCTGAAGATCAACAGCCTGCAGCCTGAGGATTTTG GGAGTTATTACTGTCAACATCATTATGGTACTCCGCTCACGTTCGGTGCTGGGACCAAGCTGGAGCTGAAA | 56 |
| SC57.12 | Heavy chain | CAGGTGCAGCTGAAGGAGTCAGGACCTGGCCTGGTGGCGCCCTCACAGAGCCTGTCCATCACTTGCACTGTCTCTGGGTTTTCATTAACCAGTTATGGTGTACTAGTTTCGCCAGCCTCCAGG AAAGGGTCTGGAGTGGCTGGGAATTTATAGGGCTGGTGGAACCACAAATTATAATTCGGCTCTCATGTCCAGACTGAGCATCAGAAAAGACAACTCCAAGAGCCAAGTTTCTTAAAAATGAACA GTCTGCAAACTGATGACACAGCCATGTACTACTGTGCCAGAGATAGGGGCTATGATGGTTACTTCGACTATGCTGTGGACTACTGGGGTCAAGGAACCTCAGTCACCGTCTCCTCA | 58 |
| SC57.14 | Light chain | GACATTGTGATGTCACAGTCTCCATCTCCCTGGCTGTGTCAGCAGGAGAAGGTCACTATGAGCTGCAAATCCAGTCTGCTCAACAGTAGAACCGAAAGAACTACTTGGCTTGGTA CCAGCAGAAACCAGGGCAGTCTCCTAAACTGCTGATCTACTGGGCATCCACTAGGGAATCTGGGGTCCCTGATCGCTTCACAGGCAGTGGATCTGGGACAGATTTCACTCTCACCATCAGCAGTG TGCAGGCTGAAGACCTGGCAGTTTATTACTGCAAGCAATCTTATTACTGTGGACGTTCGGTGGAGGCACCAAGCTGGAAATCAAA | 60 |
| SC57.14 | Heavy chain | GATGTACAGCTTCAGGAGTCAGGACCTGGCCTGGTGAAACCTTCTGTCTCTGTCTCTCACCTGCTCTGTCACTGGCGACTGGATCGGCAGTTTCC AGGAAACAAACTGGAATGGGCTACATAAGCTACGACGGTTACAATAACTACGACCATCTCTCAAAATGAATTCTCCATCGTGACACATCTAAGAACCAGTTTTCCTGAAGTTGA ATTCTGTGACTACTGAGGACACAGCTACATATTACTGTGCAAGCAACTATTGGTACGGCGTTACTTTGACTACTGGGGCCAAGGCACCACTCTCACAGTCTCCTCA | 62 |
| SC57.15 | Light chain | GACATCCAGATGACTCAGTCTCCAGCTTCACCTCCCAGTCTGCATCTGTGGGAGAAACATCGTCACCATCACATGTCGAGCAAGTGAGAATATTTACGGTGCTTTAAATTGGTATCAGCGGAAACAGGGGAAA ATCTCCTCGATCTCCTGATCTATGGTGCAACCAACTGGCAGATGGCATGTCATCGAGGTTCAGTGGCAGTGGATCTGGTGACAGTATTCTCTCAAGATCAGTGGCCTGCATCCTGCCGATGTTG CAACGTATTACTGTCAAAATGTATTAAATACTCCGTGGAGGCACCAAGCTGGAAATCAAA | 64 |
| SC57.15 | Heavy chain | GATGTGCAGCTTCAGGAGTCAGGACCTGGCCTGGTGAAACCTTCACTCACTTTCACTGTCGTCACCTGCGCTGTCACTGGCTACTCCATCACCAGTGCTTATACCTGGCACTGGATCCGGCAGTTTCC AGGAAACAAACTGGAATGGATGGGCTACATGCACTACAACTCTCATACCAAACCCATCTCTCAAAAGTGAATCTATCACTCGAGACACATCCAAGAACCAGTTCTTCCTGCAGTTGA ATTCTGTGACTACTGAGGACACAGCTACATATTACTGTACCGGTTGTACTGGTACTTCGATGTCTGGGGCGCAGGGACCACGGTCACCGTCTCCTCA | 66 |

FIG. 6C Cont.

Anti-MFI2 Murine Antibody Nucleotide Variable Region Sequences

| Name | Chain | Nucleic Acid Sequence | SEQ ID NO |
|---|---|---|---|
| SC57.17 | Light chain | GATATCCAGATGACACAGACTACATCTCCCTGTCTGCCTCTGTCAGTTGCAGTGCAAGTCAGGACATAAACAATTATTTAAACTGGTATCAACAGAAACCAGATGG AACTGTTAAACTCCTGATCCATTACACATCAAGTTTACACTCAGGAGTCCCATCAAGGTTCAGTGGCAGTGGGTCTGGGACAGATTATTCTCTCACCATCAGCAACCTGAAGATATTG CCACTTACTATTGTCAGCAGTATAGTAAGGTTCCGTGGACGTTCGGTGGAGGCACCAAGCTGGAAATCAAA | 68 |
| SC57.17 | Heavy Chain | GAAGTTCAGCTGCAGCAGTCTGGGGCAGAGCTTGTGAAGCCAGGGGCCTCAGTCAAGTTGTCCTGCACAGCTTCTGGCTTCAACATTTAAAGACACCTATATGCACTGGGTGAAGCAGAGGCCTGA ACAGGGCCTGGAGTGGATTGGAAGGATTGATCCAGCGAATGTAAATACTAGCGATGACCCGAAGTTCCAGGGCAAGGCCACTATAGCAGACACATCCTCCAACACAGTTTACCTGCAGCTCA GCAGCCTGACATCTGAGGACACTGCCGTCTATTATTGTGCTAGAGACTAGGTACGACGGATATTACTATGCTATGGACTACTGGGGTCAAGGAACCTCAGTCACCGTCTCCTCA | 70 |
| SC57.20 | Light chain | GACATTGTGATGACCCAGTCTCACAAATTCATGTCCACATCAGTAGGAGACAGGGTCAGCATCACCTGCAAGGCCAGTCAGAATGTGGGTTCTGTTGCCTGGTCTCAACAGAAACCAGGACA ATCTCCTAAACTACTGATTTACTGGGCATCTCCCGGCACAGTTTTACCTAATCTGGAGTCCCTGATCGTTCACAGGCAGTGGATCTGGGACAGATTTCACTCTCACCATTAGCAATGTGCAGTCTGAAGACTTGG CAGATTATTTCTGTCAGCAATATAGCAACTATCCTCTCACGTTCGGTGCTGGGACCAAGCTGGAGCTGAAA | 72 |
| SC57.20 | Heavy Chain | GATGTGCAGCTACAGGAGTCAGGACCTGACCTGGTGAAACCTTCTCAGTCACTTTCACTGACTGTCACTGGCTACTCCATCACCAGTGGTTATAGCTGGCACTGGATCCGGCAGTTTCC AGGAAACAAACTGGAATGGATGGGCTTCATACACTACAGTGGTCTCTAACTACACAACCCATTTCTAACAAAGTCGAATCTCTATCACTCGAGACACTCAAGAAACCAGTTCTTCCTGCAGATGA ATTCTGTGAATACAGAGGACACAGCCACATATTACTGTTCAAGAAAAGGCTCCTTCTATCTATGGACTACTGGGGTCAAGGAACCTCAGTCACCGTCTCCTCA | 74 |
| SC57.27 | Light chain | GACATCCAGATGACTCAGTCTCCAGCTCCCTGTCTGCATCTGTGGGAGAAACTGTCACCATCACATGTCGAGCAAGTGAGAATATTTACAGTTATTTAGCATGGTATCAGCAGAAACAGGGAAA ATCTCCTCAGCTCCTGGTCTATAATGCAAAAACCTTAGCAGAAGGTGTGCCATCAAGGTTCAGTGGCAGTGGATCAGGCACACAGTTTCTCTGAAGATCAAGCCTGCAGCCTGAAGATTTTG GGACTTATTACTGTCAACATCATTATGGTGTTCCTGTCACGTTCGGTGCTGGGACCAAGCTGGAGCTGAAA | 76 |
| SC57.27 | Heavy Chain | GAACTGAAACTGGTGGAGTCTGGGGGAGACTTAGTGAAGCCTGGAGGGTCCCTGAAACTCTCTGTGCAGCCTCTGGATTCTCTTTCAATAACTATGCCATGTCTTGGGTTCGTCAGACTCCAGA GAAGAGGCTGGAGTGGGTCGCATCCATTAGTAGTGGTGGAACTACGTTCTATCCAGACAGTGTGAAGGGCCGATTTACCATCTCCAGAGATCATGCCAGGAACATCCTGTACCTGCAAATGAACA GTCGAGGTCTGAGGACACGGCCATGTATTACTGTGTAAGAGGCCAATGGTTATCACTCTATTCTATGGTTATCACTCTATTCTATGGACTACTGGGGTCAAGGAACCTCAGTCACCGTCTCCTCA | 78 |

FIG. 6C Cont.

Anti-MFI2 Murine Antibody Nucleotide Variable Region Sequences

| Name | Chain | Nucleic Acid Sequence | SEQ ID NO |
|---|---|---|---|
| SC57.31 | Light Chain | GATATTGTGCTAACTCAGTCTCCAGCCACCCTGTCTGTGACTCCAGGAGATAGCGTCAGTCTTTCCTGCAGGGCCAGCCAAAGTGTTGGCAACAGCCTACACTGGTATCAACAAAAATCACATGA GTCTCCAAGGCTTCTCATCAAGTATGCTTCCCAGTCCATCTCGGGATCCCCTCCAGGTTCAGTGGCAGTGGATCAGGGACAGATTTCACTCTCAGTATCAACAGTGTGGAGACTGAAGATTTTG GAATGTATTTCTGTCAACAGAGTGACAGCTGGCCGCTCACGTTCGGCTCGGGACCAAGCTGGAGCTGAAA | 80 |
| SC57.31 | Heavy Chain | CAGGTGCACCTGACCTGAAGGAGTCAGGACCTGGCCTGGTGGCGCCCTCACGAGCCTGTCCATCACTTGCACTGTCTCTGGGTTTTCATTAACCACCTATGGTGTACACTGGGTTCGCCAGCCTCCAGG AAAGGGTCTGGAGTGGCTGGGAGTAATATGGGCTGGTGGAAGCACAAAATATAATTCGGCTTTCATGTCCAGACTGAGCATCAGCAAAGACAACTCCAAGACCCAAGTTCTCTAAAAATGAACA GTCTGCAAACTGATGACACAGCCATGTACTACTGTGCCAGAGTGGCCTCCCACGGTAGTAGCTCCTGGTTTGCTTACTGGGCCAAGGGACTCTGGTCACTGTCTCTGCA | 82 |
| SC57.43 | Light Chain | GATGTTGTGATGACCCAAACTCCACTCTCCCTGCCTGTCAGTCTTGGAGATCAAGCCTCCATCTCTTGCAGATCTAGTCACAGTAATGGAAACACCTATTTACATTGGTACCT GCAGAAGCCAGGCCAGTCTCCAAAGCTCCTGATCTACAAAGTTTCCAACCGATTTTCTGGGGTCCCAGACAGGTTCAGTGGCAGTGGATCAGGGACAGATTTCACACTCAAGATCAGCAGAGTGG AGGCTGAGGATCTGGGAGTTTATTTCTGCTCTCAAAGTACACATGTTCCTCGTACACGTTCGGAGGGGGGACCAAGCTGGAAATAAAA | 84 |
| SC57.43 | Heavy Chain | GAAGTGAAGCTGGTGGAGTCTGGGGGAGGTTTAGTGCAGCCTGGAGGGTCCCTGAAACTCTCTGTGCAGCCTCTGGATTCACTTTCGGTAGCTATACCATGTCTTGGGTTCGCCAGACTCCAGA GAAGAGGCTGGAGTGGGTCGCATACATTAGTAATGGTGTTATGTCACCAGACACTGTAAAGGGCCGATTCACCATCTCCAGAGACAATGCCAAGAATACCCTGTACCTGCAAATGA GCAGTCTGAAGTCTGAGGACTCTGCAGTCTATTACTGTCAAGAGGATACGACTGGTACTTCGATGTCTGGGGCGCAGGGACCACGGTCACCGTCTCCTCA | 86 |
| SC57.60 | Light Chain | GACATCCAGATGACTCAGTCTCCAGCCTCCCTATCTGCATCTGTGGGAGAAACTGTCACCATCACATGTCGAGCAAGTGAGAATATTTACAGTTATTTAGCATGGTCTCAGCAGAAGCAGGGAAA ATCTCCTCACCTCCTGGTCTATAATGCAAAAACCTTAGCAGAAGGTGTGCCATCAAGGTTCAGTGGCAGTGGATCAGGCACACAGTTTTCTGAAGATCAACAGCCTGAGCCTGAAGATTTTG GGAGTTATTACTGTCAACATCATTATGGTATTCCGCTCACGTTCGGTGCTGGGACCAAGCTGGAGCTGAAA | 88 |
| SC57.60 | Heavy Chain | CAGGTTCAGCTGCAGCAGTCTGGGGCTGAGCTGGTGAGGCCTGGGGCTTCAGTGAAGATGTCCTGCAAGGCTTCTGGCTATGCATTCAGTAGCTACTGGATGAACTGGGTGAAGCAGAGGCCTGG ACAGGGTCTTGAGTGGATTGGACAGATTTATCCTGGAGATGGTGATACTAACTACAATGGAAAGTTCAAGGGTAAAGCCACATTGACTGCAGACAAATCCTCCAGCACAGCCTACATGCAGCTCA GCAGTCTAACATCTGAGGACTCTGCGGTCTACTTCTGTGCAAGAGCTTACTACGGAAACCTCTATGTTATGGACTACTGGGGTCAAGGAACCTCAGTCACCGTCTCCTCA | 90 |

FIG. 6C Cont.

Anti-MFI2 Humanized Antibody Nucleotide Variable Region Sequences

| Name | Chain | Nucleic Acid Sequence | SEQ ID NO |
|---|---|---|---|
| hSC57.5 | Light Chain | GACATCCAGATGACACAGTCTCCATCCTTCAAGTCTGAGTGCCTCCGTAGGTGATAGAGTCACCATTACATGCAAAGCATCTCAAGACGTTTACGCTGCCGTGGCTTGGTACCAGCAGAAACCC GGCAAGGCTCCAAAGTTGCTGATTTACTGGGCAGCACTTCGCTCACGTGGCGTTCCTTCACGTTTTTCAGGCAGTGGAAGCGGGACCGACTTCACCCTGACCATCTCTAGTCTCCAGCCC GAGGACTTTGCTACCTACTGCCAGCAGCATTACCGTACACCTTGGACTTTCGGCCAAGGCACCAAGGTCGAGATTAAA | 92 |
| hSC57.5 | Heavy Chain | GAAGTGCAACTCGTGCAGAGCGGGGCCGAAGTAAAAAAACCAGGCGAGCTTGAAAATTTCTTGCAAGGGATCCGGCTACTCCTTCACAGACTATATCCTCACTGGGTCCGCCAGATG CCCGGCAAAGGCCTTGAATGGATGGGCAGAATAAATCCCTACAACGGCCTACCTCCTATAATCAGATCTCCAAGGATCAAGTGACCATCTCCGCGATAAGTCCATCTCCACAGCTTAT CTTCAGTGGAGCTCACTGAAGGCTAGCGATACTGCCATGTATTACTGTGCAAGGGGCGGACTACGATTTCCCTTGGTATTGGGGCCAGGGAACTACCGTCACTGTTAGCAGC | 94 |
| hSC57.5v1 | Heavy Chain | GAAGTGCAACTCGTGCAGAGCGGGGCCGAAGTAAAAAAACCAGGCGAGCTTGAAAATTTCTTGCAAGGGATCCGGCTACTCCTTCACAGACTATATCCTCACTGGGTCCGCCAGATG CCCGGCAAAGGCCTTGAATGGATGGCAGAATAAATCCCTACAACGCCTACCTCCTATAATCAGATCTTCAAGGATCAGATTCTCGCCGATAAGTCCATCTCCACAGCTTAT CTTCAGTGGAGCTCACTGAAGGCTAGCGATACTGCCATGTATTACTGTGCAAGGGGCGGACTACGATTTCCCTTGGTATTGGGGCCAGGGAACTACCGTCACTGTTAGCAGC | 96 |
| hSC57.32 | Light Chain | GATATTCAGATGACTCAGTCTCCCAGCAGCCTTAGCGCACTTGTGGGAGATCGTGTCACCATTACCTGCCGCGCTTCACAGGACATTTCTAACTACCTCAACTGGTATCAGCAGAAGCCA GGTAAGGCACCCAAAGCTCCTGATCTACTATACTTCCTACAGCGTGCACAGCGGTGTCCATCTAGATTCTCTGGAAGTGGGAGCGGCACAGACTACACACTCACAATCAGCTCCTTGCAGCCT GAAGATTTTGCAACTTATTATTGCCAGCAGGGAAACACACTCGCCACCAACCTTCGGCGGTGGGACCAAGGTGGAGATCAAG | 98 |
| hSC57.32 | Heavy Chain | CAAGTGCAGTTGGTACAGTCTGGCGCAGAGGTCAAAAAGCCCGGAGCTTCAGTGAAAGTGTCCTGCAAAGCCAGTGGATATACATTCACTAACTACCGTATTGAGTGGGTCCGTCAGGCT CCAGGCCAGGGCTGGAGTGGATGGGTGAAATACTGCCTCCGCGGCGGCAATACTAACTACATGAGAAGTTTAAGGGGAGAGTTACATTCACCGCGATACTAGTACTTCCACCGCTAT ATGGAGCTCCGTTCCTCCGAGGCGATGACACTGCCGTGTACTATTGCGCCGTGACGACGGTTATTCGGGGACAGGGTACATTGGTGACAGTATCATCT | 100 |
| hSC57.32v1 | Heavy Chain | CAAGTGCAGTTGGTACAGTCTGGCGCAGAGGTCAAAAAACCCGGAGCTTCAGTGAAAGTGTCCTGCAAAGCCAGTGGATATACATTCACTAACTACCGGATATACATTCACTAACTACCGATACTAGTACTTCCACCGCTAT CCAGGCCAGGGCTGGAGTGGATGGGTGAAATACTGCCTCCGCGGCGGCAATACTAACTGCCGCGTGACGACGGTTATTCGGGGACAGGGTACATTGGTGACAGTATCATCT ATGGAGCTCCGTTCCTCCGAGGCGATGACACTGCCGTGTACTATTGCGCCGTGACGACGGTTATTCGGGGACAGGGTACATTGGTGACAGTATCATCT | 102 |

FIG. 6C Cont.

Anti-MFI2 Humanized Antibody Nucleotide Variable Region Sequences

| Name | Chain | Nucleic Acid Sequence | SEQ ID NO |
|---|---|---|---|
| hSC57.43 | Light Chain | GACATCGTAATGACACAGTCTCCAGATAGTCTCGCCGTGAGTCTGGGAGAGGCGTGCTACTATCAACTGTCGGTCTTCTCAGTCCCTCGTCCCTCGTCCATTCTAATGGAAACACTTACCTCCATTGGTATCAGCAGAAACCCGGTCAGCCACCAAAGTTGCTGATATACAAAGTTCTCAACCGCTTTAGCGGGGTGCCTGATCGTTTCAGCGGGTCAGGAAGCGGGACAGAGCGGAAGCGGGACAGAGACTTTCACCTTGACAATATCATCTCTGCAGGCAGAAGATGTAGCCGTGTATTACTGCTCCCAGTCTACACACGTACCCTCTGTACACATTCGGGGGCGGCACCAAGGTGGAGATTAAG | 104 |
| hSC57.43 | Heavy Chain | CAGGTGCAGCTGGTGGAATCTGGTGGCGGAGTGGTGCAGCCTGGCAGCCTGAGACTGTCTTGTGCCGCCTCCGGCTTCACCTTCGGCTTCACCTTCGCCTATCATGTCCTACACCATGTCCTGGGTGCGACAGGCTCCTGGCAAGGGCCTGGAATGGGTGGCCTACATCTCCAACGGCGGCTACTACTCCAACCGTGAAGGGCCGGTTCACCATCTCTCGGGACAACCTCCAAGAACACCCTGTACCTGCAGATGAACTCCCTGCGGGCCGAGGACACCGCCGTGTACTATTGTGCCAGAGGCTACGACTGGCTTCGACAGAGGCTACGACTGGCTTCGACAGAGGCTACGACTGGTACTTTGCCGAGAGGCTACGACTGGTACTTTGACTACTGGGGCCAGGGCACCACCGTGACAGTGTCATCT | 106 |

FIG. 6C Cont.

Anti-MFI2 Humanized Antibody Full Length Amino Acid Sequences

| Name | Chain | Full Sequence | SEQ ID NO |
|---|---|---|---|
| hSC57.5 | Light Chain | DIQMTQSPSSLSASVGDRVTITCKASQDVVAAVANVQQKPGKAPKLLIYWASTRHAGVPSRFSGSGSGTDFTLTISSLQPEDFATYYCQQHYRTPWTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 108 |
| hSC57.5 | Heavy Chain | EVQLVQSGAEVKKPGESLKISCKGSGYSFTDYYLHWVRQMPGKGLEWMGRINPYNGATSYNQIFKDQVTISADKSISTAYLQWSSLKASDTAMYYCARGGDYDFPWYWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG | 109 |
| hSC57.5v1ss1 | Heavy Chain | EVQLVQSGAEVKKPGESLKISCKGSGYSFTDYYLHWVRQMPGKGLEWMGRINPYNAATSYNQIFKDQVTISADKSISTAYLQWSSLKASDTAMYYCARGGDYDFPWYWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSSDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG | 110 |
| hSC57.5v1 | Heavy Chain | EVQLVQSGAEVKKPGESLKISCKGSGYSFTDYYLHWVRQMPGKGLEWMGRINPYNAATSYNQIFKDQVTISADKSISTAYLQWSSLKASDTAMYYCARGGDYDFPWYWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG | 111 |
| hSC57.32 | Light Chain | DIQMTQSPSSLSASVGDRVTITCRASQDISNYLNWYQQKPGKAPKLLIYYTSRLHSGVPSRFSGSGSGTDYTLTISSLQPEDFATYYCQQGNTLPPTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 112 |
| hSC57.32 | Heavy Chain | QVQLVQSGAEVKKPGASVKVSCKASGYTFTNYRIEWVRQAPGQGLEWMGEILPRGGNTNVYNEKFKGRVTFTADTSTSTAYMELRSLRSDDTAVYYCARDDGYYGRFAYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG | 113 |

FIG. 6D

Anti-MFI2 Humanized Antibody Full Length Amino Acid Sequences

| Name | Chain | Full Sequence | SEQ ID NO |
|---|---|---|---|
| hSC57.32ss1 | Heavy Chain | QVQLVQSGAEVKKPGASVKVSCKASGYTFTNYRIEWVRQAPGQGLEWMGEILPRGGNTNYNEKFKGRVTFTADTSTSTAYMELRSLRSDDTAVYYCARDDGYYGRFAYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSSDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG | 114 |
| hSC57.32v1 | Heavy Chain | QVQLVQSGAEVKKPGASVKVSCKASGYTFTNYRIEWVRQAPGQGLEWMGEILPRGGNTNYNEKFKGRVTMTADTSTSTAYMELRSLRSDDTAVYYCARDDGYYGRFAYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG | 115 |
| hSC57.43 | Light Chain | DIVMTQSPDSLAVSLGERATINCRSSQSLVHSNGNTYLHWYQQKPGQPPKLLIYKVSNRFSGVPDRFSGSGSGTDFTLTISSLQAEDVAVYYCSQSTHVPLYTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 116 |
| hSC57.43 | Heavy Chain | QVQLVESGGGVVQPGRSLRLSCAASGFTFGSYTMSWVRQAPGKGLEWVAYISNGGVVTYYPDTVKGRFTISRDNSKNTLYLQMNSLRAEDTAVYYCARGYDWVFDVWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSQDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG | 117 |
| hSC57.43ss1 | Heavy Chain | QVQLVESGGGVVQPGRSLRLSCAASGFTFGSYTMSWVRQAPGKGLEWVAYISNGGVVTYYPDTVKGRFTISRDNSKNTLYLQMNSLRAEDTAVYYCARGYDWVFDVWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSNTKVDKKVEPKSSDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG | 118 |

FIG. 6D Cont.

CDRs of SC57.5
Light and Heavy Chain Variable Regions

FIG. 6E

CDRs of SC57.32
Light and Heavy Chain Variable Regions

Light Chain

Heavy Chain

FIG. 6F

CDRs of SC57.43
Light and Heavy Chain Variable Regions

FIG. 6G

Light Chain

Heavy Chain

Alignment of Murine and Humanized SC57.5 Amino Acid Sequences
Light Chain
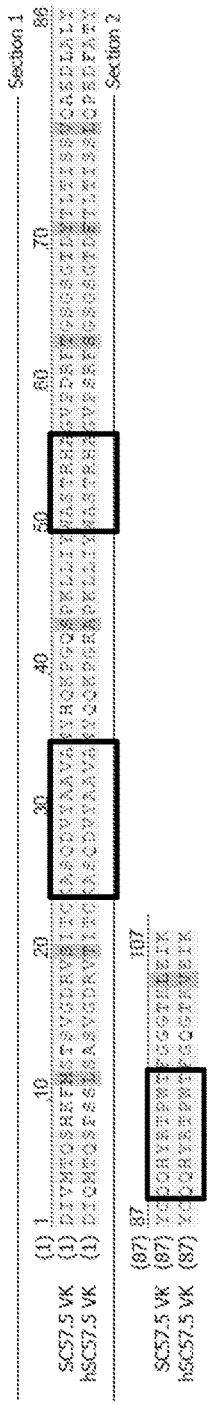
Heavy Chain
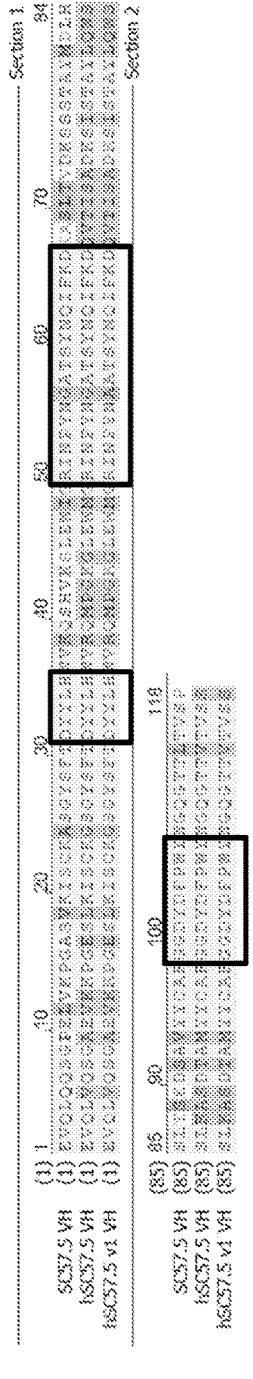
FIG. 6H

Alignment of Murine and Humanized SC57.32 Amino Acid Sequences

Light Chain

Heavy Chain

FIG. 6I

Alignment of Murine and Humanized SC57.43 Amino Acid Sequences

Light Chain

Heavy Chain

FIG. 6J

Anti-MFI2 Antibodies Detect MFI2 Protein on PDX Tumors by Immunohistochemistry

| Annotation Name | H-Score For Membrane Staining |
|---|---|
| BR13 | 85 |
| BR133 | 150 |
| BR134 | 135 |
| BR144 | 24 |
| BR145 | 0 |
| BR22 | 10 |
| BR25 | 35 |
| BR31 | 150 |
| BR5 | 0 |
| BR56 | 60 |
| BR64 | 2 |
| BR86 | 35 |
| LU104 | 0 |
| LU120 | 0 |
| LU123 | 2 |
| LU134 | 0 |
| LU187 | 0 |
| LU205 | 4 |
| LU206 | 0 |
| LU58 | 0 |
| LU92 | 2 |
| SK11 | 0 |
| SK19 | 110 |
| SK3 | 0 |
| SK30 | 0 |
| SK40 | 140 |
| SK43 | 0 |
| SK44 | 106 |
| SK46 | 185 |
| SK55 | 14 |
| SK67 | 160 |
| SK70 | 0 |
| SK79 | 0 |

FIG. 8A

ANTI-MFI2 ANTIBODIES AND METHODS OF USE

CROSS REFERENCED APPLICATIONS

This application claims the benefit of U.S. Provisional Application No. 62/046,610 filed on 5 Sep. 2014, and U.S. Provisional Application No. 62/203,836 filed on 11 Aug. 2015, each of which is incorporated herein by reference in its entirety.

SEQUENCE LISTING

This application contains a sequence listing which has been submitted in ASCII format via EFS-Web and is hereby incorporated by reference in its entirety. Said ASCII copy, created on Jul. 19, 2017 is named SUBS_SEQL_07192017.txt and is 129,495 bytes 129,463 bytes in size.

FIELD OF THE INVENTION

This application generally relates to novel anti-MFI2 antibodies or immunoreactive fragments thereof and compositions, including antibody drug conjugates, comprising the same for the treatment, diagnosis or prophylaxis of cancer and any recurrence or metastasis thereof. Selected embodiments of the invention provide for the use of such anti-MFI2 antibodies or antibody drug conjugates for the treatment of cancer comprising a reduction in tumorigenic cell frequency.

BACKGROUND OF THE INVENTION

Differentiation and proliferation of stem cells and progenitor cells are normal ongoing processes that act in concert to support tissue growth during organogenesis, cell repair and cell replacement. The system is tightly regulated to ensure that only appropriate signals are generated based on the needs of the organism. Cell proliferation and differentiation normally occur only as necessary for the replacement of damaged or dying cells or for growth. However, disruption of these processes can be triggered by many factors including the under- or overabundance of various signaling chemicals, the presence of altered microenvironments, genetic mutations or a combination thereof. Disruption of normal cellular proliferation and/or differentiation can lead to various disorders including proliferative diseases such as cancer.

Conventional therapeutic treatments for cancer include chemotherapy, radiotherapy and immunotherapy. Often these treatments are ineffective and surgical resection may not provide a viable clinical alternative. Limitations in the current standard of care are particularly evident in those cases where patients undergo first line treatments and subsequently relapse. In such cases refractory tumors, often aggressive and incurable, frequently arise. The overall survival rates for many solid tumors have remained largely unchanged over the years due, at least in part, to the failure of existing therapies to prevent relapse, tumor recurrence and metastasis. There remains therefore a great need to develop more targeted and potent therapies for proliferative disorders. The current invention addresses this need.

SUMMARY OF THE INVENTION

In selected embodiments the invention comprises an antibody that competes for binding with an isolated antibody that binds to a cell expressing human MFI2 having SEQ ID NO: 3, wherein the isolated antibody comprises: (1) a light chain variable region (VL) of SEQ ID NO: 21 and a heavy chain variable region (VH) of SEQ ID NO: 23; or (2) a VL of SEQ ID NO: 25 and a VH of SEQ ID NO: 27; or (3) a VL of SEQ ID NO: 29 and a VH of SEQ ID NO: 31; or (4) a VL of SEQ ID NO: 33 and a VH of SEQ ID NO: 35; or (5) a VL of SEQ ID NO: 37 and a VH of SEQ ID NO: 39; or (6) a VL of SEQ ID NO: 41 and a VH of SEQ ID NO: 43; or (7) a VL of SEQ ID NO: 45 and a VH of SEQ ID NO: 47; or (8) a VL of SEQ ID NO: 49 and a VH of SEQ ID NO: 51; or (9) a VL of SEQ ID NO: 53 and a VH of SEQ ID NO: 55; or (10) a VL of SEQ ID NO: 57 and a VH of SEQ ID NO: 59; or (11) a VL of SEQ ID NO: 61 and a VH of SEQ ID NO: 63; or (12) a VL of SEQ ID NO: 65 and a VH of SEQ ID NO: 67; or (13) a VL of SEQ ID NO: 69 and a VH of SEQ ID NO: 71; or (14) a VL of SEQ ID NO: 73 and a VH of SEQ ID NO: 75; or (15) a VL of SEQ ID NO: 77 and a VH of SEQ ID NO: 79; or (16) a VL of SEQ ID NO: 81 and a VH of SEQ ID NO: 83; or (17) a VL of SEQ ID NO: 85 and a VH of SEQ ID NO: 87; or (18) a VL of SEQ ID NO: 89 and a VH of SEQ ID NO: 91.

In another embodiment, the invention comprises an antibody that binds to the TFLD2 domain of MFI2. In some embodiments the anti-MFI2 antibodies of the invention bind to an epitope in an MFI2 protein, wherein the epitope comprises amino acids D460, H463 and N566. In another embodiment, the anti-MFI2 antibodies of the invention bind to tumor initiating cells expressing MFI2 having SEQ ID NO: 3. In another aspect the invention comprises an anti-MFI2 antibody of that is a chimeric, CDR grafted, human or humanized antibody, or a fragment thereof. In another embodiment, the anti-MFI2 antibody of the invention is an internalizing antibody. In one aspect the anti-MFI2 antibody of the invention does not bind to a human transferrin protein.

In a further aspect, the invention comprises a mouse antibody that binds to MFI2 comprising a light chain variable region and a heavy chain variable region, wherein the light chain variable region has three CDRs of a light chain variable region set forth as SEQ ID NO: 21, SEQ ID NO: 25, SEQ ID NO: 29, SEQ ID NO: 33, SEQ ID NO: 37, SEQ ID NO: 41, SEQ ID NO: 45, SEQ ID NO: 49, SEQ ID NO: 53 SEQ ID NO: 57, SEQ ID NO: 61, SEQ ID NO: 65, SEQ ID NO: 69, SEQ ID NO: 73, SEQ ID NO: 77, SEQ ID NO: 81, SEQ ID NO: 85, or SEQ ID NO: 89; and the heavy chain variable region has three CDRs of a heavy chain variable region set forth as SEQ ID NO: 23, SEQ ID NO: 27, SEQ ID NO: 31, SEQ ID NO: 35, SEQ ID NO: 39, SEQ ID NO: 43, SEQ ID NO: 47, SEQ ID NO: 51, SEQ ID NO: 55, SEQ ID NO:59, SEQ ID NO: 63, SEQ ID NO: 67, SEQ ID NO: 71, SEQ ID NO: 75, SEQ ID NO: 79, SEQ ID NO: 83, SEQ ID NO: 87 or SEQ ID NO: 91.

In a further embodiment, the invention comprises a humanized antibody that binds to MFI2 comprising a light chain variable region and a heavy chain variable region, wherein the light chain variable region has three CDRs of a light chain variable region set forth as SEQ ID NO: 93, SEQ ID NO: 99, or SEQ ID NO: 105; and the heavy chain variable region has three CDRs of a heavy chain variable region set forth as SEQ ID NO: 95, SEQ ID NO: 97, SEQ ID NO: 101, SEQ ID NO: 103 or SEQ ID NO: 107.

In one aspect the invention comprises a nucleic acid encoding an anti-MFI2 antibody of the invention. In another embodiment, the invention comprises a vector comprising one or more of the above described nucleic acids or a host cell comprising said vector.

In one embodiment the invention comprises an antibody drug conjugate (ADC) of the formula Ab-[L-D]n or a pharmaceutically acceptable salt thereof wherein: Ab comprises an anti-MFI2 antibody; L comprises an optional linker; D comprises a drug; and n is an integer from 1 to 20. In one aspect the ADC of the invention comprises an anti-MFI2 antibody such as those described above or an immunoreactive fragment thereof. In other embodiments the ADCs of the invention comprise a cytotoxic compound selected from calicheamicins, pyrrolobenzodiazepines, auristatins, duocarmycins, maytansinoids or an additional therapeutic moiety described herein.

In one embodiment the invention comprises a pharmaceutical composition comprising an ADC described above. Another aspect of the invention is a method of treating cancer comprising administering a pharmaceutical composition such as those described herein to a subject in need thereof. In one aspect, the cancer is selected from breast cancer (e.g. triple negative breast cancer), lung cancer, colorectal cancer or skin cancer such as melanoma (e.g. skin cancer expressing wild type or mutated BRAF). In one embodiment the method of treating cancer described above comprises administering to the subject at least one additional therapeutic moiety in addition to the pharmaceutical composition described above.

In one embodiment the invention comprises a method of reducing tumor initiating cells in a tumor cell population, wherein the method comprises contacting (e.g. in vitro or in vivo) a tumor initiating cell population with an ADCs as described herein whereby the frequency of the tumor initiating cells is reduced.

In one aspect, the invention comprises a method of delivering a cytotoxin to a cell comprising contacting the cell with any of the above described ADCs.

In another aspect, the invention comprises a method of detecting, diagnosing, or monitoring cancer (e.g. breast cancer, lung cancer, colorectal cancer or skin cancer) in a subject, the method comprising the steps of contacting (e.g. in vitro or in vivo) tumor cells with an MFI2 detection agent and detecting the detection agent associated with the tumor cells. In selected embodiments the detection agent shall comprise an anti-MFI2 antibody or a nucleic acid probe that associates with an MFI2 genotypic determinant.

The foregoing is a summary and thus contains, by necessity, simplifications, generalizations, and omissions of detail; consequently, those skilled in the art will appreciate that the summary is illustrative only and is not intended to be in any way limiting. Other aspects, features, and advantages of the methods, compositions and/or devices and/or other subject matter described herein will become apparent in the teachings set forth herein. The summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

BRIEF DESCRIPTION OF THE FIGURES

FIG. 5 shows binning, domain binding, isotype, and rat cross reactivity characteristics of exemplary anti-MFI2 antibodies.

FIGS. 6A-6J provide annotated amino acid and nucleic acid sequences of murine and humanized anti-MFI2 antibodies. More particularly FIGS. 6A and 6B show contiguous amino acid sequences of the light chain (FIG. 6A) and heavy chain (FIG. 6B) variable regions (SEQ ID NOS: 21-107, odd numbers) of exemplary murine and humanized anti-MFI2 antibodies. FIG. 6C shows the nucleic acid sequences of the light and heavy chain variable regions (SEQ ID NOS: 20-106, even numbers) of exemplary murine and humanized anti-MFI2 antibodies. FIG. 6D shows the full length amino acid sequences of the light and heavy chains of humanized anti-MFI2 antibodies (SEQ ID NOS: 108-117). FIGS. 6E-6G depict the CDRs of the light and heavy chain variable regions of the SC57.5 (FIG. 6E), SC57.32 (FIG. 6F) and SC57.43 (FIG. 6G) murine antibodies, numbered according to Kabat, as determined using Kabat, Chothia, ABM and Contact methodology. Finally, FIGS. 6H-6J provide aligned amino acid sequences for murine and derived humanized heavy and light chain variable regions for SC57.5 (FIG. 6H), SC57.32 (FIG. 6I) and SC57.43 (FIG. 6J).

FIG. 8A shows the H-score of membranous hMFI2 protein expression in various PDX tumor samples using immunohistochemistry.

FIG. 10C is a concentration dependent curve showing the ability of selected anti-MFI2 humanized antibodies indirectly linked to saporin to internalize into HEK293T cells overexpressing MFI2 protein and kill such cells. Finally, FIG. 10D compares the ability of exemplary anti-MFI2 murine antibodies in Bins A-E to internalize and kill HEK293T cells overexpressing MFI2 protein.

DETAILED DESCRIPTION OF THE INVENTION

Figure 1A:
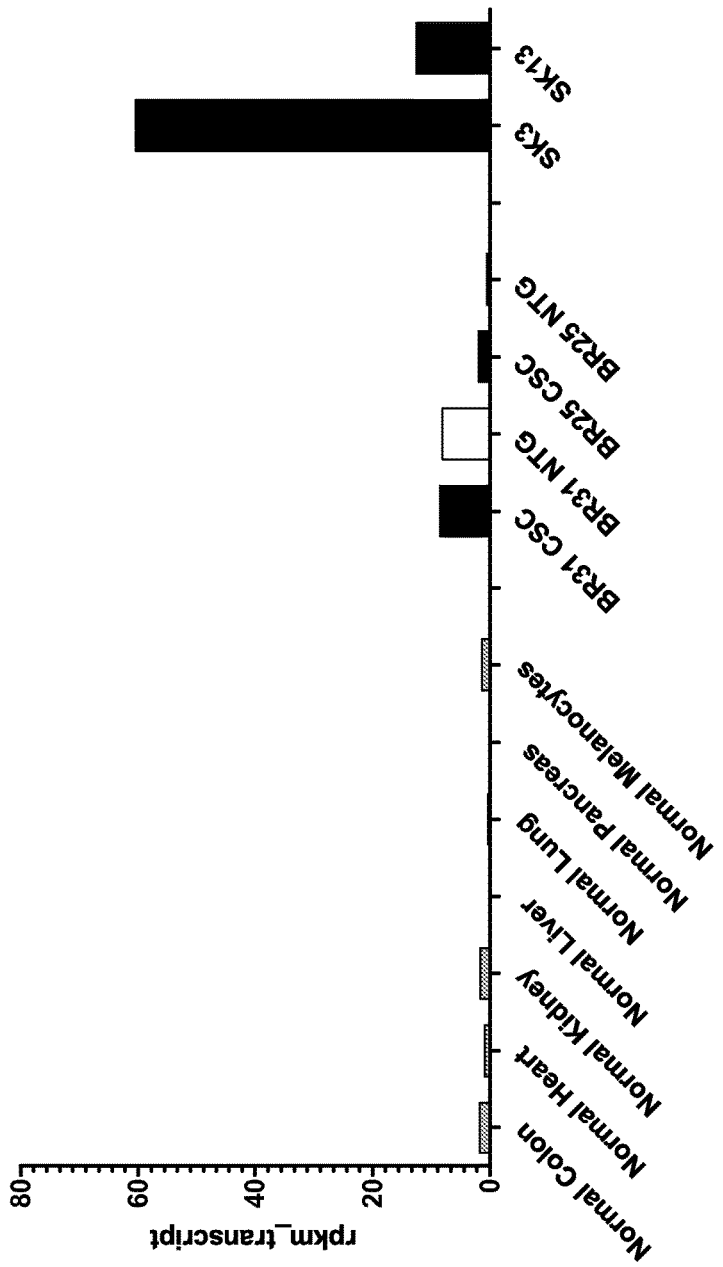
FIG. 1A depicts expression levels of MFI2 as measured using whole transcriptome (SOLiD) sequencing of RNA derived from patient derived xenograft (PDX) cancer stem cell (CSC) and non-tumorigenic (NTG) tumor cells.

The invention may be embodied in many different forms. Disclosed herein are non-limiting, illustrative embodiments of the invention that exemplify the principles thereof. Any section headings used herein are for organizational purposes only and are not to be construed as limiting the subject matter described. For the purposes of the instant disclosure all identifying sequence accession numbers may be found in the NCBI Reference Sequence (RefSeq) database and/or the NCBI GenBank® archival sequence database unless otherwise noted.

MFI2 expression has surprisingly been found to correlate with a number of tumor types and, as a determinant, may be exploited in the treatment of such tumors. It has also unexpectedly been found that MFI2 expression is associated with tumorigenic cells and, as such, may be effectively exploited to inhibit or eliminate such cells. Tumorigenic cells, which will be described in more detail below, are known to exhibit resistance to many conventional treatments. In contrast to the teachings of the prior art, the disclosed compounds and methods effectively overcome this inherent resistance.

The invention provides anti-MFI2 antibodies (including antibody drug conjugates) and their use in the prognosis, diagnosis, theragnosis, treatment and/or prevention of a variety of MFI2-associated cancers regardless of any particular mechanism of action or specifically targeted cellular or molecular component.

I. MFI2 PHYSIOLOGY

Melanotransferrin (MFI2; also known as MTF1, CD228, MAP97, and melanoma-associated antigen p97) is a cell-surface glycosylphosphatidylinositol (GPI)-anchored glycoprotein that shares sequence similarity to members of the transferrin family of non-heme iron-binding proteins (Suryo Rahmanto et al., 2007; PMID: 17452986). Representative MFI2 protein orthologs include, but are not limited to, human (NP_005920), chimpanzee (XP_003310242), rhesus monkey (XP_001096034), rat (NP_001099342), and mouse (NP_038928). In humans, the MFI2 gene consists of 16 exons spanning approximately 28 kBp at chromosome 3q28-q29. Transcription of the human MFI2 locus yields at least two known RNA transcripts, a longer 3.96 kBp transcript (NM_005929) encoding a 738 amino acid preprotein (NP_005920; hMFI2 in FIG. 3A), and an alternatively spliced shorter 1.67 kBp transcript (NM_033316) thought to encode a 302 amino acid preprotein (NM_201573; hΔMFI2 in FIG. 3A). For either protein isoform, processing of the preprotein is predicted to involve the removal of the first 19 amino acids comprising the secretion signal peptide. In the case of the longer 738 amino acid protein isoform, the final 29 amino acids are removed as part of the processing to link the mature protein to the cell membrane via a GPI anchor. It is unclear whether the shorter 302 amino acid protein isoform is made, although it would be predicted to be secreted. Structurally, the longer isoform is predicted to contain tandem transferrin-like domains (labelled TFLD1 and TFLD2, FIG. 3A), although only the first domain is capable of binding iron. Three N-linked glycosylation sites have been mapped—two to the first transferrin-like domain, and one two the second transferrin-like domain. A soluble form of melanotransferrin has been identified in cell culture supernatants and in serum, although the biological origin of this form remains unclear.

Melanoma-associated antigen p97 was one of the first cell surface markers discovered for melanoma, and based upon its sequence similarity with transferrin proteins, it was named melanotransferrin. But despite the sequence conservation with other members of the transferrin family of proteins and its apparent ability to bind iron, a variety of cell culture and in vivo experiments have shown that melanotransferrin does not play an essential role in iron transport or metabolism in normal or melanoma cells (reviewed in Suryo Rahmanto et al., 2012; PMID: 21933697). It is possible that the protein binds iron for structural reasons rather than to mediate transport functions. Other ions, including Zn(II), have been suggested to bind melanotransferrin as well. Additional functions suggested for melanotransferrin include stimulation of angiogenesis, of plasminogen activation, and cell proliferation and migration. Recently, melanotransferrin has been linked to the assembly of epithelial septal junctions in *Drosophila*, structures that provide diffusion barriers between epithelial cells in insects, analogous to tight junctions formed in epithelial sheets found in vertebrates. However, the precise biological function(s) of melanotransferrin remains unknown.

II. CANCER STEM CELLS

According to the current models, a tumor comprises non-tumorigenic cells and tumorigenic cells. Non-tumorigenic cells do not have the capacity to self-renew and are incapable of reproducibly forming tumors, even when transplanted into immunocompromised mice in excess cell numbers. Tumorigenic cells, also referred to herein as "tumor initiating cells" (TICs), which make up 0.1-40% (more typically 0.1-10%) of a tumor's cell population, have the ability to form tumors. Tumorigenic cells encompass both tumor perpetuating cells (TPCs), referred to interchangeably as cancer stem cells (CSCs) and tumor progenitor cells (TProgs).

CSCs, like normal stem cells that support cellular hierarchies in normal tissue, are able to self-replicate indefinitely while maintaining the capacity for multilineage differentiation. CSCs are able to generate both tumorigenic progeny and non-tumorigenic progeny and are able to completely recapitulate the heterogeneous cellular composition of the parental tumor as demonstrated by serial isolation and transplantation of low numbers of isolated CSCs into immunocompromised mice.

TProgs, like CSCs have the ability to fuel tumor growth in a primary transplant. However, unlike CSCs, they are not able to recapitulate the cellular heterogeneity of the parental tumor and are less efficient at reinitiating tumorigenesis in subsequent transplants because TProgs are typically only capable of a finite number of cell divisions as demonstrated by serial transplantation of low numbers of highly purified TProg into immunocompromised mice. TProgs may further be divided into early TProgs and late TProgs, which may be distinguished by phenotype (e.g., cell surface markers) and their different capacities to recapitulate tumor cell architecture. While neither can recapitulate a tumor to the same extent as CSCs, early TProgs have a greater capacity to recapitulate the parental tumor's characteristics than late TProgs. Notwithstanding the foregoing distinctions, it has been shown that some TProg populations can, on rare occasion, gain self-renewal capabilities normally attributed to CSCs and can themselves become CSCs.

CSCs exhibit higher tumorigenicity and are relatively more quiescent than: (i) TProgs (both early and late TProgs); and (ii) non-tumorigenic cells such as tumor-infiltrating cells, for example, fibroblasts/stroma, endothelial and hematopoietic cells that may be derived from CSCs and typically comprise the bulk of a tumor. Given that conventional therapies and regimens have, in large part, been designed to debulk tumors and attack rapidly proliferating cells, CSCs are more resistant to conventional therapies and regimens than the faster proliferating TProgs and other bulk tumor cell populations such as non-tumorigenic cells. Other characteristics that may make CSCs relatively chemoresistant to conventional therapies are increased expression of multi-drug resistance transporters, enhanced DNA repair mechanisms and anti-apoptotic gene expression. Such CSC properties have been implicated in the failure of standard treatment regimens to provide a lasting response in patients with advanced stage neoplasia as standard chemotherapy does not effectively target the CSCs that actually fuel continued tumor growth and recurrence.

It has surprisingly been discovered that MFI2 expression is associated with various tumorigenic cell subpopulations. The invention provides anti-MFI2 antibodies that may be particularly useful for targeting tumorigenic cells and may be used to silence, sensitize, neutralize, reduce the frequency, block, abrogate, interfere with, decrease, hinder, restrain, control, deplete, moderate, mediate, diminish, reprogram, eliminate, or otherwise inhibit (collectively, "inhibit") tumorigenic cells, thereby facilitating the treatment, management and/or prevention of proliferative disorders (e.g. cancer). Advantageously, the novel anti-MFI2 antibodies of the invention may be selected so they preferably reduce the frequency or tumorigenicity of tumorigenic cells upon administration to a subject regardless of the form of the MFI2 determinant (e.g., phenotypic or genotypic). The reduction in tumorigenic cell frequency may occur as a result of (i) inhibition or eradication of tumorigenic cells; (ii) controlling the growth, expansion or recurrence of tumorigenic cells; (iii) interrupting the initiation, propagation, maintenance, or proliferation of tumorigenic cells; or (iv) by otherwise hindering the survival, regeneration and/or metastasis of the tumorigenic cells. In some embodiments, the inhibition of tumorigenic cells may occur as a result of a change in one or more physiological pathways. The change in the pathway, whether by inhibition of the tumorigenic cells, modification of their potential (for example, by induced differentiation or niche disruption) or otherwise interfering with the ability of tumorigenic cells to influence the tumor environment or other cells, allows for the more effective treatment of MFI2 associated disorders by inhibiting tumorigenesis, tumor maintenance and/or metastasis and recurrence. It will further be appreciated that the same characteristics of the disclosed antibodies make them particularly effective at treating recurrent tumors which have proved resistant or refractory to standard treatment regimens.

Methods that can be used to assess the reduction in the frequency of tumorigenic cells, include but are not limited to, cytometric or immunohistochemical analysis, preferably by in vitro or in vivo limiting dilution analysis (Dylla et al. 2008, PMID: PMC2413402 and Hoey et al. 2009, PMID: 19664991).

In vitro limiting dilution analysis may be performed by culturing fractionated or unfractionated tumor cells (e.g. from treated and untreated tumors, respectively) on solid medium that fosters colony formation and counting and characterizing the colonies that grow. Alternatively, the tumor cells can be serially diluted onto plates with wells containing liquid medium and each well can be scored as either positive or negative for colony formation at any time after inoculation but preferably more than 10 days after inoculation.

In vivo limiting dilution is performed by transplanting tumor cells, from either untreated controls or from tumors exposed to selected therapeutic agents, into immunocompromised mice in serial dilutions and subsequently scoring each mouse as either positive or negative for tumor formation. The scoring may occur at any time after the implanted tumors are detectable but is preferably done 60 or more days after the transplant. The analysis of the results of limiting dilution experiments to determine the frequency of tumorigenic cells is preferably done using Poisson distribution statistics or assessing the frequency of predefined definitive events such as the ability to generate tumors in vivo or not (Fazekas et al., 1982, PMID: 7040548).

Flow cytometry and immunohistochemistry may also be used to determine tumorigenic cell frequency. Both techniques employ one or more antibodies or reagents that bind art recognized cell surface proteins or markers known to enrich for tumorigenic cells (see WO 2012/031280). As known in the art, flow cytometry (e.g. florescence activated cell sorting (FACS)) can also be used to characterize, isolate, purify, enrich or sort for various cell populations including tumorigenic cells. Flow cytometry measures tumorigenic cell levels by passing a stream of fluid, in which a mixed population of cells is suspended, through an electronic detection apparatus which is able to measure the physical and/or chemical characteristics of up to thousands of particles per second. Immunohistochemistry provides additional information in that it enables visualization of tumorigenic cells in situ (e.g., in a tissue section) by staining the tissue sample with labeled antibodies or reagents which bind to tumorigenic cell markers.

As such, the antibodies of the invention may be useful for identifying, characterizing, monitoring, isolating, sectioning or enriching populations or subpopulations of tumorigenic cells through methods such as, for example, flow cytometry, magnetic activated cell sorting (MACS), laser mediated sectioning or FACS. FACS is a reliable method used to isolate cell subpopulations at more than 99.5% purity based on specific cell surface markers. Other compatible techniques for the characterization and manipulation of tumorigenic cells including CSCs can be seen, for example, in U.S. patent Ser. Nos. 12/686,359, 12/669,136 and 12/757,649.

Listed below are markers that have been associated with CSC populations and have been used to isolate or characterize CSCs: ABCA1, ABCA3, ABCG2, ADAM9, ADCY9, ADORA2A, AFP, AXIN1, B7H3, BCL9, Bmi-1, BMP-4, C20orf52, C4.4A, carboxypeptidase M, CAV1, CAV2, CD105, CD133, CD14, CD16, CD166, CD16a, CD16b, CD2, CD20, CD24, CD29, CD3, CD31, CD324, CD325, CD34, CD38, CD44, CD45, CD46, CD49b, CD49f, CD56, CD64, CD74, CD9, CD90, CEACAM6, CELSR1, CPD, CRIM1, CX3CL1, CXCR4, DAF, decorin, easyh1, easyh2, EDG3, eed, EGFR, ENPP1, EPCAM, EPHA1, EPHA2, FLJ10052, FLVCR, FZD1, FZD10, FZD2, FZD3, FZD4, FZD6, FZD7, FZD8, FZD9, GD2, GJA1, GLI1, GL12, GPNMB, GPR54, GPRC5B, IL1R1, IL1RAP, JAMS, Lgr5, Lgr6, LRP3, LY6E, MCP, mf2, mIlt3, MPZL1, MUC1, MUC16, MYC, N33, Nanog, NB84, nestin, NID2, NMA, NPC1, oncostatin M, OCT4, OPN3, PCDH7, PCDHA10, PCDHB2, PPAP2C, PTPN3, PTS, RARRES1, SEMA4B, SLC19A2, SLC1A1, SLC39A1, SLC4A11, SLC6A14, SLC7A8, smarcA3, smarcD3, smarcE1, smarcA5, Sox1, STAT3, STEAP, TCF4, TEM8, TGFBR3, TMEPAI, TMPRSS4, transferrin receptor, TrkA, WNT10B, WNT16, WNT2, WNT2B, WNT3, WNT5A, YY1 and β-catenin. See, for example, Schulenburg et al., 2010, PMID: 20185329, U.S. Pat. No. 7,632,678 and U.S.P.N.s. 2007/0292414, 2008/0175870, 2010/0275280, 2010/0162416 and 2011/0020221.

Similarly, non-limiting examples of cell surface phenotypes associated with CSCs of certain tumor types include $CD44^{hi}CD24^{low}$, $ALDH^+$, $CD133^+$, $CD123^+$, $CD34^+CD38^-$, $CD44^+CD24^-$, $CD46^{hi}CD324^+CD660c^-$, $CD133^+CD34^+CD10^-CD19^-$, $CD138^-CD34^-CD19^+$, $CD133^+RC2^+$, $CD44^+\alpha_2\beta_1^{hi}CD133^+$, $CD44^+CD24^+ESA^+$, $CD271^+$, $ABCB5^+$ as well as other CSC surface phenotypes that are known in the art. See, for example, Schulenburg et al., 2010, supra, Visvader et al., 2008, PMID: 18784658 and U.S.P.N. 2008/0138313. Of particular interest with respect to the instant invention are CSC preparations comprising $CD46^{hi}CD324^+$ phenotypes.

"Positive," "low" and "negative" expression levels as they apply to markers or marker phenotypes are defined as follows. Cells with negative expression (i.e. "−") are herein defined as those cells expressing less than, or equal to, the 95th percentile of expression observed with an isotype control antibody in the channel of fluorescence in the presence of the complete antibody staining cocktail labeling for other proteins of interest in additional channels of fluorescence emission. Those skilled in the art will appreciate that this procedure for defining negative events is referred to as "fluorescence minus one", or "FMO", staining. Cells with expression greater than the 95th percentile of expression observed with an isotype control antibody using the FMO staining procedure described above are herein defined as "positive" (i.e. "+"). As defined herein there are various populations of cells broadly defined as "positive." A cell is defined as positive if the mean observed expression of the antigen is above the 95th percentile determined using FMO staining with an isotype control antibody as described above. The positive cells may be termed cells with low expression (i.e. "lo") if the mean observed expression is above the $95^{th}$ percentile determined by FMO staining and is within one standard deviation of the $95^{th}$ percentile. Alternatively, the positive cells may be termed cells with high expression (i.e. "hi") if the mean observed expression is above the $95^{th}$ percentile determined by FMO staining and greater than one standard deviation above the $95^{th}$ percentile. In other embodiments the 99th percentile may preferably be used as a demarcation point between negative and positive FMO staining and in some embodiments the percentile may be greater than 99%.

The $CD46^{hi}CD324^+$ marker phenotype and those exemplified immediately above may be used in conjunction with standard flow cytometric analysis and cell sorting techniques to characterize, isolate, purify or enrich TIC and/or TPC cells or cell populations for further analysis.

The ability of the antibodies of the current invention to reduce the frequency of tumorigenic cells can therefore be determined using the techniques and markers described above. In some instances, the anti-MFI2 antibodies may reduce the frequency of tumorigenic cells by 10%, 15%, 20%, 25%, 30% or even by 35%. In other embodiments, the reduction in frequency of tumorigenic cells may be in the order of 40%, 45%, 50%, 55%, 60% or 65%. In certain embodiments, the disclosed compounds my reduce the frequency of tumorigenic cells by 70%, 75%, 80%, 85%, 90% or even 95%. It will be appreciated that any reduction of the frequency of tumorigenic cells is likely to result in a corresponding reduction in the tumorigenicity, persistence, recurrence and aggressiveness of the neoplasia.

III. ANTIBODIES

A. Antibody Structure

Antibodies and variants and derivatives thereof, including accepted nomenclature and numbering systems, have been extensively described, for example, in Abbas et al. (2010), *Cellular and Molecular Immunology* ($6^{th}$ Ed.), W.B. Saunders Company; or Murphey et al. (2011), *Janeway's Immunobiology* ($8^{th}$ Ed.), Garland Science.

An "antibody" or "intact antibody" typically refers to a Y-shaped tetrameric protein comprising two heavy (H) and two light (L) polypeptide chains held together by covalent disulfide bonds and non-covalent interactions. Each light chain is composed of one variable domain (VL) and one constant domain (CL). Each heavy chain comprises one variable domain (VH) and a constant region, which in the case of IgG, IgA, and IgD antibodies, comprises three domains termed CH1, CH2, and CH3 (IgM and IgE have a fourth domain, CH4). In IgG, IgA, and IgD classes the CH1 and CH2 domains are separated by a flexible hinge region, which is a proline and cysteine rich segment of variable length (from about 10 to about 60 amino acids in various IgG subclasses). The variable domains in both the light and heavy chains are joined to the constant domains by a "J" region of about 12 or more amino acids and the heavy chain also has a "D" region of about 10 additional amino acids. Each class of antibody further comprises inter-chain and intra-chain disulfide bonds formed by paired cysteine residues.

As used herein the term "antibody" includes polyclonal antibodies, multiclonal antibodies, monoclonal antibodies, chimeric antibodies, humanized and primatized antibodies, CDR grafted antibodies, human antibodies, recombinantly produced antibodies, intrabodies, multispecific antibodies, bispecific antibodies, monovalent antibodies, multivalent antibodies, anti-idiotypic antibodies, synthetic antibodies, including muteins and variants thereof, immunospecific antibody fragments such as Fd, Fab, $F(ab')_2$, F(ab') fragments, single-chain fragments (e.g. ScFv and ScFvFc); and derivatives thereof including Fc fusions and other modifications, and any other immunoreactive molecule so long as it exhibits preferential association or binding with a determinant. Moreover, unless dictated otherwise by contextual constraints the term further comprises all classes of antibodies (i.e. IgA, IgD, IgE, IgG, and IgM) and all subclasses (i.e., IgG1, IgG2, IgG3, IgG4, IgA1, and IgA2). Heavy-chain constant domains that correspond to the different classes of antibodies are typically denoted by the corresponding lower case Greek letter α, δ, ε, γ, and μ, respectively. Light chains of the antibodies from any vertebrate species can be assigned to one of two clearly distinct types, called kappa (κ) and lambda (λ), based on the amino acid sequences of their constant domains.

The variable domains of antibodies show considerable variation in amino acid composition from one antibody to another and are primarily responsible for antigen recognition and binding. Variable regions of each light/heavy chain pair form the antibody binding site such that an intact IgG antibody has two binding sites (i.e. it is bivalent). VH and VL domains comprise three regions of extreme variability, which are termed hypervariable regions, or more commonly, complementarity-determining regions (CDRs), framed and separated by four less variable regions known as framework regions (FRs). The non-covalent association between the VH and the VL region forms the Fv fragment (for "fragment variable") which contains one of the two antigen-binding sites of the antibody. ScFv fragments (for single chain fragment variable), which can be obtained by genetic engineering, associates in a single polypeptide chain, the VH and the VL region of an antibody, separated by a peptide linker.

As used herein, the assignment of amino acids to each domain, framework region and CDR may be in accordance with one of the numbering schemes provided by Kabat et al. (1991) *Sequences of Proteins of Immunological Interest* (5$^{th}$ Ed.), US Dept. of Health and Human Services, PHS, NIH, NIH Publication no. 91-3242; Chothia et al., 1987, PMID: 3681981; Chothia et al., 1989, PMID: 2687698; MacCallum et al., 1996, PMID: 8876650; or Dubel, Ed. (2007) *Handbook of Therapeutic Antibodies*, 3$^{rd}$ Ed., Wily-VCH Verlag GmbH and Co or AbM (Oxford Molecular/MSI Pharmacopia) unless otherwise noted. The amino acid residues which comprise CDRs as defined by Kabat, Chothia, MacCallum (also known as Contact) and AbM as obtained from the Abysis website database (infra.) are set out below.

TABLE 1

|  | Kabat | Chothia | MacCallum | AbM |
|---|---|---|---|---|
| VH CDR1 | 31-35 | 26-32 | 30-35 | 26-35 |
| VH CDR2 | 50-65 | 52-56 | 47-58 | 50-58 |
| VH CDR3 | 95-102 | 95-102 | 93-101 | 95-102 |
| VL CDR1 | 24-34 | 24-34 | 30-36 | 24-34 |
| VL CDR2 | 50-56 | 50-56 | 46-55 | 50-56 |
| VL CDR3 | 89-97 | 89-97 | 89-96 | 89-97 |

Figure 6E:
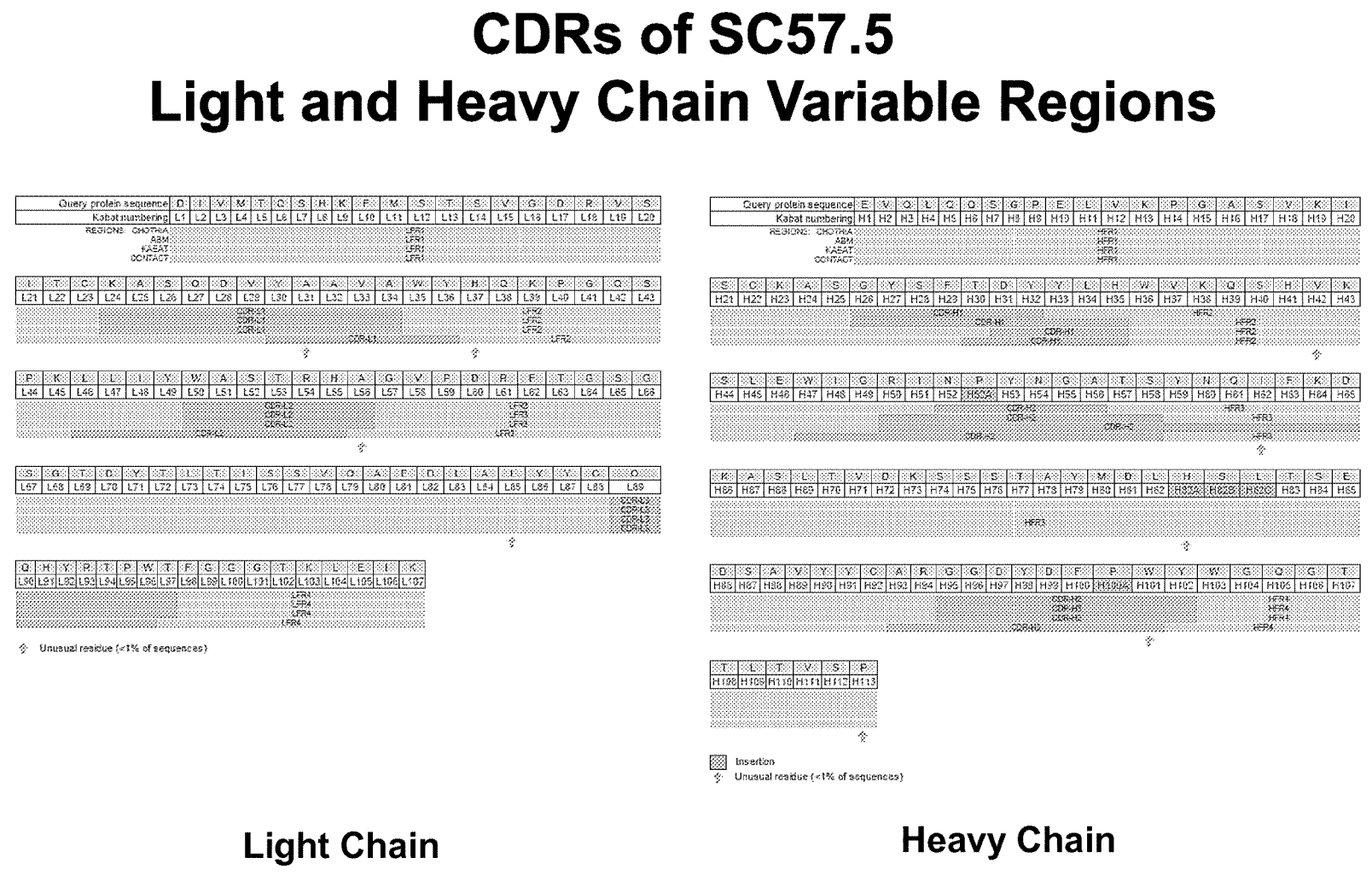
Figure 6F:
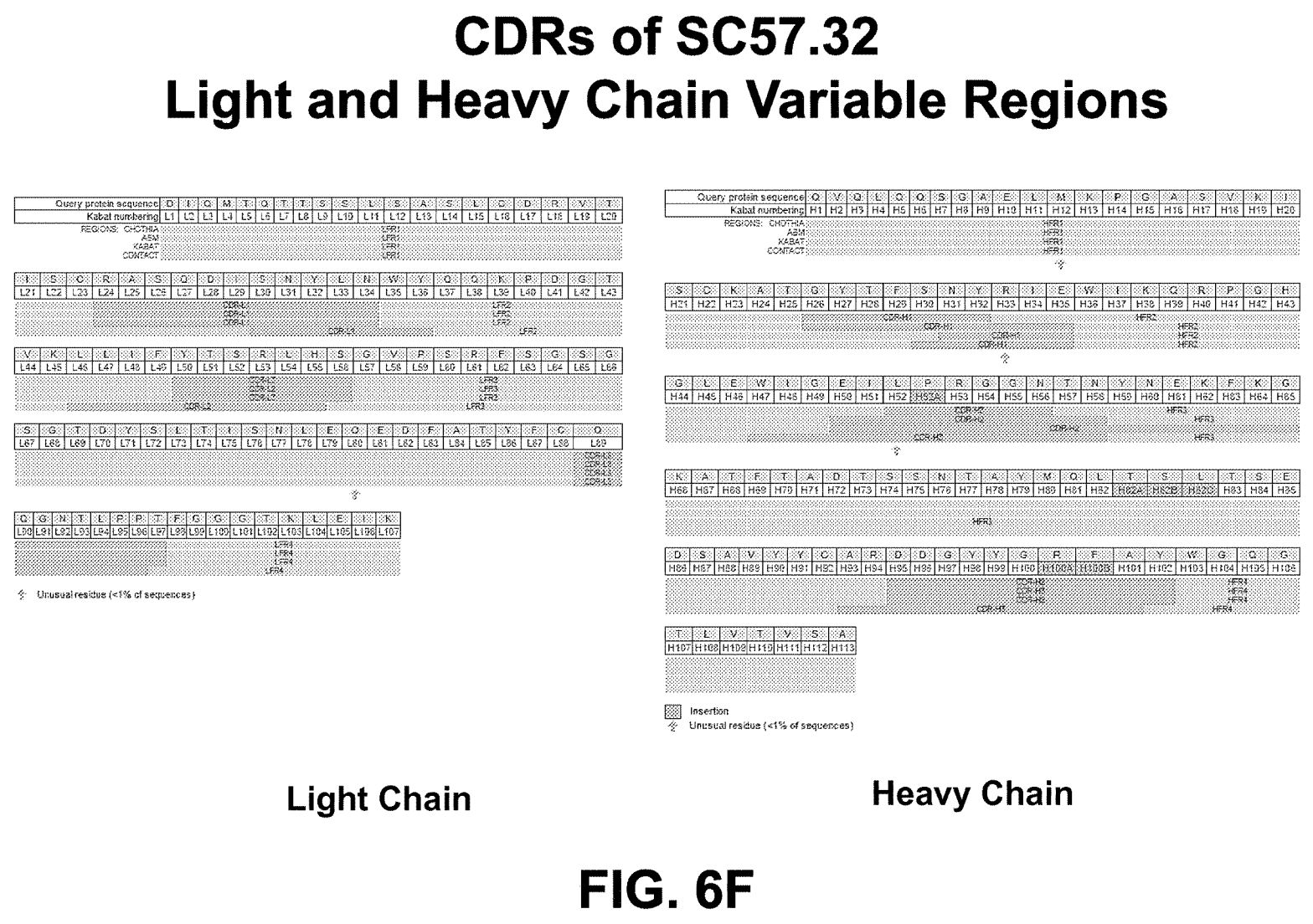
Figure 6G:
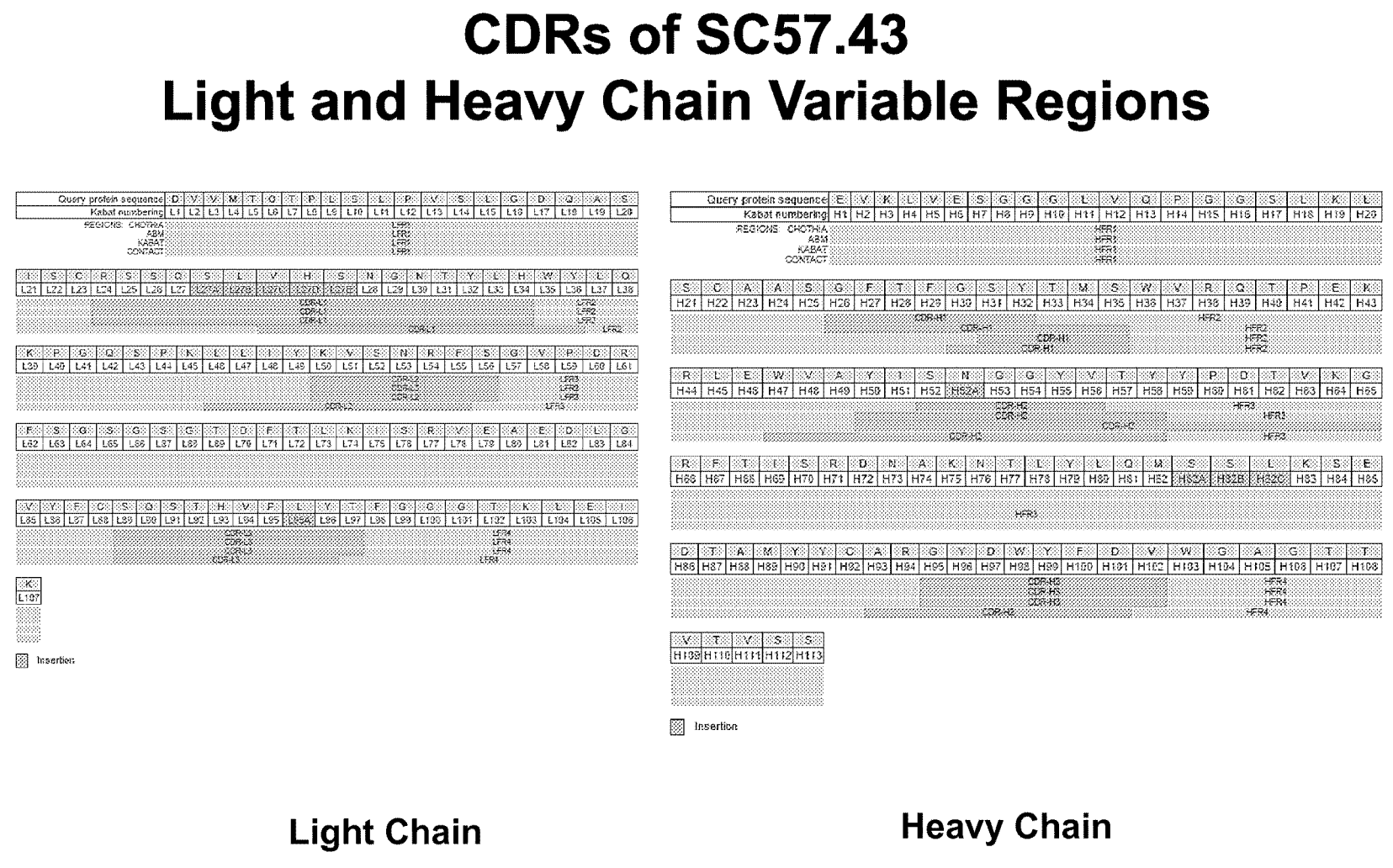

Variable regions and CDRs in an antibody sequence can be identified according to general rules that have been developed in the art (as set out above, such as, for example, the Kabat numbering system) or by aligning the sequences against a database of known variable regions. Methods for identifying these regions are described in Kontermann and Dubel, eds., Antibody Engineering, Springer, New York, N.Y., 2001 and Dinarello et al., Current Protocols in Immunology, John Wiley and Sons Inc., Hoboken, N.J., 2000. Exemplary databases of antibody sequences are described in, and can be accessed through, the "Abysis" website at www.bioinf.org.uk/abs (maintained by A. C. Martin in the Department of Biochemistry & Molecular Biology University College London, London, England) and the VBASE2 website at www.vbase2.org, as described in Retter et al., Nucl. Acids Res., 33 (Database issue): D671-D674 (2005). Preferably the sequences are analyzed using the Abysis database, which integrates sequence data from Kabat, IMGT and the Protein Data Bank (PDB) with structural data from the PDB. See Dr. Andrew C. R. Martin's book chapter *Protein Sequence and Structure Analysis of Antibody Variable Domains*. In: *Antibody Engineering Lab Manual* (Ed.: Duebel, S. and Kontermann, R., Springer-Verlag, Heidelberg, ISBN-13: 978-3540413547, also available on the website bioinforg.uk/abs). The Abysis database website further includes general rules that have been developed for identifying CDRs which can be used in accordance with the teachings herein. FIGS. 6E to 6G appended hereto show the results of such analysis in the annotation of exemplary heavy and light chain variable regions. Unless otherwise indicated, all CDRs set forth herein are derived according to the Abysis database website as per Kabat et al.

For heavy chain constant region amino acid positions discussed in the invention, numbering is according to the Eu index first described in Edelman et al., 1969, Proc. Natl. Acad. Sci. USA 63(1): 78-85 describing the amino acid sequence of the myeloma protein Eu, which reportedly was the first human IgG1 sequenced. The Eu index of Edelman is also set forth in Kabat et al., 1991 (supra.). Thus, the terms "Eu index as set forth in Kabat" or "Eu index of Kabat" or "Eu index" or "Eu numbering" in the context of the heavy chain refers to the residue numbering system based on the human IgG1 Eu antibody of Edelman et aL as set forth in Kabat et al., 1991 (supra.) The numbering system used for the light chain constant region amino acid sequence is similarly set forth in Kabat et al., (supra.) An exemplary kappa light chain constant region amino acid sequence compatible with the present invention is set forth immediately below:

```
                                            (SEQ ID NO: 1)
RTVAAPSVFIFPPSDEQLKSGTASVVCLLNNFYPREAKVQWKVDNALQS

GNSQESVTEQDSKDSTYSLSSTLTLSKADYEKHKVYACEVTHQGLSSPV

TKSFNRGEC.
```

Similarly, an exemplary IgG1 heavy chain constant region amino acid sequence compatible with the present invention is set forth immediately below:

```
                                            (SEQ ID NO: 2)
ASTKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDKKV

EPKSCDKTHTCPPCPAPELLGGPSVFLFPPKPKDTLMISRTPEVTCVVV

DVSHEDPEVKFNWYVDGVEVHNAKTKPREEQYNSTYRVVSVLTVLHQDW

LNGKEYKCKVSNKALPAPIEKTISKAKGQPREPQVYTLPPSRDELTKNQ

VSLTCLVKGFYPSDIAVEWESNGQPENNYKTTPPVLDSDGSFFLYSKLT

VDKSRWQQGNVFSCSVMHEALHNHYTQKSLSLSPG.
```

The disclosed constant region sequences, or variations or derivatives thereof, may be operably associated with the disclosed heavy and light chain variable regions using standard molecular biology techniques to provide full-length antibodies that may be used as such or incorporated in the anti-MFI2 ADCs of the invention.

The antibodies or immunoglobulins of the invention may be generated from an antibody that specifically recognizes or associates with any relevant determinant. As used herein "determinant" or "target" means any detectable trait, property, marker or factor that is identifiably associated with, or specifically found in or on a particular cell, cell population or tissue. Determinants or targets may be morphological, functional or biochemical in nature and are preferably phenotypic. In some embodiments a determinant is a protein that is differentially expressed (over- or under-expressed) by specific cell types or by cells under certain conditions (e.g., during specific points of the cell cycle or cells in a particular niche). For the purposes of the instant invention a determinant preferably is differentially expressed on aberrant cancer cells and may comprise a MFI2 protein, or any of its splice variants, isoforms, homologs or family members, or specific domains, regions or epitopes thereof. An "antigen", "immunogenic determinant", "antigenic determinant" or "immunogen" means any protein or any fragment, region or domain thereof that can stimulate an immune response when introduced into an immunocompetent animal and is recognized by the antibodies produced from the immune response. The presence or absence of the MFI2 determinants contemplated herein may be used to identify a cell, cell subpopulation or tissue (e.g., tumors, tumorigenic cells or CSCs).

There are two types of disulfide bridges or bonds in immunoglobulin molecules: interchain and intrachain disulfide bonds. As is well known in the art the location and number of interchain disulfide bonds vary according to the immunoglobulin class and species. While the invention is not limited to any particular class or subclass of antibody, the IgG1 immunoglobulin shall be used throughout the instant disclosure for illustrative purposes. In wild-type IgG1 molecules there are twelve intrachain disulfide bonds (four on each heavy chain and two on each light chain) and four interchain disulfide bonds. Intrachain disulfide bonds are generally somewhat protected and relatively less susceptible to reduction than interchain bonds. Conversely, interchain disulfide bonds are located on the surface of the immunoglobulin, are accessible to solvent and are usually relatively easy to reduce. Two interchain disulfide bonds exist between the heavy chains and one from each heavy chain to its respective light chain. It has been demonstrated that interchain disulfide bonds are not essential for chain association. The IgG1 hinge region contain the cysteines in the heavy chain that form the interchain disulfide bonds, which provide structural support along with the flexibility that facilitates Fab movement. The heavy/heavy IgG1 interchain disulfide bonds are located at residues C226 and C229 (Eu numbering) while the IgG1 interchain disulfide bond between the light and heavy chain of IgG1 (heavy/light) are formed between C214 of the kappa or lambda light chain and C220 in the upper hinge region of the heavy chain.

B. Antibody Generation and Production

Antibodies of the invention can be produced using a variety of methods known in the art.

1. Generation of Polyclonal Antibodies in Host Animals

The production of polyclonal antibodies in various host animals is well known in the art (see for example, Harlow and Lane (Eds.) (1988) Antibodies: A Laboratory Manual, CSH Press; and Harlow et al. (1989) Antibodies, N.Y., Cold Spring Harbor Press). In order to generate polyclonal antibodies, an immunocompetent animal (e.g., mouse, rat, rabbit, goat, non-human primate, etc.) is immunized with an antigenic protein or cells or preparations comprising an antigenic protein. After a period of time, polyclonal antibody-containing serum is obtained by bleeding or sacrificing the animal. The serum may be used in the form obtained from the animal or the antibodies may be partially or fully purified to provide immunoglobulin fractions or isolated antibody preparations.

Any form of antigen, or cells or preparations containing the antigen, can be used to generate an antibody that is specific for a determinant. The term "antigen" is used in a broad sense and may comprise any immunogenic fragment or determinant of the selected target including a single epitope, multiple epitopes, single or multiple domains or the entire extracellular domain (ECD). The antigen may be an isolated full-length protein, a cell surface protein (e.g., immunizing with cells expressing at least a portion of the antigen on their surface), or a soluble protein (e.g., immunizing with only the ECD portion of the protein). The antigen may be produced in a genetically modified cell. Any of the aforementioned antigens may be used alone or in combination with one or more immunogenicity enhancing adjuvants known in the art. The DNA encoding the antigen may be genomic or non-genomic (e.g., cDNA) and may encode at least a portion of the ECD, sufficient to elicit an immunogenic response. Any vectors may be employed to transform the cells in which the antigen is expressed, including but not limited to adenoviral vectors, lentiviral vectors, plasmids, and non-viral vectors, such as cationic lipids.

2. Monoclonal Antibodies

In selected embodiments, the invention contemplates use of monoclonal antibodies. As known in the art, the term "monoclonal antibody" or "mAb" refers to an antibody obtained from a population of substantially homogeneous antibodies, i.e., the individual antibodies comprising the population are identical except for possible mutations (e.g., naturally occurring mutations), that may be present in minor amounts.

Monoclonal antibodies can be prepared using a wide variety of techniques known in the art including hybridoma techniques, recombinant techniques, phage display technologies, transgenic animals (e.g., a XenoMouse®) or some combination thereof. For example, monoclonal antibodies can be produced using hybridoma and biochemical and genetic engineering techniques such as described in more detail in An, Zhigiang (ed.) *Therapeutic Monoclonal Antibodies: From Bench to Clinic*, John Wiley and Sons, 1' ed. 2009; Shire et. al. (eds.) *Current Trends in Monoclonal Antibody Development and Manufacturing*, Springer Science+Business Media LLC, $1^{st}$ ed. 2010; Harlow et al., *Antibodies*: A Laboratory Manual, Cold Spring Harbor Laboratory Press, 2nd ed. 1988; Hammerling, et al., in: *Monoclonal Antibodies and T-Cell Hybridomas* 563-681 (Elsevier, N.Y., 1981). Following production of multiple monoclonal antibodies that bind specifically to a determinant, particularly effective antibodies may be selected through various screening processes, based on, for example, its affinity for the determinant or rate of internalization. Antibodies produced as described herein may be used as "source" antibodies and further modified to, for example, improve affinity for the target, improve its production in cell culture, reduce immunogenicity in vivo, create multispecific constructs, etc. A more detailed description of monoclonal antibody production and screening is set out below and in the appended Examples.

3. Human Antibodies

In another embodiment, the antibodies may comprise fully human antibodies. The term "human antibody" refers to an antibody which possesses an amino acid sequence that corresponds to that of an antibody produced by a human and/or has been made using any of the techniques for making human antibodies described below.

Human antibodies can be produced using various techniques known in the art. In one embodiment, recombinant human antibodies may be isolated by screening a recombinant combinatorial antibody library prepared using phage display. In one embodiment, the library is a scFv phage or yeast display library, generated using human VL and VH cDNAs prepared from mRNA isolated from B-cells.

Human antibodies can also be made by introducing human immunoglobulin loci into transgenic animals, e.g., mice in which the endogenous immunoglobulin genes have been partially or completely inactivated and human immunoglobulin genes have been introduced. Upon challenge, human antibody production is observed, which closely resembles that seen in humans in all respects, including gene rearrangement, assembly and fully human antibody repertoire. This approach is described, for example, in U.S. Pat. Nos. 5,545,807; 5,545,806; 5,569,825; 5,625,126; 5,633, 425; 5,661,016, and U.S. Pat. Nos. 6,075,181 and 6,150,584 regarding XenoMouse® technology; and Lonberg and Huszar, 1995, PMID: 7494109). Alternatively, a human antibody may be prepared via immortalization of human B lymphocytes producing an antibody directed against a target antigen (such B lymphocytes may be recovered from an individual suffering from a neoplastic disorder or may have been immunized in vitro). See, e.g., Cole et al., *Monoclonal Antibodies and Cancer Therapy*, Alan R. Liss, p. 77 (1985); Boerner et al., 1991, PMID: 2051030; and U.S. Pat. No. 5,750,373. As with other monoclonal antibodies such human antibodies may be used as source antibodies.

4. Derived Antibodies:

Once source antibodies have been generated, selected and isolated as described above they may be further altered to provide anti-MFI2 antibodies having improved pharmaceutical characteristics. Preferably the source antibodies are modified or altered using known molecular engineering techniques to provide derived antibodies having the desired therapeutic properties.

4.1. Chimeric and Humanized Antibodies

Selected embodiments of the invention comprise murine monoclonal antibodies that immunospecifically bind to MFI2 and which can be considered "source" antibodies. In selected embodiments, antibodies of the invention can be derived from such "source" antibodies through optional modification of the constant region and/or the epitope-binding amino acid sequences of the source antibody. In certain embodiments an antibody is "derived" from a source antibody if selected amino acids in the source antibody are altered through deletion, mutation, substitution, integration or combination. In another embodiment, a "derived" antibody is one in which fragments of the source antibody (e.g., one or more CDRs or the entire heavy and light chain variable regions) are combined with or incorporated into an acceptor antibody sequence to provide the derivative antibody (e.g. chimeric or humanized antibodies). These "derived" antibodies can be generated using standard molecular biological techniques as described below, such as, for example, to improve affinity for the determinant; to improve antibody stability; to improve production and yield in cell culture; to reduce immunogenicity in vivo; to reduce toxicity; to facilitate conjugation of an active moiety; or to create a multispecific antibody. Such antibodies may also be derived from source antibodies through modification of the mature molecule (e.g., glycosylation patterns or pegylation) by chemical means or post-translational modification.

In one embodiment, the antibodies of the invention comprise chimeric antibodies that are derived from protein segments from at least two different species or class of antibodies that have been covalently joined. The term "chimeric" antibody is directed to constructs in which a portion of the heavy and/or light chain is identical or homologous to corresponding sequences in antibodies from a particular species or belonging to a particular antibody class or subclass, while the remainder of the chain(s) is identical or homologous to corresponding sequences in antibodies from another species or belonging to another antibody class or subclass, as well as fragments of such antibodies (U.S. Pat. No. 4,816,567; Morrison et al., 1984, PMID: 6436822). In some embodiments chimeric antibodies of the instant invention may comprise all or most of the selected murine heavy and light chain variable regions operably linked to human light and heavy chain constant regions. In other selected embodiments, anti-MFI2 antibodies may be "derived" from the mouse antibodies disclosed herein.

In other embodiments, chimeric antibodies of the invention are "CDR-grafted" antibodies, where the CDRs (as defined using Kabat, Chothia, McCallum, etc.) are derived from a particular species or belonging to a particular antibody class or subclass, while the remainder of the antibody is largely derived from an antibody from another species or belonging to another antibody class or subclass. For use in humans, one or more selected rodent CDRs (e.g., mouse CDRs) may be grafted into a human acceptor antibody, replacing one or more of the naturally occurring CDRs of the human antibody. These constructs generally have the advantages of providing full strength human antibody functions, e.g., complement dependent cytotoxicity (CDC) and antibody-dependent cell-mediated cytotoxicity (ADCC) while reducing unwanted immune responses to the antibody by the subject. In one embodiment the CDR grafted antibodies will comprise one or more CDRs obtained from a mouse incorporated in a human framework sequence.

Similar to the CDR-grafted antibody is a "humanized" antibody. As used herein, a "humanized" antibody is a human antibody (acceptor antibody) comprising one or more amino acid sequences (e.g. CDR sequences) derived from one or more non-human antibodies (donor or source antibody). In certain embodiments, "back mutations" can be introduced into the humanized antibody, in which residues in one or more FRs of the variable region of the recipient human antibody are replaced by corresponding residues from the non-human species donor antibody. Such back mutations may to help maintain the appropriate three-dimensional configuration of the grafted CDR(s) and thereby improve affinity and antibody stability. Antibodies from various donor species may be used including, without limitation, mouse, rat, rabbit, or non-human primate. Furthermore, humanized antibodies may comprise new residues that are not found in the recipient antibody or in the donor antibody to, for example, further refine antibody performance. CDR grafted and humanized antibodies compatible with the instant invention comprising murine components from source antibodies and human components from acceptor antibodies are provided as set forth in the Examples below.

Various art-recognized techniques can be used to determine which human sequences to use as acceptor antibodies to provide humanized constructs in accordance with the instant invention. Compilations of compatible human germline sequences and methods of determining their suitability as acceptor sequences are disclosed, for example, in Dubel and Reichert (Eds.) (2014) *Handbook of Therapeutic Antibodies*, 2$^{nd}$ Edition, Wiley-Blackwell GmbH; Tomlinson, I. A. et al. (1992) *J. Mol. Biol.* 227:776-798; Cook, G. P. et al. (1995) *Immunol. Today* 16: 237-242; Chothia, D. et al. (1992) *J. Mol. Biol.* 227:799-817; and Tomlinson et al. (1995) *EMBO J* 14:4628-4638). The V-BASE directory (VBASE2—Retter et al., Nucleic Acid Res. 33; 671-674, 2005) which provides a comprehensive directory of human immunoglobulin variable region sequences (compiled by Tomlinson, I. A. et al. MRC Centre for Protein Engineering, Cambridge, UK) may also be used to identify compatible acceptor sequences. Additionally, consensus human framework sequences described, for example, in U.S. Pat. No. 6,300,064 may also prove to be compatible acceptor sequences are can be used in accordance with the instant teachings. In general, human framework acceptor sequences are selected based on homology with the murine source framework sequences along with an analysis of the CDR canonical structures of the source and acceptor antibodies. The derived sequences of the heavy and light chain variable regions of the derived antibody may then be synthesized using art recognized techniques.

By way of example CDR grafted and humanized antibodies, and associated methods, are described in U.S. Pat. Nos. 6,180,370 and 5,693,762. For further details, see, e.g., Jones et al., 1986, (PMID: 3713831); and U.S. Pat. Nos. 6,982,321 and 7,087,409.

The sequence identity or homology of the CDR grafted or humanized antibody variable region to the human acceptor variable region may be determined as discussed herein and, when measured as such, will preferably share at least 60% or 65% sequence identity, more preferably at least 70%, 75%, 80%, 85%, or 90% sequence identity, even more preferably at least 93%, 95%, 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution.

It will be appreciated that the annotated CDRs and framework sequences as provided in the appended FIGS. 6A and 6B are defined as per Kabat et al. using a proprietary Abysis database. Similarly, the CDRs shown in the annotated aligned sequences of FIGS. 6H-6J are also defined as per Kabat et al. However, as discussed herein and shown in FIGS. 6E-6G one skilled in the art could readily identify CDRs in accordance with definitions provided by Chothia et al., ABM or MacCallum et al as well as Kabat et al. As such, anti-MFI2 humanized antibodies comprising one or more CDRs derived according to any of the aforementioned systems are explicitly held to be within the scope of the instant invention.

4.2. Site-Specific Antibodies

The antibodies of the instant invention may be engineered to facilitate conjugation to a cytotoxin or other anti-cancer agent (as discussed in more detail below). It is advantageous for the antibody drug conjugate (ADC) preparation to comprise a homogenous population of ADC molecules in terms of the position of the cytotoxin on the antibody and the drug to antibody ratio (DAR). Based on the instant disclosure one skilled in the art could readily fabricate site-specific engineered constructs as described herein. As used herein a "site-specific antibody" or "site-specific construct" means an antibody, or immunoreactive fragment thereof, wherein at least one amino acid in either the heavy or light chain is deleted, altered or substituted (preferably with another amino acid) to provide at least one free cysteine. Similarly, a "site-specific conjugate" shall be held to mean an ADC comprising a site-specific antibody and at least one cytotoxin or other compound conjugated to the unpaired or free cysteine(s). In certain embodiments the unpaired cysteine residue will comprise an unpaired intrachain residue. In other embodiments the free cysteine residue will comprise an unpaired interchain cysteine residue. In still other embodiments the free cysteine may be engineered into the amino acid sequence of the antibody (e.g., in the CH3 domain). In any event the site-specific antibody can be of various isotypes, for example, IgG, IgE, IgA or IgD; and within those classes the antibody can be of various subclasses, for example, IgG1, IgG2, IgG3 or IgG4. For IgG constructs the light chain of the antibody can comprise either a kappa or lambda isotype each incorporating a C214 that, in selected embodiments, may be unpaired due to a lack of a C220 residue in the IgG1 heavy chain.

Thus, as used herein, the terms "free cysteine" or "unpaired cysteine" may be used interchangeably unless otherwise dictated by context and shall mean any cysteine (or thiol containing) constituent of an antibody, whether naturally present or specifically incorporated in a selected residue position using molecular engineering techniques. In certain selected embodiments the free cysteine may comprise a naturally occurring cysteine whose native interchain or intrachain disulfide bridge partner has been substituted, eliminated or otherwise altered to disrupt the naturally occurring disulfide bride under physiological conditions thereby rendering the unpaired cysteine suitable for site-specific conjugation. In other preferred embodiments the free or unpaired cysteine will comprise a cysteine residue that is selectively placed at a predetermined site within the antibody heavy or light chain amino acid sequences. It will be appreciated that, prior to conjugation, free or unpaired cysteines may be present as a thiol (reduced cysteine), as a capped cysteine (oxidized) or as a non-natural intramolecular disulfide bond (oxidized) with another free cysteine on the same antibody depending on the oxidation state of the system. As discussed in more detail below, mild reduction of this antibody construct will provide thiols available for site-specific conjugation. In particularly preferred embodiments the free or unpaired cysteines (whether naturally occurring or incorporated) will be subject to selective reduction and subsequent conjugation to provide homogenous DAR compositions.

It will be appreciated that the favorable properties exhibited by the disclosed engineered conjugate preparations is predicated, at least in part, on the ability to specifically direct the conjugation and largely limit the fabricated conjugates in terms of conjugation position and absolute DAR of the composition. Unlike most conventional ADC preparations the present invention does not rely entirely on partial or total reduction of the antibody to provide random conjugation sites and relatively uncontrolled generation of DAR species. Rather, the present invention provides one or more predetermined unpaired (or free) cysteine sites by engineering the targeting antibody to disrupt one or more of the naturally occurring (i.e., "native") interchain or intrachain disulfide bridges or to introduce a cysteine residue at any position. To this end it will be appreciated that, in selected embodiments, a cysteine residue may be incorporated anywhere along the antibody (or immunoreactive fragment thereof) heavy or light chain or appended thereto using standard molecular engineering techniques. In other preferred embodiments disruption of native disulfide bonds may be effected in combination with the introduction of a non-native cysteine (which will then comprise the free cysteine) that may then be used as a conjugation site.

In one embodiment the engineered antibody comprises at least one amino acid deletion or substitution of an intrachain or interchain cysteine residue. As used herein "interchain cysteine residue" means a cysteine residue that is involved in a native disulfide bond either between the light and heavy chain of an antibody or between the two heavy chains of an antibody while an "intrachain cysteine residue" is one naturally paired with another cysteine in the same heavy or light chain. In one embodiment the deleted or substituted interchain cysteine residue is involved in the formation of a disulfide bond between the light and heavy chain. In another embodiment the deleted or substituted cysteine residue is involved in a disulfide bond between the two heavy chains. In a typical embodiment, due to the complementary structure of an antibody, in which the light chain is paired with the VH and CH1 domains of the heavy chain and wherein the CH2 and CH3 domains of one heavy chain are paired with the CH2 and CH3 domains of the complementary heavy chain, a mutation or deletion of a single cysteine in either the light chain or in the heavy chain would result in two unpaired cysteine residues in the engineered antibody.

In some embodiments an interchain cysteine residue is deleted. In other embodiments an interchain cysteine is substituted for another amino acid (e.g., a naturally occurring amino acid). For example, the amino acid substitution can result in the replacement of an interchain cysteine with a neutral (e.g. serine, threonine or glycine) or hydrophilic (e.g. methionine, alanine, valine, leucine or isoleucine) residue. In one embodiment an interchain cysteine is replaced with a serine.

In some embodiments contemplated by the invention the deleted or substituted cysteine residue is on the light chain (either kappa or lambda) thereby leaving a free cysteine on the heavy chain. In other embodiments the deleted or substituted cysteine residue is on the heavy chain leaving the free cysteine on the light chain constant region. Upon assembly it will be appreciated that deletion or substitution of a single cysteine in either the light or heavy chain of an intact antibody results in a site-specific antibody having two unpaired cysteine residues.

In one embodiment the cysteine at position 214 (C214) of the IgG light chain (kappa or lambda) is deleted or substituted. In another embodiment the cysteine at position 220 (C220) on the IgG heavy chain is deleted or substituted. In further embodiments the cysteine at position 226 or position 229 on the heavy chain is deleted or substituted. In one embodiment C220 on the heavy chain is substituted with serine (C220S) to provide the desired free cysteine in the light chain. In another embodiment C214 in the light chain is substituted with serine (C214S) to provide the desired free cysteine in the heavy chain. Such site-specific constructs provided in Example 15. A summary of these constructs is shown in Table 2 immediately below where numbering is generally according to the Eu index as set forth in Kabat and WT stands for "wild-type" or native constant region sequences without alterations and delta (Δ) designates the deletion of an amino acid residue (e.g., C214Δ indicates that the cysteine at position 214 has been deleted).

TABLE 2

| Designation | Antibody Component | Alteration |
| --- | --- | --- |
| ss1 | Heavy Chain | C220S |
|  | Light Chain | WT |
| ss2 | Heavy Chain | C220Δ |
|  | Light Chain | WT |
| ss3 | Heavy Chain | WT |
|  | Light Chain | C214Δ |
| ss4 | Heavy Chain | WT |
|  | Light Chain | C214S |

With regard to the introduction or addition of a cysteine residue or residues to provide a free cysteine (as opposed to disrupting a native disulfide bond) compatible position(s) on the antibody or antibody fragment may readily be discerned by one skilled in the art. Accordingly, in selected embodiments the cysteine(s) may be introduced in the CH1 domain, the CH2 domain or the CH3 domain or any combination thereof depending on the desired DAR, the antibody construct, the selected payload and the antibody target. In other preferred embodiments the cysteines may be introduced into a kappa or lambda CL domain and, in particularly preferred embodiments, in the c-terminal region of the CL domain. In each case other amino acid residues proximal to the site of cysteine insertion may be altered, removed or substituted to facilitate molecular stability, conjugation efficiency or provide a protective environment for the payload once it is attached. In particular embodiments, the substituted residues occur at any accessible sites of the antibody. By substituting such surface residues with cysteine, reactive thiol groups are thereby positioned at readily accessible sites on the antibody and may be selectively reduced as described further herein. In particular embodiments, the substituted residues occur at accessible sites of the antibody. By substituting those residues with cysteine, reactive thiol groups are thereby positioned at accessible sites of the antibody and may be used to selectively conjugate the antibody. In certain embodiments, any one or more of the following residues may be substituted with cysteine: V205 (Kabat numbering) of the light chain; A118 (Eu numbering) of the heavy chain; and S400 (Eu numbering) of the heavy chain Fc region. Additional substitution positions and methods of fabricating compatible site-specific antibodies are set forth in U.S. Pat. No. 7,521,541 which is incorporated herein in its entirety.

The strategy for generating antibody-drug conjugates with defined sites and stoichiometries of drug loading, as disclosed herein, is broadly applicable to all anti-MFI2 antibodies as it primarily involves engineering of the conserved constant domains of the antibody. As the amino acid sequences and native disulfide bridges of each class and subclass of antibody are well documented, one skilled in the art could readily fabricate engineered constructs of various antibodies without undue experimentation and, accordingly, such constructs are expressly contemplated as being within the scope of the instant invention.

4.3. Constant Region Modifications and Altered Glycosylation

Selected embodiments of the present invention may also comprise substitutions or modifications of the constant region (i.e. the Fc region), including without limitation, amino acid residue substitutions, mutations and/or modifications, which result in a compound with characteristics including, but not limited to: altered pharmacokinetics, increased serum half-life, increase binding affinity, reduced immunogenicity, increased production, altered Fc ligand binding to an Fc receptor (FcR), enhanced or reduced ADCC or CDC, altered glycosylation and/or disulfide bonds and modified binding specificity.

Compounds with improved Fc effector functions can be generated, for example, through changes in amino acid residues involved in the interaction between the Fc domain and an Fc receptor (e.g., FcγRI, FcγRIIA and B, FcγRIII and FcRn), which may lead to increased cytotoxicity and/or altered pharmacokinetics, such as increased serum half-life (see, for example, Ravetch and Kinet, Annu. Rev. Immunol 9:457-92 (1991); Capel et al., Immunomethods 4:25-34 (1994); and de Haas et al., J. Lab. Clin. Med. 126:330-41 (1995).

In selected embodiments, antibodies with increased in vivo half-lives can be generated by modifying (e.g., substituting, deleting or adding) amino acid residues identified as involved in the interaction between the Fc domain and the FcRn receptor (see, e.g., International Publication Nos. WO 97/34631; WO 04/029207; U.S. Pat. No. 6,737,056 and U.S.P.N. 2003/0190311). With regard to such embodiments, Fc variants may provide half-lives in a mammal, preferably a human, of greater than 5 days, greater than 10 days, greater than 15 days, preferably greater than 20 days, greater than 25 days, greater than 30 days, greater than 35 days, greater than 40 days, greater than 45 days, greater than 2 months, greater than 3 months, greater than 4 months, or greater than 5 months. The increased half-life results in a higher serum titer which thus reduces the frequency of the administration of the antibodies and/or reduces the concentration of the antibodies to be administered. Binding to human FcRn in vivo and serum half-life of human FcRn high affinity binding polypeptides can be assayed, e.g., in transgenic mice or transfected human cell lines expressing human FcRn, or in primates to which the polypeptides with a variant Fc region are administered. WO 2000/42072 describes antibody variants with improved or diminished binding to FcRns. See also, e.g., Shields et al. J. Biol. Chem. 9(2):6591-6604 (2001).

In other embodiments, Fc alterations may lead to enhanced or reduced ADCC or CDC activity. As in known in the art, CDC refers to the lysing of a target cell in the presence of complement, and ADCC refers to a form of cytotoxicity in which secreted Ig bound onto FcRs present on certain cytotoxic cells (e.g., Natural Killer cells, neutrophils, and macrophages) enables these cytotoxic effector cells to bind specifically to an antigen-bearing target cell and subsequently kill the target cell with cytotoxins. In the context of the instant invention antibody variants are provided with "altered" FcR binding affinity, which is either enhanced or diminished binding as compared to a parent or unmodified antibody or to an antibody comprising a native sequence FcR. Such variants which display decreased binding may possess little or no appreciable binding, e.g., 0-20% binding to the FcR compared to a native sequence, e.g. as determined by techniques well known in the art. In other embodiments the variant will exhibit enhanced binding as compared to the native immunoglobulin Fc domain. It will be appreciated that these types of Fc variants may advantageously be used to enhance the effective anti-neoplastic properties of the disclosed antibodies. In yet other embodiments, such alterations lead to increased binding affinity, reduced immunogenicity, increased production, altered glycosylation and/or disulfide bonds (e.g., for conjugation sites), modified binding specificity, increased phagocytosis; and/or down regulation of cell surface receptors (e.g. B cell receptor; BCR), etc.

Still other embodiments comprise one or more engineered glycoforms, e.g., a site-specific antibody comprising an altered glycosylation pattern or altered carbohydrate composition that is covalently attached to the protein (e.g., in the Fc domain). See, for example, Shields, R. L. et al. (2002) *J. Biol. Chem.* 277:26733-26740. Engineered glycoforms may be useful for a variety of purposes, including but not limited to enhancing or reducing effector function, increasing the affinity of the antibody for a target or facilitating production of the antibody. In certain embodiments where reduced effector function is desired, the molecule may be engineered to express an aglycosylated form. Substitutions that may result in elimination of one or more variable region framework glycosylation sites to thereby eliminate glycosylation at that site are well known (see e.g. U.S. Pat. Nos. 5,714,350 and 6,350,861). Conversely, enhanced effector functions or improved binding may be imparted to the Fc containing molecule by engineering in one or more additional glycosylation sites.

Other embodiments include an Fc variant that has an altered glycosylation composition, such as a hypofucosylated antibody having reduced amounts of fucosyl residues or an antibody having increased bisecting GlcNAc structures. Such altered glycosylation patterns have been demonstrated to increase the ADCC ability of antibodies. Engineered glycoforms may be generated by any method known to one skilled in the art, for example by using engineered or variant expression strains, by co-expression with one or more enzymes (for example N-acetylglucosaminyltransferase III (GnTIII)), by expressing a molecule comprising an Fc region in various organisms or cell lines from various organisms or by modifying carbohydrate(s) after the molecule comprising Fc region has been expressed (see, for example, WO 2012/117002).

4.4. Fragments

Regardless of which form of antibody (e.g. chimeric, humanized, etc.) is selected to practice the invention it will be appreciated that immunoreactive fragments, either by themselves or as part of an antibody drug conjugate, of the same may be used in accordance with the teachings herein. An "antibody fragment" comprises at least a portion of an intact antibody. As used herein, the term "fragment" of an antibody molecule includes antigen-binding fragments of antibodies, and the term "antigen-binding fragment" refers to a polypeptide fragment of an immunoglobulin or antibody that immunospecifically binds or reacts with a selected antigen or immunogenic determinant thereof or competes with the intact antibody from which the fragments were derived for specific antigen binding.

Exemplary site-specific fragments include: variable light chain fragments (VL), an variable heavy chain fragments (VH), scFv, F(ab')2 fragment, Fab fragment, Fd fragment, Fv fragment, single domain antibody fragments, diabodies, linear antibodies, single-chain antibody molecules and multispecific antibodies formed from antibody fragments. In addition, an active site-specific fragment comprises a portion of the antibody that retains its ability to interact with the antigen/substrates or receptors and modify them in a manner similar to that of an intact antibody (though maybe with somewhat less efficiency). Such antibody fragments may further be engineered to comprise one or more free cysteines as described herein.

In other embodiments, an antibody fragment is one that comprises the Fc region and that retains at least one of the biological functions normally associated with the Fc region when present in an intact antibody, such as FcRn binding, antibody half-life modulation, ADCC function and complement binding. In one embodiment, an antibody fragment is a monovalent antibody that has an in vivo half-life substantially similar to an intact antibody. For example, such an antibody fragment may comprise an antigen binding arm linked to an Fc sequence comprising at least one free cysteine capable of conferring in vivo stability to the fragment.

As would be well recognized by those skilled in the art, fragments can be obtained by molecular engineering or via chemical or enzymatic treatment (such as papain or pepsin) of an intact or complete antibody or antibody chain or by recombinant means. See, e.g., Fundamental Immunology, W. E. Paul, ed., Raven Press, N.Y. (1999), for a more detailed description of antibody fragments.

In selected embodiments antibody fragments of the invention will comprise ScFv constructs which may be used in various configurations. For example such anti-MFI2 ScFv constructs may be used in adoptive immunity gene therapy to treat tumors. In certain embodiments the antibodies of the invention (e.g. ScFv fragments) may be used to generate a chimeric antigen receptors (CAR) that immunoselectively react with MFI2. In accordance with the instant disclosure an anti-MFI2 CAR is a fused protein comprising the anti-MFI2 antibodies of the invention or immunoreactive fragments thereof (e.g. ScFv fragments), a transmembrane domain, and at least one intracellular domain. In certain embodiments, T-cells, natural killer cells or dendritic cells that have been genetically engineered to express an anti-MFI2 CAR can be introduced into a subject suffering from cancer in order to stimulate the immune system of the subject to specifically target tumor cells expressing MFI2. In some embodiments the CARs of the invention will comprise an intracellular domain that initiates a primary cytoplasmic signaling sequence, that is, a sequence for initiating antigen-dependent primary activation via a T-cell receptor complex, for example, intracellular domains derived from CD3$\zeta$, FcR$\gamma$, FcR$\beta$, CD3$\gamma$, CD3$\delta$, CD3$\varepsilon$, CD5, CD22, CD79a, CD79b, and CD66d. In other embodiments, the CARs of the invention will comprise an intracellular domain that initiates a secondary or co-stimulating signal, for example, intracellular domains derived from CD2, CD4, CD5, CD8$\alpha$, CD8$\beta$, CD28, CD134, CD137, ICOS, CD154, 4-1BB and glucocorticoid-induced tumor necrosis factor receptor (see U.S.P.N. US/2014/0242701).

4.5. Multivalent Constructs

In other embodiments, the antibodies and conjugates of the invention may be monovalent or multivalent (e.g., bivalent, trivalent, etc.). As used herein, the term "valency" refers to the number of potential target binding sites associated with an antibody. Each target binding site specifically binds one target molecule or specific position or locus on a target molecule. When an antibody is monovalent, each binding site of the molecule will specifically bind to a single antigen position or epitope. When an antibody comprises more than one target binding site (multivalent), each target binding site may specifically bind the same or different molecules (e.g., may bind to different ligands or different antigens, or different epitopes or positions on the same antigen). See, for example, U.S.P.N. 2009/0130105.

In one embodiment, the antibodies are bispecific antibodies in which the two chains have different specificities, as described in Millstein et al., 1983, *Nature,* 305:537-539. Other embodiments include antibodies with additional specificities such as trispecific antibodies. Other more sophisticated compatible multispecific constructs and methods of their fabrication are set forth in U.S.P.N. 2009/0155255, as well as WO 94/04690; Suresh et al., 1986, *Methods in Enzymology,* 121:210; and WO96/27011.

Multivalent antibodies may immunospecifically bind to different epitopes of the desired target molecule or may immunospecifically bind to both the target molecule as well as a heterologous epitope, such as a heterologous polypeptide or solid support material. While selected embodiments may only bind two antigens (i.e. bispecific antibodies), antibodies with additional specificities such as trispecific antibodies are also encompassed by the instant invention. Bispecific antibodies also include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

5. Recombinant Production of Antibodies

Antibodies and fragments thereof may be produced or modified using genetic material obtained from antibody producing cells and recombinant technology (see, for example; Dubel and Reichert (Eds.) (2014) *Handbook of Therapeutic Antibodies,* $2^{nd}$ Edition, Wiley-Blackwell GmbH; Sambrook and Russell (Eds.) (2000) *Molecular Cloning: A Laboratory Manual* ($3^{rd}$ Ed.), NY, Cold Spring Harbor Laboratory Press; Ausubel et al. (2002) *Short Protocols in Molecular Biology: A Compendium of Methods from Current Protocols in Molecular Biology*, Wiley, John & Sons, Inc.; and U.S. Pat. No. 7,709,611).

Another aspect of the invention pertains to nucleic acid molecules that encode the antibodies of the invention. The nucleic acids may be present in whole cells, in a cell lysate, or in a partially purified or substantially pure form. A nucleic acid is "isolated" or rendered substantially pure when separated from other cellular components or other contaminants, e.g., other cellular nucleic acids or proteins, by standard techniques, including alkaline/SDS treatment, CsCl banding, column chromatography, agarose gel electrophoresis and others well known in the art. A nucleic acid of the invention can be, for example, DNA (e.g. genomic DNA, cDNA), RNA and artificial variants thereof (e.g., peptide nucleic acids), whether single-stranded or double-stranded or RNA, RNA and may or may not contain introns. In selected embodiments the nucleic acid is a cDNA molecule.

Nucleic acids of the invention can be obtained using standard molecular biology techniques. For antibodies expressed by hybridomas (e.g., hybridomas prepared as described in the Examples below), cDNAs encoding the light and heavy chains of the antibody can be obtained by standard PCR amplification or cDNA cloning techniques. For antibodies obtained from an immunoglobulin gene library (e.g., using phage display techniques), nucleic acid encoding the antibody can be recovered from the library.

DNA fragments encoding VH and VL segments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, means that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (CH1, CH2 and CH3 in the case of IgG1). The sequences of human heavy chain constant region genes are known in the art (see e.g., Kabat, et al. (1991) (supra)) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. An exemplary IgG1 constant region is set forth in SEQ ID NO: 2. For a Fab fragment heavy chain gene, the VH-encoding DNA can be operatively linked to another DNA molecule encoding only the heavy chain CH1 constant region.

Isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, et al. (1991) (supra)) and DNA fragments encompassing these regions can be obtained by standard PCR amplification. The light chain constant region can be a kappa or lambda constant region, but most preferably is a kappa constant region. An exemplary compatible kappa light chain constant region is set forth in SEQ ID NO: 1.

Contemplated herein are certain polypeptides (e.g. antigens or antibodies) that exhibit "sequence identity", sequence similarity" or "sequence homology" to the polypeptides of the invention. For example, a derived humanized antibody VH or VL domain may exhibit a sequence similarity with the source (e.g., murine) or acceptor (e.g., human) VH or VL domain. A "homologous" polypeptide may exhibit 65%, 70%, 75%, 80%, 85%, or 90% sequence identity. In other embodiments a "homologous" polypeptides may exhibit 93%, 95% or 98% sequence identity. As used herein, the percent homology between two amino acid sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two amino acid sequences can be determined using the algorithm of E. Meyers and W. Miller (*Comput. Appl. Biosci.*, 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* 48:444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6.

Additionally or alternatively, the protein sequences of the present invention can further be used as a "query sequence" to perform a search against public databases to, for example, identify related sequences. Such searches can be performed using the XBLAST program (version 2.0) of Altschul, et al. (1990) *J. Mol. Biol.* 215:403-10. BLAST protein searches can be performed with the XBLAST program, score=50, wordlength=3 to obtain amino acid sequences homologous to the antibody molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used.

Residue positions which are not identical may differ by conservative amino acid substitutions or by non-conservative amino acid substitutions. A "conservative amino acid substitution" is one in which an amino acid residue is substituted by another amino acid residue having a side chain with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. In cases where there is a substitution with a non-conservative amino acid, in embodiments the polypeptide exhibiting sequence identity will retain the desired function or activity of the polypeptide of the invention (e.g., antibody.)

Also contemplated herein are nucleic acids that that exhibit "sequence identity", sequence similarity" or "sequence homology" to the nucleic acids of the invention. A "homologous sequence" means a sequence of nucleic acid molecules exhibiting at least about 65%, 70%, 75%, 80%, 85%, or 90% sequence identity. In other embodiments, a "homologous sequence" of nucleic acids may exhibit 93%, 95% or 98% sequence identity to the reference nucleic acid.

The instant invention also provides vectors comprising such nucleic acids described above, which may be operably linked to a promoter (see, e.g., WO 86/05807; WO 89/01036; and U.S. Pat. No. 5,122,464); and other transcriptional regulatory and processing control elements of the eukaryotic secretory pathway. The invention also provides host cells harboring those vectors and host-expression systems.

As used herein, the term "host-expression system" includes any kind of cellular system that can be engineered to generate either the nucleic acids or the polypeptides and antibodies of the invention. Such host-expression systems include, but are not limited to microorganisms (e.g., *E. coli* or *B. subtilis*) transformed or transfected with recombinant bacteriophage DNA or plasmid DNA; yeast (e.g., Saccharomyces) transfected with recombinant yeast expression vectors; or mammalian cells (e.g., COS, CHO-S, HEK293T, 3T3 cells) harboring recombinant expression constructs containing promoters derived from the genome of mammalian cells or viruses (e.g., the adenovirus late promoter). The host cell may be co-transfected with two expression vectors, for example, the first vector encoding a heavy chain derived polypeptide and the second vector encoding a light chain derived polypeptide.

Methods of transforming mammalian cells are well known in the art. See, for example, U.S. Pat. Nos. 4,399,216, 4,912,040, 4,740,461, and 4,959,455. The host cell may also be engineered to allow the production of an antigen binding molecule with various characteristics (e.g. modified glycoforms or proteins having GnTIII activity).

For long-term, high-yield production of recombinant proteins stable expression is preferred. Accordingly, cell lines that stably express the selected antibody may be engineered using standard art recognized techniques and form part of the invention. Rather than using expression vectors that contain viral origins of replication, host cells can be transformed with DNA controlled by appropriate expression control elements (e.g., promoter or enhancer sequences, transcription terminators, polyadenylation sites, etc.), and a selectable marker. Any of the selection systems well known in the art may be used, including the glutamine synthetase gene expression system (the GS system) which provides an efficient approach for enhancing expression under selected conditions. The GS system is discussed in whole or part in connection with EP 0 216 846, EP 0 256 055, EP 0 323 997 and EP 0 338 841 and U.S. Pat. Nos. 5,591,639 and 5,879,936. Another compatible expression system for the development of stable cell lines is the Freedom™ CHO-S Kit (Life Technologies).

Once an antibody of the invention has been produced by recombinant expression or any other of the disclosed techniques, it may be purified or isolated by methods known in the art in that it is identified and separated and/or recovered from its natural environment and separated from contaminants that would interfere with diagnostic or therapeutic uses for the antibody or related ADC. Isolated antibodies include antibodies in situ within recombinant cells.

These isolated preparations may be purified using various art-recognized techniques, such as, for example, ion exchange and size exclusion chromatography, dialysis, diafiltration, and affinity chromatography, particularly Protein A or Protein G affinity chromatography. Compatible methods are discussed more fully in the Examples below.

6. Post-Production Selection

No matter how obtained, antibody-producing cells (e.g., hybridomas, yeast colonies, etc.) may be selected, cloned and further screened for desirable characteristics including, for example, robust growth, high antibody production and desirable antibody characteristics such as high affinity for the antigen of interest. Hybridomas can be expanded in vitro in cell culture or in vivo in syngeneic immunocompromised animals. Methods of selecting, cloning and expanding hybridomas and/or colonies are well known to those of ordinary skill in the art. Once the desired antibodies are identified the relevant genetic material may be isolated, manipulated and expressed using common, art-recognized molecular biology and biochemical techniques.

The antibodies produced by naïve libraries (either natural or synthetic) may be of moderate affinity ($K_a$ of about $10^6$ to $10^7$ M$^{-1}$). To enhance affinity, affinity maturation may be mimicked in vitro by constructing antibody libraries (e.g., by introducing random mutations in vitro by using error-prone polymerase) and reselecting antibodies with high affinity for the antigen from those secondary libraries (e.g. by using phage or yeast display). WO 9607754 describes a method for inducing mutagenesis in a CDR of an immunoglobulin light chain to create a library of light chain genes.

Various techniques can be used to select antibodies, including but not limited to, phage or yeast display in which a library of human combinatorial antibodies or scFv fragments is synthesized on phages or yeast, the library is screened with the antigen of interest or an antibody-binding portion thereof, and the phage or yeast that binds the antigen is isolated, from which one may obtain the antibodies or immunoreactive fragments (Vaughan et al., 1996, PMID: 9630891; Sheets et al., 1998, PMID: 9600934; Boder et al., 1997, PMID: 9181578; Pepper et al., 2008, PMID: 18336206). Kits for generating phage or yeast display libraries are commercially available. There also are other methods and reagents that can be used in generating and screening antibody display libraries (see U.S. Pat. No. 5,223,409; WO 92/18619, WO 91/17271, WO 92/20791, WO 92/15679, WO 93/01288, WO 92/01047, WO 92/09690; and Barbas et al., 1991, PMID: 1896445). Such techniques advantageously allow for the screening of large numbers of candidate antibodies and provide for relatively easy manipulation of sequences (e.g., by recombinant shuffling).

IV. CHARACTERISTICS OF ANTIBODIES

In certain embodiments, antibody-producing cells (e.g., hybridomas or yeast colonies) may be selected, cloned and further screened for favorable properties including, for example, robust growth, high antibody production and, as discussed in more detail below, desirable site-specific antibody characteristics. In other cases characteristics of the antibody may be imparted by selecting a particular antigen (e.g., a specific MFI2 isoform) or immunoreactive fragment of the target antigen for inoculation of the animal. In still other embodiments the selected antibodies may be engineered as described above to enhance or refine immunochemical characteristics such as affinity or pharmacokinetics.

A. Neutralizing Antibodies

In selected embodiments the antibodies of the invention may be "antagonists" or "neutralizing" antibodies, meaning that the antibody may associate with a determinant and block or inhibit the activities of said determinant either directly or by preventing association of the determinant with a binding partner such as a ligand or a receptor, thereby interrupting the biological response that otherwise would result from the interaction of the molecules. A neutralizing or antagonist antibody will substantially inhibit binding of the determinant to its ligand or substrate when an excess of antibody reduces the quantity of binding partner bound to the determinant by at least about 20%, 30%, 40%, 50%, 60%, 70%, 80%, 85%, 90%, 95%, 97%, 99% or more as measured, for example, by target molecule activity or in an in vitro competitive binding assay. It will be appreciated that the modified activity may be measured directly using art recognized techniques or may be measured by the impact the altered activity has downstream (e.g., oncogenesis or cell survival).

B. Internalizing Antibodies

In certain embodiments the antibodies may comprise internalizing antibodies such that the antibody will bind to a determinant and will be internalized (along with any conjugated pharmaceutically active moiety) into a selected target cell including tumorigenic cells. The number of antibody molecules internalized may be sufficient to kill an antigen-expressing cell, especially an antigen-expressing tumorigenic cell. Depending on the potency of the antibody or, in some instances, antibody drug conjugate, the uptake of a single antibody molecule into the cell may be sufficient to kill the target cell to which the antibody binds. With regard to the instant invention there is evidence that a substantial portion of expressed MFI2 protein remains associated with the tumorigenic cell surface, thereby allowing for localization and internalization of the disclosed antibodies or ADCs. In selected embodiments such antibodies will be associated with, or conjugated to, one or more drugs that kill the cell upon internalization. In some embodiments the ADCs of the instant invention will comprise an internalizing site-specific ADC.

As used herein, an antibody that "internalizes" is one that is taken up (along with any conjugated cytotoxin) by a target cell upon binding to an associated determinant. The number of such ADCs internalized will preferably be sufficient to kill the determinant-expressing cell, especially a determinant-expressing cancer stem cell. Depending on the potency of the cytotoxin or ADC as a whole, in some instances the uptake of a few antibody molecules into the cell is sufficient to kill the target cell to which the antibody binds. For example, certain drugs such as PBDs or calicheamicin are so potent that the internalization of a few molecules of the toxin conjugated to the antibody is sufficient to kill the target cell. Whether an antibody internalizes upon binding to a mammalian cell can be determined by various art-recognized assays including those described in the Examples below.

Methods of detecting whether an antibody internalizes into a cell are also described in U.S. Pat. No. 7,619,068.

C. Depleting Antibodies

In other embodiments the antibodies of the invention are depleting antibodies. The term "depleting" antibody refers to an antibody that preferably binds to an antigen on or near the cell surface and induces, promotes or causes the death of the cell (e.g., by CDC, ADCC or introduction of a cytotoxic agent). In embodiments, the selected depleting antibodies will be conjugated to a cytotoxin.

Preferably a depleting antibody will be able to kill at least 20%, 30%, 40%, 50%, 60%, 70%, 80%, 85%, 90%, 95%, 97%, or 99% of MFI2-expressing cells in a defined cell population. In some embodiments the cell population may comprise enriched, sectioned, purified or isolated tumorigenic cells, including cancer stem cells. In other embodiments the cell population may comprise whole tumor samples or heterogeneous tumor extracts that comprise cancer stem cells. Standard biochemical techniques may be used to monitor and quantify the depletion of tumorigenic cells in accordance with the teachings herein.

D. Binding Affinity

Disclosed herein are antibodies that have a high binding affinity for a specific determinant e.g. MFI2. The term "$K_D$" refers to the dissociation constant or apparent affinity of a particular antibody-antigen interaction. An antibody of the invention can immunospecifically bind its target antigen when the dissociation constant $K_D$ ($k_{off}/k_{on}$) is $\leq 10^{-7}$ M. The antibody specifically binds antigen with high affinity when the $K_D$ is $\leq 5\times 10^{-9}$ M, and with very high affinity when the $K_D$ is $\leq 5\times 10^{-10}$ M. In one embodiment of the invention, the antibody has a $K_D$ of $\leq 10^{-9}$ M and an off-rate of about $1\times 10^{-4}$/sec. In one embodiment of the invention, the off-rate is $<1\times 10^{-5}$/sec. In other embodiments of the invention, the antibodies will bind to a determinant with a $K_D$ of between about $10^{-7}$ M and $10^{-10}$ M, and in yet another embodiment it will bind with a $K_D \leq 2\times 10^{-10}$ M. Still other selected embodiments of the invention comprise antibodies that have a $K_D$ ($k_{off}/k_{on}$) of less than $10^{-6}$ M, less than $5\times 10^{-6}$ M, less than $10^{-7}$ M, less than $5\times 10^{-7}$ M, less than $10^{-8}$ M, less than $5\times 10^{-8}$ M, less than $10^{-9}$ M, less than $5\times 10^{-9}$ M, less than $10^{-10}$ M, less than $5\times 10^{-10}$ M, less than $10^{-11}$ M, less than $5\times 10^{-11}$ M, less than $10^{-12}$ M, less than $5\times 10^{-12}$ M, less than $10^{-13}$ M, less than $5\times 10^{-13}$ M, less than $10^{-14}$ M, less than $5\times 10^{-14}$ M, less than $10^{-15}$ M or less than $5\times 10^{-15}$ M.

In certain embodiments, an antibody of the invention that immunospecifically binds to a determinant e.g. MFI2 may have an association rate constant or $k_{on}$ (or $k_a$) rate (antibody+antigen $(Ag)^k_{on}\leftarrow$ antibody-Ag) of at least $10^5 M^{-1}s^{-1}$, at least $2\times 10^5$ $M^{-1}s^{-1}$, at least $5\times 10^5$ $M^{-1}s^{-1}$, at least $10^6 M^{-1}s^{-1}$, at least $5\times 10^6 M^{-1}s^{-1}$, at least $10^7$ $M^{-1}s^{-1}$, at least $5\times 10^7$ $M^{-1}s^{-1}$, or at least $10^8$ $M^{-1}s^{-1}$.

In another embodiment, an antibody of the invention that immunospecifically binds to a determinant e.g. MFI2 may have a disassociation rate constant or $k_{off}$ (or $k_d$) rate (antibody+antigen $(Ag)^k_{off}\leftarrow$ antibody-Ag) of less than $10^{-1}$ $s^{-1}$, less than $5\times 10^{-1}$ $s^{-1}$, less than $10^{-2}$ $s^{-1}$, less than $5\times 10^{-2}$ $s^{-1}$, less than $10^{-3}$ $s^{-1}$, less than $5\times 10^{-3}$ $s^{-1}$, less than $10^{-4}$ $s^{-1}$, less than $5\times 10^4$ $s^{-1}$, less than $10^{-5}$ $s^{-1}$, less than $5\times 10^{-5}$ $s^{-1}$, less than $10^{-6}$ $s^{-1}$, less than $5\times 10^{-6}$ $s^{-1}$ less than $10^{-7}$ $s^{-1}$, less than $5\times 10^{-7}$ $s^{-1}$, less than $10^{-8}$ $s^{-1}$, less than $5\times 10^{-8}$ $s^{-1}$, less than $10^{-9}$ $s^{-1}$, less than $5\times 10^{-9}$ $s^{-1}$ or less than $10^{-10}$ $s^{-1}$.

Binding affinity may be determined using various techniques known in the art, for example, surface plasmon resonance, bio-layer interferometry, dual polarization interferometry, static light scattering, dynamic light scattering, isothermal titration calorimetry, ELISA, analytical ultracentrifugation, and flow cytometry.

E. Binning and Epitope Mapping

Antibodies disclosed herein may be characterized in terms of the discrete epitope with which they associate. An "epitope" is the portion(s) of a determinant to which the antibody or immunoreactive fragment specifically binds. Immunospecific binding can be confirmed and defined based on binding affinity, as described above, or by the preferential recognition by the antibody of its target antigen in a complex mixture of proteins and/or macromolecules (e.g. in competition assays). A "linear epitope", is formed by contiguous amino acids in the antigen that allow for immunospecific binding of the antibody. The ability to preferentially bind linear epitopes is typically maintained even when the antigen is denatured. Conversely, a "conformational epitope", usually comprises non-contiguous amino acids in the antigen's amino acid sequence but, in the context of the antigen's secondary, tertiary or quaternary structure, are sufficiently proximate to be bound concomitantly by a single antibody. When antigens with conformational epitopes are denatured, the antibody will typically no longer recognize the antigen. An epitope (contiguous or non-contiguous) typically includes at least 3, and more usually, at least 5 or 8-10 or 12-20 amino acids in a unique spatial conformation.

It is also possible to characterize the antibodies of the invention in terms of the group or "bin" to which they belong. "Binning" refers to the use of competitive antibody binding assays to identify pairs of antibodies that are incapable of binding an immunogenic determinant simultaneously, thereby identifying antibodies that "compete" for binding. Competing antibodies may be determined by an assay in which the antibody or immunologically functional fragment being tested prevents or inhibits specific binding of a reference antibody to a common antigen. Typically, such an assay involves the use of purified antigen (e.g., MFI2 or a domain or fragment thereof) bound to a solid surface or cells, an unlabeled test antibody and a labeled reference antibody. Competitive inhibition is measured by determining the amount of label bound to the solid surface or cells in the presence of the test antibody. Additional details regarding methods for determining competitive binding are provided in the Examples herein. Usually, when a competing antibody is present in excess, it will inhibit specific binding of a reference antibody to a common antigen by at least 30%, 40%, 45%, 50%, 55%, 60%, 65%, 70% or 75%. In some instance, binding is inhibited by at least 80%, 85%, 90%, 95%, or 97% or more. Conversely, when the reference antibody is bound it will preferably inhibit binding of a subsequently added test antibody (i.e., a MFI2 antibody) by at least 30%, 40%, 45%, 50%, 55%, 60%, 65%, 70% or 75%. In some instance, binding of the test antibody is inhibited by at least 80%, 85%, 90%, 95%, or 97% or more.

Generally binning or competitive binding may be determined using various art-recognized techniques, such as, for example, immunoassays such as western blots, radioimmunoassays, enzyme linked immunosorbent assay (ELISA), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays and protein A immunoassays. Such immunoassays are routine and well known in the art (see, Ausubel et al, eds, (1994) *Current Protocols in Molecular Biology*, Vol. 1, John Wiley & Sons, Inc., New York). Additionally, cross-blocking assays may be used (see, for example, WO 2003/48731; and Harlow et al. (1988) *Antibodies, A Laboratory Manual*, Cold Spring Harbor Laboratory, Ed Harlow and David Lane).

Other technologies used to determine competitive inhibition (and hence "bins"), include: surface plasmon resonance using, for example, the BIAcore™ 2000 system (GE Healthcare); bio-layer interferometry using, for example, a ForteBio® Octet RED (ForteBio); or flow cytometry bead arrays using, for example, a FACSCanto II (BD Biosciences) or a multiplex LUMINEX™ detection assay (Luminex).

Luminex is a bead-based immunoassay platform that enables large scale multiplexed antibody pairing. The assay compares the simultaneous binding patterns of antibody pairs to the target antigen. One antibody of the pair (capture mAb) is bound to Luminex beads, wherein each capture mAb is bound to a bead of a different color. The other antibody (detector mAb) is bound to a fluorescent signal (e.g. phycoerythrin (PE)). The assay analyzes the simultaneous binding (pairing) of antibodies to an antigen and groups together antibodies with similar pairing profiles. Similar profiles of a detector mAb and a capture mAb indicates that the two antibodies bind to the same or closely related epitopes. In one embodiment, pairing profiles can be determined using Pearson correlation coefficients to identify the antibodies which most closely correlate to any particular antibody on the panel of antibodies that are tested. In embodiments a test/detector mAb will be determined to be in the same bin as a reference/capture mAb if the Pearson's correlation coefficient of the antibody pair is at least 0.9. In other embodiments the Pearson's correlation coefficient is at least 0.8, 0.85, 0.87 or 0.89. In further embodiments, the Pearson's correlation coefficient is at least 0.91, 0.92, 0.93, 0.94, 0.95, 0.96, 0.97, 0.98, 0.99 or 1. Other methods of analyzing the data obtained from the Luminex assay are described in U.S. Pat. No. 8,568,992. The ability of Luminex to analyze 100 different types of beads (or more) simultaneously provides almost unlimited antigen and/or antibody surfaces, resulting in improved throughput and resolution in antibody epitope profiling over a biosensor assay (Miller, et al., 2011, PMID: 21223970).

Similarly binning techniques comprising surface plasmon resonance are compatible with the instant invention. As used herein "surface plasmon resonance," refers to an optical phenomenon that allows for the analysis of real-time specific interactions by detection of alterations in protein concentrations within a biosensor matrix. Using commercially available equipment such as the BIAcore™ 2000 system it may readily be determined if selected antibodies compete with each other for binding to a defined antigen.

In other embodiments, a technique that can be used to determine whether a test antibody "competes" for binding with a reference antibody is "bio-layer interferometry", an optical analytical technique that analyzes the interference pattern of white light reflected from two surfaces: a layer of immobilized protein on a biosensor tip, and an internal reference layer. Any change in the number of molecules bound to the biosensor tip causes a shift in the interference pattern that can be measured in real-time. Such biolayer interferometry assays may be conducted using a ForteBio® Octet RED machine as follows. A reference antibody (Ab1) is captured onto an anti-mouse capture chip, a high concentration of non-binding antibody is then used to block the chip and a baseline is collected. Monomeric, recombinant target protein is then captured by the specific antibody (Ab1) and the tip is dipped into a well with either the same antibody (Ab1) as a control or into a well with a different test antibody (Ab2). If no further binding occurs, as determined by comparing binding levels with the control Ab1, then Ab1 and Ab2 are determined to be "competing" antibodies. If additional binding is observed with Ab2, then Ab1 and Ab2 are determined not to compete with each other. This process can be expanded to screen large libraries of unique antibodies using a full row of antibodies in a 96-well plate representing unique bins. In embodiments a test antibody will compete with a reference antibody if the reference antibody inhibits specific binding of the test antibody to a common antigen by at least 40%, 45%, 50%, 55%, 60%, 65%, 70% or 75%. In other embodiments, binding is inhibited by at least 80%, 85%, 90%, 95%, or 97% or more.

Once a bin, encompassing a group of competing antibodies, has been defined further characterization can be carried out to determine the specific domain or epitope on the antigen to which that group of antibodies binds. Domain-level epitope mapping may be performed using a modification of the protocol described by Cochran et al., 2004, PMID: 15099763. Fine epitope mapping is the process of determining the specific amino acids on the antigen that comprise the epitope of a determinant to which the antibody binds.

In certain embodiments fine epitope mapping can be performed using phage or yeast display. Other compatible epitope mapping techniques include alanine scanning mutants, peptide blots (Reineke, 2004, PMID: 14970513), or peptide cleavage analysis. In addition, methods such as epitope excision, epitope extraction and chemical modification of antigens can be employed (Tomer, 2000, PMID: 10752610) using enzymes such as proteolytic enzymes (e.g., trypsin, endoproteinase Glu-C, endoproteinase Asp-N, chymotrypsin, etc.); chemical agents such as succinimidyl esters and their derivatives, primary amine-containing compounds, hydrazines and carbohydrazines, free amino acids, etc. In another embodiment Modification-Assisted Profiling, also known as Antigen Structure-based Antibody Profiling (ASAP) can be used to categorize large numbers of monoclonal antibodies directed against the same antigen according to the similarities of the binding profile of each antibody to chemically or enzymatically modified antigen surfaces (U.S.P.N. 2004/0101920).

Once a desired epitope on an antigen is determined, it is possible to generate additional antibodies to that epitope, e.g., by immunizing with a peptide comprising the selected epitope using techniques described herein.

V. ANTIBODY CONJUGATES

In some embodiments the antibodies of the invention may be conjugated with pharmaceutically active or diagnostic moieties to form an "antibody drug conjugate" (ADC) or "antibody conjugate". The term "conjugate" is used broadly and means the covalent or non-covalent association of any pharmaceutically active or diagnostic moiety with an antibody of the instant invention regardless of the method of association. In certain embodiments the association is effected through a lysine or cysteine residue of the antibody. In some embodiments the pharmaceutically active or diagnostic moieties may be conjugated to the antibody via one or more site-specific free cysteine(s). The disclosed ADCs may be used for therapeutic and diagnostic purposes.

The ADCs of the instant invention may be used to deliver cytotoxins or other payloads to the target location (e.g., tumorigenic cells and/or cells expressing MFI2). As used herein the terms "drug" or "warhead" may be used interchangeably and will mean a biologically active or detectable molecule or drug, including anti-cancer agents as described below. A "payload" may comprise a drug or "warhead" in combination with an optional linker compound. The "warhead" on the conjugate may comprise peptides, proteins or prodrugs which are metabolized to an active agent in vivo, polymers, nucleic acid molecules, small molecules, binding agents, mimetic agents, synthetic drugs, inorganic molecules, organic molecules and radioisotopes. In an advantageous embodiment, the disclosed ADCs will direct the bound payload to the target site in a relatively unreactive, non-toxic state before releasing and activating the warhead. This targeted release of the warhead is preferably achieved through stable conjugation of the payloads (e.g., via one or more cysteines on the antibody) and the relatively homogeneous composition of the ADC preparations which minimize over-conjugated toxic species. Coupled with drug linkers that are designed to largely release the warhead once it has been delivered to the tumor site, the conjugates of the instant invention can substantially reduce undesirable non-specific toxicity. This advantageously provides for relatively high levels of the active cytotoxin at the tumor site while minimizing exposure of non-targeted cells and tissue thereby providing an enhanced therapeutic index.

It will be appreciated that, while some embodiments of the invention comprise payloads incorporating therapeutic moieties (e.g., cytotoxins), other payloads incorporating diagnostic agents and biocompatible modifiers may benefit from the targeted release provided by the disclosed conjugates. Accordingly, any disclosure directed to exemplary therapeutic payloads is also applicable to payloads comprising diagnostic agents or biocompatible modifiers as discussed herein unless otherwise dictated by context. The selected payload may be covalently or non-covalently linked to, the antibody and exhibit various stoichiometric molar ratios depending, at least in part, on the method used to effect the conjugation. Conjugates of the instant invention may be generally represented by the formula:

Ab-[L-D]n or a pharmaceutically acceptable salt thereof wherein:
  a) Ab comprises an anti-MFI2 antibody;
  b) L comprises an optional linker;
  c) D comprises a drug; and
  d) n is an integer from about 1 to about 20.

Those of skill in the art will appreciate that conjugates according to the aforementioned formula may be fabricated using a number of different linkers and drugs and that conjugation methodology will vary depending on the selection of components. As such, any drug or drug linker compound that associates with a reactive residue (e.g., cysteine or lysine) of the disclosed antibodies are compatible with the teachings herein. Similarly, any reaction conditions that allow for conjugation (including site-specific conjugation) of the selected drug to an antibody are within the scope of the present invention. Notwithstanding the foregoing, some embodiments of the instant invention comprise selective conjugation of the drug or drug linker to free cysteines using stabilization agents in combination with mild reducing agents as described herein. Such reaction conditions tend to provide more homogeneous preparations with less non-specific conjugation and contaminants and correspondingly less toxicity.

A. Payloads and Warheads

1. Therapeutic Agents

The antibodies of the invention may be conjugated, linked or fused to or otherwise associated with a pharmaceutically active moiety which is a therapeutic moiety or a drug such as an anti-cancer agent including, but not limited to, cytotoxic agents, cytostatic agents, anti-angiogenic agents, debulking agents, chemotherapeutic agents, radiotherapeutic agents, targeted anti-cancer agents, biological response modifiers, cancer vaccines, cytokines, hormone therapies, anti-metastatic agents and immunotherapeutic agents.

Exemplary anti-cancer agents (including homologs and derivatives thereof) comprise 1-dehydrotestosterone, anthramycins, actinomycin D, bleomycin, calicheamicin, colchicin, cyclophosphamide, cytochalasin B, dactinomycin (formerly actinomycin), dihydroxy anthracin, dione, duocarmycin, emetine, epirubicin, ethidium bromide, etoposide, glucocorticoids, gramicidin D, lidocaine, maytansinoids such as DM-1 and DM-4 (Immunogen), mithramycin, mitomycin, mitoxantrone, paclitaxel, procaine, propranolol, puromycin, tenoposide, tetracaine and pharmaceutically acceptable salts or solvates, acids or derivatives of any of the above.

Additional compatible cytotoxins comprise dolastatins and auristatins, including monomethyl auristatin E (MMAE) and monomethyl auristatin F (MMAF) (Seattle Genetics), amanitins such as alpha-amanitin, beta-amanitin, gamma-amanitin or epsilon-amanitin (Heidelberg Pharma), DNA minor groove binding agents such as duocarmycin derivatives (Syntarga), alkylating agents such as modified or dimeric pyrrolobenzodiazepines (PBD), mechlorethamine, thioepa, chlorambucil, melphalan, carmustine (BCNU), lomustine (CCNU), cyclophosphamide, busulfan, dibromomannitol, streptozotocin, mitomycin C and cisdichlorodiamine platinum (II) (DDP) cisplatin, splicing inhibitors such as meayamycin analogs or derivatives (e.g., FR901464 as set forth in U.S. Pat. No. 7,825,267), tubular binding agents such as epothilone analogs and tubulysins, paclitaxel and DNA damaging agents such as calicheamicins and esperamicins, antimetabolites such as methotrexate, 6-mercaptopurine, 6-thioguanine, cytarabine, and 5-fluorouracil decarbazine, anti-mitotic agents such as vinblastine and vincristine and anthracyclines such as daunorubicin (formerly daunomycin) and doxorubicin and pharmaceutically acceptable salts or solvates, acids or derivatives of any of the above.

In one embodiment the antibodies of the instant invention may be associated with anti-CD3 binding molecules to recruit cytotoxic T-cells and have them target tumorigenic cells (BiTE technology; see e.g., Fuhrmann et. al. (2010) Annual Meeting of AACR Abstract No. 5625).

In further embodiments ADCs of the invention may comprise therapeutic radioisotopes conjugated using appropriate linkers. Exemplary radioisotopes that may be compatible with such embodiments include, but are not limited to, iodine ($^{131}$I, $^{125}$I, $^{123}$I, $^{121}$I), carbon ($^{14}$C), copper ($^{62}$Cu, $^{64}$Cu, $^{67}$Cu), sulfur ($^{35}$S), tritium ($^{3}$H), indium ($^{115}$In, $^{113}$In, $^{112}$In, $^{111}$In,), bismuth (212Bi, $^{213}$Bi, technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine (18F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, $^{117}$Sn, $^{225}$Ac, $^{76}$Br, and $^{211}$At. Other radionuclides are also available as diagnostic and therapeutic agents, especially those in the energy range of 60 to 4,000 keV.

In certain some embodiments, the ADCs of the invention may comprise PBDs, and pharmaceutically acceptable salts or solvates, acids or derivatives thereof, as warheads. PBDs are alkylating agents that exert antitumor activity by covalently binding to DNA in the minor groove and inhibiting nucleic acid synthesis. PBDs have been shown to have potent antitumor properties while exhibiting minimal bone marrow depression. PBDs compatible with the invention may be linked to an antibody using several types of linkers (e.g., a peptidyl linker comprising a maleimido moiety with a free sulfhydryl), and in certain embodiments are dimeric in form (i.e., PBD dimers). Compatible PBDs (and optional linkers) that may be conjugated to the disclosed antibodies are described, for example, in U.S. Pat. Nos. 6,362,331, 7,049,311, 7,189,710, 7,429,658, 7,407,951, 7,741,319, 7,557,099, 8,034,808, 8,163,736, 2011/0256157 and PCT filings WO2011/130613, WO2011/128650, WO2011/130616, WO2014/057073 and WO2014/057074. Examples of PBD compounds compatible with the instant invention are shown below.

More specifically, in selected embodiments the present invention provides PBD dimers comprising a linker (as described below) connected to a position on one of the PBD moieties and conjugated to an MFI2 antibody. Through carefully engineered configurations the conjugate allows release of an active PBD compound that preferably does not retain any part of the linker. That is, there is no stub or linker residue present that could adversely impact the reactivity of the PBD payload. Accordingly selected MFI2 conjugates release the following dimeric PBD compounds upon cleavage of the linker:

It will be appreciated that each of the aforementioned dimeric PBD warheads would be preferably be released upon internalization by the target cell and destruction of the linker. As described in more detail below, preferable linkers will comprise cleavable linkers incorporating a self-immolation moiety that allows release of the active PBD warhead without retention of any part of the linker. Upon release the PBD warhead will then bind and cross-link with the target cell's DNA. Such binding apparently blocks division of the target cancer cell without distorting its DNA helix, thus potentially avoiding the common phenomenon of emergent drug resistance.

In addition to the aforementioned agents the antibodies of the present invention may also be conjugated to biological response modifiers. For example, in some embodiments the drug moiety can be a polypeptide possessing a desired biological activity. Such proteins may include, for example, a toxin such as abrin, ricin A, Onconase (or another cytotoxic RNase), *pseudomonas* exotoxin, cholera toxin, diphtheria toxin; an apoptotic agent such as tumor necrosis factor e.g. TNF-α or TNF-β, α-interferon, β-interferon, nerve

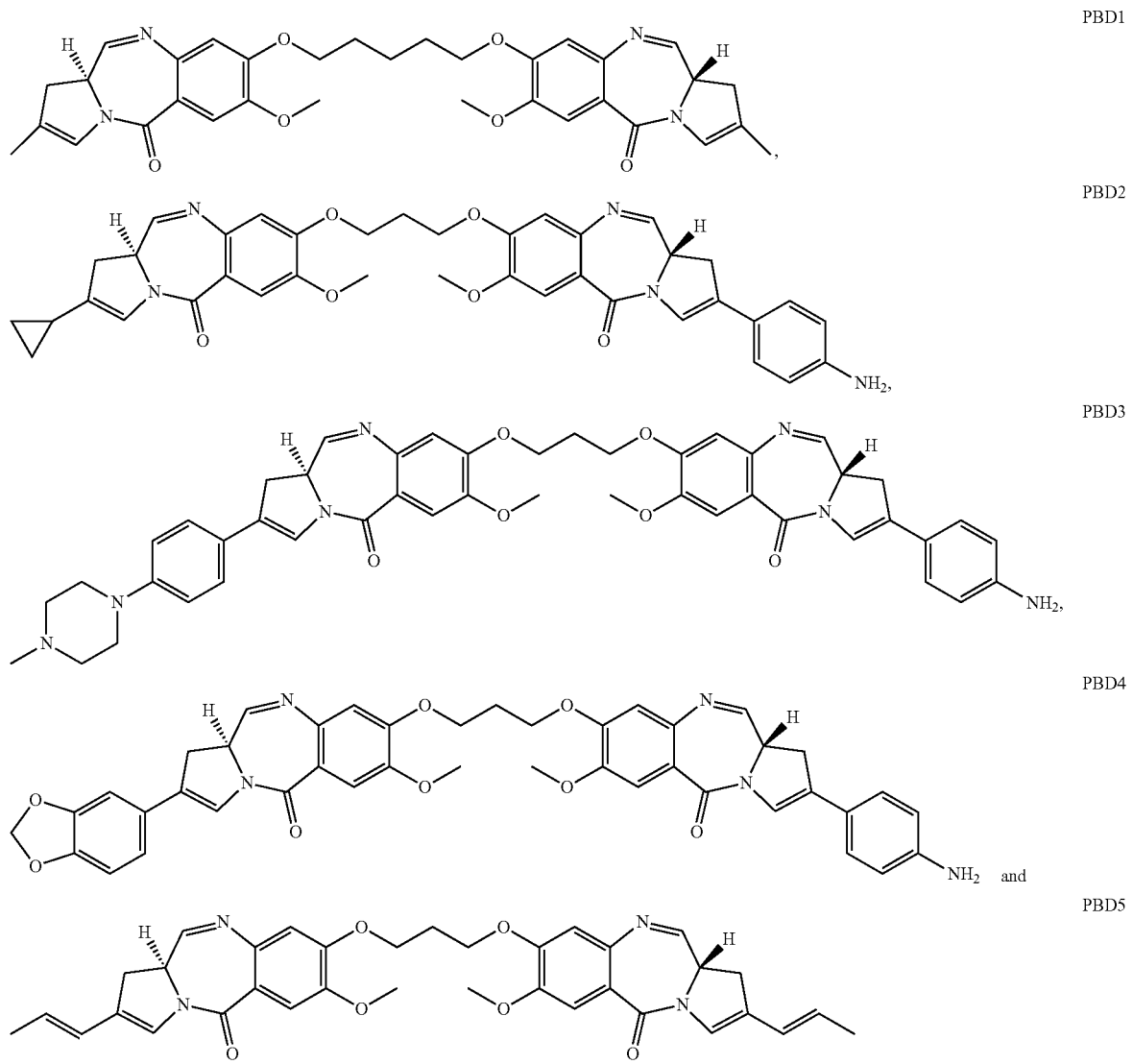

growth factor, platelet derived growth factor, tissue plasminogen activator, AIM I (WO 97/33899), AIM II (WO 97/34911), Fas Ligand (Takahashi et al., 1994, PMID: 7826947), and VEGI (WO 99/23105), a thrombotic agent, an anti-angiogenic agent, e.g., angiostatin or endostatin, a lymphokine, for example, interleukin-1 (IL-1), interleukin-2 (IL-2), interleukin-6 (IL-6), granulocyte macrophage colony stimulating factor (GM-CSF), and granulocyte colony stimulating factor (G-CSF), or a growth factor e.g., growth hormone (GH).

2. Diagnostic or Detection Agents

In other embodiments, the antibodies of the invention, or fragments or derivatives thereof, are conjugated to a diagnostic or detectable agent, marker or reporter which may be, for example, a biological molecule (e.g., a peptide or nucleotide), a small molecule, fluorophore, or radioisotope. Labeled antibodies can be useful for monitoring the development or progression of a hyperproliferative disorder or as part of a clinical testing procedure to determine the efficacy of a particular therapy including the disclosed antibodies (i.e. theragnostics) or to determine a future course of treatment. Such markers or reporters may also be useful in purifying the selected antibody, for use in antibody analytics (e.g., epitope binding or antibody binning), separating or isolating tumorigenic cells or in preclinical procedures or toxicology studies.

Such diagnosis, analysis and/or detection can be accomplished by coupling the antibody to detectable substances including, but not limited to, various enzymes comprising for example horseradish peroxidase, alkaline phosphatase, beta-galactosidase, or acetylcholinesterase; prosthetic groups, such as but not limited to streptavidinlbiotin and avidin/biotin; fluorescent materials, such as but not limited to, umbelliferone, fluorescein, fluorescein isothiocynate, rhodamine, dichlorotriazinylamine fluorescein, dansyl chloride or phycoerythrin; luminescent materials, such as but not limited to, luminol; bioluminescent materials, such as but not limited to, luciferase, luciferin, and aequorin; radioactive materials, such as but not limited to iodine ($^{131}$I, $^{125}$I, $^{123}$I, $^{121}$I), carbonl ($^{14}$C), sulfur ($^{35}$S), tritium ($^{3}$H), indium ($^{115}$In, $^{113}$In, $^{112}$In, $^{111}$In), and technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine (18F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Tin; positron emitting metals using various positron emission tomographies, non-radioactive paramagnetic metal ions, and molecules that are radiolabeled or conjugated to specific radioisotopes. In such embodiments appropriate detection methodology is well known in the art and readily available from numerous commercial sources.

In other embodiments the antibodies or fragments thereof can be fused or conjugated to marker sequences or compounds, such as a peptide or fluorophore to facilitate purification or diagnostic or analytic procedures such as immunohistochemistry, bio-layer interferometry, surface plasmon resonance, flow cytometry, competitive ELISA, FACs, etc. In some embodiments, the marker comprises a histidine tag such as that provided by the pQE vector (Qiagen), among others, many of which are commercially available. Other peptide tags useful for purification include, but are not limited to, the hemagglutinin "HA" tag, which corresponds to an epitope derived from the influenza hemagglutinin protein (Wilson et al., 1984, Cell 37:767) and the "flag" tag (U.S. Pat. No. 4,703,004).

3. Biocompatible Modifiers

In selected embodiments the antibodies of the invention may be conjugated with biocompatible modifiers that may be used to adjust, alter, improve or moderate antibody characteristics as desired. For example, antibodies or fusion constructs with increased in vivo half-lives can be generated by attaching relatively high molecular weight polymer molecules such as commercially available polyethylene glycol (PEG) or similar biocompatible polymers. Those skilled in the art will appreciate that PEG may be obtained in many different molecular weights and molecular configurations that can be selected to impart specific properties to the antibody (e.g. the half-life may be tailored). PEG can be attached to antibodies or antibody fragments or derivatives with or without a multifunctional linker either through conjugation of the PEG to the N- or C-terminus of said antibodies or antibody fragments or via epsilon-amino groups present on lysine residues. Linear or branched polymer derivatization that results in minimal loss of biological activity may be used. The degree of conjugation can be closely monitored by SDS-PAGE and mass spectrometry to ensure optimal conjugation of PEG molecules to antibody molecules. Unreacted PEG can be separated from antibody-PEG conjugates by, e.g., size exclusion or ion-exchange chromatography. In a similar manner, the disclosed antibodies can be conjugated to albumin in order to make the antibody or antibody fragment more stable in vivo or have a longer half-life in vivo. The techniques are well known in the art, see e.g., WO 93/15199, WO 93/15200, and WO 01/77137; and EP 0 413, 622. Other biocompatible conjugates are evident to those of ordinary skill and may readily be identified in accordance with the teachings herein.

B. Linker Compounds

Numerous linker compounds can be used to conjugate the antibodies of the invention to the relevant warhead. The linkers merely need to covalently bind with the reactive residue on the antibody (preferably a cysteine or lysine) and the selected drug compound. Accordingly, any linker that reacts with the selected antibody residue and may be used to provide the relatively stable conjugates (site-specific or otherwise) of the instant invention is compatible with the teachings herein.

Compatible linkers can advantageously bind to reduced cysteines and lysines, which are nucleophilic. Conjugation reactions involving reduced cysteines and lysines include, but are not limited to, thiol-maleimide, thiol-halogeno (acyl halide), thiol-ene, thiol-yne, thiol-vinylsulfone, thiol-bisulfone, thiol-thiosulfonate, thiol-pyridyl disulfide and thiol-parafluoro reactions. As further discussed herein, thiol-maleimide bioconjugation is one of the most widely used approaches due to its fast reaction rates and mild conjugation conditions. One issue with this approach is the possibility of the retro-Michael reaction and loss or transfer of the maleimido-linked payload from the antibody to other proteins in the plasma, such as, for example, human serum albumin. However, in some embodiments the use of selective reduction and site-specific antibodies as set forth herein in Examples 18 and 19 may be used to stabilize the conjugate and reduce this undesired transfer. Thiol-acyl halide reactions provide bioconjugates that cannot undergo retro-Michael reaction and therefore are more stable. However, the thiol-halide reactions in general have slower reaction rates compared to maleimide-based conjugations and are thus not as efficient in providing undesired drug to antibody ratios. Thiol-pyridyl disulfide reaction is another popular bioconjugation route. The pyridyl disulfide undergoes fast exchange with free thiol resulting in the mixed disulfide and release of pyridine-2-thione. Mixed disulfides can be cleaved in the reductive cell environment releasing the payload. Other approaches gaining more attention in bioconjugation are thiol-vinylsulfone and thiol-bisulfone reactions, each of which are compatible with the teachings herein and expressly included within the scope of the invention.

In some embodiments compatible linkers will confer stability on the ADCs in the extracellular environment, prevent aggregation of the ADC molecules and keep the ADC freely soluble in aqueous media and in a monomeric state. Before transport or delivery into a cell, the ADC is preferably stable and remains intact, i.e. the antibody remains linked to the drug moiety. While the linkers are stable outside the target cell they are designed to be cleaved or degraded at some efficacious rate inside the cell. Accordingly an effective linker will: (i) maintain the specific binding properties of the antibody; (ii) allow intracellular delivery of the conjugate or drug moiety; (iii) remain stable and intact, i.e. not cleaved or degraded, until the conjugate has been delivered or transported to its targeted site; and (iv) maintain a cytotoxic, cell-killing effect or a cytostatic effect of the drug moiety (including, in some cases, any bystander effects). The stability of the ADC may be measured by standard analytical techniques such as HPLC/UPLC, mass spectroscopy, HPLC, and the separation/analysis techniques LC/MS and LC/MS/MS. As set forth above covalent attachment of the antibody and the drug moiety requires the linker to have two reactive functional groups, i.e. bivalency in a reactive sense. Bivalent linker reagents which are useful to attach two or more functional or biologically active moieties, such as MMAE and antibodies are known, and methods have been described to provide their resulting conjugates.

Linkers compatible with the present invention may broadly be classified as cleavable and non-cleavable linkers. Cleavable linkers, which may include acid-labile linkers, protease cleavable linkers and disulfide linkers, are internalized into the target cell and are cleaved in the endosomal—lysosomal pathway inside the cell. Release and activation of the cytotoxin relies on endosome/lysosome acidic compartments that facilitate cleavage of acid-labile chemical linkages such as hydrazone or oxime. If a lysosomal-specific protease cleavage site is engineered into the linker the cytotoxins will be released in proximity to their intracellular targets. Alternatively, linkers containing mixed disulfides provide an approach by which cytotoxic payloads are released intracellularly as they are selectively cleaved in the reducing environment of the cell, but not in the oxygen-rich environment in the bloodstream. By way of contrast, compatible non-cleavable linkers containing amide linked polyethyleneglycol or alkyl spacers liberate toxic payloads during lysosomal degradation of the ADC within the target cell. In some respects the selection of linker will depend on the particular drug used in the conjugate, the particular indication and the antibody target.

Accordingly, certain embodiments of the invention comprise a linker that is cleavable by a cleaving agent that is present in the intracellular environment (e.g., within a lysosome or endosome or caveolae). The linker can be, for example, a peptidyl linker that is cleaved by an intracellular peptidase or protease enzyme, including, but not limited to, a lysosomal or endosomal protease. In some embodiments, the peptidyl linker is at least two amino acids long or at least three amino acids long. Cleaving agents can include cathepsins B and D and plasmin, each of which is known to hydrolyze dipeptide drug derivatives resulting in the release of active drug inside target cells. Exemplary peptidyl linkers that are cleavable by the thiol-dependent protease Cathepsin-B are peptides comprising Phe-Leu since cathepsin-B has been found to be highly expressed in cancerous tissue. Other examples of such linkers are described, for example, in U.S. Pat. No. 6,214,345. In specific embodiments, the peptidyl linker cleavable by an intracellular protease is a Val-Cit linker, a Val-Ala linker or a Phe-Lys linker. One advantage of using intracellular proteolytic release of the therapeutic agent is that the agent is typically attenuated when conjugated and the serum stabilities of the conjugates are relatively high.

In other embodiments, the cleavable linker is pH-sensitive. Typically, the pH-sensitive linker will be hydrolyzable under acidic conditions. For example, an acid-labile linker that is hydrolyzable in the lysosome (e.g., a hydrazone, oxime, semicarbazone, thiosemicarbazone, cis-aconitic amide, orthoester, acetal, ketal, or the like) can be used (See, e.g., U.S. Pat. Nos. 5,122,368; 5,824,805; 5,622,929). Such linkers are relatively stable under neutral pH conditions, such as those in the blood, but are unstable (e.g., cleavable) at below pH 5.5 or 5.0 which is the approximate pH of the lysosome.

In yet other embodiments, the linker is cleavable under reducing conditions (e.g., a disulfide linker). A variety of disulfide linkers are known in the art, including, for example, those that can be formed using SATA (N-succinimidyl-S-acetylthioacetate), SPDP (N-succinimidyl-3-(2-pyridyldithio)propionate), SPDB (N-succinimidyl-3-(2-pyridyldithio) butyrate) and SMPT (N-succinimidyl-oxycarbonyl-alpha-methyl-alpha-(. 2-pyridyl-dithio) toluene). In yet other specific embodiments, the linker is a malonate linker (Johnson et al., 1995, Anticancer Res. 15:1387-93), a maleimidobenzoyl linker (Lau et al., 1995, *Bioorg-Med-Chem.* 3(10):1299-1304), or a 3'-N-amide analog (Lau et al., 1995, *Bioorg-Med-Chem.* 3(10):1305-12).

In some embodiments (such as those set forth in U.S.P.N. 2011/0256157) compatible peptidyl linkers will comprise:

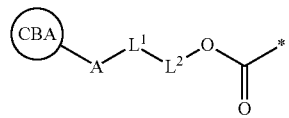

where the asterisk indicates the point of attachment to the drug, CBA (i.e. cell binding agent) comprises the anti-MFI2 antibody, $L^1$ comprises a linker and optionally a cleavable linker, A is a connecting group (optionally comprising a spacer) connecting $L^1$ to a reactive residue on the antibody and $L^2$ is a covalent bond or together with —OC(=O)— forms a self-immolative moiety.

It will be appreciated that the nature of $L^1$ and $L^2$, where present, can vary widely. These groups are chosen on the basis of their cleavage characteristics, which may be dictated by the conditions at the site to which the conjugate is delivered. Those linkers that are cleaved by the action of enzymes are preferred, although linkers that are cleavable by changes in pH (e.g. acid or base labile), temperature or upon irradiation (e.g. photolabile) may also be used. Linkers that are cleavable under reducing or oxidizing conditions may also find use in the present invention.

In certain embodiments $L^1$ may comprise a contiguous sequence of amino acids. The amino acid sequence may be the target substrate for enzymatic cleavage, thereby allowing release of the drug.

In one embodiment, $L^1$ is cleavable by the action of an enzyme. In one embodiment, the enzyme is an esterase or a peptidase.

In another embodiment $L^1$ is as a cathepsin labile linker.

In one embodiment, $L^1$ comprises a dipeptide. The dipeptide may be represented as —NH—$X_1$-$X_2$—CO—, where —NH— and —CO— represent the N- and C-terminals of the amino acid groups $X_1$ and $X_2$ respectively. The amino acids in the dipeptide may be any combination of natural amino acids. Where the linker is a cathepsin labile linker, the dipeptide may be the site of action for cathepsin-mediated cleavage.

Additionally, for those amino acids groups having carboxyl or amino side chain functionality, for example Glu and Lys respectively, CO and NH may represent that side chain functionality.

In one embodiment, the group —$X_1$-$X_2$— in dipeptide, —NH—$X_1$-$X_2$—CO—, is selected from: -Phe- Lys-, -Val-Ala-, -Val-Lys-, -Ala-Lys-, -Val-Cit-, -Phe-Cit-, -Leu-Cit-, -Ile-Cit-, -Phe- Arg- and -Trp-Cit- where Cit is citrulline.

Preferably, the group —$X_1$-$X_2$— in dipeptide, —NH—$X_1$-$X_2$—CO—, is selected from: -Phe-Lys-, -Val-Ala-, -Val-Lys-, -Ala-Lys-, and -Val-Cit-.

Most preferably, the group —$X_1$-$X_2$— in dipeptide, —NH—$X_1$-$X_2$—CO—, is -Phe-Lys- or -Val-Ala- or Val-Cit.

In one embodiment, $L^2$ is present and together with —C(=O)O— forms a self-immolative linker.

In one embodiment, $L^2$ is a substrate for enzymatic activity, thereby allowing release of the warhead.

In one embodiment, where $L^1$ is cleavable by the action of an enzyme and $L^2$ is present, the enzyme cleaves the bond between $L^1$ and $L^2$.

$L^1$ and $L^2$, where present, may be connected by a bond selected from: —C(=O)NH—, —C(=O)O—, —NHC(=O)—, —OC(=O)—, —OC(=O)O—, —NHC(=O)O—, —OC(=O)NH—, and —NHC(=O)NH—.

An amino group of $L^1$ that connects to $L^2$ may be the N-terminus of an amino acid or may be derived from an amino group of an amino acid side chain, for example a lysine amino acid side chain.

A carboxyl group of $L^1$ that connects to $L^2$ may be the C-terminus of an amino acid or may be derived from a carboxyl group of an amino acid side chain, for example a glutamic acid amino acid side chain.

A hydroxyl group of $L^1$ that connects to $L^2$ may be derived from a hydroxyl group of an amino acid side chain, for example a serine amino acid side chain.

The term "amino acid side chain" includes those groups found in: (i) naturally occurring amino acids such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine; (ii) minor amino acids such as ornithine and citrulline; (iii) unnatural amino acids, beta-amino acids, synthetic analogs and derivatives of naturally occurring amino acids; and (iv) all enantiomers, diastereomers, isomerically enriched, isotopically labelled (e.g. $^2$H, $^3$H, $^{14}$C, $^{15}$N), protected forms, and racemic mixtures thereof.

In one embodiment, —C(=O)O— and $L^2$ together form the group:

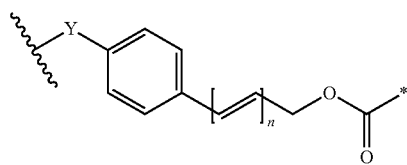

where the asterisk indicates the point of attachment to the drug or cytotoxic agent position, the wavy line indicates the point of attachment to the linker $L^1$, Y is —N(H)—, —O—, —C(=O)N(H)— or —C(=O)O—, and n is 0 to 3. The phenylene ring is optionally substituted with one, two or three substituents. In one embodiment, the phenylene group is optionally substituted with halo, $NO_2$, alkyl or hydroxyalkyl.

In one embodiment, Y is NH.

In one embodiment, n is 0 or 1. Preferably, n is 0.

Where Y is NH and n is 0, the self-immolative linker may be referred to as a p-aminobenzylcarbonyl linker (PABC).

In other embodiments the linker may include a self-immolative linker and the dipeptide together form the group —NH-Val-Cit-CO—NH—PABC—. In other selected embodiments the linker may comprise the group —NH-Val-Ala-CO—NH—PABC—, which is illustrated below:

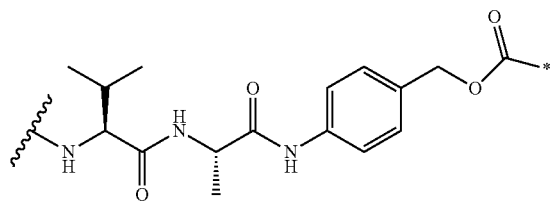 [SMILES: *N[C@H](C(=O)N[C@@H](C)C(=O)Nc1ccc(COC(*)=O)cc1)C(C)C]

where the asterisk indicates the point of attachment to the selected cytotoxic moiety, and the wavy line indicates the point of attachment to the remaining portion of the linker (e.g., the spacer-antibody binding segments) which may be conjugated to the antibody. Upon enzymatic cleavage of the dipeptide, the self-immolative linker will allow for clean release of the protected compound (i.e., the cytotoxin) when a remote site is activated, proceeding along the lines shown below:

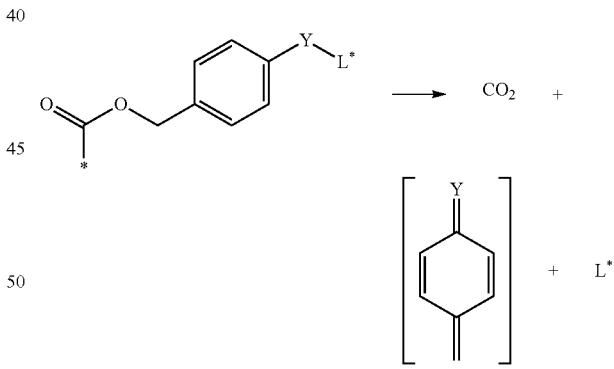

where the asterisk indicates the point of attachment to the selected cytotoxic moiety and where $L^-$ is the activated form of the remaining portion of the linker comprising the now cleaved peptidyl unit. The clean release of the warhead ensures it will maintain the desired toxic activity.

In one embodiment, A is a covalent bond. Thus, $L^1$ and the antibody are directly connected. For example, where $L^1$ comprises a contiguous amino acid sequence, the N-terminus of the sequence may connect directly to the antibody residue.

In another embodiment, A is a spacer group. Thus, $L^1$ and the antibody are indirectly connected.

In certain embodiments L¹ and A may be connected by a bond selected from: —C(=O)NH—, —C(=O)O—, —NHC(=O)—, —OC(=O)—, —OC(=O)O—, —NHC(=O)O—, —OC(=O)NH—, and —NHC(=O)NH—.

As will be discussed in more detail below the drug linkers of the instant invention will preferably be linked to reactive thiol nucleophiles on cysteines, including free cysteines. To this end the cysteines of the antibodies may be made reactive for conjugation with linker reagents by treatment with various reducing agent such as DTT or TCEP or mild reducing agents as set forth herein. In other embodiments the drug linkers of the instant invention will preferably be linked to a lysine.

Preferably, the linker contains an electrophilic functional group for reaction with a nucleophilic functional group on the antibody. Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) maleimide groups (ii) activated disulfides, (iii) active esters such as NHS (N-hydroxysuccinimide) esters, HOBt (N-hydroxybenzotriazole) esters, haloformates, and acid halides; (iv) alkyl and benzyl halides such as haloacetamides; and (v) aldehydes, ketones and carboxyl groups.

Exemplary functional groups compatible with the invention are illustrated immediately below:

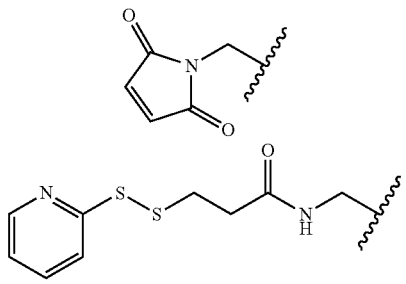

-continued

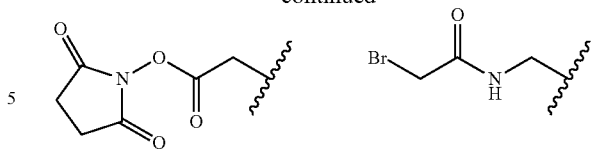

In some embodiments the connection between a cysteine (including a free cysteine of a site-specific antibody) and the drug-linker moiety is through a thiol residue and a terminal maleimide group of present on the linker. In such embodiments, the connection between the antibody and the drug-linker may be:

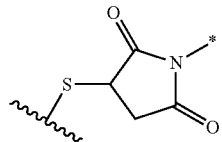 [SMILES: *SC1CC(=O)N(*)C1=O]

where the asterisk indicates the point of attachment to the remaining portion of drug-linker and the wavy line indicates the point of attachment to the remaining portion of the antibody. In this embodiment, the S atom is preferably derived from a site-specific free cysteine.

With regard to other compatible linkers the binding moiety may comprise a terminal iodoacetamide that may be reacted with activated residues on the antibody to provide the desired conjugate. In any event one skilled in the art could readily conjugate each of the disclosed drug-linker compounds with a compatible anti-MFI2 antibody (including site-specific antibodies) in view of the instant disclosure.

In accordance with the instant disclosure the invention provides methods of making compatible antibody drug conjugates comprising conjugating an anti-MFI2 antibody with a drug-linker compound selected from the group consisting of:

DL1

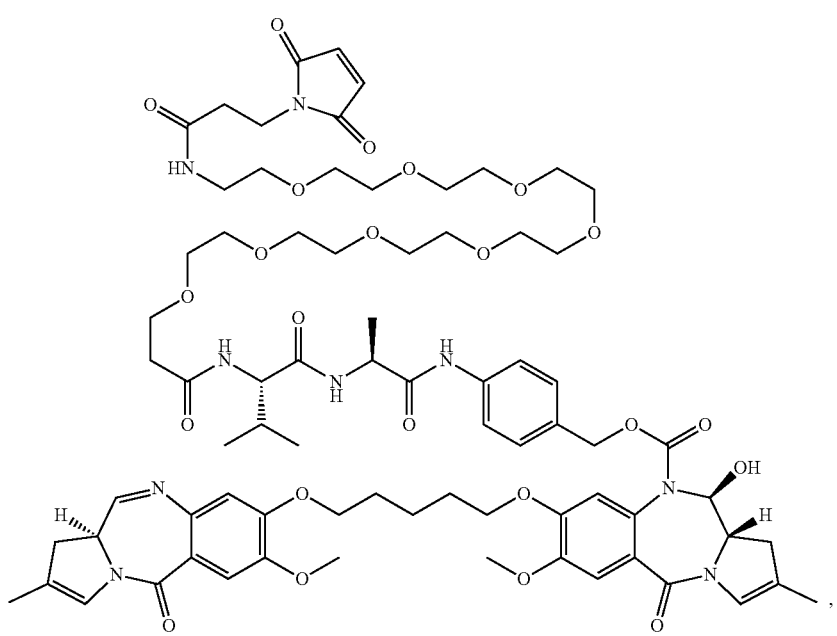

-continued

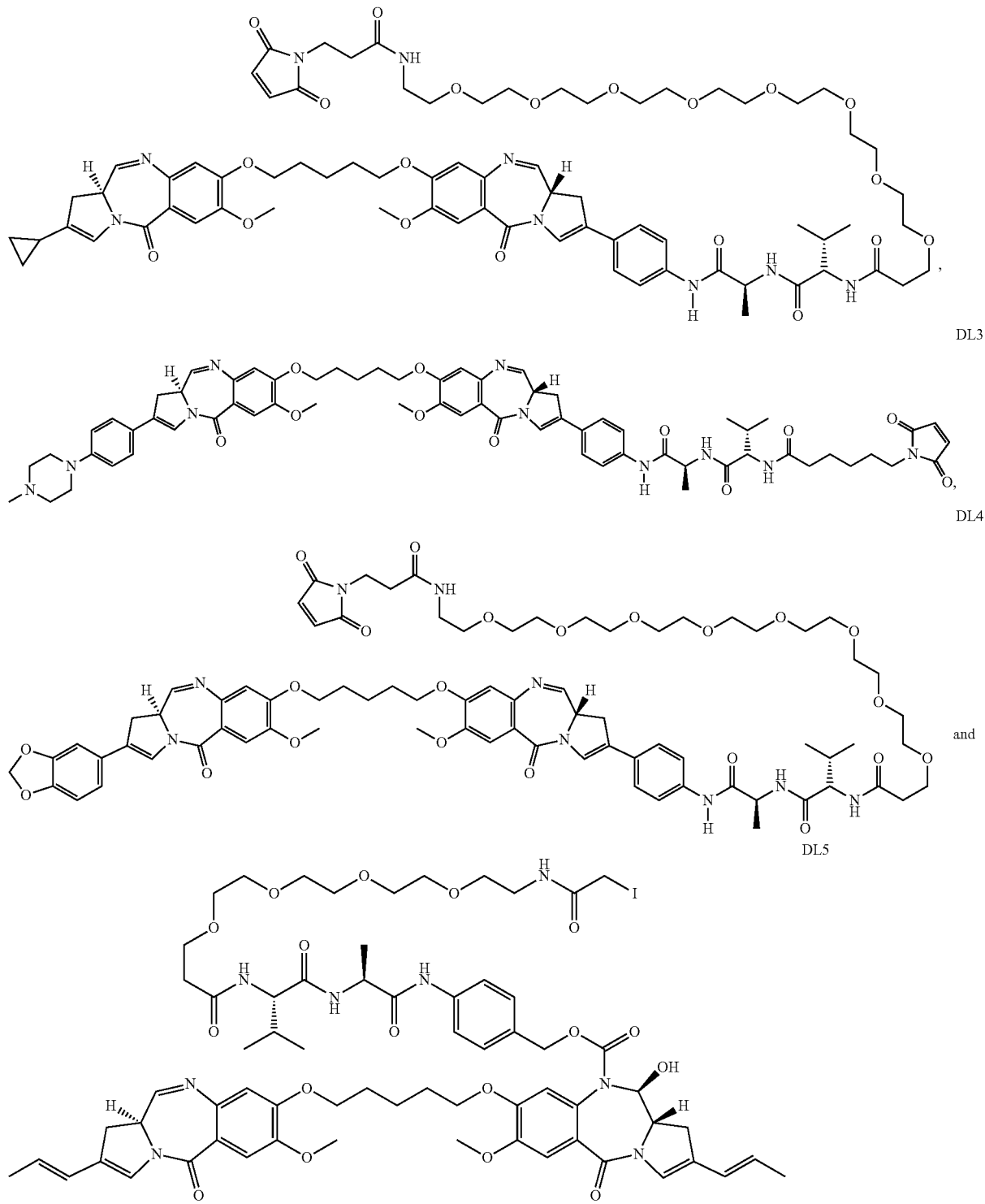

For the purposes of then instant application DL will be used as an abbreviation for "drug-linker" and will comprise drug linkers 1-5 (i.e., DL1, DL2, DL3, DL4 and DL5) as set forth above.

It will be appreciated that the linker appended terminal maleimido moiety (DL1-DL4) or iodoacetamide moiety (DL5) may be conjugated to free sulfhydryl(s) on the selected MFI2 antibody using art-recognized techniques. Synthetic routes for the aforementioned compounds are set forth in WO2014/130879 which is incorporated herein by reference while specific methods of conjugating such PBDs are set forth in the Examples below.

Thus, in selected aspects the present invention relates to MFI2 antibodies conjugated to the disclosed pyrrolobenzodiazepines to provide MFI2 immunoconjugates substantially set forth in ADCs 1-5 immediately below. Accordingly, in certain aspects the invention is directed to a conjugate selected from the group consisting of
ADC 1
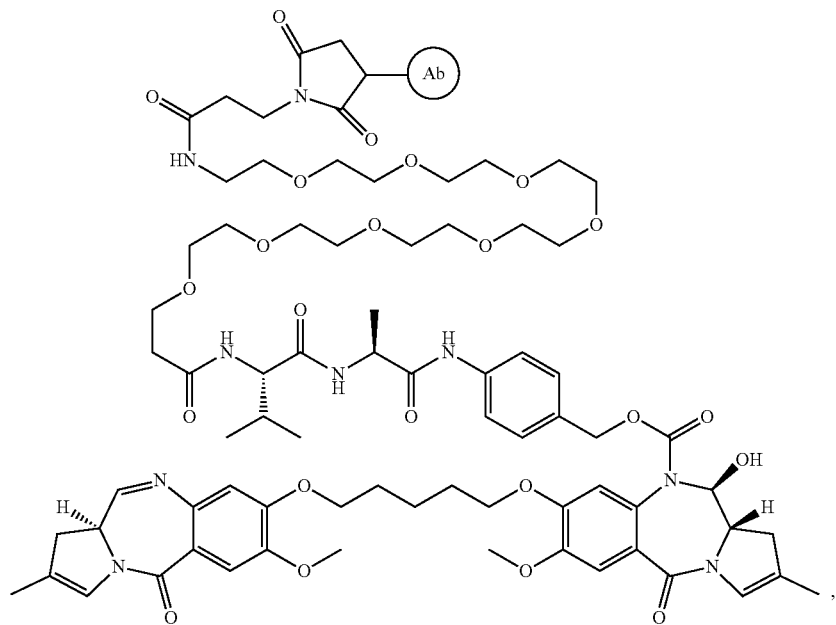
ADC 2
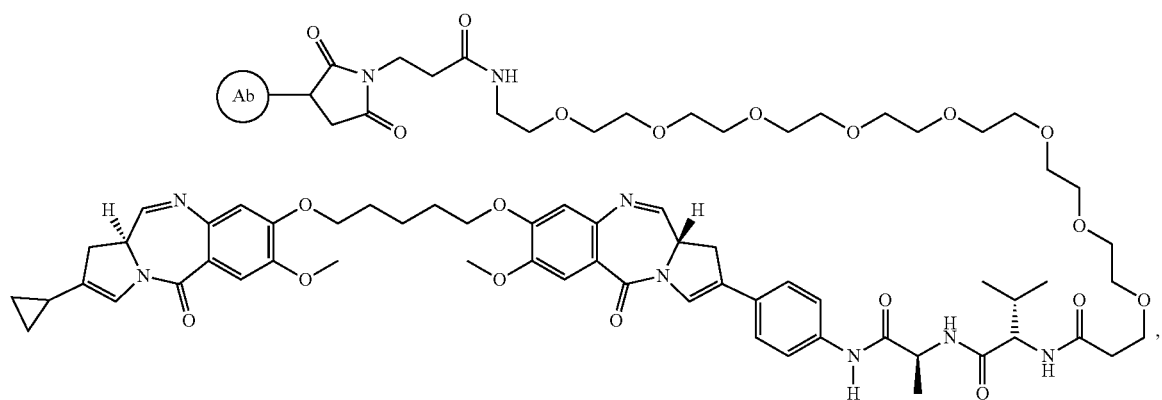
ADC 3
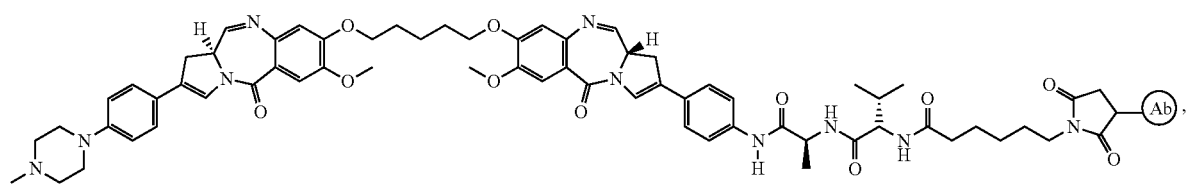

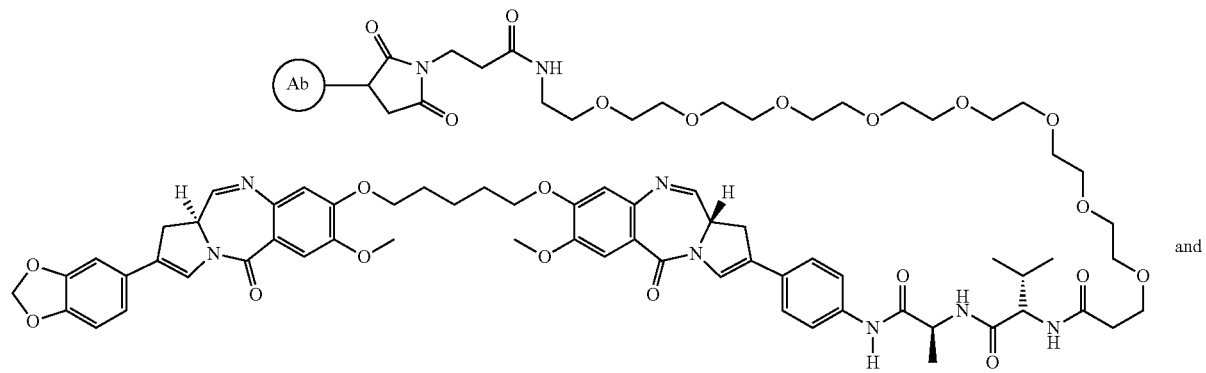

ADC 4

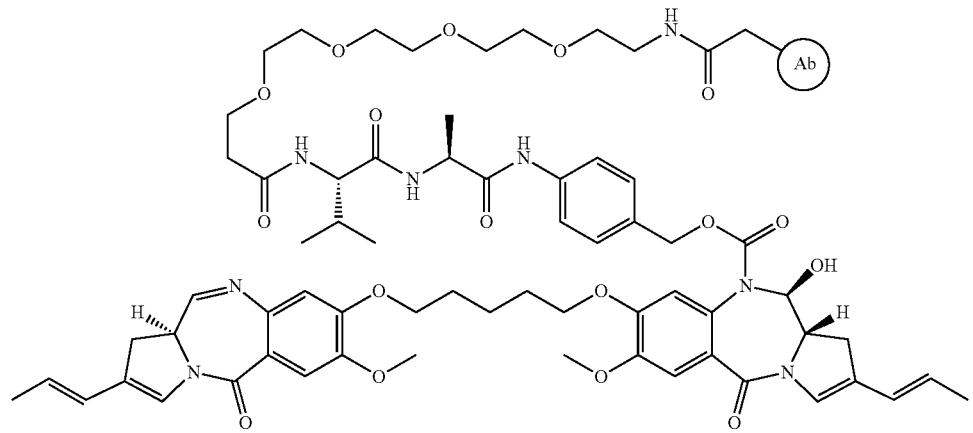

and

ADC 5 wherein Ab comprises an anti-MFI2 antibody or immunoreactive fragment thereof.

C. Conjugation

It will be appreciated that a number of well-known different reactions may be used to attach the drug moiety and/or linker to the selected antibody. For example, various reactions exploiting sulfhydryl groups of cysteines may be employed to conjugate the desired moiety. Some embodiments will comprise conjugation of antibodies comprising one or more free cysteines as discussed in detail below. In other embodiments ADCs of the instant invention may be generated through conjugation of drugs to solvent-exposed amino groups of lysine residues present in the selected antibody. Still other embodiments comprise activation of N-terminal threonine and serine residues which may then be used to attach the disclosed payloads to the antibody. The selected conjugation methodology will preferably be tailored to optimize the number of drugs attached to the antibody and provide a relatively high therapeutic index.

Various methods are known in the art for conjugating a therapeutic compound to a cysteine residue and will be apparent to the skilled artisan. Under basic conditions the cysteine residues will be deprotonated to generate a thiolate nucleophile which may be reacted with soft electrophiles such as maleimides and iodoacetamides. Generally reagents for such conjugations may react directly with a cysteine thiol to form the conjugated protein or with a linker-drug to form a linker-drug intermediate. In the case of a linker, several routes, employing organic chemistry reactions, conditions, and reagents are known to those skilled in the art, including: (1) reaction of a cysteine group of the protein of the invention with a linker reagent, to form a protein-linker intermediate, via a covalent bond, followed by reaction with an activated compound; and (2) reaction of a nucleophilic group of a compound with a linker reagent, to form a drug-linker intermediate, via a covalent bond, followed by reaction with a cysteine group of a protein of the invention. As will be apparent to the skilled artisan from the foregoing, bifunctional (or bivalent) linkers are useful in the present invention. For example, the bifunctional linker may comprise a thiol modification group for covalent linkage to the cysteine residue(s) and at least one attachment moiety (e.g., a second thiol modification moiety) for covalent or non-covalent linkage to the compound.

Prior to conjugation, antibodies may be made reactive for conjugation with linker reagents by treatment with a reducing agent such as dithiothreitol (DTT) or (tris(2-carboxyethyl)phosphine (TCEP). In other embodiments additional nucleophilic groups can be introduced into antibodies through the reaction of lysines with reagents, including but not limited to, 2-iminothiolane (Traut's reagent), SATA, SATP or SAT(PEG)4, resulting in conversion of an amine into a thiol.

With regard to such conjugations cysteine thiol or lysine amino groups are nucleophilic and capable of reacting to form covalent bonds with electrophilic groups on linker reagents or compound-linker intermediates or drugs including: (i) active esters such as NHS esters, HOBt esters, haloformates, and acid halides; (ii) alkyl and benzyl halides, such as haloacetamides; (iii) aldehydes, ketones, carboxyl, and maleimide groups; and (iv) disulfides, including pyridyl disulfides, via sulfide exchange. Nucleophilic groups on a compound or linker include, but are not limited to amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents.

Conjugation reagents include maleimide, haloacetyl, iodoacetamide succinimidyl ester, isothiocyanate, sulfonyl chloride, 2,6-dichlorotriazinyl, pentafluorophenyl ester, and phosphoramidite, although other functional groups can also be used. In certain embodiments methods include, for example, the use of maleimides, iodoacetimides or haloacetyl/alkyl halides, aziridne, acryloyl derivatives to react with the thiol of a cysteine to produce a thioether that is reactive with a compound. Disulphide exchange of a free thiol with an activated piridyldisulphide is also useful for producing a conjugate (e.g., use of 5-thio-2-nitrobenzoic (TNB) acid). Preferably, a maleimide is used.

As indicated above, lysine may also be used as a reactive residue to effect conjugation as set forth herein. The nucleophilic lysine residue is commonly targeted through amine-reactive succinimidylesters. To obtain an optimal number of deprotonated lysine residues, the pH of the aqueous solution must be below the pKa of the lysine ammonium group, which is around 10.5, so the typical pH of the reaction is about 8 and 9. The common reagent for the coupling reaction is NHS-ester which reacts with nucleophilic lysine through a lysine acylation mechanism. Other compatible reagents that undergo similar reactions comprise isocyanates and isothiocyanates which also may be used in conjunction with the teachings herein to provide ADCs. Once the lysines have been activated, many of the aforementioned linking groups may be used to covalently bind the warhead to the antibody.

Methods are also known in the art for conjugating a compound to a threonine or serine residue (preferably a N-terminal residue). For example methods have been described in which carbonyl precursors are derived from the 1,2-aminoalcohols of serine or threonine, which can be selectively and rapidly converted to aldehyde form by periodate oxidation. Reaction of the aldehyde with a 1,2-aminothiol of cysteine in a compound to be attached to a protein of the invention forms a stable thiazolidine product. This method is particularly useful for labeling proteins at N-terminal serine or threonine residues.

In some embodiments reactive thiol groups may be introduced into the selected antibody (or fragment thereof) by introducing one, two, three, four, or more free cysteine residues (e.g., preparing antibodies comprising one or more free non-native cysteine amino acid residues). Such site-specific antibodies or engineered antibodies, allow for conjugate preparations that exhibit enhanced stability and substantial homogeneity due, at least in part, to the provision of engineered free cysteine site(s) and/or the novel conjugation procedures set forth herein. Unlike conventional conjugation methodology that fully or partially reduces each of the intrachain or interchain antibody disulfide bonds to provide conjugation sites (and is fully compatible with the instant invention), the present invention additionally provides for the selective reduction of certain prepared free cysteine sites and direction of the drug-linker to the same. The conjugation specificity promoted by the engineered sites and the selective reduction allows for a high percentage of site directed conjugation at the desired positions. Significantly some of these conjugation sites, such as those present in the terminal region of the light chain constant region, are typically difficult to conjugate effectively as they tend to cross-react with other free cysteines. However, through molecular engineering and selective reduction of the resulting free cysteines, efficient conjugation rates may be obtained which considerably reduces unwanted high-DAR contaminants and non-specific toxicity. More generally the engineered constructs and disclosed novel conjugation methods comprising selective reduction provide ADC preparations having improved pharmacokinetics and/or pharmacodynamics and, potentially, an improved therapeutic index.

In certain embodiments site-specific constructs present free cysteine(s), which when reduced comprise thiol groups that are nucleophilic and capable of reacting to form covalent bonds with electrophilic groups on linker moieties such as those disclosed above. As discussed above antibodies of the instant invention may have reducible unpaired interchain or intrachain cysteines or introduced non-native cysteines, i.e. cysteines providing such nucleophilic groups. Thus, in certain embodiments the reaction of free sulfhydryl groups of the reduced free cysteines and the terminal maleimido or haloacetamide groups of the disclosed drug-linkers will provide the desired conjugation. In such cases free cysteines of the antibodies may be made reactive for conjugation with linker reagents by treatment with a reducing agent such as dithiothreitol (DTT) or (tris (2-carboxyethyl)phosphine (TCEP). Each free cysteine will thus present, theoretically, a reactive thiol nucleophile. While such reagents are compatible it will be appreciated that conjugation of site-specific antibodies may be effected using various reactions, conditions and reagents generally known to those skilled in the art.

In addition it has been found that the free cysteines of engineered antibodies may be selectively reduced to provide enhanced site-directed conjugation and a reduction in unwanted, potentially toxic contaminants. More specifically "stabilizing agents" such as arginine have been found to modulate intra- and inter-molecular interactions in proteins and may be used, in conjunction with selected reducing agents (preferably relatively mild), to selectively reduce the free cysteines and to facilitate site-specific conjugation as set forth herein. As used herein the terms "selective reduction" or "selectively reducing" may be used interchangeably and shall mean the reduction of free cysteine(s) without substantially disrupting native disulfide bonds present in the engineered antibody. In selected embodiments this may be affected by certain reducing agents. In other embodiments selective reduction of an engineered construct will comprise the use of stabilization agents in combination with reducing agents (including mild reducing agents). It will be appreciated that the term "selective conjugation" shall mean the conjugation of an engineered antibody that has been selectively reduced with a cytotoxin as described herein. In this respect the use of such stabilizing agents in combination with selected reducing agents can markedly improve the efficiency of site-specific conjugation as determined by extent of conjugation on the heavy and light antibody chains and DAR distribution of the preparation. Compatible antibody constructs and selective conjugation techniques and reagents are extensively disclosed in WO2015/031698 as to such methodology and constructs.

While not wishing to be bound by any particular theory, such stabilizing agents may act to modulate the electrostatic microenvironment and/or modulate conformational changes at the desired conjugation site, thereby allowing relatively mild reducing agents (which do not materially reduce intact native disulfide bonds) to facilitate conjugation at the desired free cysteine site(s). Such agents (e.g., certain amino acids) are known to form salt bridges (via hydrogen bonding and electrostatic interactions) and can modulate protein-protein interactions in such a way as to impart a stabilizing effect that may cause favorable conformation changes and/or reduce unfavorable protein-protein interactions. Moreover, such agents may act to inhibit the formation of undesired intramolecular (and intermolecular) cysteine-cysteine bonds after reduction thus facilitating the desired conjugation reaction wherein the engineered site-specific cysteine is bound to the drug (preferably via a linker). Since selective reduction conditions do not provide for the significant reduction of intact native disulfide bonds, the subsequent conjugation reaction is naturally driven to the relatively few reactive thiols on the free cysteines (e.g., preferably 2 free thiols per antibody). As previously alluded to, such techniques may be used to considerably reduce levels of non-specific conjugation and corresponding impurities in conjugate preparations fabricated in accordance with the instant disclosure.

In selected embodiments stabilizing agents compatible with the present invention will generally comprise compounds with at least one moiety having a basic pKa. In certain embodiments the moiety will comprise a primary amine while in other embodiments the amine moiety will comprise a secondary amine. In still other embodiments the amine moiety will comprise a tertiary amine or a guanidinium group. In other selected embodiments the amine moiety will comprise an amino acid while in other compatible embodiments the amine moiety will comprise an amino acid side chain. In yet other embodiments the amine moiety will comprise a proteinogenic amino acid. In still other embodiments the amine moiety comprises a non-proteinogenic amino acid. In some embodiments, compatible stabilizing agents may comprise arginine, lysine, proline and cysteine. In addition compatible stabilizing agents may include guanidine and nitrogen containing heterocycles with basic pKa.

In certain embodiments compatible stabilizing agents comprise compounds with at least one amine moiety having a pKa of greater than about 7.5, in other embodiments the subject amine moiety will have a pKa of greater than about 8.0, in yet other embodiments the amine moiety will have a pKa greater than about 8.5 and in still other embodiments the stabilizing agent will comprise an amine moiety having a pKa of greater than about 9.0. Other embodiments will comprise stabilizing agents where the amine moiety will have a pKa of greater than about 9.5 while certain other embodiments will comprise stabilizing agents exhibiting at least one amine moiety having a pKa of greater than about 10.0. In still other embodiments the stabilizing agent will comprise a compound having the amine moiety with a pKa of greater than about 10.5, in other embodiments the stabilizing agent will comprise a compound having a amine moiety with a pKa greater than about 11.0, while in still other embodiments the stabilizing agent will comprise a amine moiety with a pKa greater than about 11.5. In yet other embodiments the stabilizing agent will comprise a compound having an amine moiety with a pKa greater than about 12.0, while in still other embodiments the stabilizing agent will comprise an amine moiety with a pKa greater than about 12.5. Those of skill in the art will understand that relevant pKa's may readily be calculated or determined using standard techniques and used to determine the applicability of using a selected compound as a stabilizing agent.

The disclosed stabilizing agents are shown to be particularly effective at targeting conjugation to free site-specific cysteines when combined with certain reducing agents. For the purposes of the instant invention, compatible reducing agents may include any compound that produces a reduced free site-specific cysteine for conjugation without significantly disrupting the native disulfide bonds of the engineered antibody. Under such conditions, preferably provided by the combination of selected stabilizing and reducing agents, the activated drug linker is largely limited to binding to the desired free site-specific cysteine site(s). Relatively mild reducing agents or reducing agents used at relatively low concentrations to provide mild conditions are particularly preferred. As used herein the terms "mild reducing agent" or "mild reducing conditions" shall be held to mean any agent or state brought about by a reducing agent (optionally in the presence of stabilizing agents) that provides thiols at the free cysteine site(s) without substantially disrupting native disulfide bonds present in the engineered antibody. That is, mild reducing agents or conditions (preferably in combination with a stabilizing agent) are able to effectively reduce free cysteine(s) (provide a thiol) without significantly disrupting the protein's native disulfide bonds. The desired reducing conditions may be provided by a number of sulfhydryl-based compounds that establish the appropriate environment for selective conjugation. In embodiments mild reducing agents may comprise compounds having one or more free thiols while in some embodiments mild reducing agents will comprise compounds having a single free thiol. Non-limiting examples of reducing agents compatible with the selective reduction techniques of the instant invention comprise glutathione, n-acetyl cysteine, cysteine, 2-aminoethane-1-thiol and 2-hydroxyethane-1-thiol.

It will be appreciated that selective reduction process set forth above is particularly effective at targeted conjugation to the free cysteine. In this respect the extent of conjugation to the desired target site (defined here as "conjugation efficiency") in site-specific antibodies may be determined by various art-accepted techniques. The efficiency of the site-specific conjugation of a drug to an antibody may be determined by assessing the percentage of conjugation on the target conjugation site(s) (e.g. free cysteines on the c-terminus of each light chain) relative to all other conjugated sites. In certain embodiments, the method herein provides for efficiently conjugating a drug to an antibody comprising free cysteines. In some embodiments, the conjugation efficiency is at least 5%, at least 10%, at least 15%, at least 20%, at least 25%, at least 30%, at least 35%, at least 40%, at least 45%, at least 50%, at least 55%, at least 60%, at least 70%, at least 75%, at least 80%, at least 85%, at least 90%, at least 95%, at least 98% or more as measured by the percentage of target conjugation relative to all other conjugation sites.

It will further be appreciated that engineered antibodies capable of conjugation may contain free cysteine residues that comprise sulfhydryl groups that are blocked or capped as the antibody is produced or stored. Such caps include small molecules, proteins, peptides, ions and other materials that interact with the sulfhydryl group and prevent or inhibit conjugate formation. In some cases the unconjugated engineered antibody may comprise free cysteines that bind other free cysteines on the same or different antibodies. As discussed herein such cross-reactivity may lead to various contaminants during the fabrication procedure. In some embodiments, the engineered antibodies may require uncapping prior to a conjugation reaction. In specific embodiments, antibodies herein are uncapped and display a free sulfhydryl group capable of conjugation. In specific embodiments, antibodies herein are subjected to an uncapping reaction that does not disturb or rearrange the naturally occurring disulfide bonds. It will be appreciated that in most cases the uncapping reactions will occur during the normal reduction reactions (reduction or selective reduction).

D. DAR Distribution and Purification

In selected embodiments conjugation with site specific antibodies of the present invention advantageously provides the ability to generate relatively homogeneous ADC preparations comprising a narrow DAR distribution. In this regard the disclosed constructs and/or selective conjugation provides for homogeneity of the ADC species within a sample in terms of the stoichiometric ratio between the drug and the engineered antibody and with respect to the toxin location. As briefly discussed above the term "drug to antibody ratio" or "DAR" refers to the molar ratio of drug to antibody. In some embodiments a conjugate preparation may be substantially homogeneous with respect to its DAR distribution, meaning that within the ADC preparation is a predominant species of site-specific ADC with a particular DAR (e.g., a DAR of 2 or 4) that is also uniform with respect to the site of loading (i.e., on the free cysteines). In certain embodiments of the invention it is possible to achieve the desired homogeneity through the use of site-specific antibodies and/or selective reduction and conjugation. In other embodiments the desired homogeneity may be achieved through the use of site-specific constructs in combination with selective reduction. In yet other embodiments the preparations may be further purified using analytical or preparative chromatography techniques. In each of these embodiments the homogeneity of the ADC sample can be analyzed using various techniques known in the art including but not limited to mass spectrometry, HPLC (e.g. size exclusion HPLC, RP-HPLC, HIC-HPLC etc.) or capillary electrophoresis.

With regard to the purification of ADC preparations it will be appreciated that standard pharmaceutical preparative methods may be employed to obtain the desired purity. As discussed herein liquid chromatography methods such as reverse phase (RP) and hydrophobic interaction chromatography (HIC) may separate compounds in the mixture by drug loading value. In some cases, ion-exchange (IEC) or mixed-mode chromatography (MMC) may also be used to isolate species with a specific drug load.

The disclosed ADCs and preparations thereof may comprise drug and antibody moieties in various stoichiometric molar ratios depending on the configuration of the antibody and, at least in part, on the method used to effect conjugation. In certain embodiments the drug loading per ADC may comprise from 1-20 warheads (i.e., n is 1-20). Other selected embodiments may comprise ADCs with a drug loading of from 1 to 15 warheads. In still other embodiments the ADCs may comprise from 1-12 warheads or, more preferably, from 1-10 warheads. In some embodiments the ADCs will comprise from 1 to 8 warheads.

While theoretical drug loading may be relatively high, practical limitations such as free cysteine cross reactivity and warhead hydrophobicity tend to limit the generation of homogeneous preparations comprising such DAR due to aggregates and other contaminants. That is, higher drug loading, e.g. >6 or 8, may cause aggregation, insolubility, toxicity, or loss of cellular permeability of certain antibody-drug conjugates. In view of such concerns practical drug loading provided by the instant invention preferably ranges from 1 to 8 drugs per conjugate, i.e. where 1, 2, 3, 4, 5, 6, 7, or 8 drugs are covalently attached to each antibody (e.g., for IgG1, other antibodies may have different loading capacity depending the number of disulfide bonds). Preferably the DAR of compositions of the instant invention will be approximately 2, 4 or 6 and in some embodiments the DAR will comprise approximately 2.

Despite the relatively high level of homogeneity provided by the instant invention the disclosed compositions actually comprise a mixture of conjugates with a range of drugs compounds (potentially from 1 to 8 in the case of a IgG1). As such, the disclosed ADC compositions include mixtures of conjugates where most of the constituent antibodies are covalently linked to one or more drug moieties and (despite the relative conjugate specificity provided by engineered constructs and selective reduction) where the drug moieties may be attached to the antibody by various thiol groups. That is, following conjugation ADC compositions of the invention will comprise a mixture of conjugates with different drug loads (e.g., from 1 to 8 drugs per IgG1 antibody) at various concentrations (along with certain reaction contaminants primarily caused by free cysteine cross reactivity). However using selective reduction and post-fabrication purification the conjugate compositions may be driven to the point where they largely contain a single predominant desired ADC species (e.g., with a drug loading of 2) with relatively low levels of other ADC species (e.g., with a drug loading of 1, 4, 6, etc.). The average DAR value represents the weighted average of drug loading for the composition as a whole (i.e., all the ADC species taken together). Due to inherent uncertainty in the quantification methodology employed and the difficulty in completely removing the non-predominant ADC species in a commercial setting, acceptable DAR values or specifications are often presented as an average, a range or distribution (i.e., an average DAR of 2+/−0.5). Preferably compositions comprising a measured average DAR within the range (i.e., 1.5 to 2.5) would be used in a pharmaceutical setting.

Thus, in some embodiments the present invention will comprise compositions having an average DAR of 1, 2, 3, 4, 5, 6, 7 or 8 each +/−0.5. In other embodiments the present invention will comprise an average DAR of 2, 4, 6 or 8+/−0.5. Finally, in selected embodiments the present invention will comprise an average DAR of 2+/−0.5 or 4+/−0.5. It will be appreciated that the range or deviation may be less than 0.4 in some embodiments. Thus, in other embodiments the compositions will comprise an average DAR of 1, 2, 3, 4, 5, 6, 7 or 8 each +/−0.3, an average DAR of 2, 4, 6 or 8+/−0.3, even more preferably an average DAR of 2 or 4+/−0.3 or even an average DAR of 2+/−0.3. In other embodiments IgG1 conjugate compositions will preferably comprise a composition with an average DAR of 1, 2, 3, 4, 5, 6, 7 or 8 each +/−0.4 and relatively low levels (i.e., less than 30%) of non-predominant ADC species. In other embodiments the ADC composition will comprise an average DAR of 2, 4, 6 or 8 each +/−0.4 with relatively low levels (<30%) of non-predominant ADC species. In some embodiments the ADC composition will comprise an average DAR of 2+/−0.4 with relatively low levels (<30%) of non-predominant ADC species. In yet other embodiments the predominant ADC species (e.g., DAR of 2 or DAR of 4) will be present at a concentration of greater than 65%, at a concentration of greater than 70%, at a concentration of greater than 75%, at a concentration of greater that 80%, at a concentration of greater than 85%, at a concentration of greater than 90%, at a concentration of greater than 93%, at a concentration of greater than 95% or even at a concentration of greater than 97% when measured against other DAR species.

As detailed in the Examples below the distribution of drugs per antibody in preparations of ADC from conjugation reactions may be characterized by conventional means such as UV-Vis spectrophotometry, reverse phase HPLC, HIC, mass spectroscopy, ELISA, and electrophoresis. The quantitative distribution of ADC in terms of drugs per antibody may also be determined. By ELISA, the averaged value of the drugs per antibody in a particular preparation of ADC may be determined. However, the distribution of drug per antibody values is not discernible by the antibody-antigen binding and detection limitation of ELISA. Also, ELISA assay for detection of antibody-drug conjugates does not determine where the drug moieties are attached to the antibody, such as the heavy chain or light chain fragments, or the particular amino acid residues.

VI. DIAGNOSTICS AND SCREENING

A. Diagnostics

The invention provides in vitro and in vivo methods for detecting, diagnosing or monitoring proliferative disorders and methods of screening cells from a patient to identify tumor cells including tumorigenic cells. Such methods include identifying an individual having cancer for treatment or monitoring progression of a cancer, comprising contacting the patient or a sample obtained from a patient (either in vivo or in vitro) with a detection agent (e.g., an antibody or nucleic acid probe) capable of specifically recognizing and associating with MFI2 and detecting the presence or absence, or level of association of the detection agent in the sample. In selected embodiments the detection agent will comprise an antibody associated with a detectable label or reporter molecule as described herein. In yet other embodiments (e.g., In situ hybridization or ISH) a nucleic acid probe that reacts with a genomic MFI2 determinant will be used in the detection, diagnosis or monitoring of the proliferative disorder.

More generally the presence and/or levels of MFI2 determinants may be measured using any of a number of techniques available to the person of ordinary skill in the art for protein or nucleic acid analysis, e.g., direct physical measurements (e.g., mass spectrometry), binding assays (e.g., immunoassays, agglutination assays, and immunochromatographic assays), Polymerase Chain Reaction (PCR, RT-PCR; RT-qPCR) technology, branched oligonucleotide technology, Northern blot technology, oligonucleotide hybridization technology and in situ hybridization technology. The method may also comprise measuring a signal that results from a chemical reaction, e.g., a change in optical absorbance, a change in fluorescence, the generation of chemiluminescence or electrochemiluminescence, a change in reflectivity, refractive index or light scattering, the accumulation or release of detectable labels from the surface, the oxidation or reduction or redox species, an electrical current or potential, changes in magnetic fields, etc. Suitable detection techniques may detect binding events by measuring the participation of labeled binding reagents through the measurement of the labels via their photoluminescence (e.g., via measurement of fluorescence, time-resolved fluorescence, evanescent wave fluorescence, up-converting phosphors, multi-photon fluorescence, etc.), chemiluminescence, electrochemiluminescence, light scattering, optical absorbance, radioactivity, magnetic fields, enzymatic activity (e.g., by measuring enzyme activity through enzymatic reactions that cause changes in optical absorbance or fluorescence or cause the emission of chemiluminescence). Alternatively, detection techniques may be used that do not require the use of labels, e.g., techniques based on measuring mass (e.g., surface acoustic wave measurements), refractive index (e.g., surface plasmon resonance measurements), or the inherent luminescence of an analyte.

In some embodiments, the association of the detection agent with particular cells or cellular components in the sample indicates that the sample may contain tumorigenic cells, thereby denoting that the individual having cancer may be effectively treated with an antibody or ADC as described herein.

In certain preferred embodiments the assays may comprise immunohistochemistry (IHC) assays or variants thereof (e.g., fluorescent, chromogenic, standard ABC, standard LSAB, etc.), immunocytochemistry or variants thereof (e.g., direct, indirect, fluorescent, chromogenic, etc.) or In situ hybridization (ISH) or variants thereof (e.g., chromogenic in situ hybridization (CISH) or fluorescence in situ hybridization (DNA-FISH or RNA-FISH]))

In this regard certain aspects of the instant invention comprise the use of labeled MFI2 for immunohistochemistry (IHC). More particularly MFI2 IHC may be used as a diagnostic tool to aid in the diagnosis of various proliferative disorders and to monitor the potential response to treatments including MFI2 antibody therapy. As discussed herein and shown in the Examples below compatible diagnostic assays may be performed on tissues that have been chemically fixed (including but not limited to: formaldehyde, gluteraldehyde, osmium tetroxide, potassium dichromate, acetic acid, alcohols, zinc salts, mercuric chloride, chromium tetroxide and picric acid) and embedded (including but not limited to: glycol methacrylate, paraffin and resins) or preserved via freezing. Such assays can be used to guide treatment decisions and determine dosing regimens and timing.

Other particularly compatible aspects of the invention involve the use of in situ hybridization to detect or monitor MFI2 determinants. In situ hybridization technology or ISH is well known to those of skill in the art. Briefly, cells are fixed and detectable probes which contain a specific nucleotide sequence are added to the fixed cells. If the cells contain complementary nucleotide sequences, the probes, which can be detected, will hybridize to them. Using the sequence information set forth herein, probes can be designed to identify cells that express genotypic MFI2 determinants. Probes preferably hybridize to a nucleotide sequence that corresponds to such determinants. Hybridization conditions can be routinely optimized to minimize background signal by non-fully complementary hybridization though preferably the probes are preferably fully complementary to the selected MFI2 determinant. In selected embodiments the probes are labeled with fluorescent dye attached to the probes that is readily detectable by standard fluorescent methodology.

Compatible in vivo theragnostics or diagnostic assays may comprise art-recognized imaging or monitoring techniques such as magnetic resonance imaging, computerized tomography (e.g. CAT scan), positron tomography (e.g., PET scan) radiography, ultrasound, etc., as would be known by those skilled in the art.

In certain embodiments the antibodies of the instant invention may be used to detect and quantify levels of a particular determinant (e.g., MFI2 protein) in a patient sample (e.g., plasma or blood) which may, in turn, be used to detect, diagnose or monitor proliferative disorders that are associated with the relevant determinant. In related embodiments the antibodies of the instant invention may be used to detect, monitor and/or quantify circulating tumor cells either in vivo or in vitro (WO 2012/0128801). In still other embodiments the circulating tumor cells may comprise tumorigenic cells.

In certain embodiments of the invention, the tumorigenic cells in a subject or a sample from a subject may be assessed or characterized using the disclosed antibodies prior to therapy or regimen to establish a baseline. In other examples, the tumorigenic cells can be assessed from a sample that is derived from a subject that was treated.

In another embodiment, the invention provides a method of analyzing cancer progression and/or pathogenesis in vivo. In another embodiment, analysis of cancer progression and/or pathogenesis in vivo comprises determining the extent of tumor progression. In another embodiment, analysis comprises the identification of the tumor. In another embodiment, analysis of tumor progression is performed on the primary tumor. In another embodiment, analysis is performed over time depending on the type of cancer as known to one skilled in the art. In another embodiment, further analysis of secondary tumors originating from metastasizing cells of the primary tumor is analyzed in vivo. In another embodiment, the size and shape of secondary tumors are analyzed. In some embodiments, further ex vivo analysis is performed.

In another embodiment, the invention provides a method of analyzing cancer progression and/or pathogenesis in vivo including determining cell metastasis or detecting and quantifying the level of circulating tumor cells. In yet another embodiment, analysis of cell metastasis comprises determination of progressive growth of cells at a site that is discontinuous from the primary tumor. In another embodiment, the site of cell metastasis analysis comprises the route of neoplastic spread. In some embodiment, cells can disperse via blood vasculature, lymphatics, within body cavities or combinations thereof. In another embodiment, cell metastasis analysis is performed in view of cell migration, dissemination, extravasation, proliferation or combinations thereof.

In certain examples, the tumorigenic cells in a subject or a sample from a subject may be assessed or characterized using the disclosed antibodies prior to therapy to establish a baseline. In other examples the sample is derived from a subject that was treated. In some examples the sample is taken from the subject at least about 1, 2, 4, 6, 7, 8, 10, 12, 14, 15, 16, 18, 20, 30, 60, 90 days, 6 months, 9 months, 12 months, or >12 months after the subject begins or terminates treatment. In certain examples, the tumorigenic cells are assessed or characterized after a certain number of doses (e.g., after 2, 5, 10, 20, 30 or more doses of a therapy). In other examples, the tumorigenic cells are characterized or assessed after 1 week, 2 weeks, 1 month, 2 months, 1 year, 2 years, 3 years, 4 years or more after receiving one or more therapies.

B. Screening

In certain embodiments, antibodies of the instant invention can be used to screen samples in order to identify compounds or agents (e.g., antibodies or ADCs) that alter a function or activity of tumor cells by interacting with a determinant. In one embodiment, tumor cells are put in contact with an antibody or ADC and the antibody or ADC can be used to screen the tumor for cells expressing a certain target (e.g. MFI2) in order to identify such cells for purposes, including but not limited to, diagnostic purposes, to monitor such cells to determine treatment efficacy or to enrich a cell population for such target-expressing cells.

In yet another embodiment, a method includes contacting, directly or indirectly, tumor cells with a test agent or compound and determining if the test agent or compound modulates an activity or function of the determinant-associated tumor cells for example, changes in cell morphology or viability, expression of a marker, differentiation or de-differentiation, cell respiration, mitochondrial activity, membrane integrity, maturation, proliferation, viability, apoptosis or cell death. One example of a direct interaction is physical interaction, while an indirect interaction includes, for example, the action of a composition upon an intermediary molecule that, in turn, acts upon the referenced entity (e.g., cell or cell culture).

Screening methods include high throughput screening, which can include arrays of cells (e.g., microarrays) positioned or placed, optionally at pre-determined locations, for example, on a culture dish, tube, flask, roller bottle or plate. High-throughput robotic or manual handling methods can probe chemical interactions and determine levels of expression of many genes in a short period of time. Techniques have been developed that utilize molecular signals, for example via fluorophores or microarrays (Mocellin and Rossi, 2007, PMID: 17265713) and automated analyses that process information at a very rapid rate (see, e.g., Pinhasov et al., 2004, PMID: 15032660). Libraries that can be screened include, for example, small molecule libraries, phage display libraries, fully human antibody yeast display libraries (Adimab), siRNA libraries, and adenoviral transfection vectors.

VII. PHARMACEUTICAL PREPARATIONS AND THERAPEUTIC USES

A. Formulations and routes of administration

The antibodies or ADCs of the invention can be formulated in various ways using art recognized techniques. In some embodiments, the therapeutic compositions of the invention can be administered neat or with a minimum of additional components while others may optionally be formulated to contain suitable pharmaceutically acceptable carriers. As used herein, "pharmaceutically acceptable carriers" comprise excipients, vehicles, adjuvants and diluents that are well known in the art and can be available from commercial sources for use in pharmaceutical preparation (see, e.g., Gennaro (2003) Remington: *The Science and Practice of Pharmacy with Facts and Comparisons: Drugfacts Plus*, 20th ed., Mack Publishing; Ansel et al. (2004) *Pharmaceutical Dosage Forms and Drug Delivery Systems*, $7^{th}$ ed., Lippencott Williams and Wilkins; Kibbe et al. (2000) *Handbook of Pharmaceutical Excipients*, $3^{rd}$ ed., Pharmaceutical Press.)

Suitable pharmaceutically acceptable carriers comprise substances that are relatively inert and can facilitate administration of the antibody or can aid processing of the active compounds into preparations that are pharmaceutically optimized for delivery to the site of action.

Such pharmaceutically acceptable carriers include agents that can alter the form, consistency, viscosity, pH, tonicity, stability, osmolarity, pharmacokinetics, protein aggregation or solubility of the formulation and include buffering agents, wetting agents, emulsifying agents, diluents, encapsulating agents and skin penetration enhancers. Certain non-limiting examples of carriers include saline, buffered saline, dextrose, arginine, sucrose, water, glycerol, ethanol, sorbitol, dextran, sodium carboxymethyl cellulose and combinations thereof. Antibodies for systemic administration may be formulated for enteral, parenteral or topical administration. Indeed, all three types of formulation may be used simultaneously to achieve systemic administration of the active ingredient. Excipients as well as formulations for parenteral and nonparenteral drug delivery are set forth in *Remington: The Science and Practice of Pharmacy* (2000) 20th Ed. Mack Publishing.

Suitable formulations for enteral administration include hard or soft gelatin capsules, pills, tablets, including coated tablets, elixirs, suspensions, syrups or inhalations and controlled release forms thereof.

Formulations suitable for parenteral administration (e.g., by injection), include aqueous or non-aqueous, isotonic, pyrogen-free, sterile liquids (e.g., solutions, suspensions), in which the active ingredient is dissolved, suspended, or otherwise provided (e.g., in a liposome or other microparticulate). Such liquids may additionally contain other pharmaceutically acceptable carriers, such as anti-oxidants, buffers, preservatives, stabilizers, bacteriostats, suspending agents, thickening agents, and solutes that render the formulation isotonic with the blood (or other relevant bodily fluid) of the intended recipient. Examples of excipients include, for example, water, alcohols, polyols, glycerol, vegetable oils, and the like. Examples of suitable isotonic pharmaceutically acceptable carriers for use in such formulations include Sodium Chloride Injection, Ringer's Solution, or Lactated Ringer's Injection.

Compatible formulations for parenteral administration (e.g., intravenous injection) may comprise ADC or antibody concentrations of from about 10 µg/mL to about 100 mg/mL. In certain selected embodiments antibody or ADC concentrations will comprise 20 µg/mL, 40 µg/mL, 60 µg/mL, 80 µg/mL, 100 µg/mL, 200 µg/mL, 300, µg/mL, 400 µg/mL, 500 µg/mL, 600 µg/mL, 700 µg/mL, 800 µg/mL, 900 µg/mL or 1 mg/mL. In other embodiments ADC concentrations will comprise 2 mg/mL, 3 mg/mL, 4 mg/mL, 5 mg/mL, 6 mg/mL, 8 mg/mL, 10 mg/mL, 12 mg/mL, 14 mg/mL, 16 mg/mL, 18 mg/mL, 20 mg/mL, 25 mg/mL, 30 mg/mL, 35 mg/mL, 40 mg/mL, 45 mg/mL, 50 mg/mL, 60 mg/mL, 70 mg/mL, 80 mg/mL, 90 mg/mL or 100 mg/mL.

The compounds and compositions of the invention may be administered in vivo, to a subject in need thereof, by various routes, including, but not limited to, oral, intravenous, intra-arterial, subcutaneous, parenteral, intranasal, intramuscular, intracardiac, intraventricular, intratracheal, buccal, rectal, intraperitoneal, intradermal, topical, transdermal, and intrathecal, or otherwise by implantation or inhalation. The subject compositions may be formulated into preparations in solid, semi-solid, liquid, or gaseous forms; including, but not limited to, tablets, capsules, powders, granules, ointments, solutions, suppositories, enemas, injections, inhalants, and aerosols. The appropriate formulation and route of administration may be selected according to the intended application and therapeutic regimen.

B. Dosages

The particular dosage regimen, i.e., dose, timing and repetition, will depend on the particular individual, as well as empirical considerations such as pharmacokinetics (e.g., half-life, clearance rate, etc.). Determination of the frequency of administration may be made by persons skilled in the art, such as an attending physician based on considerations of the condition and severity of the condition being treated, age and general state of health of the subject being treated and the like. Frequency of administration may be adjusted over the course of therapy based on assessment of the efficacy of the selected composition and the dosing regimen. Such assessment can be made on the basis of markers of the specific disease, disorder or condition. In embodiments where the individual has cancer, these include direct measurements of tumor size via palpation or visual observation; indirect measurement of tumor size by x-ray or other imaging techniques; an improvement as assessed by direct tumor biopsy and microscopic examination of a tumor sample; the measurement of an indirect tumor marker (e.g., PSA for prostate cancer) or an antigen identified according to the methods described herein; reduction in the number of proliferative or tumorigenic cells, maintenance of the reduction of such neoplastic cells; reduction of the proliferation of neoplastic cells; or delay in the development of metastasis.

The MFI2 antibodies or ADCs of the invention may be administered in various ranges. These include about 5 µg/kg body weight to about 100 mg/kg body weight per dose; about 50 µg/kg body weight to about 5 mg/kg body weight per dose; about 100 µg/kg body weight to about 10 mg/kg body weight per dose. Other ranges include about 100 µg/kg body weight to about 20 mg/kg body weight per dose and about 0.5 mg/kg body weight to about 20 mg/kg body weight per dose. In certain embodiments, the dosage is at least about 100 µg/kg body weight, at least about 250 µg/kg body weight, at least about 750 µg/kg body weight, at least about 3 mg/kg body weight, at least about 5 mg/kg body weight, at least about 10 mg/kg body weight.

In selected embodiments the MFI2 antibodies or ADCs will be administered (preferably intravenously) at approximately 10, 20, 30, 40, 50, 60, 70, 80, 90 or 100 µg/kg body weight per dose. Other embodiments may comprise the administration of antibodies or ADCs at about 200, 300, 400, 500, 600, 700, 800, 900, 1000, 1100, 1200, 1300, 1400, 1500, 1600, 1700, 1800, 1900 or 2000 µg/kg body weight per dose. In other embodiments the disclosed conjugates will be administered at 2.5, 3, 3.5, 4, 4.5, 5, 5.5, 6, 6.5, 7, 7.5, 8, 9 or 10 mg/kg. In still other embodiments the conjugates may be administered at 12, 14, 16, 18 or 20 mg/kg body weight per dose. In yet other embodiments the conjugates may be administered at 25, 30, 35, 40, 45, 50, 55, 60, 65, 70, 75, 80, 90 or 100 mg/kg body weight per dose. With the teachings herein one of skill in the art could readily determine appropriate dosages for various MFI2 antibodies or ADCs based on preclinical animal studies, clinical observations and standard medical and biochemical techniques and measurements.

Other dosing regimens may be predicated on Body Surface Area (BSA) calculations as disclosed in U.S. Pat. No. 7,744,877. As is well known, the BSA is calculated using the patient's height and weight and provides a measure of a subject's size as represented by the surface area of his or her body. In certain embodiments, the conjugates may be administered in dosages from 1 mg/m$^2$ to 800 mg/m$^2$, from 50 mg/m$^2$ to 500 mg/m$^2$ and at dosages of 100 mg/m$^2$, 150 mg/m$^2$, 200 mg/m$^2$, 250 mg/m$^2$, 300 mg/m$^2$, 350 mg/m$^2$, 400 mg/m$^2$ or 450 mg/m$^2$. It will also be appreciated that art recognized and empirical techniques may be used to determine appropriate dosage.

Anti-MFI2 antibodies or ADCs may be administered on a specific schedule. Generally, an effective dose of the MFI2 conjugate is administered to a subject one or more times. More particularly, an effective dose of the ADC is administered to the subject once a month, more than once a month, or less than once a month. In certain embodiments, the effective dose of the MFI2 antibody or ADC may be administered multiple times, including for periods of at least a month, at least six months, at least a year, at least two years or a period of several years. In yet other embodiments, several days (2, 3, 4, 5, 6 or 7), several weeks (1, 2, 3, 4, 5, 6, 7 or 8) or several months (1, 2, 3, 4, 5, 6, 7 or 8) or even a year or several years may lapse between administration of the disclosed antibodies or ADCs.

In some embodiments the course of treatment involving conjugated antibodies will comprise multiple doses of the selected drug product over a period of weeks or months. More specifically, antibodies or ADCs of the instant invention may administered once every day, every two days, every four days, every week, every ten days, every two weeks, every three weeks, every month, every six weeks, every two months, every ten weeks or every three months. In this regard it will be appreciated that the dosages may be altered or the interval may be adjusted based on patient response and clinical practices. The invention also contemplates discontinuous administration or daily doses divided into several partial administrations. The compositions of the instant invention and anti-cancer agent may be administered interchangeably, on alternate days or weeks; or a sequence of antibody treatments may be given, followed by one or more treatments of anti-cancer agent therapy. In any event, as will be understood by those of ordinary skill in the art, the appropriate doses of chemotherapeutic agents will be generally around those already employed in clinical therapies wherein the chemotherapeutics are administered alone or in combination with other chemotherapeutics.

In another embodiment the MFI2 antibodies or ADCs of the instant invention may be used in maintenance therapy to reduce or eliminate the chance of tumor recurrence following the initial presentation of the disease. Preferably the disorder will have been treated and the initial tumor mass eliminated, reduced or otherwise ameliorated so the patient is asymptomatic or in remission. At such time the subject may be administered pharmaceutically effective amounts of the disclosed antibodies one or more times even though there is little or no indication of disease using standard diagnostic procedures.

In another preferred embodiment the modulators of the present invention may be used to prophylactically or as an adjuvant therapy to prevent or reduce the possibility of tumor metastasis following a debulking procedure. As used in the instant disclosure a "debulking procedure" means any procedure, technique or method that reduces, or ameliorates a tumor or tumor proliferation. Exemplary debulking procedures include, but are not limited to, surgery, radiation treatments (i.e., beam radiation), chemotherapy, immunotherapy or ablation. At appropriate times readily determined by one skilled in the art in view of the instant disclosure the disclosed ADCs may be administered as suggested by clinical, diagnostic or theragnostic procedures to reduce tumor metastasis.

Yet other embodiments of the invention comprise administering the disclosed ADCs to subjects that are asymptomatic but at risk of developing cancer. That is, the ADCs of the instant invention may be used in a truly preventative sense and given to patients that have been examined or tested and have one or more noted risk factors (e.g., genomic indications, family history, in vivo or in vitro test results, etc.) but have not developed neoplasia.

Dosages and regimens may also be determined empirically for the disclosed therapeutic compositions in individuals who have been given one or more administration(s). For example, individuals may be given incremental dosages of a therapeutic composition produced as described herein. In selected embodiments the dosage may be gradually increased or reduced or attenuated based respectively on empirically determined or observed side effects or toxicity. To assess efficacy of the selected composition, a marker of the specific disease, disorder or condition can be followed as described previously. For cancer, these include direct measurements of tumor size via palpation or visual observation, indirect measurement of tumor size by x-ray or other imaging techniques; an improvement as assessed by direct tumor biopsy and microscopic examination of the tumor sample; the measurement of an indirect tumor marker (e.g., PSA for prostate cancer) or a tumorigenic antigen identified according to the methods described herein, a decrease in pain or paralysis; improved speech, vision, breathing or other disability associated with the tumor; increased appetite; or an increase in quality of life as measured by accepted tests or prolongation of survival. It will be apparent to one of skill in the art that the dosage will vary depending on the individual, the type of neoplastic condition, the stage of neoplastic condition, whether the neoplastic condition has begun to metastasize to other location in the individual, and the past and concurrent treatments being used.

C. Combination Therapies

Combination therapies may be useful in preventing or treating cancer and in preventing metastasis or recurrence of cancer. "Combination therapy", as used herein, means the administration of a combination comprising at least one anti-MFI2 antibody or ADC and at least one therapeutic moiety (e.g., anti-cancer agent) wherein the combination preferably has therapeutic synergy or improves the measurable therapeutic effects in the treatment of cancer over (i) the anti-MFI2 antibody or ADC used alone, or (ii) the therapeutic moiety used alone, or (iii) the use of the therapeutic moiety in combination with another therapeutic moiety without the addition of an anti-MFI2 antibody or ADC. The term "therapeutic synergy", as used herein, means the combination of an anti-MFI2 antibody or ADC and one or more therapeutic moiety(ies) having a therapeutic effect greater than the additive effect of the combination of the anti-MFI2 antibody or ADC and the one or more therapeutic moiety(ies).

Desired outcomes of the disclosed combinations are quantified by comparison to a control or baseline measurement. As used herein, relative terms such as "improve," "increase," or "reduce" indicate values relative to a control, such as a measurement in the same individual prior to initiation of treatment described herein, or a measurement in a control individual (or multiple control individuals) in the absence of the anti-MFI2 antibodies or ADCs described herein but in the presence of other therapeutic moiety(ies) such as standard of care treatment. A representative control individual is an individual afflicted with the same form of cancer as the individual being treated, who is about the same age as the individual being treated (to ensure that the stages of the disease in the treated individual and the control individual are comparable.)

Changes or improvements in response to therapy are generally statistically significant. As used herein, the term "significance" or "significant" relates to a statistical analysis of the probability that there is a non-random association between two or more entities. To determine whether or not a relationship is "significant" or has "significance," a "p-value" can be calculated. P-values that fall below a user-defined cut-off point are regarded as significant. A p-value less than or equal to 0.1, less than 0.05, less than 0.01, less than 0.005, or less than 0.001 may be regarded as significant.

A synergistic therapeutic effect may be an effect of at least about two-fold greater than the therapeutic effect elicited by a single therapeutic moiety or anti-MFI2 antibody or ADC, or the sum of the therapeutic effects elicited by the anti-MFI2 antibody or ADC or the single therapeutic moiety(ies) of a given combination, or at least about five-fold greater, or at least about ten-fold greater, or at least about twenty-fold greater, or at least about fifty-fold greater, or at least about one hundred-fold greater. A synergistic therapeutic effect may also be observed as an increase in therapeutic effect of at least 10% compared to the therapeutic effect elicited by a single therapeutic moiety or anti-MFI2 antibody or ADC, or the sum of the therapeutic effects elicited by the anti-MFI2 antibody or ADC or the single therapeutic moiety(ies) of a given combination, or at least 20%, or at least 30%, or at least 40%, or at least 50%, or at least 60%, or at least 70%, or at least 80%, or at least 90%, or at least 100%, or more. A synergistic effect is also an effect that permits reduced dosing of therapeutic agents when they are used in combination.

In practicing combination therapy, the anti-MFI2 antibody or ADC and therapeutic moiety(ies) may be administered to the subject simultaneously, either in a single composition, or as two or more distinct compositions using the same or different administration routes. Alternatively, treatment with the anti-MFI2 antibody or ADC may precede or follow the therapeutic moiety treatment by, e.g., intervals ranging from minutes to weeks. In one embodiment, both the therapeutic moiety and the antibody or ADC are administered within about 5 minutes to about two weeks of each other. In yet other embodiments, several days (2, 3, 4, 5, 6 or 7), several weeks (1, 2, 3, 4, 5, 6, 7 or 8) or several months (1, 2, 3, 4, 5, 6, 7 or 8) may lapse between administration of the antibody and the therapeutic moiety.

The combination therapy can be administered until the condition is treated, palliated or cured on various schedules such as once, twice or three times daily, once every two days, once every three days, once weekly, once every two weeks, once every month, once every two months, once every three months, once every six months, or may be administered continuously. The antibody and therapeutic moiety(ies) may be administered on alternate days or weeks; or a sequence of anti-MFI2 antibody or ADC treatments may be given, followed by one or more treatments with the additional therapeutic moiety. In one embodiment an anti-MFI2 antibody or ADC is administered in combination with one or more therapeutic moiety(ies) for short treatment cycles. In other embodiments the combination treatment is administered for long treatment cycles. The combination therapy can be administered via any route.

In selected embodiments the compounds and compositions of the present invention may be used in conjunction with checkpoint inhibitors such as PD-1 inhibitors or PDL-1 inhibitors. PD-1, together with its ligand PD-L1, are negative regulators of the antitumor T lymphocyte response. In one embodiment the combination therapy may comprise an anti-MFI2 antibody or ADC together with an anti-PD-1 antibody (e.g. lambrolizumab, nivolumab, pidilizumab) and optionally one or more other therapeutic moiety(ies). In another embodiment the combination therapy may comprise an anti-MFI2 antibody or ADC together with an anti-PD-L1 antibody (e.g. MPDL3280A, MED14736, MSB0010718C) and optionally one or more other therapeutic moiety(ies). In yet another embodiment, the combination therapy may comprise an anti-MFI2 antibody or ADC together with an anti PD-1 antibody (e.g., pembrolizumab) administered to patients who continue progress following treatments with other anti-PD-1 and/or targeted BRAF combination therapies (e.g., ipilimumab and vemurafenib or dabrafinib).

In some embodiments the anti-MFI2 antibodies or ADCs may be used in combination with various first line cancer treatments. In one embodiment the combination therapy comprises the use of an anti-MFI2 antibody or ADC and a cytotoxic agent such as ifosfamide, mytomycin C, vindesine, vinblastine, etoposide, ironitecan, gemcitabine, taxanes, vinorelbine, methotrexate, and pemetrexed) and optionally one or more other therapeutic moiety(ies).

In another embodiment the combination therapy comprises the use of an anti-MFI2 antibody or ADC and a platinum-based drug (e.g. carboplatin or cisplatin) and optionally one or more other therapeutic moiety(ies) (e.g. vinorelbine; gemcitabine; a taxane such as, for example, docetaxel or paclitaxel; irinotican; or pemetrexed).

In one embodiment, for example, in the treatment of BR-ERPR, BR-ER or BR-PR cancer, the combination therapy comprises the use of an anti-MFI2 antibody or ADC and one or more therapeutic moieties described as "hormone therapy". "Hormone therapy" as used herein, refers to, e.g., tamoxifen; gonadotropin or luteinizing releasing hormone (GnRH or LHRH); everolimus and exemestane; toremifene; or aromatase inhibitors (e.g. anastrozole, letrozole, exemestane or fulvestrant).

In another embodiment, for example, in the treatment of BR-HER2, the combination therapy comprises the use of an anti-MFI2 antibody or ADC and trastuzumab or ado-trastuzumab emtansine and optionally one or more other therapeutic moiety(ies) (e.g. pertuzumab and/or docetaxel).

In some embodiments, for example, in the treatment of metastatic breast cancer, the combination therapy comprises the use of an anti-MFI2 antibody or ADC and a taxane (e.g. docetaxel or paclitaxel) and optionally an additional therapeutic moiety(ies), for example, an anthracycline (e.g. doxorubicin or epirubicin) and/or eribulin.

In another embodiment, for example, in the treatment of metastatic or recurrent breast cancer or BRCA-mutant breast cancer, the combination therapy comprises the use of an anti-MFI2 antibody or ADC and megestrol and optionally an additional therapeutic moiety(ies).

In further embodiments, for example, in the treatment of BR-TNBC, the combination therapy comprises the use of an anti-MFI2 antibody or ADC and a poly ADP ribose polymerase (PARP) inhibitor (e.g. BMN-673, olaparib, rucaparib and veliparib) and optionally an additional therapeutic moiety(ies).

In another embodiment, for example, in the treatment of breast cancer, the combination therapy comprises the use of an anti-MFI2 antibody or ADC and cyclophosphamide and optionally an additional therapeutic moiety(ies) (e.g. doxorubicin, a taxane, epirubicin, 5-FU and/or methotrexate.

In another embodiment combination therapy for the treatment of EGFR-positive NSCLC comprises the use of an anti-MFI2 antibody or ADC and afatinib and optionally one or more other therapeutic moiety(ies) (e.g. erlotinib and/or bevacizumab).

In another embodiment combination therapy for the treatment of EGFR-positive NSCLC comprises the use of an anti-MFI2 antibody or ADC and erlotinib and optionally one or more other therapeutic moiety(ies) (e.g. bevacizumab).

In another embodiment combination therapy for the treatment of ALK-positive NSCLC comprises the use of an anti-MFI2 antibody or ADC and ceritinib and optionally one or more other therapeutic moiety(ies).

In another embodiment combination therapy for the treatment of ALK-positive NSCLC comprises the use of an anti-MFI2 antibody or ADC and crizotinib and optionally one or more other therapeutic moiety(ies).

In another embodiment the combination therapy comprises the use of an anti-MFI2 antibody or ADC and bevacizumab and optionally one or more other therapeutic moiety(ies) (e.g. a taxane such as, for example, docetaxel or paclitaxel; and/or a platinum analog).

In another embodiment the combination therapy comprises the use of an anti-MFI2 antibody or ADC and bevacizumab and optionally one or more other therapeutic moiety(ies) (e.g. gemcitabine and/or a platinum analog).

In one embodiment the combination therapy comprises the use of an anti-MFI2 antibody or ADC and a platinum-based drug (e.g. carboplatin or cisplatin) analog and optionally one or more other therapeutic moiety(ies) (e.g. a taxane such as, for example, docetaxel and paclitaxel).

In one embodiment the combination therapy comprises the use of an anti-MFI2 antibody or ADC and platinum-based drug (e.g. carboplatin or cisplatin) analog and optionally one or more other therapeutic moiety(ies) (e.g. a taxane such, for example, docetaxel and paclitaxel and/or gemcitabine and/or doxorubicin).

In a particular embodiment the combination therapy for the treatment of platinum-resistant tumors comprises the use of an anti-MFI2 antibody or ADC and doxorubicin and/or etoposide and/or gemcitabine and/or vinorelbine and/or ifosfamide and/or leucovorin-modulated 5-fluoroucil and/or bevacizumab and/or tamoxifen; and optionally one or more other therapeutic moiety(ies).

In another embodiment the combination therapy comprises the use of an anti-MFI2 antibody or ADC and a PARP inhibitor and optionally one or more other therapeutic moiety(ies).

In another embodiment the combination therapy comprises the use of an anti-MFI2 antibody or ADC and bevacizumab and optionally cyclophosphamide.

The combination therapy may comprise an anti-MFI2 antibody or ADC and a chemotherapeutic moiety that is effective on a tumor (e.g. melanoma) comprising a mutated or aberrantly expressed gene or protein (e.g. BRAF V600E).

T lymphocytes (e.g., cytotoxic lymphocytes (CTL)) play an important role in host defense against malignant tumors. CTL are activated by the presentation of tumor associated antigens on antigen presenting cells. Active specific immunotherapy is a method that can be used to augment the T lymphocyte response to cancer by vaccinating a patient with peptides derived from known cancer associated antigens. In one embodiment the combination therapy may comprise an anti-MFI2 antibody or ADC and a vaccine to a cancer associated antigen (e.g. melanocyte-lineage specific antigen tyrosinase, gp100, Melan-A/MART-1 or gp75.) In other embodiments the combination therapy may comprise administration of an anti-MFI2 antibody or ADC together with in vitro expansion, activation, and adoptive reintroduction of autologous CTLs or natural killer cells. CTL activation may also be promoted by strategies that enhance tumor antigen presentation by antigen presenting cells. Granulocyte macrophage colony stimulating factor (GM-CSF) promotes the recruitment of dendritic cells and activation of dendritic cell cross-priming. In one embodiment the combination therapy may comprise the isolation of antigen presenting cells, activation of such cells with stimulatory cytokines (e.g. GM-CSF), priming with tumor-associated antigens, and then adoptive reintroduction of the antigen presenting cells into patients in combination with the use of anti-MFI2 antibodies or ADCs and optionally one or more different therapeutic moiety(ies).

In some embodiments the anti-MFI2 antibodies or ADCs may be used in combination with various first line melanoma treatments. In one embodiment the combination therapy comprises the use of an anti-MFI2 antibody or ADC and dacarbazine and optionally one or more therapeutic moiety(ies). In further embodiments the combination therapy comprises the use of an anti-MFI2 antibody or ADC and temozolamide and optionally one or more therapeutic moiety(ies). In another embodiment the combination therapy comprises the use of an anti-MFI2 antibody or ADC and a platinum-based therapeutic moiety (e.g. carboplatin or cisplatin) and optionally one or more other therapeutic moiety(ies). In some embodiments the combination therapy comprises the use of an anti-MFI2 antibody or ADC and a vinca alkaloid therapeutic moiety (e.g. vinblastine, vinorelbine, vincristine, or vindesine) and optionally one or more other therapeutic moiety(ies). In one embodiment the combination therapy comprises the use of an anti-MFI2 antibody or ADC and interleukin-2 and optionally one or more other therapeutic moiety(ies). In another embodiment the combination therapy comprises the use of an anti-MFI2 antibody or ADC and interferon-alpha and optionally one or more other therapeutic moiety(ies).

In other embodiments, the anti-MFI2 antibodies or ADCs may be used in combination with adjuvant melanoma treatments and/or a surgical procedure (e.g. tumor resection.) In one embodiment the combination therapy comprises the use of an anti-MFI2 antibody or ADC and interferon-alpha and optionally one or more other therapeutic moiety(ies).

The invention also provides for the combination of anti-MFI2 antibodies or ADCs with radiotherapy. The term "radiotherapy", as used herein, means, any mechanism for inducing DNA damage locally within tumor cells such as gamma-irradiation, X-rays, UV-irradiation, microwaves, electronic emissions and the like. Combination therapy using the directed delivery of radioisotopes to tumor cells is also contemplated, and may be used in combination or as a conjugate of the anti-MFI2 antibodies disclosed herein. Typically, radiation therapy is administered in pulses over a period of time from about 1 to about 2 weeks. Optionally, the radiation therapy may be administered as a single dose or as multiple, sequential doses.

In other embodiments an anti-MFI2 antibody or ADC may be used in combination with one or more of the chemotherapeutic agents described below.

D. Anti-Cancer Agents

The term "anti-cancer agent" or "chemotherapeutic agent" as used herein is one subset of "therapeutic moieties", which in turn is a subset of the agents described as "pharmaceutically active moieties". More particularly "anti-cancer agent" means any agent that can be used to treat a cell proliferative disorder such as cancer, and includes, but is not limited to, cytotoxic agents, cytostatic agents, anti-angiogenic agents, debulking agents, chemotherapeutic agents, radiotherapy and radiotherapeutic agents, targeted anti-cancer agents, biological response modifiers, therapeutic antibodies, cancer vaccines, cytokines, hormone therapy, anti-metastatic agents and immunotherapeutic agents. It will be appreciated that in selected embodiments as discussed above, such anti-cancer agents may comprise conjugates and may be associated with antibodies prior to administration. In certain embodiments the disclosed anti-cancer agent will be linked to an antibody to provide an ADC as disclosed herein.

The term "cytotoxic agent", which can also be an anti-cancer agent means a substance that is toxic to the cells and decreases or inhibits the function of cells and/or causes destruction of cells. Typically, the substance is a naturally occurring molecule derived from a living organism (or a synthetically prepared natural product). Examples of cytotoxic agents include, but are not limited to, small molecule toxins or enzymatically active toxins of bacteria (e.g., Diptheria toxin, *Pseudomonas* endotoxin and exotoxin, *Staphylococcal* enterotoxin A), fungal (e.g., α-sarcin, restrictocin), plants (e.g., abrin, ricin, modeccin, viscumin, pokeweed anti-viral protein, saporin, gelonin, momoridin, trichosanthin, barley toxin, Aleurites fordii proteins, dianthin proteins, Phytolacca mericana proteins (PAPI, PAPII, and PAP-S), *Momordica charantia* inhibitor, curcin, crotin, saponaria officinalis inhibitor, mitegellin, restrictocin, phenomycin, neomycin, and the tricothecenes) or animals, (e.g., cytotoxic RNases, such as extracellular pancreatic RNases; DNase I, including fragments and/or variants thereof).

An anti-cancer agent can include any chemical agent that inhibits, or is designed to inhibit, a cancerous cell or a cell likely to become cancerous or generate tumorigenic progeny (e.g., tumorigenic cells). Such chemical agents are often directed to intracellular processes necessary for cell growth or division, and are thus particularly effective against cancerous cells, which generally grow and divide rapidly. For example, vincristine depolymerizes microtubules, and thus inhibits cells from entering mitosis. Such agents are often administered, and are often most effective, in combination, e.g., in the formulation CHOP. Again, in selected embodiments such anti-cancer agents may be conjugated to the disclosed antibodies to provide ADCs.

Examples of anti-cancer agents that may be used in combination with (or conjugated to) the antibodies of the invention include, but are not limited to, alkylating agents, alkyl sulfonates, anastrozole, amanitins, aziridines, ethylenimines and methylamelamines, acetogenins, a camptothecin, BEZ-235, bortezomib, bryostatin, callystatin, CC-1065, ceritinib, crizotinib, cryptophycins, dolastatin, duocarmycin, eleutherobin, erlotinib, pancratistatin, a sarcodictyin, spongistatin, nitrogen mustards, antibiotics, enediyne dynemicin, bisphosphonates, esperamicin, chromoprotein enediyne antibiotic chromophores, aclacinomysins, actinomycin, authramycin, azaserine, bleomycins, cactinomycin, canfosfamide, carabicin, carminomycin, carzinophilin, chromomycinis, cyclosphosphamide, dactinomycin, daunorubicin, detorubicin, 6-diazo-5-oxo-L-norleucine, doxorubicin, epirubicin, esorubicin, exemestane, fluorouracil, fulvestrant, gefitinib, idarubicin, lapatinib, letrozole, lonafarnib, marcellomycin, megestrol acetate, mitomycins, mycophenolic acid, nogalamycin, olivomycins, pazopanib, peplomycin, potfiromycin, puromycin, quelamycin, rapamycin, rodorubicin, sorafenib, streptonigrin, streptozocin, tamoxifen, tamoxifen citrate, temozolomide, tepodina, tipifarnib, tubercidin, ubenimex, vandetanib, vorozole, XL-147, zinostatin, zorubicin; anti-metabolites, folic acid analogues, purine analogs, androgens, anti-adrenals, folic acid replenisher such as frolinic acid, aceglatone, aldophosphamide glycoside, aminolevulinic acid, eniluracil, amsacrine, bestrabucil, bisantrene, edatraxate, defofamine, demecolcine, diaziquone, elfornithine, elliptinium acetate, epothilone, etoglucid, gallium nitrate, hydroxyurea, lentinan, lonidainine, maytansinoids, mitoguazone, mitoxantrone, mopidanmol, nitraerine, pentostatin, phenamet, pirarubicin, losoxantrone, podophyllinic acid, 2-ethylhydrazide, procarbazine, polysaccharide complex, razoxane; rhizoxin; SF-1126, sizofiran; spirogermanium; tenuazonic acid; triaziquone; 2,2',2"-trichlorotriethylamine; trichothecenes (T-2 toxin, verracurin A, roridin A and anguidine); urethan; vindesine; dacarbazine; mannomustine; mitobronitol; mitolactol; pipobroman; gacytosine; arabinoside; cyclophosphamide; thiotepa; taxoids, chloranbucil; gemcitabine; 6-thioguanine; mercaptopurine; methotrexate; platinum analogs, vinblastine; platinum; etoposide; ifosfamide; mitoxantrone; vincristine; vinorelbine; novantrone; teniposide; edatrexate; daunomycin; aminopterin; xeloda; ibandronate; irinotecan, topoisomerase inhibitor RFS 2000; difluorometlhylornithine; retinoids; capecitabine; combretastatin; leucovorin; oxaliplatin; XL518, inhibitors of PKC-alpha, Raf, H-Ras, EGFR and VEGF-A that reduce cell proliferation and pharmaceutically acceptable salts or solvates, acids or derivatives of any of the above. Also included in this definition are anti-hormonal agents that act to regulate or inhibit hormone action on tumors such as anti-estrogens and selective estrogen receptor antibodies, aromatase inhibitors that inhibit the enzyme aromatase, which regulates estrogen production in the adrenal glands, and anti-androgens; as well as troxacitabine (a 1,3-dioxolane nucleoside cytosine analog); antisense oligonucleotides, ribozymes such as a VEGF expression inhibitor and a HER2 expression inhibitor; vaccines, PROLEUKIN® rIL-2; LURTOTECAN® topoisomerase 1 inhibitor; ABARELIX® rmRH; Vinorelbine and Esperamicins and pharmaceutically acceptable salts or solvates, acids or derivatives of any of the above.

Anti-cancer agents comprise commercially or clinically available compounds such as erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine, dichloroplatinum(II), CAS No. 15663-27-1), carboplatin (CAS No. 41575-94-4), paclitaxel (TAXOL®, Bristol-Myers Squibb Oncology, Princeton, N.J.), trastuzumab (HERCEPTIN®, Genentech), temozolomide (4-methyl-5-oxo-2,3,4,6,8-pentazabicyclo [4.3.0] nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethylethanamine, NOLVADEX®, ISTUBAL®, VALODEX®), and doxorubicin (ADRIAMYCIN®). Additional commercially or clinically available anti-cancer agents comprise oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (Mek inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafarnib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, Ill.), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSAR®); vinorelbine (NAVELBINE®); capecitabine (XELODA®, Roche), tamoxifen (including NOLVADEX®; tamoxifen citrate, FARESTON® (toremifene citrate) MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca).

The term "pharmaceutically acceptable salt" or "salt" means organic or inorganic salts of a molecule or macromolecule. Acid addition salts can be formed with amino groups. Exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1' methylene bis-(2-hydroxy 3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Where multiple charged atoms are part of the pharmaceutically acceptable salt, the salt can have multiple counter ions. Hence, a pharmaceutically acceptable salt can have one or more charged atoms and/or one or more counterion.

"Pharmaceutically acceptable solvate" or "solvate" refers to an association of one or more solvent molecules and a molecule or macromolecule. Examples of solvents that form pharmaceutically acceptable solvates include, but are not limited to, water, isopropanol, ethanol, methanol, DMSO, ethyl acetate, acetic acid, and ethanolamine.

In other embodiments the antibodies or ADCs of the instant invention may be used in combination with any one of a number of antibodies (or immunotherapeutic agents) presently in clinical trials or commercially available. The disclosed antibodies may be used in combination with an antibody selected from the group consisting of abagovomab, adecatumumab, afutuzumab, alemtuzumab, altumomab, amatuximab, anatumomab, arcitumomab, atezolizumab, bavituximab, bectumomab, bevacizumab, bivatuzumab, blinatumomab, brentuximab, cantuzumab, catumaxomab, cetuximab, citatuzumab, cixutumumab, clivatuzumab, conatumumab, daratumumab, drozitumab, duligotumab, dusigitumab, detumomab, dacetuzumab, dalotuzumab, ecromeximab, elotuzumab, ensituximab, ertumaxomab, etaracizumab, farletuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab, iratumumab, labetuzumab, lambrolizumab, lexatumumab, lintuzumab, lorvotuzumab, lucatumumab, mapatumumab, matuzumab, milatuzumab, minretumomab, mitumomab, moxetumomab, narnatumab, naptumomab, necitumumab, nimotuzumab, nivolumab, nofetumomabn, obinutuzumab, ocaratuzumab, ofatumumab, olaratumab, olaparib, onartuzumab, oportuzumab, oregovomab, panitumumab, parsatuzumab, patritumab, pembrolizumab pemtumomab, pertuzumab, pidilizumab, pintumomab, pritumumab, racotumomab, radretumab, ramucirumab, rilotumumab, rituximab, robatumumab, satumomab, selumetinib, sibrotuzumab, siltuximab, simtuzumab, solitomab, tacatuzumab, taplitumomab, tenatumomab, teprotumumab, tigatuzumab, tositumomab, trastuzumab, tucotuzumab, ublituximab, veltuzumab, vorsetuzumab, votumumab, zalutumumab, CC49, 3F8, MDX-1105 and MED14736 and combinations thereof.

Other embodiments comprise the use of antibodies approved for cancer therapy including, but not limited to, rituximab, gemtuzumab ozogamcin, alemtuzumab, ibritumomab tiuxetan, tositumomab, bevacizumab, cetuximab, patitumumab, ofatumumab, ipilimumab and brentuximab vedotin. Those skilled in the art will be able to readily identify additional anti-cancer agents that are compatible with the teachings herein.

E. Radiotherapy

The present invention also provides for the combination of antibodies or ADCs with radiotherapy (i.e., any mechanism for inducing DNA damage locally within tumor cells such as gamma-irradiation, X-rays, UV-irradiation, microwaves, electronic emissions and the like). Combination therapy using the directed delivery of radioisotopes to tumor cells is also contemplated, and the disclosed antibodies or ADCs may be used in connection with a targeted anti-cancer agent or other targeting means. Typically, radiation therapy is administered in pulses over a period of time from about 1 to about 2 weeks. The radiation therapy may be administered to subjects having head and neck cancer for about 6 to 7 weeks. Optionally, the radiation therapy may be administered as a single dose or as multiple, sequential doses.

VIII. INDICATIONS

The invention provides for the use of antibodies and ADCs of the invention for the diagnosis, theragnosis, treatment and/or prophylaxis of various disorders including neoplastic, inflammatory, angiogenic and immunologic disorders and disorders caused by pathogens. In certain embodiments the diseases to be treated comprise neoplastic conditions comprising solid tumors. In other embodiments the diseases to be treated comprise hematologic malignancies. In certain embodiments the antibodies or ADCs of the invention will be used to treat tumors or tumorigenic cells expressing an MFI2 determinant. Preferably the "subject" or "patient" to be treated will be human although, as used herein, the terms are expressly held to comprise any mammalian species.

Neoplastic conditions subject to treatment in accordance with the instant invention may be benign or malignant; solid tumors or hematologic malignancies; and may be selected from the group including, but not limited to: adrenal gland tumors, AIDS-associated cancers, alveolar soft part sarcoma, astrocytic tumors, autonomic ganglia tumors, bladder cancer (squamous cell carcinoma and transitional cell carcinoma), blastocoelic disorders, bone cancer (adamantinoma, aneurismal bone cysts, osteochondroma, osteosarcoma), brain and spinal cord cancers, metastatic brain tumors, breast cancer, carotid body tumors, cervical cancer, chondrosarcoma, chordoma, chromophobe renal cell carcinoma, clear cell carcinoma, colon cancer, colorectal cancer, cutaneous benign fibrous histiocytomas, desmoplastic small round cell tumors, ependymomas, epithelial disorders, Ewing's tumors, extraskeletal myxoid chondrosarcoma, fibrogenesis imperfecta ossium, fibrous dysplasia of the bone, gallbladder and bile duct cancers, gastric cancer, gastrointestinal, gestational trophoblastic disease, germ cell tumors, glandular disorders, head and neck cancers, hypothalamic, intestinal cancer, islet cell tumors, Kaposi's Sarcoma, kidney cancer (nephroblastoma, papillary renal cell carcinoma), leukemias, lipoma/benign lipomatous tumors, liposarcoma/malignant lipomatous tumors, liver cancer (hepatoblastoma, hepatocellular carcinoma), lymphomas, lung cancers (small cell carcinoma, adenocarcinoma, squamous cell carcinoma, large cell carcinoma etc.), macrophagal disorders, medulloblastoma, melanoma, meningiomas, multiple endocrine neoplasia, multiple myeloma, myelodysplastic syndrome, neuroblastoma, neuroendocrine tumors, ovarian cancer, pancreatic cancers, papillary thyroid carcinomas, parathyroid tumors, pediatric cancers, peripheral nerve sheath tumors, phaeochromocytoma, pituitary tumors, prostate cancer, posterious unveal melanoma, rare hematologic disorders, renal metastatic cancer, rhabdoid tumor, rhabdomysarcoma, sarcomas, skin cancer, soft-tissue sarcomas, squamous cell cancer, stomach cancer, stromal disorders, synovial sarcoma, testicular cancer, thymic carcinoma, thymoma, thyroid metastatic cancer, and uterine cancers (carcinoma of the cervix, endometrial carcinoma, and leiomyoma).

In certain embodiments the compounds and compositions of the instant invention will be used as a front line therapy and administered to subjects who have not previously been treated for the cancerous condition. In other embodiments the compounds and compositions of the present invention will be used to treat subjects that have previously been treated (with antibodies or ADCs of the present invention or with other anti-cancer agents) and have relapsed or determined to be refractory to the previous treatment. In selected embodiments the compounds and compositions of the instant invention may be used to treat subjects that have recurrent tumors.

In certain selected embodiments the proliferative disorder to be treated will comprise a solid tumor including, but not limited to, adrenal, liver, kidney, bladder, breast, gastric, ovarian, cervical, uterine, esophageal, colorectal, prostate, pancreatic, lung (both small cell and non-small cell), thyroid, carcinomas, sarcomas, glioblastomas and various head and neck tumors.

In other selected embodiments, and as shown in the Examples below, the disclosed antibody drug conjugates are particularly effective at treating breast cancer, including triple negative breast cancer. In certain embodiments the breast cancer comprises BR-Basal-Like, BR-HER2, BR-LumA, BR-LumB or BR-undefined tumors, In one embodiment, the subject suffering from breast cancer is refractory, relapsed or resistant to treatment with a drug selected from the group consisting of capecitabine (e.g., Xeloda), carboplatin (e.g., Paraplatin), cisplatin (e.g., Platinol), cyclophosphamide (e.g., Neosar), docetaxel (e.g., Docefrez or Taxotere), doxorubicin (e.g., Adriamycin), pegylated liposomal doxorubicin (e.g., Doxil), epirubicin (e.g., Ellence), fluorouracil (e.g., 5-FU or Adrucil), gemcitabine (e.g., Gemzar), methotrexate, paclitaxel (e.g., Taxol), protein-bound paclitaxel (e.g., Abraxane), vinorelbine (e.g., Navelbine), eribulin (e.g., Halaven), and ixabepilone (e.g., Ixempra). In other embodiments the subject is suffering from a recurrent breast tumor that arose following treatment with one or more drugs selected from the group consisting of capecitabine (e.g., Xeloda), carboplatin (e.g., Paraplatin), cisplatin (e.g., Platinol), cyclophosphamide (e.g., Neosar), docetaxel (e.g., Docefrez or Taxotere), doxorubicin (e.g., Adriamycin), pegylated liposomal doxorubicin (e.g., Doxil), epirubicin (e.g., Ellence), fluorouracil (e.g., 5-FU or Adrucil), gemcitabine (e.g., Gemzar), methotrexate, paclitaxel (e.g., Taxol), protein-bound paclitaxel (e.g., Abraxane), vinorelbine (e.g., Navelbine), eribulin (e.g., Halaven), and ixabepilone (e.g., Ixempra).

In still other preferred embodiments the compounds or compositions will be administered to a subject suffering from melanoma. More generally the compositions and methods disclosed herein may be used to diagnose, monitor, treat or prevent melanoma. The term "melanoma", as used herein, includes all types of melanoma including, but not limited to, primary melanoma, malignant melanoma, cutaneous melanoma, extracutaneous melanoma, superficial spreading melanoma, polypoid melanoma, melanocarcinomas, melanoepitheliomas, melanosarcomas, melanoma in situ, nodular malignant melanoma, lentigo maligna melanoma, lentiginous melanoma, lentiginous malignant melanoma, mucosal lentiginous melanoma, mucosal melanoma, acral lentiginous melanoma, soft tissue melanoma, ocular melanoma, invasive melanoma, familial atypical mole and melanoma (FAM-M) syndrome, desmoplastic malignant melanoma or uveal melanoma.

Metastatic melanoma may be derived from melanocytes, melanocytic nevi or dysplastic nevi and can evolve through different phases of tumor progression (e.g. radial growth phase or vertical growth phase. Melanoma can be caused by chromosomal abnormalities, degenerative growth and/or developmental disorders, mitogenic agents, ultraviolet radiation, viral infections, carcinogenic agents, various genetic mutations or abnormal expression of a gene.

In other embodiments, the disclosed antibodies and ADCs are especially effective at treating lung cancer, including the following subtypes: small cell lung cancer and non-small cell lung cancer (e.g. squamous cell non-small cell lung cancer or squamous cell small cell lung cancer). In selected embodiments the antibodies and ADCs can be administered to patients exhibiting limited stage disease or extensive stage disease. In other embodiments the disclosed conjugated antibodies will be administered to refractory patients (i.e., those whose disease recurs during or shortly after completing a course of initial therapy); sensitive patients (i.e., those whose relapse is longer than 2-3 months after primary therapy); or patients exhibiting resistance to a platinum based agent (e.g. carboplatin, cisplatin, oxaliplatin) and/or a taxane (e.g. docetaxel, paclitaxel, larotaxel or cabazitaxel).

With regard to hematologic malignancies it will be further be appreciated that the compounds and methods of the present invention may be particularly effective in treating a variety of B-cell lymphomas, including low grade/NHL follicular cell lymphoma (FCC), mantle cell lymphoma (MCL), diffuse large cell lymphoma (DLCL), small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL, Waldenstrom's Macroglobulinemia, lymphoplasmacytoid lymphoma (LPL), mantle cell lymphoma (MCL), follicular lymphoma (FL), diffuse large cell lymphoma (DLCL), Burkitt's lymphoma (BL), AIDS-related lymphomas, monocytic B cell lymphoma, angioimmunoblastic lymphoadenopathy, small lymphocytic, follicular, diffuse large cell, diffuse small cleaved cell, large cell immunoblastic lymphoblastoma, small, non-cleaved, Burkitt's and non-Burkitt's, follicular, predominantly large cell; follicular, predominantly small cleaved cell; and follicular, mixed small cleaved and large cell lymphomas. See, Gaidono et al., "Lymphomas", IN CANCER: PRINCIPLES & PRACTICE OF ONCOLOGY, Vol. 2: 2131-2145 (DeVita et al., eds., 5.sup.th ed. 1997). It should be clear to those of skill in the art that these lymphomas will often have different names due to changing systems of classification, and that patients having lymphomas classified under different names may also benefit from the combined therapeutic regimens of the present invention.

IX. ARTICLES OF MANUFACTURE

The invention includes pharmaceutical packs and kits comprising one or more containers, wherein a container can comprise one or more doses of an antibody or ADC of the invention. In certain embodiments, the pack or kit contains a unit dosage, meaning a predetermined amount of a composition comprising, for example, an antibody or ADC of the invention, with or without one or more additional agents and optionally, one or more anti-cancer agents.

The kit of the invention will generally contain in a suitable container a pharmaceutically acceptable formulation of the antibody or ADC of the invention and, optionally, one or more anti-cancer agents in the same or different containers. The kits may also contain other pharmaceutically acceptable formulations or devices, either for diagnosis or combination therapy. Examples of diagnostic devices or instruments include those that can be used to detect, monitor, quantify or profile cells or markers associated with proliferative disorders (for a full list of such markers, see above). In some embodiments the devices may be used to detect, monitor and/or quantify circulating tumor cells either in vivo or in vitro (see, for example, WO 2012/0128801). In still other embodiments the circulating tumor cells may comprise tumorigenic cells. The kits contemplated by the invention can also contain appropriate reagents to combine the antibody or ADC of the invention with an anti-cancer agent or diagnostic agent (e.g., see U.S. Pat. No. 7,422,739).

When the components of the kit are provided in one or more liquid solutions, the liquid solution can be non-aqueous, however, an aqueous solution is preferred, with a sterile aqueous solution being some. The formulation in the kit can also be provided as dried powder(s) or in lyophilized form that can be reconstituted upon addition of an appropriate liquid. The liquid used for reconstitution can be contained in a separate container. Such liquids can comprise sterile, pharmaceutically acceptable buffer(s) or other diluent(s) such as bacteriostatic water for injection, phosphate-buffered saline, Ringer's solution or dextrose solution. Where the kit comprises the antibody or ADC of the invention in combination with additional therapeutics or agents, the solution may be pre-mixed, either in a molar equivalent combination, or with one component in excess of the other. Alternatively, the antibody or ADC of the invention and any optional anti-cancer agent or other agent can be maintained separately within distinct containers prior to administration to a patient.

The kit can comprise one or multiple containers and a label or package insert in, on or associated with the container(s), indicating that the enclosed composition is used for diagnosing or treating the disease condition of choice. Suitable containers include, for example, bottles, vials, syringes, etc. The containers can be formed from a variety of materials such as glass or plastic. The container(s) can comprise a sterile access port, for example, the container may be an intravenous solution bag or a vial having a stopper that can be pierced by a hypodermic injection needle.

In some embodiments the kit can contain a means by which to administer the antibody and any optional components to a patient, e.g., one or more needles or syringes (pre-filled or empty), an eye dropper, pipette, or other such like apparatus, from which the formulation may be injected or introduced into the subject or applied to a diseased area of the body. The kits of the invention will also typically include a means for containing the vials, or such like, and other components in close confinement for commercial sale, such as, e.g., blow-molded plastic containers into which the desired vials and other apparatus are placed and retained.

X. MISCELLANEOUS

Unless otherwise defined herein, scientific and technical terms used in connection with the invention shall have the meanings that are commonly understood by those of ordinary skill in the art. Further, unless otherwise required by context, singular terms shall include pluralities and plural terms shall include the singular. In addition, ranges provided in the specification and appended claims include both end points and all points between the end points. Therefore, a range of 2.0 to 3.0 includes 2.0, 3.0, and all points between 2.0 and 3.0.

Generally, techniques of cell and tissue culture, molecular biology, immunology, microbiology, genetics and chemistry described herein are those well known and commonly used in the art. The nomenclature used herein, in association with such techniques, is also commonly used in the art. The methods and techniques of the invention are generally performed according to conventional methods well known in the art and as described in various references that are cited throughout the present specification unless otherwise indicated.

XI. REFERENCES

The complete disclosure of all patents, patent applications, and publications, and electronically available material (including, for example, nucleotide sequence submissions in, e.g., GenBank and RefSeq, and amino acid sequence submissions in, e.g., SwissProt, PIR, PRF, PBD, and translations from annotated coding regions in GenBank and RefSeq) cited herein are incorporated by reference, regardless of whether the phrase "incorporated by reference" is or is not used in relation to the particular reference. The foregoing detailed description and the examples that follow have been given for clarity of understanding only. No unnecessary limitations are to be understood therefrom. The invention is not limited to the exact details shown and described. Variations obvious to one skilled in the art are included in the invention defined by the claims. Any section headings used herein are for organizational purposes only and are not to be construed as limiting the subject matter described.

XII. SEQUENCE LISTING SUMMARY

Appended to the instant application is a sequence listing comprising a number of nucleic acid and amino acid sequences. The following TABLE 3 provides a summary of the included sequences.

TABLE 3

| SEQ ID NO | Description |
| --- | --- |
| 1 | Kappa light chain constant region protein |
| 2 | IgG1 heavy chain constant region protein |
| 3 | Amino acid sequence of MFI2 (Accession # NP_005920) |
| 4-19 | Reserved |
| 20 | SC57.1 VL DNA |
| 21 | SC57.1 VL protein |
| 22 | SC57.1 VH DNA |
| 23 | SC57.1 VH protein |
| 24-91 | Additional murine clones |
| 92-95 | hSC57.5 humanized clone (DNA and protein) |
| 96-97 | hSC57.5v1 humanized clone VH (DNA and protein) |
| 98-101 | hSC57.32 humanized clone (DNA and protein) |
| 102-103 | hSC57.32v1 humanized clone VH (DNA and protein) |
| 104-107 | hSC57.43 humanized clone (DNA and protein) |
| 108 | hSC57.5 full length light chain protein (same for hSC57.5v1 and hSC57.5ss1) |
| 109 | hSC57.5 full length heavy chain protein |
| 110 | hSC57.5v1ss1 full length heavy chain protein |

TABLE 3-continued

| SEQ ID NO | Description |
|---|---|
| 111 | hSC57.5v1 full length heavy chain protein |
| 112 | hSC57.32 full length light chain protein (same for hSC57.v1 and hSC57.32ss1) |
| 113 | hSC57.32 full length heavy chain protein |
| 114 | hSC57.32ss1 full length heavy chain protein |
| 115 | hSC57.32v1 full length heavy chain protein |
| 116 | hSC57.43 full length light chain protein (same for hSC57.43ss1) |
| 117 | hSC57.43 full length heavy chain protein |
| 118 | hSC57.43ss1 full length heavy chain protein |
| 119-121 | CDRL1, CDRL2, CDRL3 of hSC57.5 (same for hSC57.5v1 and hSC57.5v1ss1) |
| 122 | CDRH1 of hSC57.5 (same for hSC57.5v1ss1) |
| 123 | CDRH2 of hSC57.5 |
| 124 | CDRH2 of hSC57.5v1 (same for hSC57.5v1ss1) |
| 125 | CDRH3 of hSC57.5 (same for hSC57.5v1 and hSC57.5v1ss1) |
| 126-128 | CDRL1, CDRL2, CDRL3 of hSC57.32 (same for hSC57.32ss1 and hSC57.32v1) |
| 129-131 | CDRH1, CDRH2, CDRH3 of hSC57.32 (same for hSC57.32ss1 and hSC57.32v1) |
| 132-134 | CDRL1, CDRL2, CDRL3 of hSC57.43 (same for hSC57.43ss1) |
| 135-137 | CDRH1, CDRH2, CDRH3 of hSC57.43 (same for hSC57.43ss1) |

XIII. EXAMPLES

The invention, generally described above, will be understood more readily by reference to the following examples, which are provided by way of illustration and are not intended to be limiting of the instant invention. The examples are not intended to represent that the experiments below are all or the only experiments performed. Unless indicated otherwise, parts are parts by weight, molecular weight is weight average molecular weight, temperature is in degrees Centigrade, and pressure is at or near atmospheric.

PDX tumor cell types are denoted by an abbreviation followed by a number, which indicates the particular tumor cell line. The passage number of the tested sample is indicated by p0-p# appended to the sample designation where p0 is indicative of an unpassaged sample obtained directly from a patient tumor and p# is indicative of the number of times the tumor has been passaged through a mouse prior to testing. As used herein, the abbreviations of the tumor types and subtypes are shown in TABLE 4 as follows:

TABLE 4

| Tumor Type | Abbreviation | Tumor subtype | Abbreviation |
|---|---|---|---|
| Bladder | BD | | |
| Breast | BR | | |
| | | basal-like | BR-Basal-Like |
| | | estrogen receptor positive and/or progesterone receptor positive | BR-ERPR |
| | | ERBB2/Neu positive | BR-ERBB2/Neu |
| | | HER2 positive | BR-HER2 |
| | | triple-negative | TNBC |
| | | luminal A | BR-LumA |
| | | luminal B | BR-LumB |
| | | claudin subtype of triple-negative | TNBC-CL |
| | | claudin low | BR-CLDN-Low |
| | | normal-like | BR-NL |
| Cervical | CER | | |
| Colorectal | CR | | |
| | | rectum adenocarcinoma | RE-Ad |
| Endometrial | EM | | |
| Esophageal | ES | | |
| Gastric | GA | | |
| | | diffuse adenocarcinoma | GA-Ad-Dif/Muc |
| | | intestinal adenocarcinoma | GA-Ad-Int |
| | | stromal tumors | GA-GIST |
| Glioblastoma | GB | | |
| Head and neck | HN | | |
| Kidney | KDY | | |
| | | clear renal cell carcinoma | KDY-CC |
| | | papillary renal cell carcinoma | KDY-PAP |
| | | transitional cell or urothelial carcinoma | KDY-URO |
| | | unknown | KDY-UNK |
| Liver | LIV | | |
| | | hepatocellular carcinoma | LIV-HCC |
| | | cholangiocarcinoma | LIV-CHOL |
| Lymphoma | LN | | |
| Lung | LU | | |
| | | adenocarcinoma | LU-Ad |
| | | carcinoid | LU-CAR |
| | | large cell neuroendocrine | LU-LCC |
| | | non-small cell | NSCLC |
| | | squamous cell | LU-SCC |
| | | small cell | SCLC |
| | | spindle cell | LU-SPC |
| Ovarian | OV | | |
| | | clear cell | OV-CC |
| | | endometroid | OV-END |
| | | mixed subtype | OV-MIX |
| | | malignant mixed mesodermal | OV-MMMT |
| | | mucinous | OV-MUC |
| | | neuroendocrine | OV-NET |
| | | papillary serous | OV-PS |
| | | serous | OV-S |
| | | small cell | OV-SC |
| | | transitional cell carcinoma | OV-TCC |
| Pancreatic | PA | | |
| | | acinar cell carcinoma | PA-ACC |
| | | duodenal carcinoma | PA-DC |
| | | mucinous adenocarcinoma | PA-MAD |
| | | neuroendocrine | PA-NET |
| | | adenocarcinoma | PA-PAC |
| | | adenocarcinoma exocrine type | PA-PACe |
| | | ductal adenocarcinoma | PA-PDAC |
| | | ampullary adenocarcinoma | PA-AAC |
| Prostate | PR | | |
| Skin | SK | | |
| | | melanoma | MEL |
| | | squamous cell carcinomas | SK-SCC |
| | | uveal melanoma | UVM |

TABLE 4-continued

| Tumor Type | Abbreviation | Tumor subtype | Abbreviation |
|---|---|---|---|
| Testicular | TES | | |
| Thyroid | THY | | |
| | | medullary thyroid carcinoma | MTC |

Example 1

Identification of MFI2 Expression Using Whole Transcriptome Sequencing

To characterize the cellular heterogeneity of solid tumors as they exist in cancer patients and identify clinically relevant therapeutic targets, a large PDX tumor bank was developed and maintained using art recognized techniques. The PDX tumor bank, comprising a large number of discrete tumor cell lines, was propagated in immunocompromised mice through multiple passages of tumor cells originally obtained from cancer patients afflicted by a variety of solid tumor malignancies. Low passage PDX tumors are representative of tumors in their native environments, providing clinically relevant insight into underlying mechanisms driving tumor growth and resistance to current therapies.

Tumor cells can be divided broadly into two types of cell subpopulations: non-tumorigenic cells (NTG) and tumor initiating cells (TICs). TICs have the ability to form tumors when implanted into immunocompromised mice. Cancer stem cells (CSCs) are a subset of TICs that are able to self-replicate indefinitely while maintaining the capacity for multilineage differentiation. NTGs, while sometimes able to grow in vivo, will not form tumors that recapitulate the heterogeneity of the original tumor when implanted.

In order to perform whole transcriptome analysis, PDX tumors from the tumor bank were resected from mice after they reached 800-2,000 mm$^3$. Resected PDX tumors were dissociated into single cell suspensions using art-recognized enzymatic digestion techniques (see, for example, U.S.P.N. 2007/0292414). Dissociated bulk tumor cells were incubated with 4',6-diamidino-2-phenylindole (DAPI) to detect dead cells, anti-mouse CD45 and H-2K$^d$ antibodies to identify mouse cells and anti-human EPCAM antibody to identify human cells. In addition the tumor cells were incubated with fluorescently conjugated anti-human CD46 and/or CD324 antibodies to identify CD46$^{hi}$CD324$^+$ CSCs or CD46$^{lo/-}$CD324$^-$ NTG cells and were then sorted using a FACSAria cell sorter (BD Biosciences) (see U.S.P.Ns 2013/0260385, 2013/0061340 and 2013/0061342).

RNA was extracted from tumor cells by lysing the cells in RLTplus RNA lysis buffer (Qiagen) supplemented with 1% 2-mercaptoethanol, freezing the lysates at −80° C. and then thawing the lysates for RNA extraction using an RNeasy isolation kit (Qiagen). RNA was quantified using a Nanodrop spectrophotometer (Thermo Scientific) and/or a Bioanalyzer 2100 (Agilent Technologies). Normal tissue RNA was purchased from various sources (Life Technology, Agilent, ScienCell, BioChain, and Clontech). The resulting total RNA preparations were assessed by genetic sequencing and gene expression analyses.

Whole transcriptome sequencing of high quality RNA was performed using two different systems. Certain BR and SK PDX tumor samples were analyzed using an Applied Biosystems (ABI) Sequencing by Oligo Ligation/Detection (SOLiD) 4.5 or SOLiD 5500xl next generation sequencing system (Life Technologies). LU PDX tumor samples were analyzed using an Illumina HiSeq 2000 or 2500 next generation sequencing system (Illumina).

SOLiD whole transcriptome analysis was performed with cDNA, generated from 1 ng RNA from sorted BR or bulk SK tumor samples using either a modified whole transcriptome protocol from ABI designed for low input total RNA or the Ovation RNA-Seq System V2™ (NuGEN Technologies). The resulting cDNA library was fragmented, and barcode adapters were added to allow pooling of fragment libraries from different samples during sequencing runs. Data generated by the SOLiD platform mapped to 34,609 genes as annotated by RefSeq version 47 using NCBI version hg19.2 of the published human genome and provided verifiable measurements of RNA levels in most samples. Sequencing data from the SOLiD platform is nominally represented as a transcript expression value using the metric RPKM (read per kilobase per million) mapped to exon regions of genes, enabling basic gene expression analysis to be normalized and enumerated as RPKM_Transcript. MFI2 mRNA expression was higher in BR CSCs compared to NTG cells and normal tissues in the following PDX lines: BR31 and BR25. MFI2 mRNA expression was higher in bulk SK PDX compared to normal tissues, including melanocytes in the following PDX lines: SK3 and SK13 (FIG. 1A).

Figure 1B:
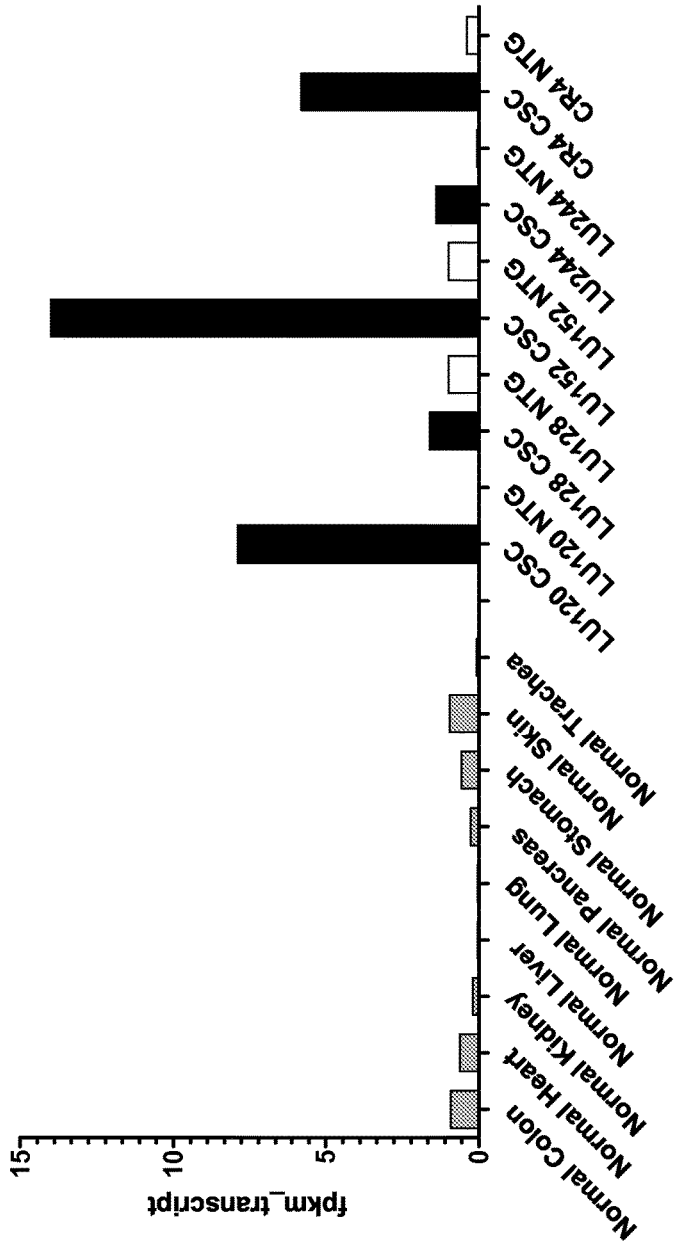
FIG. 1B shows expression levels of MFI2 as measured using whole transcriptome (Illumina) sequencing of RNA derived from PDX CSC and NTG tumor cells.

Illumina whole transcriptome analysis was performed with cDNA that was generated using 5 ng total RNA extracted from either NTG or CSC tumor subpopulations that were isolated as described above in this Example 1. The library was created using the TruSeq RNA Sample Preparation Kit v2 (Illumina). The resulting cDNA library was fragmented and barcoded. Sequencing data from the Illumina platform is nominally represented as a fragment expression value using the metric FPKM (fragment per kilobase per million) mapped to exon regions of genes, enabling basic gene expression analysis to be normalized and enumerated as FPKM_Transcript. MFI2 mRNA expression in the CSC tumor cell subpopulation was higher than expression in both normal cells and compared to the NTG cell population in the following LU and CR PDX tumor cell lines: LU120, LU128, LU152, LU244 and CR4 (FIG. 1B).

The identification of elevated MFI2 mRNA expression in BR, SK, LU and CR PDX tumors indicated that MFI2 merited further evaluation as a potential diagnostic and immunotherapeutic target. Furthermore, increased expression of MFI2 in CSC compared to NTG in BR, CR and LU PDX tumors indicates that MFI2 is a good marker of tumorigenic cells in these tumor types.

Example 2

Expression of MFI2 mRNA in Tumors Using QRT-PCR

Figure 2A:
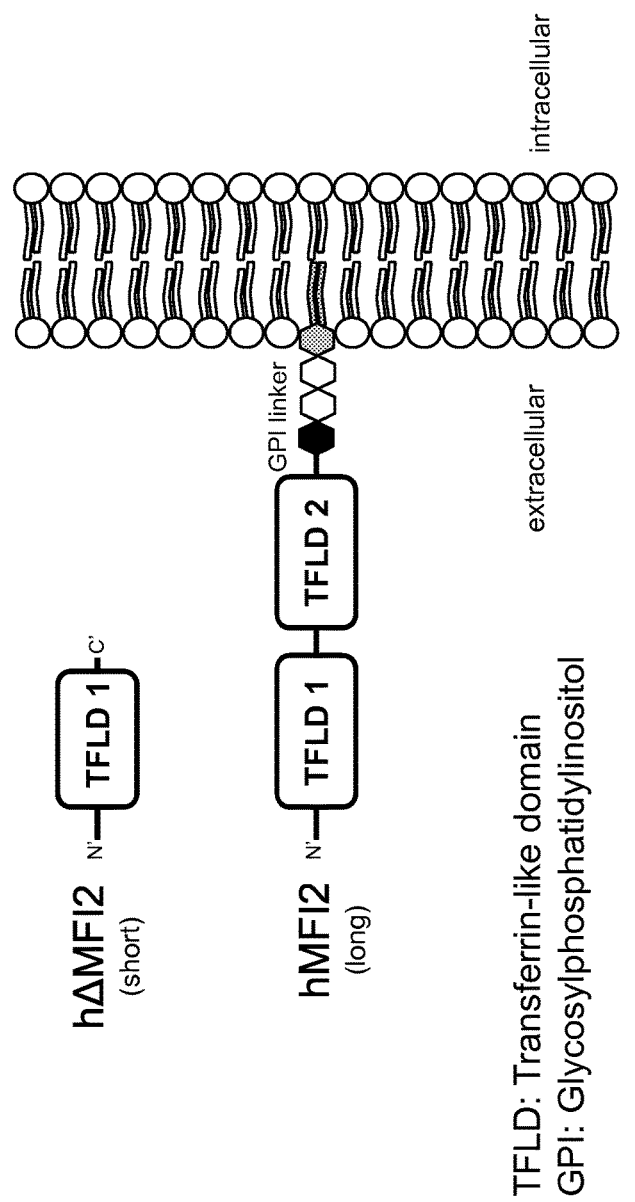
FIG. 2A is a schematic of human MFI2, showing both long (hMFI2) and short (hΔMFI2) isoforms.

The human MFI2 gene encodes two transcripts: a 16-exon long isoform of 2377 bp (Genbank Accession: NM_005929) and a shorter 7-exon isoform of 1651 bp (Genbank Accession: NM_033316). The first six exons of the short and long isoforms are identical. However, the seventh and last exon of the short isoform comprises an in-frame termination signal resulting in the truncated protein. The long isoform of the MFI2 protein ("hMFI2") is a GPI-membrane anchored protein of 738 amino acids. The short isoform ("hΔMFI2") has a predicted length of 302 amino acids and has no GPI-anchor motif; it is therefore thought to be a secreted protein. FIG. 2A is a schematic of hMFI2, showing both isoforms.

Anti-MFI2 antibodies of the invention can be used as an effective treatment or method of diagnosis of tumors regardless of whether they bind to the short or long isoform, however, it is particularly advantageous for the antibodies of the invention to bind the long membrane-anchored isoform in order to optimize localization of the antibody to the tumor location and increase antibody internalization. To confirm the results of Examples 1 and 2 and in order to determine which hMFI2 isoform was expressed in various PDX tumor cell lines.

To confirm MFI2 RNA expression in tumor cells, qRT-PCR was performed on various PDX cell lines using the Fluidigm BioMark™ HD System according to industry standard protocols. RNA was extracted from bulk PDX tumor cells or sorted CSC and NTG subpopulations as described in Example 1. 1 ng of RNA was converted to cDNA using the High Capacity cDNA Archive kit (Life Technologies) according to the manufacturer's instructions. cDNA material, pre-amplified using an MFI2 long isoform-specific Taqman assay, was then used for subsequent qRT-PCR experiments.

Figure 2B:
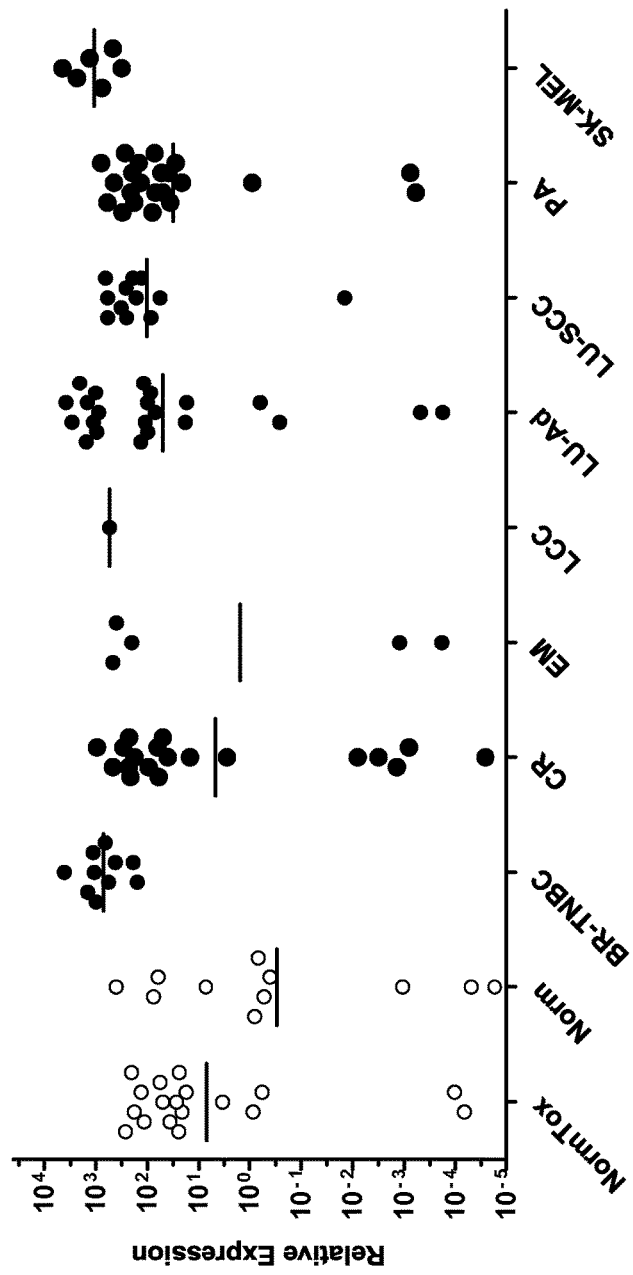
FIG. 2B depicts the relative expression levels of MFI2 transcripts as measured by qRT-PCR in RNA samples isolated from normal tissue and from a variety of PDX tumors.

Expression in normal tissues (NormTox or Norm) was compared to expression in BR, CR, EM, LU, PA and SK PDX tumor cell lines (FIG. 2B; each dot represents the average relative expression of each individual tissue or PDX cell line, with the small horizontal line representing the geometric mean). "NormTox" represents samples of various normal tissues as follows: adrenal, artery, colon, dorsal root ganglion, esophagus, heart, kidney, liver, lung, pancreas, skeletal muscle, skin, fibroblasts, keratinocytes, small intestine, spleen, stomach, trachea and vein. Another set of normal tissues designated "Norm" represents the following samples of normal tissue with a presumed lower risk for toxicity compared to "NormTox" cells in relation to ADC-type drugs: peripheral blood mononuclear cells and various sorted subpopulations (B cells, monocytes, NK cells, neutrophils, T cells), brain, breast, melanocytes, normal bone marrow and various sorted subpopulations and testes. FIG. 2B shows that on average MFI2 expression was higher in breast (BR-Basal-Like); colorectal, lung (LU-Ad, LU-LCC and LU-SCC); pancreatic and skin (SK-MEL) tumors, as well as a subset of EM tumors, compared to Norm and NormTox tissues. This data supports the earlier finding of elevated expression of MFI2 in BR, LU and SK PDX compared to normal tissues.

Figure 2C:
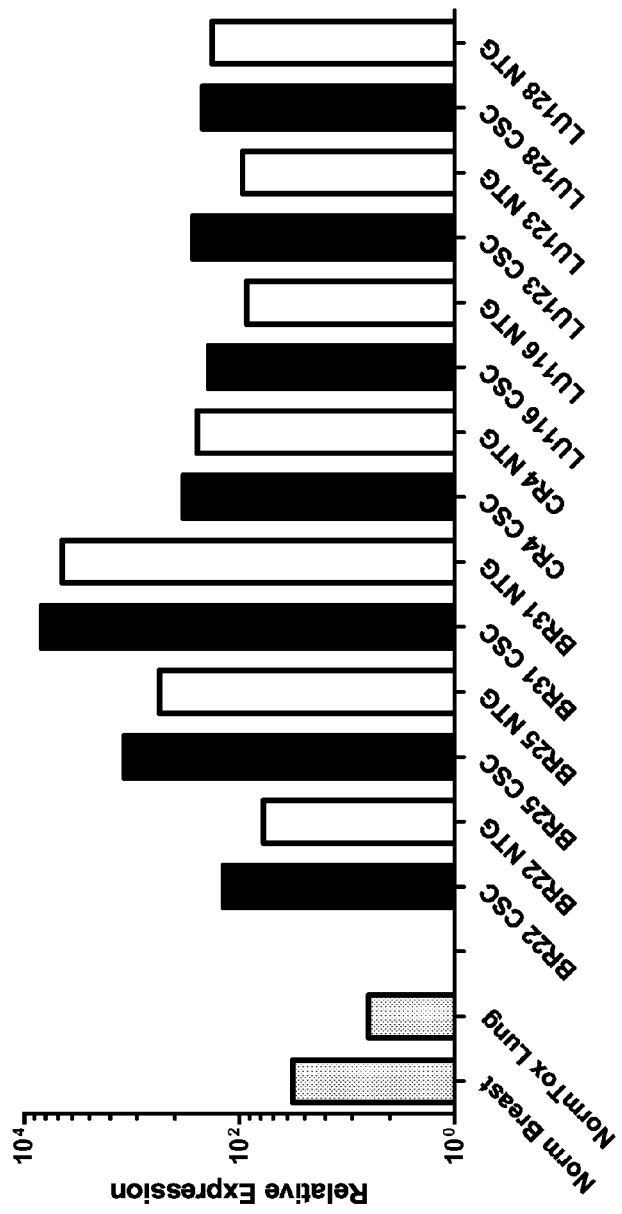
FIG. 2C depicts the relative expression levels of MFI2 transcripts as measured by qRT-PCR in RNA samples isolated from various normal tissues and from CSC and NTG cells isolated from a variety of PDX tumors.

MFI2 expression was also determined in various PDX tumor cell lines that had been sorted into CSCs and NTGs as described in Example 1 above. MFI2 expression was higher in CSCs compared to NTGs in the following tumor subtypes: BR-Basal-Like (BR22, BR31); BR-CLDN-low (BR25); CR (CR4); LU-Ad (LU123); and LU-SCC (LU116, and LU128) (FIG. 2C). In contrast to the aforementioned LU PDX tumor lines, LU206 exhibited low expression of MFI2 (FIG. 2B). This finding was later confirmed when determining the level of MFI2 protein expression in LU206 (See Example 16 below).

Such findings further support the observed association between MFI2 expression levels and various tumor subtypes including BR, CR and LU.

Example 3

Determination of Expression of MFI2 mRNA in Tumors Using Microarray

Microarray experiments for the full-length GPI anchored hMFI2 isoform were conducted and data was analyzed as follows. 1-2 µg of whole tumor total RNA was extracted, substantially as described in Example 1, from BR, CR, LU, PA and SK PDX cell lines. The samples were analyzed using the Agilent SurePrint GE Human 8×60 v2 microarray platform, which contains 50,599 biological probes designed against 27,958 genes and 7,419 lncRNAs in the human genome. Standard industry practices were used to normalize and transform the intensity values to quantify gene expression for each sample. The normalized intensity of MFI2 expression in each sample is plotted in FIG. 3 and the geometric mean derived for each tumor type is indicated by the horizontal bar.

Figure 3:
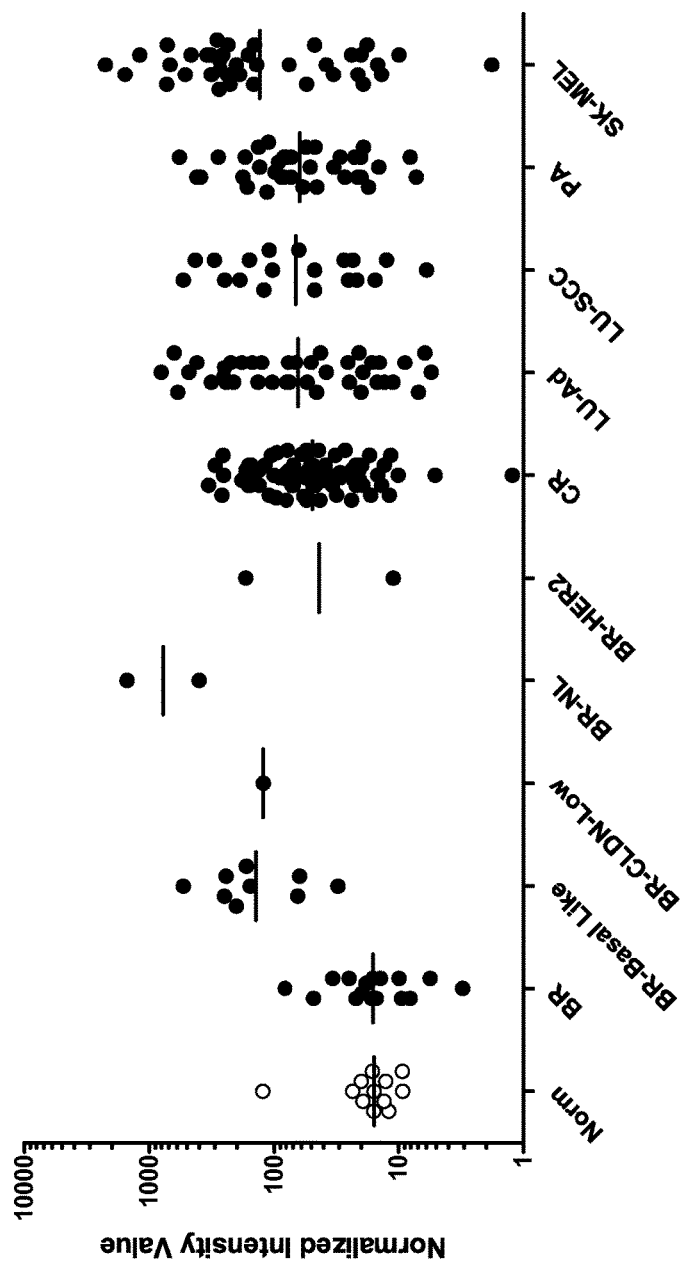
FIG. 3 shows the normalized intensity value of MFI2 transcript expression measured by microarray hybridization in normal tissues and a variety of PDX cell lines.

FIG. 3 shows that the long isoform of MFI2 is expressed in BR (BR-Basal-like, BR-CLDN-low, BR-HER2, BR-NL), CR, LU (LU-Ad, LU-SCC), PA and SK compared to normal tissues. The observation of elevated MFI2 expression in the aforementioned tumor types confirms the results of Examples 1 and 2. In addition, LU206 was shown not to express MFI2, confirming the flow cytometry results for this particular PDX tumor line that were described in Example 16. Specifically, BR25, BR31 and CR4, which were analyzed on all three platforms, show elevated MFI2 expression of the long isoform when measured by whole transcriptome RNA sequencing (Example 1), qRT-PCR (Example 2) and microarray (Example 3). These data demonstrate that the long isoform of MFI2 is expressed in a number of tumor subtypes including BR, CR, LU, PA and SK, and may be a good target for the development of an antibody-based therapeutic in these indications.

Example 4

MFI2 Expression in Tumors Using the Cancer Genome Atlas

Figure 4A:
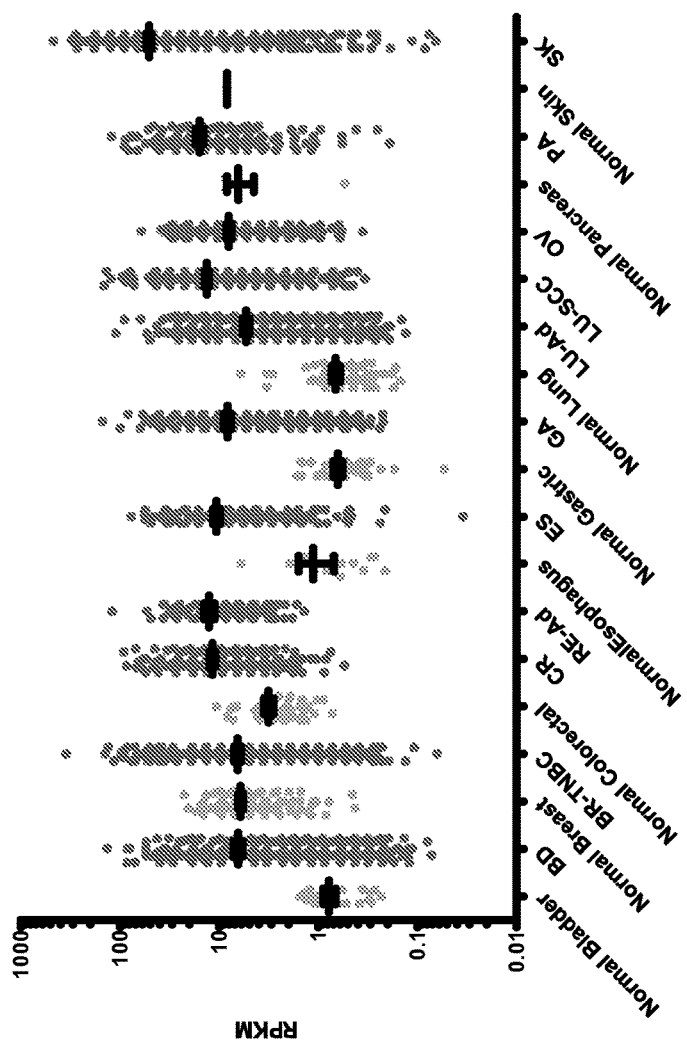
FIG. 4A shows expression of MFI2 transcripts in normal tissues and primary tumors from The Cancer Genome Atlas (TCGA), a publically available dataset.

Overexpression of hMFI2 mRNA in various tumors was confirmed using a large, publically available dataset of primary tumors and normal samples known as The Cancer Genome Atlas (TCGA). hMFI2 expression data from the IlluminaHiSeq_RNASeqV2 platform was downloaded from the TCGA Data Portal (https://tcga-data.nci.nih.gov/tcga/tcgaDownload.jsp) and parsed to aggregate the reads from the individual exons of each gene to generate a single value read per kilobase of exon per million mapped reads (RPKM). FIG. 4A shows that MFI2 expression is elevated in the following PDX tumor lines compared to normal tissue: BD, BR (BR-TNBC); CR; RE-Ad, ES, GA, LU (LU-Ad, LU-SCC); OV; PA; and SK. These data confirm that elevated levels of MFI2 mRNA may be found in the above mentioned tumor types, indicating that anti-MFI2 antibodies and ADCs may be useful therapeutics for these tumors.

Figure 4B:
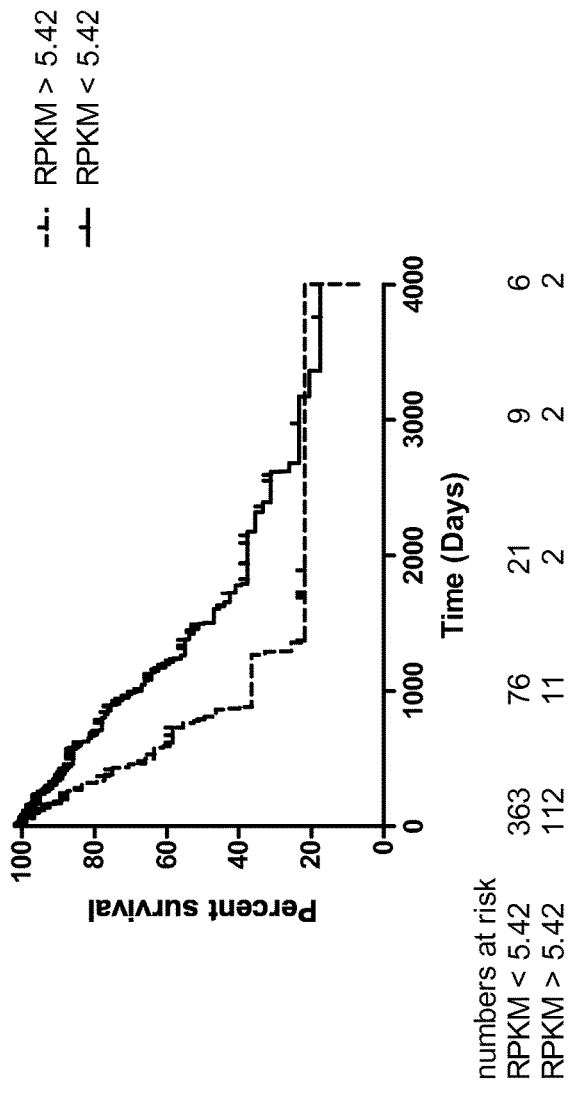
FIG. 4B depicts Kaplan-Meier survival curves based on high and low expression of MFI2 transcripts in primary melanoma tumors from the TCGA dataset wherein the threshold index value is determined using the arithmetic mean of the RPKM values.

FIG. 4B shows Kaplan Meier survival curves for a subset of LU-Ad TCGA tumors where patient survival data was available. Patients were stratified based on high expression of MFI2 mRNA i.e. expression over the threshold index value or low expression of MFI2 mRNA i.e. expression under the threshold index value in LU-Ad tumors. The threshold index value was calculated as the arithmetic mean of the RPKM values, which was calculated to be 5.42.

The "numbers at risk" listed below the plot shows the number of surviving patients remaining in the dataset every 1000 days after the day at which each patient was first diagnosed (day 0). The two survival curves are significantly different (p=0.0002) by the Log-rank (Mantel-Cox) test of p=0.0004 by the Gehan-Breslow-Wilcoxon test These data show that patients with LU-Ad tumors exhibiting high expression of MFI2 have a much shorter survival time compared to patients with LU-Ad tumors exhibiting low expression of MFI2. This suggests the usefulness of anti-MFI2 therapies to treat LU-Ad, and the usefulness of MFI2 expression as a prognostic biomarker on the basis of which treatment decisions can be made.

Example 5

Cloning and Expression of Recombinant MFI2 Proteins and Engineering of Cell Lines Overexpressing Cell Surface MFI2 Proteins Human MFI2 (hMFI2).

To generate all molecular and cellular materials of the present invention pertaining to the hMFI2 protein, a commercial human MFI2 cDNA clone was purchased from Thermo Scientific (IMAGE clone 100016036; accession BC152832), the open reading frame of which was determined by BLAST analysis to encode a protein 100% identical to the RefSeq for hMFI2, accession NP_005920. The BC152832 cDNA clone was used for all subsequent engineering of constructs expressing the mature hMFI2 protein or fragments thereof.

To produce immunoreactive antibodies to the hMFI2 protein, a chimeric fusion gene was generated in which the extracellular domain (ECD) of the hMFI2 protein was fused in-frame with either a Histidine tag or human IgG2 Fc tag. This was done as follows: a DNA fragment encoding the ECD of hMFI2 (residues G20-C709) was PCR amplified from the BC152832 cDNA clone and subcloned into a CMV driven expression vector in frame and downstream of an immunoglobulin kappa (IgK) signal peptide sequence and upstream of either a Histidine tag or a human IgG2 Fc cDNA, using standard molecular techniques.

The CMV-driven hMFI2 expression vector permits high level transient expression in HEK293T and/or CHO-S cells. Suspension or adherent cultures of HEK293T cells, or suspension CHO-S cells were transfected with expression constructs encoding either the hMFI2K-ECD-His or hMFI2 ECD-Fc proteins, using polyethylenimine polymer as the transfecting reagent. Three to five days after transfection, the hMFI2-ECD-His or hMFI2-ECD-Fc proteins were purified from clarified cell-supernatants using an AKTA explorer and either Nickel-EDTA (Qiagen) or MabSelect SuRe™ Protein A (GE Healthcare Life Sciences) columns, respectively.

Rat MFI2 (rMFI2).

In order to assemble constructs encoding the ECD of rMFI2 fused in-frame with either a Histidine tag or human IgG2 Fc tag, the sequence contained in the NCBI accession NM_001105872 was used to design three overlapping synthetic DNA pieces (gBlocks, IDT), which were then cloned into a CMV driven expression vector in frame and downstream of an IgK signal peptide sequence and upstream of either a Histidine tag or a human IgG2 Fc cDNA, using an in vitro recombination technique (In-Fusion, Clontech) according to manufacturer's instructions. Recombinant proteins were produced as described for the hMFI2 proteins, above.

Cell Line Engineering

Engineered cell lines overexpressing hMFI2 were constructed using lentiviral vectors to transduce HEK293T cell lines using art recognized techniques. First, standard molecular cloning techniques were used to introduce nucleotide sequences encoding an IgK signal peptide followed by a DDDK epitope tag upstream of the multiple cloning site of pCDH-EF1-MCS-T2A-GFP (System Biosciences), creating vector pCEMT. The T2A sequence in pCEMT promotes ribosomal skipping of a peptide bond condensation, resulting in expression of two independent proteins: high level expression of DDDK-tagged cell surface proteins encoded upstream of the T2A peptide, with co-expression of the GFP marker protein encoded downstream of the T2A peptide. pCEMT was used to create various MFI2 vectors as follows: a DNA fragment encoding the mature hMFI2 protein (residues G20-L738) was generated by PCR amplification, using the BC152832 cDNA clone as a template, with the resultant PCR product subcloned in-frame downstream of the IgK signal peptide-DDDK epitope tag in pCEMT. This yielded the pL120-hMFI2 lentiviral vector. This lentiviral vector was used to create stable HEK293T-based cell lines overexpressing hMFI2 protein using standard lentiviral transduction techniques well known to those skilled in the art, followed by MFI2-positive cell selection and fluorescent activated cell sorting (FACS) of high-expressing HEK293T subclones (e.g., cells that were strongly positive for GFP and the FLAG epitope).

Example 6

Generation of Anti-MFI2 Antibodies

To produce anti-MFI2 mouse antibodies one Balb/c mouse was inoculated with 10 µg hMFI2-His protein along with appropriate adjuvants. Following the initial inoculation the mouse was injected twice weekly for 4 weeks with 10 µg hMFI2-His protein along with appropriate adjuvants, where the final inoculation was conducted using 10 µg hMFI2-His protein along with appropriate adjuvants.

The mouse was sacrificed and draining lymph nodes (popliteal, inguinal, and medial iliac) were dissected and used as a source for antibody producing cells. A single cell suspension of B cells ($430 \times 10^6$ cells) was fused with non-secreting P3x63Ag8.653 myeloma cells (ATCC # CRL-1580) at a ratio of 1:1 by electro cell fusion using a model BTX Hybrimmune System (BTX Harvard Apparatus). Cells were re-suspended in hybridoma selection medium consisting of DMEM medium supplemented with azaserine, 15% fetal clone I serum, 10% BM conditioned medium, 1 mM nonessential amino acids, 1 mM HEPES, 100 IU penicillin-streptomycin, and 50 µM 2-mercaptoethanol, and were cultured in four T225 flasks in 100 mL selection medium per flask. The flasks were placed in a humidified 37° C. incubator containing 5% $CO_2$ and 95% air for six days.

Six days after the fusion the hybridoma library cells were collected from the flasks and the library was stored in liquid nitrogen. Frozen vials were thawed into T75 flasks and on the following day the hybridoma cells were plated at one cell per well (using the FACSAria I cell sorter) in 90 µL of supplemented hybridoma selection medium (as described above) into 15 Falcon 384-well plates.

The hybridomas were cultured for 10 days and the supernatants were screened for antibodies specific to hMFI2 using flow cytometry performed as follows. $1 \times 10^5$ per well of HEK293T cells stably transduced with hMFI2 were incubated for 30 min. with 25 µL hybridoma supernatant. Cells were washed with PBS/2% FCS and then incubated with 25 µL per sample DyeLight 649 labeled goat-anti-mouse IgG, Fc fragment specific secondary diluted 1:300 in PBS/2% FCS for 15 mins. Cells were washed twice with PBS/2% FCS and re-suspended in PBS/2% FCS with DAPI and analyzed by flow cytometry for fluorescence exceeding that of cells stained with an isotype control antibody. Remaining unused hybridoma library cells were frozen in liquid nitrogen for future library testing and screening.

The hMFI2-His immunization campaign yielded mouse antibodies that bound specifically to the surface of hMFI2-expressing HEK293T cells.

Example 7

Characteristics of Anti-MFI2 Antibodies

Various methods were used to characterize the anti-MFI2 mouse antibodies generated in Example 6 in terms of isotype, cross reactivity with rat MFI2, affinity for rat, cynomolgus, and human MFI2 and epitope binning. FIG. 5 is a table summarizing the aforementioned characteristics, where "ND" denotes 'not determined'.

The isotype of a representative number of antibodies was determined using the Milliplex mouse immunoglobulin isotyping kit (Millipore) according to the manufacturer's protocols. Results for the unique MFI2-specific antibodies can be seen in FIG. 5.

The affinity of the anti-hMFI2 mouse antibodies for rat MFI2-His was qualitatively determined from kinetics curves generated with a ForteBio RED as follows. 8 μg/mL purified anti-MFI2 antibodies were immobilized onto anti-mouse Fc capture biosensors with a contact time of 3 mins. and a shaking rate of 1000 rpm. The captured antibody loading from baseline was constant at 0.3-1 units. Following antibody capture and 50 sec. baseline, the biosensors were dipped into a 300 nM solution of purified hMFI2-His or rMFI2-His protein for a 60 sec. association phase followed by a 60 sec. dissociation phase at a shaking rate of 1000 rpm. The biosensors were regenerated by dipping into 10 mM glycine, pH 1.7 following each cycle. The data was processed by subtracting a control mouse IgG surface response from the specific antibody response and data was truncated to the association and dissociation phase. The association and dissociation curves were used to qualitatively estimate the ability of selected antibodies to bind hMFI2 and rMFI2. Of those tested, 8 antibodies were determined to cross-react with rMFI2-His with high affinity compared to the other antibodies that were screened (FIG. 5).

The affinity of select mouse and humanized anti-hMFI2 antibodies for human, cynomolgus, or rat MFI2 protein was quantitatively determined by surface plasmon resonance using a BIAcore 2000 instrument (GE Healthcare). An antibody capture kit was used to immobilize mouse or humanized anti-MFI2 antibodies on a CM5 biosensor chip. Prior to each antigen injection cycle, mouse or humanized antibodies at a concentration of 0.01-1 μg/mL were captured on the surface with a contact time of 1 min. and a flow rate of 5 μL/min. The captured antibody loading from baseline was constant at 80-120 response units. Following antibody capture and 1 min. baseline, monomeric hMFI2-His antigen, cMFI2-His, or rMFI2-His antigen was flowed over the surface at varying concentrations for a 1.5 min. association phase followed by a 5 min. dissociation phase at a flow rate of 10 μL/min. The data was processed by subtracting a control non-binding antibody surface response from the specific antibody surface response and data was truncated to the association and dissociation phase. The resulting response curves were fitted with a 1:1 Langmuir binding model to generate apparent affinity, $k_{on}$, and $k_{off}$ kinetic constants using BiaEvaluation Software 3.1 (GE Healthcare). The selected antibodies exhibited affinities for hMFI2, cMFI2, and rMFI2 in the nanomolar range (FIG. 5).

Antibodies were grouped into bins using a multiplexed competition immunoassay (Luminex). 100 μl of each unique anti-MFI2 antibody (capture mAb) at a concentration of 10 μg/mL was incubated for 1 hour with magnetic beads (Luminex) that had been conjugated to an anti-mouse kappa antibody (Miller et al., 2011, PMID: 21223970). The capture mAb/conjugated bead complexes were washed with PBSTA buffer (1% BSA in PBS with 0.05% Tween20) and then pooled. Following removal of residual wash buffer the beads were incubated for 1 hour with 2 μg/mL hMFI2-His protein, washed and then resuspended in PBSTA. The pooled bead mixture was distributed into a 96 well plate, each well containing a unique anti-MFI2 antibody (detector mAb) and incubated for 1 hour with shaking. Following a wash step, anti-mouse kappa antibody (the same as that used above), conjugated to PE, was added at a concentration of 5 μg/ml to the wells and incubated for 1 hour. Beads were washed again and resuspended in PBSTA. Mean fluorescence intensity (MFI) values were measured with a Luminex MAGPIX instrument. Antibody pairing was visualized as a dendrogram of a distance matrix computed from the Pearson correlation coefficients of the antibody pairs. Binning was determined on the basis of the dendrogram and analysis of the MFI values of antibody pairs. Antibodies that had low affinity binding for MFI2 and could not be placed in a specific Bin are denoted as being in Bin X. "ND" means that the binning experiment for the relevant antibody was not performed. FIG. 5 shows that the anti-MFI2 antibodies that were screened can be grouped into at least five unique bins (A-E) on the hMFI2 protein.

Example 8

Cross Reactivity of Anti-MFI2 Antibodies with Transferrin hMFI2 is a transferrin (Tf) homolog and shares 37-39% homology with human Tf. There are two forms of human Tf, Apo-Tf, which is iron-free, and Holo-Tf, which is iron-bound. In order to determine whether the antibodies of the invention cross reacted with either Apo-Tf or Holo-Tf, an ELISA assay was used.

Plates were coated with 5 μg/mL purified hMFI2-His, Holo-Tf (RnD cat. #2914-HT) or Apo-Tf (RnD cat. #3188-AT) in PBS buffer and incubated at 4° C. overnight. Plates were then washed with PBST (PBS plus 0.05% Tween 20) and blocked with 3% BSA in PBS for 1 hour at 37° C. The plates were washed and 10 μL of anti-MFI2 antibodies was added at 1.4 μg/mL for 1 hour at room temperature. Goat anti-mouse IgG detection antibody was sulfo-tagged using an MSD® SULFO-TAG NHS ester according to the manufacturer's protocol. MSD SULFO-TAG NHS-ester is an amine reactive, N-hydroxysuccinimide ester which readily couples to primary amine groups of proteins under mildly basic conditions to form a stable amide bond. The plate was washed and 10 μL/well of 0.5 μg/mL sulfo-tagged goat anti-mouse IgG was added for 30 min. at room temperature. The plate was washed and MSD Read Buffer T with surfactant was diluted to 1× in water and 35 μL was added to each well. Plates were read on an MSD Sector Imager 2400. A high signal indicates binding. Out of the 60 mouse anti-MFI2 antibodies that were tested, none cross reacted with either Apo-Tf or Holo-Tf. These results indicate that the antibodies of the invention do not cross react with free transferrin in plasma or normal cells expressing Tf.

Example 9

Sequencing of MFI2 Antibodies

The anti-MFI2 mouse antibodies that were generated (Example 6) were sequenced as described below. Total RNA was purified from selected hybridoma cells using the RNeasy Miniprep Kit (Qiagen) according to the manufacturer's instructions. Between $10^4$ and $10^5$ cells were used per sample. Isolated RNA samples were stored at −80° C. until used.

The variable region of the Ig heavy chain of each hybridoma was amplified using two 5' primer mixes comprising eighty-six mouse specific leader sequence primers designed to target the complete mouse VH repertoire in combination with a 3' mouse Cγ primer specific for all mouse Ig isotypes. Similarly, two primer mixes containing sixty-four 5' Vk leader sequences designed to amplify each of the Vk mouse families was used in combination with a single reverse primer specific to the mouse kappa constant region in order to amplify and sequence the kappa light chain. The VH and VL transcripts were amplified from 100 ng total RNA using the Qiagen One Step RT-PCR kit as follows. A total of four RT-PCR reactions were run for each hybridoma, two for the VK light chain and two for the VH heavy chain. PCR reaction mixtures included 1.5 μL of RNA, 0.4 μL of 100 μM of either heavy chain or kappa light chain primers (custom synthesized by IDT), 5 pL of 5x RT-PCR buffer, 1 μL dNTPs, and 0.6 μL of enzyme mix containing reverse transcriptase and DNA polymerase. The thermal cycler program was RT step 50° C. for 60 min., 95° C. for 15 min. followed by 35 cycles of (94.5° C. for 30 seconds, 57° C. for 30 seconds, 72° C. for 1 min.). There was then a final incubation at 72° C. for 10 min.

The extracted PCR products were sequenced using the same specific variable region primers as described above for the amplification of the variable regions. PCR products were sent to an external sequencing vendor (MCLAB) for PCR purification and sequencing services. Nucleotide sequences were analyzed using the IMGT sequence analysis tool (http://www.imgt.org/IMGTmedical/sequence analysis.html) to identify germline V, D and J gene members with the highest sequence homology. The derived sequences were compared to known germline DNA sequences of the Ig V- and J-regions by alignment of VH and VL genes to the mouse germline database using a proprietary antibody sequence database.

FIG. 6A depicts the contiguous amino acid sequences of numerous novel mouse light chain variable regions from anti-MFI2 antibodies and exemplary humanized light chain variable regions derived from the variable light chains of representative mouse anti-MFI2 antibodies. FIG. 6B depicts the contiguous amino acid sequences of novel mouse heavy chain variable regions from the same anti-MFI2 antibodies and humanized heavy chain variable regions derived from the same mouse antibodies providing the humanized light chains. Mouse light and heavy chain variable region amino acid sequences are provided in SEQ ID NOS: 21-91 odd numbers while humanized light and heavy chain variable region amino acid sequences are provided in SEQ ID NOS: 93-107, odd numbers.

Taken together FIGS. 6A and 6B provide the annotated sequences of several mouse anti-MFI2 antibodies, termed SC57.1 (identical sequence to SC57.2, 57.23), having a VL of SEQ ID NO: 21 and VH of SEQ ID NO: 23; SC57.3 (identical sequence to SC57.52, SC57.55), having a VL of SEQ ID NO: 25 and a VH of SEQ ID NO: 27; SC57.4 (identical sequence to SC57.16, SC57.18, SC57.25, SC57.28, SC57.37), having a VL of SEQ ID NO: 29 and a VH of SEQ ID NO: 31; SC57.5, having a VL of SEQ ID NO: 33 and a VH of SEQ ID NO: 35; SC57.6 (identical sequence to SC57.7, SC57.48), a VL of SEQ ID NO: 37 and a VH of SEQ ID NO: 39; SC57.8 having a VL of SEQ ID NO: 41 and a VH of SEQ ID NO: 43; SC57.9, having a VL of SEQ ID NO: 45 and a VH of SEQ ID NO: 47; SC57.10 (identical sequence to SC57.29, SC57.30, SC57.32, SC57.35, SC57.38, SC57.40, SC57.45, SC57.47, SC57.51, SC57.54), having a VL of SEQ ID NO: 49 and a VH of SEQ ID NO: 51; SC57.11 (identical sequence to SC57.41, SC57.56), having a VL of SEQ ID NO: 53 and a VH of SEQ ID NO: 55; SC57.12 (identical sequence to SC57.46), having a VL of SEQ ID NO: 57 and a VH of SEQ ID NO: 59; SC57.14, having a VL of SEQ ID NO: 61 and a VH of SEQ ID NO: 63; SC57.15, having a VL of SEQ ID NO: 65 and a VH of SEQ ID NO: 67; SC57.17, having a VL of SEQ ID NO: 69 and a VH of SEQ ID NO: 71; SC57.20, having a VL of SEQ ID NO: 73 and a VH of SEQ ID NO: 75; SC57.27, having a VL of SEQ ID NO: 77 and a VH of SEQ ID NO: 79; SC57.31 (identical sequence to SC57.53, SC57.57), having a VL of SEQ ID NO: 81 and a VH of SEQ ID NO: 83; SC57.43, having a VL of SEQ ID NO: 85 and a VH of SEQ ID NO: 87; and SC57.60, having a VL of SEQ ID NO: 89 and a VH of SEQ ID NO: 91. In addition, FIGS. 6A and 6B provide the annotated sequences of the humanized antibodies, termed hSC57.5, having a VL of SEQ ID NO: 93 and a VH of SEQ ID NO: 95; hSC57.5v1 (described in Example 13), having a VL of SEQ ID NO: 93 and a VH of SEQ ID NO: 97; hSC57.32, having a VL of SEQ ID NO: 99 and a VH of SEQ ID NO: 101; hSC57.32v1 (described in Example 13), having a VL of SEQ ID NO: 99 and a VH of SEQ ID NO: 103 and hSC57.43, having a VL of SEQ ID NO: 105 and a VH of SEQ ID NO: 107.

The amino acid sequences are annotated to identify the framework regions (i.e. FR1-FR4) and the complementarity determining regions (i.e., CDRL1-CDRL3 in FIG. 6A or CDRH1-CDRH3 in FIG. 6B), defined as per Kabat. The variable region sequences were analyzed using a proprietary version of the Abysis database to provide the CDR and FR designations. Though the CDRs are defined as per Kabat those skilled in the art will appreciate that the CDR and FR designations can also be defined according to Chothia, McCallum or any other accepted nomenclature system. FIG. 6C provides the nucleic acid sequences (SEQ ID NOS: 20-106 even numbers) encoding the amino acid sequences set forth in FIGS. 6A and 6B. FIG. 6D provides the amino acid sequences (SEQ ID NOS: 108-118) of exemplary full-length humanized heavy and light chains. FIGS. 6E-6G show the CDRs of the light and heavy chain variable regions of the SC57.5 (FIG. 6E), SC57.32 (FIG. 6F) and SC57.43 (FIG. 6G) murine antibodies as determined by Kabat, Chothia, ABM and Contact methods and numbered according to Kabat. Similarly, FIGS. 6H-6J provide aligned amino acid sequences for heavy and light chain variable regions of mouse source antibodies and derived humanized constructs (SC57.5—FIG. 6H, SC57.32—FIG. 6I and SC57.43—FIG. 6J) where CDRs as per Kabat are boxed.

As seen in FIGS. 6A and 6B the SEQ ID NOS. of the heavy and light chain variable region amino acid sequences for each particular murine antibody are sequential odd numbers. Thus the monoclonal anti-MFI2 antibody, SC57.1, comprises amino acid SEQ ID NOS: 21 and 23 for the light and heavy chain variable regions respectively; SC57.3 comprises SEQ ID NOS: 25 and 27; SC57.4 comprises SEQ ID NOS: 29 and 31, and so on. The corresponding nucleic acid sequence for each murine antibody amino acid sequence is included in FIG. 6C and has the SEQ ID NO. immediately preceding the corresponding amino acid SEQ ID NO. Thus, for example, the SEQ ID NOS. of the nucleic acid sequences of the VL and VH of the SC57.1 antibody are SEQ ID NOS: 20 and 22, respectively.

Example 10

Generation of Site Specific Antibodies

An engineered human IgG1/kappa anti-MFI2 site-specific antibody was constructed comprising a native light chain (LC) constant region and heavy chain (HC) constant region, wherein cysteine 220 (C220) in the upper hinge region of the HC, which forms an interchain disulfide bond with cysteine 214 (C214) in the LC, was substituted with serine (C220S). When assembled the HCs and LCs form an antibody comprising two free cysteines that are suitable for conjugation to a therapeutic agent. Unless otherwise noted, all numbering of constant region residues is in accordance with the EU numbering scheme as set forth in Kabat et al.

The engineered antibodies were generated as follows. An expression vector encoding the full length humanized anti-MFI2 antibody hSC57.5v1 HC (SEQ ID NO: 111) or hSC57.32 (SEQ ID NO: 113), was used as a template for PCR amplification and site directed mutagenesis. Site directed mutagenesis was performed using the QuickChange® system (Agilent Technologies) according to the manufacturer's instructions.

The vector encoding the mutant C220S HC of hSC57.5v1, hSC57.32, or hSC5757.43 was co-transfected with the native full length kappa LCs of hSC57.5v1, which is identical to the LC of hSC57.5 (SEQ ID NO: 108), or hSC57.32 (SEQ ID NO: 112) or hSC57.43 (SEQ ID NO: 116), respectively, in CHO-S cells and expressed using a mammalian transient expression system. The engineered anti-MFI2 site-specific antibodies containing the C220S mutant were termed hSC57.5v1ss1 and hSC57.32ss1. Amino acid sequences of the full length LC and HC of the hSC57.5v1ss1 (SEQ ID NOS: 108 and 110), hSC57.32ss1 (SEQ ID NOS: 112 and 114) and hSC57.43ss1 (SEQ ID NOS: 116 and 118) site specific antibodies are shown in FIG. 6D. The reactive cysteine in the LC is underlined as is the native or mutated residue at position 220 in the HC. The engineered anti-MFI2 antibodies were characterized by SDS-PAGE to confirm that the correct mutants had been generated. SDS-PAGE was conducted on a pre-cast 10% Tris-Glycine mini gel from life technologies in the presence and absence of a reducing agent such as DTT (dithiothreitol). Following electrophoresis, the gels were stained with a colloidal Coomassie solution. Under reducing conditions, two bands corresponding to the free LCs and free HCs, were observed (data not shown). This pattern is typical of IgG molecules in reducing conditions. Under non-reducing conditions, the band patterns were different from native IgG molecules, indicative of the absence of a disulfide bond between the HC and LC. A band around 98 kD corresponding to the HC-HC dimer was observed. In addition, a faint band corresponding to the free LC and a predominant band around 48 kD that corresponded to a LC-LC dimer was observed. The formation of some amount of LC-LC species is expected due to the free cysteines on the C-terminus of each LC.

Example 11

Generation of Chimeric and Humanized Anti-MFI2 Antibodies

Chimeric anti-MFI2 antibodies were generated using art-recognized techniques as follows. Total RNA was extracted from the anti-MFI2 antibody-producing hybridomas using the method described in Example 1 and the RNA was PCR amplified. Data regarding V, D and J gene segments of the VH and VL chains of the mouse antibodies were obtained from the nucleic acid sequences (FIG. 6C) of the anti-MFI2 antibodies of the invention. Primer sets specific to the framework sequence of the VH and VL chain of the antibodies were designed using the following restriction sites: AgeI and XhoI for the VH fragments, and XmaI and DraIn for the VL fragments. PCR products were purified with a Qiaquick PCR purification kit (Qiagen), followed by digestion with restriction enzymes AgeI and XhoI for the VH fragments and XmaI and DraIII for the VL fragments. The VH and VL digested PCR products were purified and ligated into IgH or Igk expression vectors, respectively. Ligation reactions were performed in a total volume of 10 µL with 200U T4-DNA Ligase (New England Biolabs), 7.5 µL of digested and purified gene-specific PCR product and 25 ng linearized vector DNA. Competent E. coli DH10B bacteria (Life Technologies) were transformed via heat shock at 42° C. with 3 µL ligation product and plated onto ampicillin plates at a concentration of 100 µg/mL. Following purification and digestion of the amplified ligation products, the VH fragment was cloned into the AgeI-XhoI restriction sites of the pEE6.4 expression vector (Lonza) comprising HuIgG1 (pEE6.4HuIgG1) and the VL fragment was cloned into the XmaI-DraIII restriction sites of the pEE12.4 expression vector (Lonza) comprising a human kappa light constant region (pEE12.4Hu-Kappa).

Chimeric antibodies were expressed by co-transfection of CHO-S cells with pEE6.4HuIgG1 and pEE12.4Hu-Kappa expression vectors. 2.5 µg each of pEE6.4HuIgG1 and pEE12.4Hu-Kappa vector DNA were added to 15 µg PEI transfection reagent in 400 µL Opti-MEM. The mix was incubated for 10 min. at room temperature and added to cells. Supernatants were harvested three to six days after transfection. Culture supernatants containing recombinant chimeric antibodies were cleared from cell debris by centrifugation at 800×g for 10 min. and stored at 4° C. Recombinant chimeric antibodies were purified with Protein A beads.

In addition mouse anti-MFI2 antibodies were humanized using a proprietary computer-aided CDR-grafting method (Abysis Database, UCL Business) and standard molecular engineering techniques as follows. Human framework regions of the variable regions were designed based on the highest homology between the framework sequences and CDR canonical structures of human germline antibody sequences, and the framework sequences and CDRs of the relevant mouse antibodies. For the purpose of the analysis the assignment of amino acids to each of the CDR domains was done in accordance with Kabat et al. numbering. Once the variable regions were selected, they were generated from synthetic gene segments (Integrated DNA Technologies). Humanized antibodies were cloned and expressed using the molecular methods described above for chimeric antibodies.

The VL and VH amino acid sequences of the humanized antibody hSC57.5 (SEQ ID NOS: 93 and 95), hSC57.32 (SEQ ID NOS: 99 and 101), hSC57.43 (SEQ ID NOS: 105 and 107) were derived from the VL and VH sequences of the corresponding mouse antibodies SC57.5 (SEQ ID NOS: 33 and 35), SC57.32 (SEQ ID NOS: 49 and 51), and SC57.43 (SEQ ID NOS: 85 and 87), respectively. TABLE 5 below and FIGS. 6H-6J show that relatively few framework changes were necessary to maintain the favorable properties of the antibodies.

A variation of hSC57.5 was generated in which a G55A mutation in the VH CDRH2 was introduced to produce the hSC57.5v1 antibody (SEQ ID NOS: 93 and 97). The VL of hSC57.5v1 was identical to the VL of hSC57.5 (SEQ ID NO: 93). The hSC57.5v1ss1 had identical VH and VL as hSC57.5v1. Three framework changes were introduced in the hSC57.32 and hSC57.32ss1 antibodies: two in the VH: M69F and T71A, and one in the VL: F71Y. In hSC57.32v1 two framework changes were introduced: one in the VH: T71A, and one in the VL: F71Y. A single point mutation S30G was introduced into the VH framework region of the hSC57.43 and hSC57.43ss1 antibody.

The amino acid sequences of the full length light chain and heavy chain of the humanized antibodies hSC57.5, hSC57.5v1, hSC57.5v1ss1, hSC57.32, hSC57.32v1, hSC57.32ss1, hSC57.43 and hSC57.43ss1 are shown in FIG. 6D.

minutes' incubation on ice, cells were washed twice with PBSA and analyzed on a FACSCanto II (BD Biosciences). FIG. 5 shows that of the antibodies that were tested the majority bound to TLD2 indicating that most of the antibodies are specific to the long, GPI-anchored isoform of MFI2. Of note, only those antibodies that were in Bin E (See Example 8; FIG. 5) bound to TLD1, whereas antibodies that were in Bins A-D bound to TLD2. "ND" in FIG. 5 denotes "not determined", meaning that the experiment was not performed on the specific antibody.

In order to classify an epitope as conformational (e.g., discontinuous) or linear, yeast displaying the hMFI2 domains was heat treated for 30 minutes at 80° C. and then

TABLE 5

| mAb | Isotype | human VH | human JH | VH FR changes | VH CDR changes | human VK | human JK | VK FR changes | VK CDR changes |
|---|---|---|---|---|---|---|---|---|---|
| hSC57.5 | IgG1/κ | IGHV5-51*01 | JH6 | None | None | IGKV1-39*01 | JK1 | None | None |
| hSC57.5 v1 | IgG1/κ | IGHV5-51*01 | JH6 | None | G55A | IGKV1-39*01 | JK1 | None | None |
| hSC57.5 v1ss1 | IgG1 C220S/κ | IGHV5-51*01 | JH6 | None | G55A | IGKV1-39*01 | JK1 | None | None |
| hSC57.32 | IgG1/κ | IGHV1-18*01 | JH1 | M69F T71A | None | IGKV1-39*01 | JK4 | F71Y | None |
| hSC57.32v1 | IgG1/κ | IGHV1-18*01 | JH1 | T71A | None | IGKV1-39*01 | JK4 | F71Y | None |
| hSC57.32ss1 | IgG1 C220S/κ | IGHV1-18*01 | JH1 | M69F T71A | None | IGKV1-39*01 | JK4 | F71Y | None |
| hSC57.43 | IgG1/κ | IGHV3-30*03 | JH6 | S30G | None | IGKV4-1*01 | JK4 | None | None |
| hSC57.43ss1 | IgG1 C220S/κ | IGHV3-30*03 | JH6 | S30G | None | IGKV4-1*01 | JK4 | None | None |

Example 12

Domain-Level Epitope Mapping of Anti-MFI2 Antibodies

In order to characterize the epitopes with which the disclosed anti-MFI2 antibodies associate, domain-level epitope mapping was performed using a FACS-based method with yeast displayed domains that is a modification of the protocol described by Cochran et al. (2004, PMID: 15099763).

Yeast display plasmid constructs were generated for the expression of the hMFI2 Tf-like Domain 1 (TLD1) comprising amino acids 20-357; and Tf-like Domain 2 (TLD2) comprising amino acids 366-709. The numbering of both domains included amino acids 1-19, the leader sequence of hMFI2. For domain information see generally UniProtKB/Swiss-Prot database entry P08582. The long isoform of hMFI2 comprises both TLD1 and TLD2 whereas the short isoform of hMFI2 comprises only TLD1 but not TLD2. Therefore, those antibodies that bound to TLD2 are specific to the long, GPI-anchored isoform of hMFI2.

The yeast display plasmids were transformed into yeast, which were then grown and induced as described in Cochran et aL (supra). To test for binding to a particular construct, 200,000 induced yeast cells expressing the desired construct were washed twice in PBS with 1 mg/mL BSA (PBSA). Yeast cells were incubated in 50 µL of PBSA with chicken anti c-Myc (Life Technologies) antibodies at 1 µg/mL and purified anti-MFI2 antibodies at 50 ng/mL for 90 minutes on ice and then washed twice in PBSA. Cells were then incubated in 50 µL PBSA with Alexa 488 conjugated anti-chicken and Alexa 647 conjugated goat anti-mouse antibodies (both Life Technologies) at 1 µg/mL each. After twenty washed twice in ice-cold PBSA. Yeast displaying denatured antigen (denatured yeast) were then subjected to the same staining protocol and flow cytometry analysis as described above. Anti-MFI2 antibodies that bound to both the denatured and native yeast were classified as binding to a linear epitope, whereas anti-MFI2 antibodies that bound native yeast but not denatured yeast were classified as conformationally specific. The majority of antibodies tested were found to be conformationally specific with the exceptions of SC57.2, SC57.7, SC57.31, SC57.53, and SC57.57, which bound to linear epitopes.

Example 13

Fine Epitope Mapping of Anti-MFI2 Antibodies

Fine epitope mapping was further performed on selected anti-MFI2 antibodies using a yeast display method (Chao et al., Nat Protoc. 1(2): 755-768, 2007). Briefly, libraries of hMFI2 ECD mutants were generated with error prone PCR using nucleotide analogues 8-oxo-2'deoxyguanosine-5'-triphosphate and 2'-deoxy-p-nucleoside-5'triphosphate (both from TriLink Bio) for a target mutagenesis rate of one amino acid mutation per clone. These were transformed into a yeast display format. Using the technique described above for domain-level mapping, the library was stained for c-Myc and anti-MFI2 antibody binding at 50 nM. Using a FACS Aria (BD), clones that exhibited a loss of binding compared to wild type hMFI2 ECD were re-grown, and subjected to another round of FACS sorting for loss of binding to the target antibody. Using the Zymoprep Yeast Plasmid Miniprep kit (Zymo Research), individual ECD clones were isolated and sequenced. Where necessary, mutations were reformatted as single-mutant ECD clones using the Quikchange site directed mutagenesis kit (Agilent).

Individual single-mutant ECD clones were next screened to determine whether loss of binding was due to a mutation in the epitope, or a mutation that caused misfolding. Mutations that involved cysteine, proline, and stop codons were automatically discarded due to the high likelihood of a misfolding mutation. ECD clones were then screened for binding to various non-competing, conformationally specific antibodies. ECD clones that lost binding to non-competing, conformationally specific antibodies were concluded to contain misfolding mutations, whereas ECD clones that retained equivalent binding as wild type hMFI2 ECD were concluded to be properly folded. Mutations in the ECD clones in the latter group were concluded to be in the epitope.

Results of the mapping of various antibodies are shown below in TABLE 6 where specific mutations are indicated along with the ability of the subject antibody to bind the mutated MFI2 homolog. In TABLE 7 those residues implicated as epitope constituents are indicated by a # in front of the mutated residue.

TABLE 6

| | Bins | | | | | |
|---|---|---|---|---|---|---|
| hMFI2 mutant | D Loss of binding with SC57.4 | B Loss of binding with SC57.5 | F Loss of binding with SC57.9 | C Loss of binding with SC57.32 | C Loss of binding with SC57.41 | A Loss of binding with SC57.43 |
| #D460A | None | None | None | Partial | Partial | None |
| S461A | None | None | None | None | None | None |
| S462A | None | None | None | None | None | None |
| #H463A | None | None | None | Complete | Complete | None |
| F465A | None | None | None | None | None | None |
| #N566A | None | None | None | Partial | Partial | None |
| V570A | None | None | None | None | None | None | implicated as an epitope component

Based on data derived from the mutated homologs potential epitope constituents for SC57.32, and SC57.41 are set forth in TABLE 7 immediately below.

TABLE 7

| Antibody Clone | Epitope Associated Residues |
|---|---|
| SC57.32 | D460, H463, N566 |
| SC57.41 | D460, H463, N566 |

Example 14

MFI2 Protein Expression in Tumors

Given the elevated MFI2 mRNA transcript levels associated with various tumors described in Examples 1-3, work was undertaken to test whether MFI2 protein expression was also elevated in PDX tumors. To detect and quantify MFI2 protein expression, an electrochemiluminscence MFI2 sandwich ELISA assay was developed using the MSD Discovery Platform (Meso Scale Discovery).

PDX tumors were excised from mice and flash frozen on dry ice/ethanol. Protein Extraction Buffer (Biochain Institute) was added to the thawed tumor pieces and tumors were pulverized using a TissueLyser system (Qiagen). Lysates were cleared by centrifugation (20,000 g, 20 min., 4° C.) and the total protein concentration in each lysate was quantified using bicinchoninic acid. The protein lysates were then normalized to 5 mg/mL and stored at −80° C. until used. Normal tissues were purchased from a commercial source.

MFI2 protein concentrations from the lysate samples were determined by interpolating the values from a standard protein concentration curve that was generated using purified recombinant MFI2-His protein, generated as described in Example 5. The MFI2 protein standard curve and protein quantification assay were conducted as follows:

MSD standard plates were coated overnight at 4° C. with 15 µL of SC57.2 capture antibody at 2 µg/mL in PBS. Plates were washed in PBST and blocked in 35 µL MSD 3% Blocker A solution for one hour while shaking. Plates were again washed in PBST. 10 µL of 10× diluted lysate (or serially diluted recombinant MFI2 standard) in MSD 1% Blocker A containing 10% Protein Extraction Buffer was also added to the wells and incubated for two hours while shaking. Plates were again washed in PBST. The SC57.10 detection antibody was then sulfo-tagged using an MSD® SULFO-TAG NHS Ester according to the manufacturer's protocol. 10 µL of the tagged SC57.10 antibody was added to the washed plates at 0.5 µg/mL in MSD 1% Blocker A for 1 hour at room temperature while shaking. Plates were washed in PBST. MSD Read Buffer T with surfactant was diluted to 1× in water and 35 µL was added to each well. Plates were read on an MSD Sector Imager 2400 using an integrated software analysis program to derive MFI2 concentrations in PDX samples via interpolation from the standard curve. Values were then divided by total protein concentration to yield nanograms of MFI2 per milligram of total lysate protein. The resulting concentrations are set forth in FIG. 7 wherein each spot represents MFI2 protein concentrations derived from a single PDX tumor line. While each spot is derived from a single PDX line, in most cases multiple biological samples were tested from the same PDX line and values were averaged to provide the data point.

Figure 7:
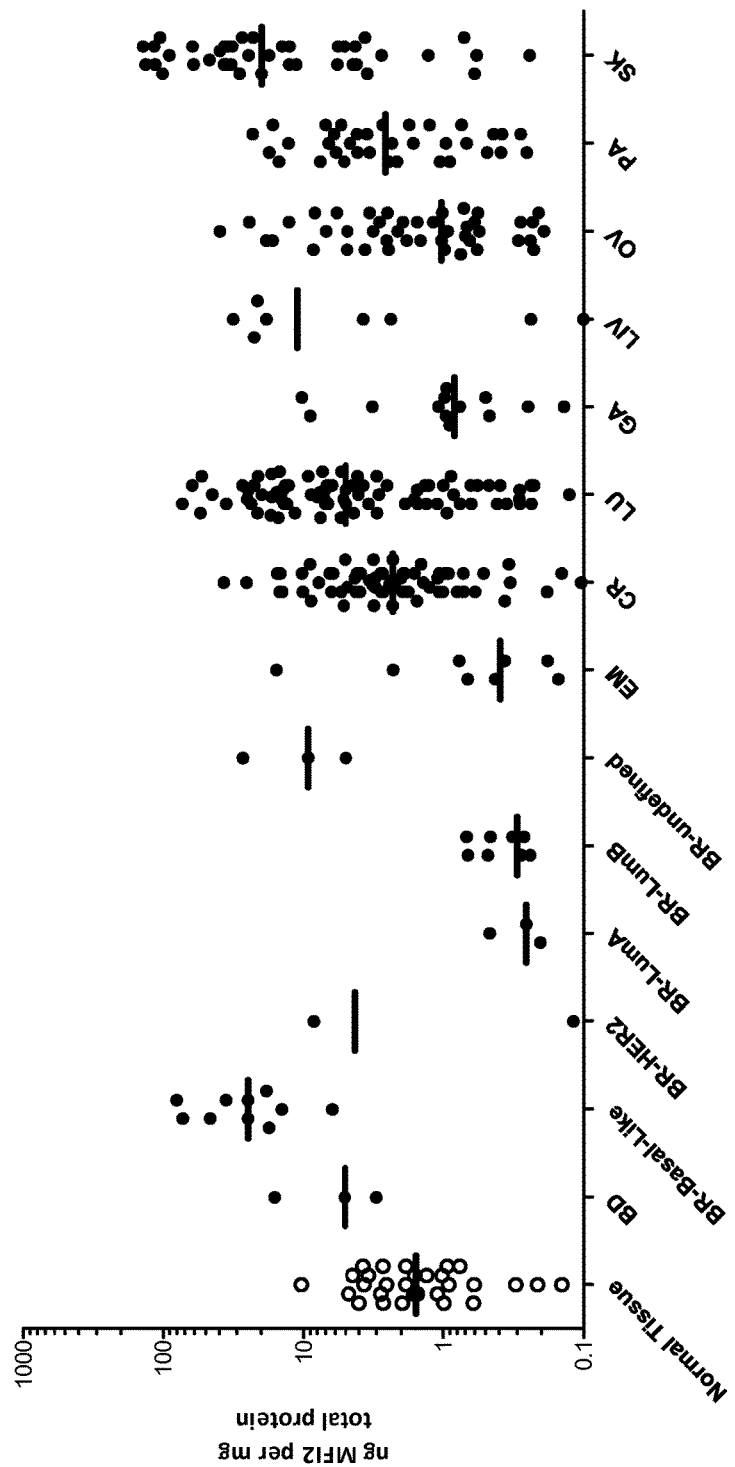
FIG. 7 shows the relative protein expression of human MFI2 in various PDX cell lines measured using an electrochemiluminescent sandwich ELISA assay.

FIG. 7 shows that representative samples of BD, BR (BR-Basal-Like, BR-HER2, BR-LumA, BR-LumB, BR-undefined), EM, CR, LU, GA, LIV, OV, PA and SK tumor samples exhibited high MFI2 protein expression. The levels of MFI2 protein expression for each sample are given in ng/mg total protein and the median derived for each tumor type is indicated by the horizontal bar. Normal tissues that were tested include adrenal gland, artery, colon, esophagus, gall bladder, heart, kidney, liver, lung, peripheral and sciatic nerve, pancreas, skeletal muscle, skin, small intestine, spleen, stomach, trachea, red and white blood cells and platelets, bladder, brain, breast, eye, lymph node, ovary, pituitary gland, prostate and spinal cord. Detectable levels of MFI2 protein were only seen in spinal cord, packed RBC and peripheral blood leukocytes. Several BD, BR, CR, LU, PA and SK PDX tumor samples were significantly higher than the average normal tissue. These data, combined with the mRNA transcription data for MFI2 expression set forth above strongly reinforce the proposition that MFI2 is an attractive target for antibody-based therapeutic intervention.

Example 15

Immunohistochemistry

Immunohistochemistry (IHC) was performed on PDX tumor and primary human tumor tissue sections to assess the expression and location of MFI2 in tumor cells.

In order to identify an IHC-compatible anti-MFI2 antibody, IHC was performed on HEK293T parental cell pellets or MFI2-expressing HEK293T cell pellets using numerous anti-MFI2 antibodies of the invention. Anti-MFI2 antibodies SC57.5, SC57.11, SC57.30, SC57.32, SC5735, SC5736 and SC57.47 were able to specifically detect MFI2-overexpressing HEK293T cell pellets more effectively than other anti-MFI2 antibodies of the invention that were tested (data not shown). The ability of these antibodies to specifically detect MFI2 was confirmed by a competition experiment in which the relevant anti-MFI2 antibody was mixed with a 5× molar ratio excess of hMFI2-His protein and then incubated with MFI2-expressing HEK293T formalin fixed and paraffin embedded (FFPE) sections. The absence of positive staining demonstrated that the hMFI2-His protein interfered with the binding of the anti-MFI2 antibody to the MFI2-overexpressing HEK293T cells (data not shown).

IHC was performed, as described below, on formalin fixed and paraffin embedded (FFPE) tissues as is standard in the art. Planar sections of tissues were cut and mounted on glass microscope slides. After xylene de-paraffinization 5 μm sections were pre-treated with Antigen Retrieval Solution (Dako) for 20 mins. at 99° C., cooled to 75° C. and then treated with 0.3% hydrogen peroxide in PBS followed by Avidin/Biotin Blocking Solution (Vector Laboratories). FFPE slides were then blocked with 10% horse serum in 3% BSA in PBS buffer and incubated with a primary anti-MFI2 antibody of the invention, diluted to 10 μg/ml in 3% BSA/PBS, for 30 mins. at room temperature. FFPE slides were incubated with biotin-conjugated horse anti-mouse antibody (Vector Laboratories), diluted to 2.5 μg/ml in 3% BSA/PBS, for 30 mins. at room temperature followed by incubation in streptavidin-HRP (ABC Elite Kit; Vector Laboratories). FFPE slides of primary human tumors were then incubated in biotinyl tyramide followed by incubation in streptavidin-HRP following manufacturers' instruction from the TSA amplification kit (TSA Amplification Kit; Perkin Elmer). Chromogenic detection was developed with 3,3'-diaminobenzidine (Thermo Scientific) for 5 mins. at room temperature and tissues were counterstained with Meyer's hematoxylin (IHC World), washed with alcohol and immersed in xylene. PDX tumors did not receive the TSA amplification. Sections were then viewed by brightfield microscopy and MFI2 membranous expression on tumor epithelium was noted by H-score. The H-score is obtained by the formula: 3× percentage of strongly staining nuclei+2× percentage of moderately staining nuclei+percentage of weakly staining nuclei, giving a range of 0 to 300.

Figure 8B:
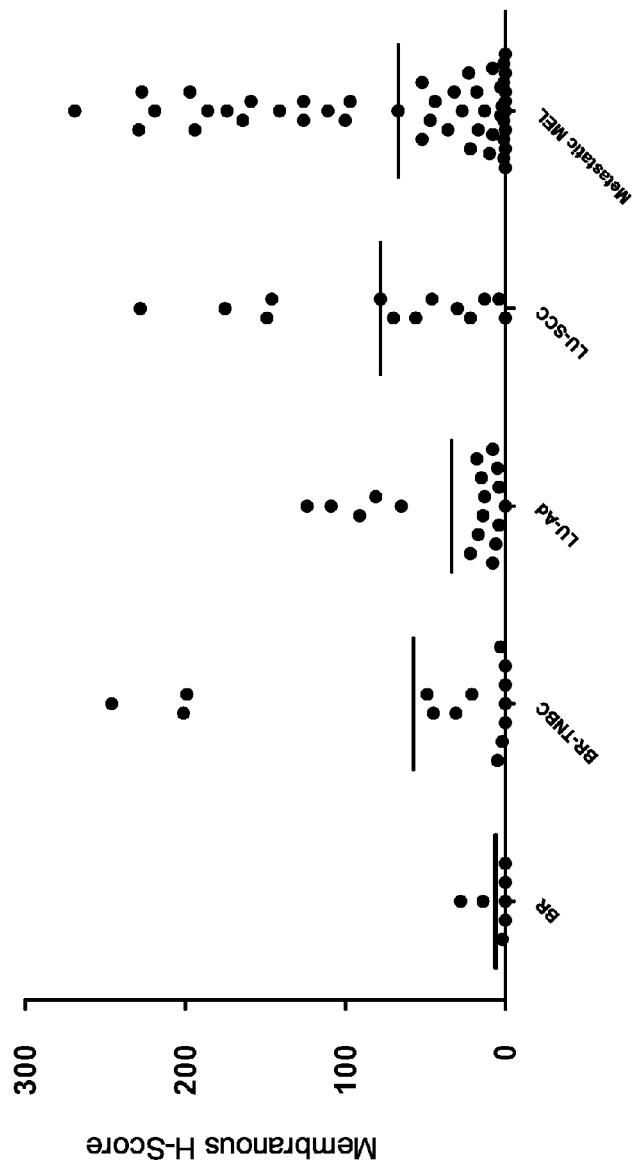
FIG. 8B depicts the H-score of hMFI2 protein expression on the membrane of cells in melanoma, breast and lung cancer samples using immunohistochemistry.

FIG. 8A lists the H-score values of membranous hMFI2 protein expression by IHC in various BR, LU and SK PDX lines. FIG. 8B depicts MFI2 expression on human primary breast cancer, lung cancer and melanoma tissue samples by IHC. MFI2 is shown to have expression in 50% of triple negative breast cancer patient samples by IHC, in 61% of lung adenocarcinoma samples, in 85% of lung squamous carcinoma samples, and in 61% of metastatic melanoma patient samples.

Example 16

Detection of MFI2 Expression on HEK293T Cells and Tumors Using Flow Cytometry

Flow cytometry was used to assess the ability of the anti-MFI2 antibodies of the invention to specifically detect the presence of human MFI2 protein on the surface of SK, BR and LU PDX tumor cell lines. In addition, the expression of MFI2 on the surface of BR and LU CSCs was also determined.

The PDX tumors were harvested and dissociated using art-recognized enzymatic tissue digestion techniques to obtain single cell suspensions of PDX tumor cells (see, for example, U.S.P.N. 2007/0292414). PDX tumor single cell suspensions were incubated with 4',6-diamidino-2-phenylindole (DAPI) to detect dead cells, anti-mouse CD45 and H-2K$^d$ antibodies to identify mouse cells and anti-human EPCAM antibodies to identify human carcinoma cells. The resulting single cell suspensions comprised a bulk sample of tumor cells including both NTG cells and CSCs. In order to partition bulk LU PDX tumor cell populations into NTG and CSC subpopulations, the PDX tumor cells were incubated with anti-human CD46 and/or CD324 and ESA antibodies (see U.S.P.N.s 2013/0260385, 2013/0061340 and 2013/0061342). Bulk or sorted tumor cells were analyzed for hMFI2 expression by flow cytometry using a BD FACS Canto II flow cytometer with SC57.43, an anti-MFI2 antibody that binds to the transferrin-like domain 2 (TFLD2) on the long isoform of the human MFI2 protein.

Figure 9A:
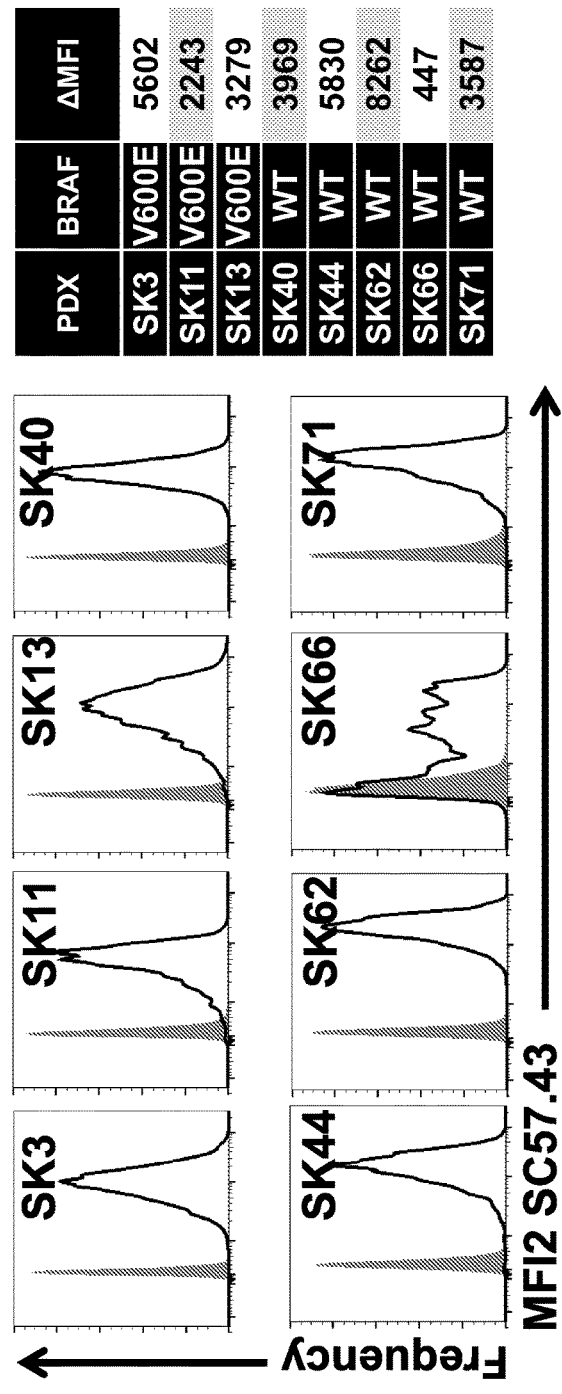
FIGS. 9A and 9B show surface protein expression of MFI2 determined by flow cytometry in melanoma (FIG. 9A), lung and breast (FIG. 9B) PDX cell lines (black line) compared to an isotype-control stained population (solid gray).

FIG. 9A shows that the SC57.43 antibody detected higher levels of surface expression of hMFI2 in a subset of live, unsorted human SK tumor cell lines (e.g. SK3, SK11, SK13, SK40, SK44, SK62, SK66, SK71) (black line) compared to the IgG isotype control antibody (gray-filled). A subset of the SK PDX lines expressed a mutated BRAF protein (V600E) (e.g. SK3, SK11, SK13), while others expressed wild type BRAF (SK40, SK44, SK62, SK66, SK71). These results indicate that the anti-MFI2 antibodies of the invention may be useful for diagnosing and treating melanoma and may also be useful in treating melanoma that expresses either wild type or mutated BRAF.

Figure 9B:
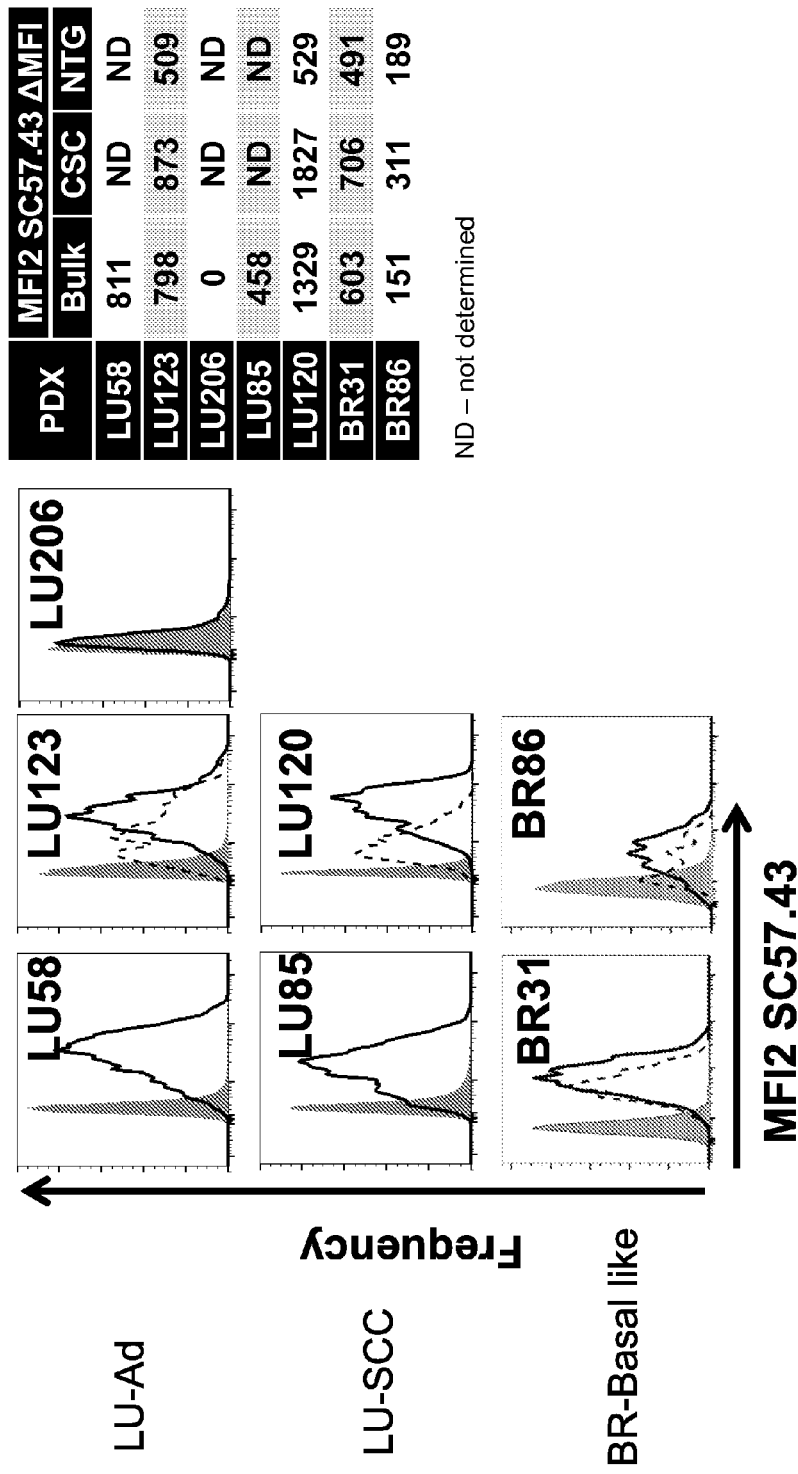

FIG. 9B shows that the anti-hMFI2 antibody SC57.43 detected expression of hMFI2 on the surface of bulk LU and BR PDX tumor cells. In all samples, the anti-MFI2 antibody (black line) detected increased MFI2 expression compared to the IgG isotype control antibody (gray-filled). For LU-Ad (LU58 and LU206) as well as for LU-SCC (LU85) the solid black line indicates staining of bulk human tumor cells of the anti-MFI2 antibody, showing that expression of hMFI2 was detected on LU58 and LU85 but not the LU206 PDX line. PDX tumor samples LU123 (LU-Ad), LU120 (LU-SCC), BR31 and BR86 (both BR-Basal-Like) showed increased hMFI2 expression on CSC (solid black line) and NTG subpopulations of LU and BR PDX tumor cells (dashed line) compared to the IgG isotype control antibody (gray-filled). This demonstrates that MFI2 is expressed on CSC in a number of LU tumor subtypes (LU-Ad and LU-SCC); and also BR tumors. Expression can be quantified as the change in geometric mean fluorescence intensity (AMFI) observed on the surface of tumor cells which have been stained with an anti-MFI2 antibody compared to the same tumor that has been stained with an isotype control antibody. A table summarizing the AMFI of for each of the tumor cell lines that were analyzed is shown as an insert in FIGS. 9A and 9B. This data confirms the IHC results in Example 15 above, in which breast cancer PDX lines BR31 and BR86 and melanoma PDX lines SK3 and SK40, also show positive staining by IHC and flow cytometry. LU206 did not show expression of hMFI2 by flow cytometry, which was expected, based on the low RNA expression data provided in Examples 1, 2 and 3 above; and further demonstrates specificity of anti-MFI2 antibody binding. Collectively, this data suggests that the long form of MFI2, which is GPI-anchored, is expressed in SK, LU and BR PDX tumor cells making these good indications for targeted therapy with an anti-MFI2 antibody drug conjugate.

Example 17

Anti-MFI2 Antibodies Facilitate Delivery of Cytotoxic Agents in Vitro

To determine whether anti-MFI2 antibodies of the invention were able to internalize in order to mediate the delivery of cytotoxic agents to live tumor cells, an in vitro cell killing assay was performed using selected anti-MFI2 antibodies and a secondary anti-mouse antibody FAB fragment linked to saporin. Saporin is a plant toxin that deactivates ribosomes, thereby inhibiting protein synthesis and resulting in the death of the cell. Saporin is only cytotoxic inside the cell where it has access to ribosomes, but is unable to internalize independently. Therefore, saporin-mediated cellular cytotoxicity in these assays is indicative of the ability of the anti-mouse FAB-saporin construct to internalize upon binding and internalization of the associated anti-MFI2 mouse antibodies into the target cells.

Figure 10A:
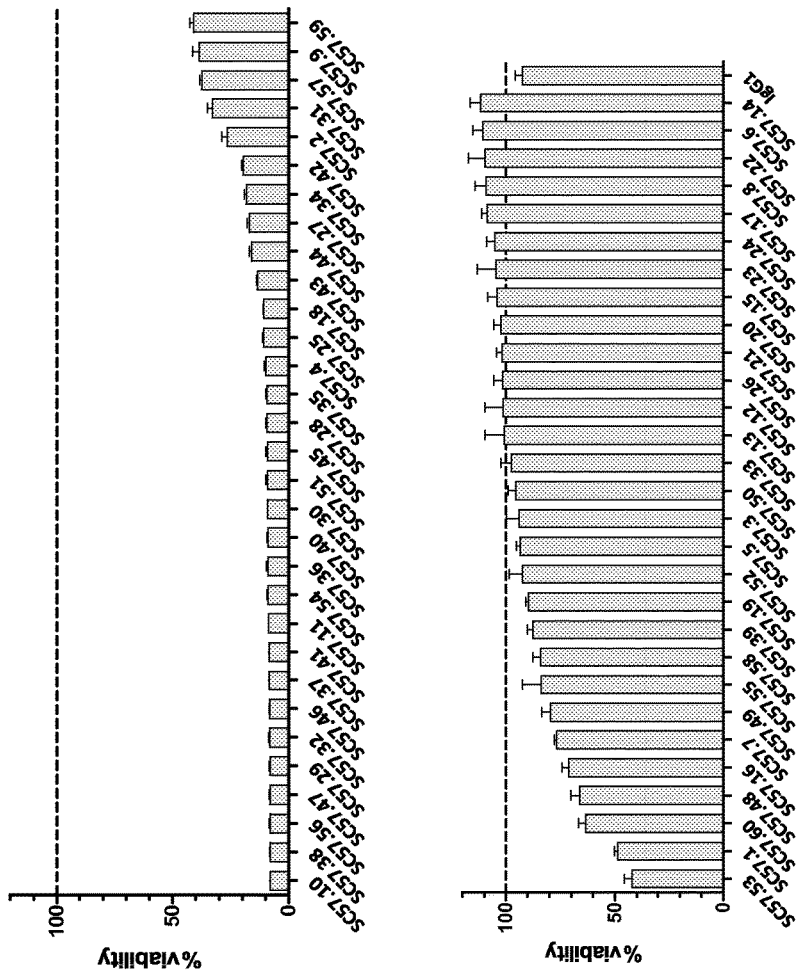
FIGS. 10A-10D show the ability of selected anti-MFI2 murine antibodies (associated with goat anti-mouse antibodies directly conjugated to saporin) to internalize into HEK293T cells overexpressing MFI2 protein (FIG. 10A) or melanoma PDX cells (FIG. 10B) and to kill such cells. Similarly

Single cell suspensions of HEK293T cells overexpressing hMFI2 were plated at 500 cells per well into BD Tissue Culture plates (BD Biosciences). One day later, various concentrations of purified anti-MFI2 antibodies (either murine or humanized) were added to the culture together with a fixed concentration of 2 nM anti-mouse IgG FAB-saporin constructs (Advanced Targeting Systems) (for testing mouse antibodies) or 2 nM anti-human IgG FAB-saporin conjugates (for testing humanized antibodies). After incubation for 96 hours viable cells were enumerated using CellTiter-Glo® (Promega) as per the manufacturer's instructions. Raw luminescence counts using cultures containing cells incubated only with the secondary FAB-saporin conjugate were set as 100% reference values and all other counts were calculated as a percentage of the reference value. A large subset of anti-MFI2 antibody-saporin conjugates at a concentration of 100 µM effectively killed HEK293T cells overexpressing hMFI2 with varying efficacy (FIG. 10A), whereas the mouse IgG1 isotype control antibody at the same concentration did not.

Figure 10B:
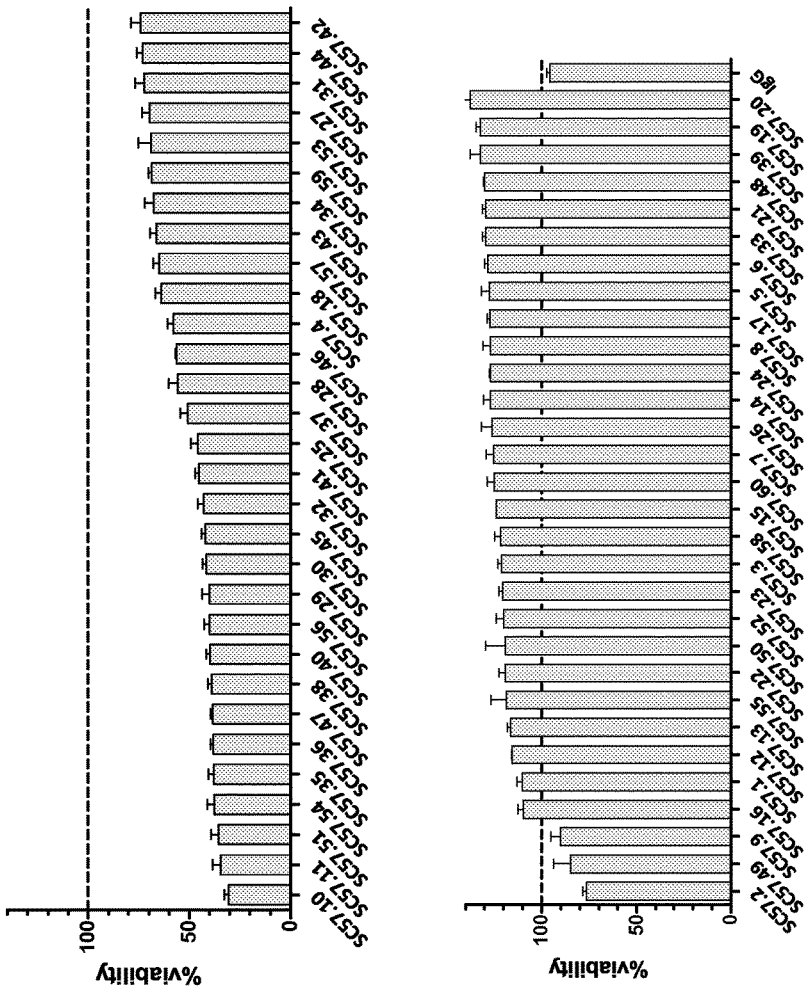

The above experiment was repeated using a melanoma PDX tumor cell line (SK43). The SK PDX tumors were harvested from mice and were magnetically depleted of mouse cells using biotinylated anti-mouse CD45 and H-2K$^d$ antibodies and streptavidin-coated ferrous beads. The tumors were then dissociated using art-recognized enzymatic tissue digestion techniques to obtain single cell suspensions of cells (see, for example, U.S.P.N. 2007/0292414). The cells were plated at 2,500 cells per well in DMEM medium as known in the art. 250 µM of purified anti-MFI2 antibodies were added to the culture together with a fixed concentration of 2 nM anti-mouse IgG FAB-saporin construct. After incubation for seven days viable cells were enumerated using CellTiter-Glo® as per the manufacturer's instructions. Raw luminescence counts using cultures containing cells incubated only with the secondary FAB-saporin conjugate were set as 100% reference values and all other counts were calculated as a percentage of the reference value. FIG. 10B shows that a significant number of anti-MFI2 mouse antibody-saporin conjugates effectively killed SK43 PDX tumor cells.

Figure 10C:
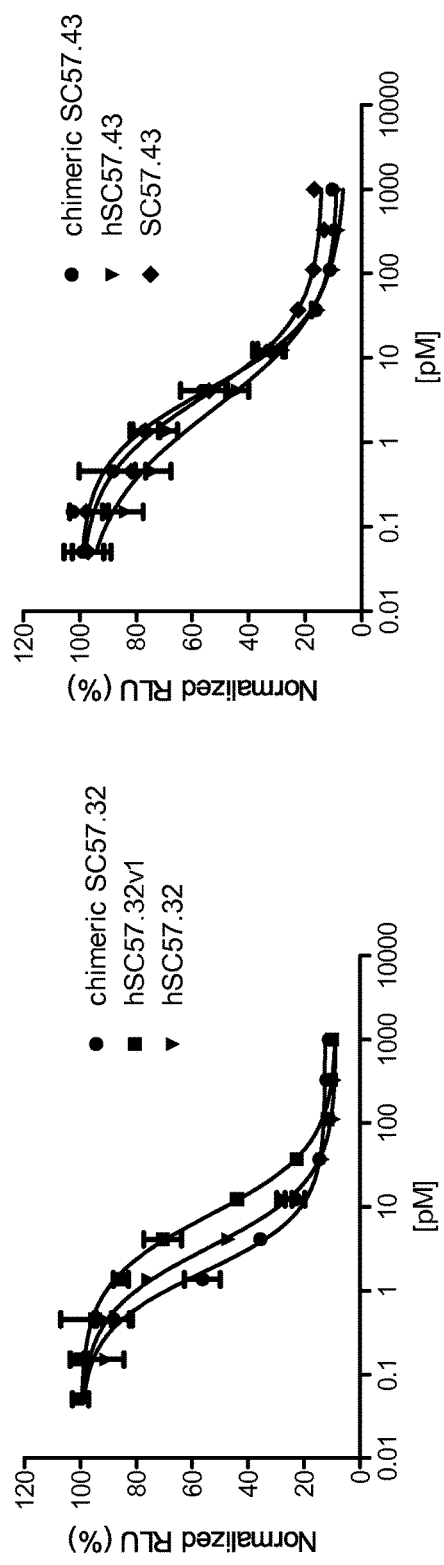

Finally, the anti-MFI2 humanized antibodies (hSC57.32, hSC57.32v1 and hSC57.43) effectively killed HEK-293T cells overexpressing MFI2. The humanized antibodies showed comparable efficacy to the chimeric antibody (in the case of hSC57.32 and hSC57.43) as well as the murine antibody (in the case of hSC57.43) from which they were derived (FIG. 10C). The above results demonstrate the ability of anti-MFI2 antibodies to mediate internalization of a conjugated cytotoxic payload, supporting the hypothesis that anti-MFI2 antibodies may have therapeutic utility as the targeting moiety for an ADC.

Figure 10D:
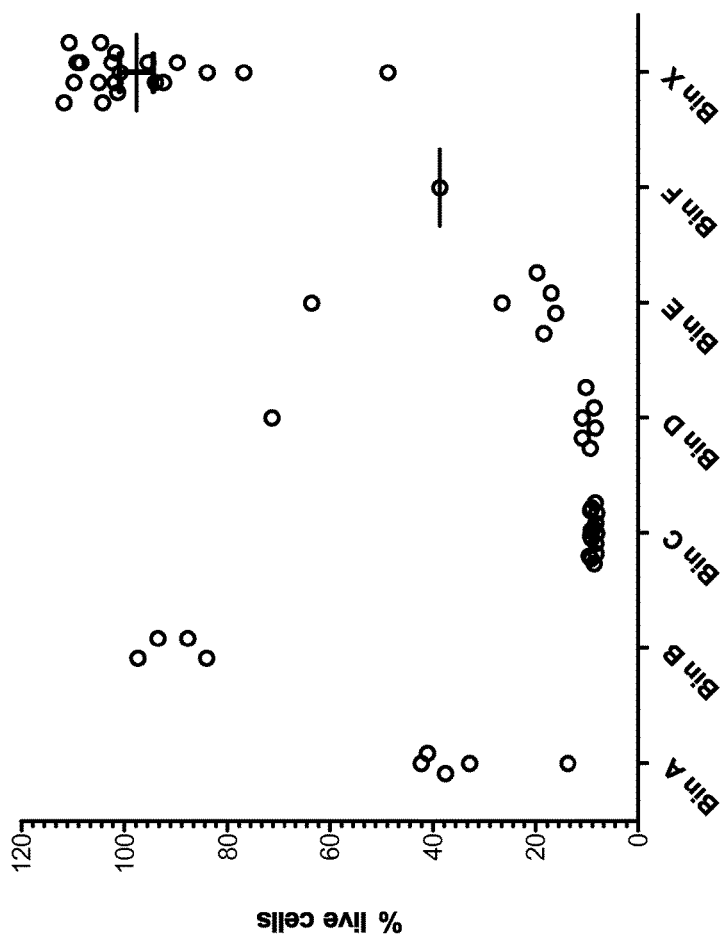

It was desirable to determine whether there was a correlation between (i) the ability of anti-MFI2 antibodies of the invention to mediate internalization and killing of cells, and (ii) the epitope on the MFI2 protein to which such anti-MFI2 antibodies bind. Such information enables the design or selection of particularly efficacious antibodies. To that end, following completion of the in vitro cell killing assay described above using HEK293T cells overexpressing MFI2, the percentage of live cells was plotted against the anti-MFI2 antibodies that were used. The antibodies were grouped into bins as determined by the binning experiment described in Example 7. Antibodies in Bins C and D were particularly effective at internalizing and mediating cell death, whereas antibodies in Bin B were less effective (FIG. 10D). The majority of antibodies in Bins A and E were able to mediate internalization and killing but to a lesser degree than those antibodies in Bins C and D. As described above in Example 7, all antibodies in Bins A, B, C and D bound to transferrin-like domain 2 (TFLD2) whereas the antibodies in Bin E bound to TFLD1. These results indicate that there may be a particular epitope within the TFLD2 domain to which the antibodies in Bins C and D bind, which makes the antibodies more efficacious, compared to, for example epitopes A and B on TFLD2 to which the antibodies in Bin B bind. Thus, the antibodies in Bins C and D, for example, SC57.32 and any antibodies that compete with such antibody comprise a subset of anti-MFI2 antibodies which may be particularly efficacious in the treatment of various tumors due to their superior ability to internalize and kill cells.

Example 18

Conjugation of Anti-MFI2 Antibodies to Pyrrolobenzodiazepines (PBD)

Seven murine anti-MFI2 antibodies (SC57.4, SC57.5, SC57.9, SC57.32, SC57.41, SC57.43 and SC57.46) and two humanized site-specific anti-MFI2 antibodies (hSC57.32ss1 and hSC57.43ss1) were conjugated to a pyrrolobenzodiazepine (PBD1) via a terminal maleimido moiety with a free sulfhydryl group to create the ADCs termed hSC57.32ss1PBD1 and hSC57.43ss1PBD1.

The murine anti-MFI2 antibody drug conjugates (ADCs) were prepared as follows. The cysteine bonds of anti-MFI2 antibodies were partially reduced with a pre-determined molar addition of mol tris(2-carboxyethyl)-phosphine (TCEP) per mol antibody for 90 min. at room temperature in phosphate buffered saline (PBS) with 5 mM EDTA. The resulting partially reduced preparations were then conjugated to PBD1 (the structure of PBD1 is provided above in the current specification) via a maleimide linker for a minimum of 30 mins. at room temperature. The reaction was then quenched with the addition of excess N-acetyl cysteine (NAC) compared to linker-drug using a 10 mM stock solution prepared in water. After a minimum quench time of 20 mins., the pH was adjusted to 6.0 with the addition of 0.5 M acetic acid. The preparations of the ADCs were buffer exchanged into diafiltration buffer by diafiltration using a 30 kDa membrane. The dialfiltered anti-MFI2 ADC was then formulated with sucrose and polysorbate-20 to the target final concentration. The resulting anti-MFI2 ADCs were analyzed for protein concentration (by measuring UV), aggregation (SEC), drug to antibody ratio (DAR) by reverse-phase HPLC (RP-HPLC) and in vitro cytotoxicity.

The site specific humanized anti-MFI2 ADCs were conjugated using a modified partial reduction process. The desired product is an ADC that is maximally conjugated on the unpaired cysteine (C214) on each LC constant region and that minimizes ADCs having a drug to antibody ratio (DAR) which is greater than 2 (DAR>2) while maximizing ADCs having a DAR of 2 (DAR=2). In order to further improve the specificity of the conjugation, the antibodies were selectively reduced using a process comprising a stabilizing agent (e.g. L-arginine) and a mild reducing agent (e.g. glutathione) prior to conjugation with the linker-drug, followed by a diafiltration and formulation step. The process is described in detail below.

A preparation of each antibody was partially reduced in a buffer containing 1 M L-arginine/5 mM EDTA with a pre-determined concentration of reduced glutathione (GSH), pH 8.0 for a minimum of two hours at room temperature. All preparations were then buffer exchanged into a 20 mM Tris/3.2 mM EDTA, pH 7.0 buffer using a 30 kDa membrane (Millipore Amicon Ultra) to remove the reducing buffer. The resulting partially reduced preparations were then conjugated to PBD1 (the structure of PBD1 is provided above in the current specification) via a maleimide linker for a minimum of 30 mins. at room temperature. The reaction was then quenched with the addition of excess NAC compared to linker-drug using a 10 mM stock solution prepared in water. After a minimum quench time of 20 mins., the pH was adjusted to 6.0 with the addition of 0.5 M acetic acid. The preparations of the ADCs were buffer exchanged into diafiltration buffer by diafiltration using a 30 kDa membrane. The dialfiltered anti-MFI2 ADC was then formulated with sucrose and polysorbate-20 to the target final concentration. The resulting anti-MFI2 ADCs were analyzed for protein concentration (by measuring UV), aggregation (SEC), drug to antibody ratio (DAR) by reverse-phase HPLC (RP-HPLC) and in vitro cytotoxicity.

Example 19

Conjugation of Anti-MFI2 Antibodies to Calicheamicin

An anti-MFI2 antibody (hSC57.32ss1) was conjugated to a calicheamicin (Cal) compound via a terminal maleimido moiety with a free sulfhydryl group to create the ADC termed hSC57.32ss1Cal.

The desired product is an ADC that is maximally conjugated on the unpaired cysteine (C214) on each LC constant region and that minimizes ADCs having a drug to antibody ratio (DAR) which is greater than 2 (DAR>2) while maximizing ADCs having a DAR of 2 (DAR=2).

In order to further improve the specificity of the conjugation, the antibodies were selectively reduced using a process comprising a stabilizing agent (e.g. L-arginine) and a mild reducing agent (e.g. glutathione) prior to conjugation with the linker-drug, followed by a diafiltration and formulation step. The process is described in detail below.

A preparation of each antibody was partially reduced in a buffer containing 1M L-arginine/5 mM EDTA with a pre-determined concentration of reduced glutathione (GSH), pH 8.0 for a minimum of two hours at room temperature. All preparations were then buffer exchanged into a 20 mM Tris/3.2 mM EDTA, pH 7.0 buffer using a 30 kDa membrane (Millipore Amicon Ultra) to remove the reducing buffer. The resulting partially reduced preparations were then conjugated to calicheamicin via a maleimide linker for a minimum of 120 mins. at room temperature. The reaction was then quenched with the addition of excess NAC compared to linker-drug using a 10 mM stock solution prepared in water. After a minimum quench time of 20 mins., the pH was adjusted to 6.0 with the addition of 0.5 M acetic acid. The preparation of the ADC was buffer exchanged into diafiltration buffer by diafiltration using a 30 kDa membrane. The dialfiltered anti-MFI2 ADC was then formulated with sucrose and polysorbate-20 to the target final concentration. The resulting anti-MFI2 ADCs were analyzed for protein concentration (by measuring UV), aggregation (SEC), drug to antibody ratio (DAR) by reverse-phase HPLC (RP-HPLC) and in vitro cytotoxicity.

Example 20

Anti-MFI2 Antibody Drug Conjugates Facilitate Delivery of Cytotoxic Agents in Vitro To determine whether anti-MFI2 ADCs of the invention were able to internalize in order to mediate the delivery of cytotoxic agents to live tumor cells, an in vitro cell killing assay was performed using the anti-MFI2 ADCs, hSC57.32ss1 PBD1 and hSC57.43ss1PBD1 (produced as described in Example 18 above) and hSC57.32ss1Cal (produced as described in Example 19 above).

Figure 11A:
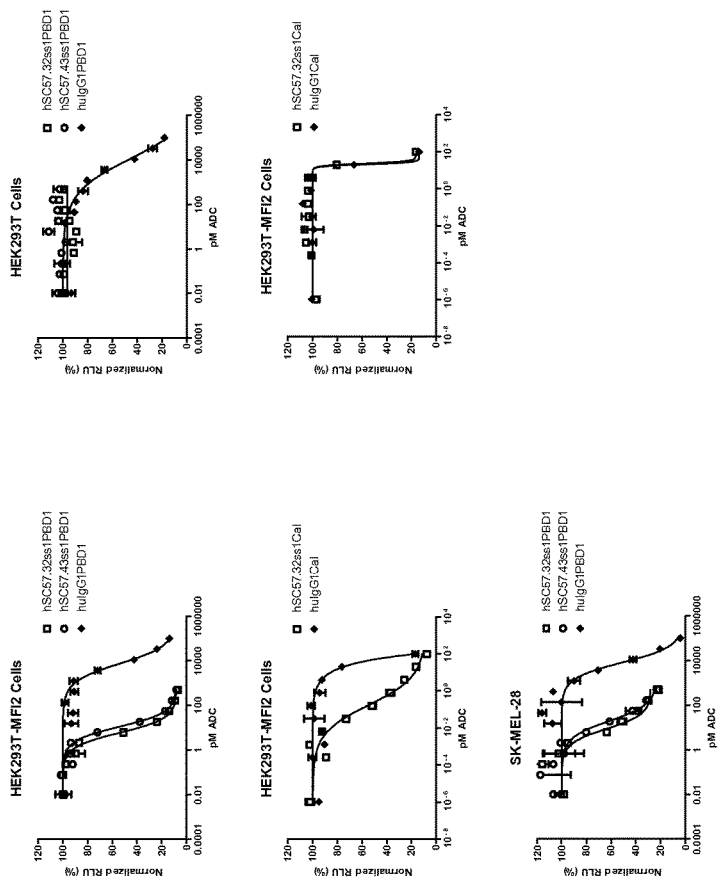
FIGS. 11A and 11B depict the ability of anti-MFI2 ADCs to internalize and kill HEK293T cells overexpressing MFI2 protein and SK-MEL-28 melanoma cells (FIG. 11A) or breast cancer and melanoma PDX lines (FIG. 11B) that endogenously overexpress MFI2 in vitro.
Figure 11B:
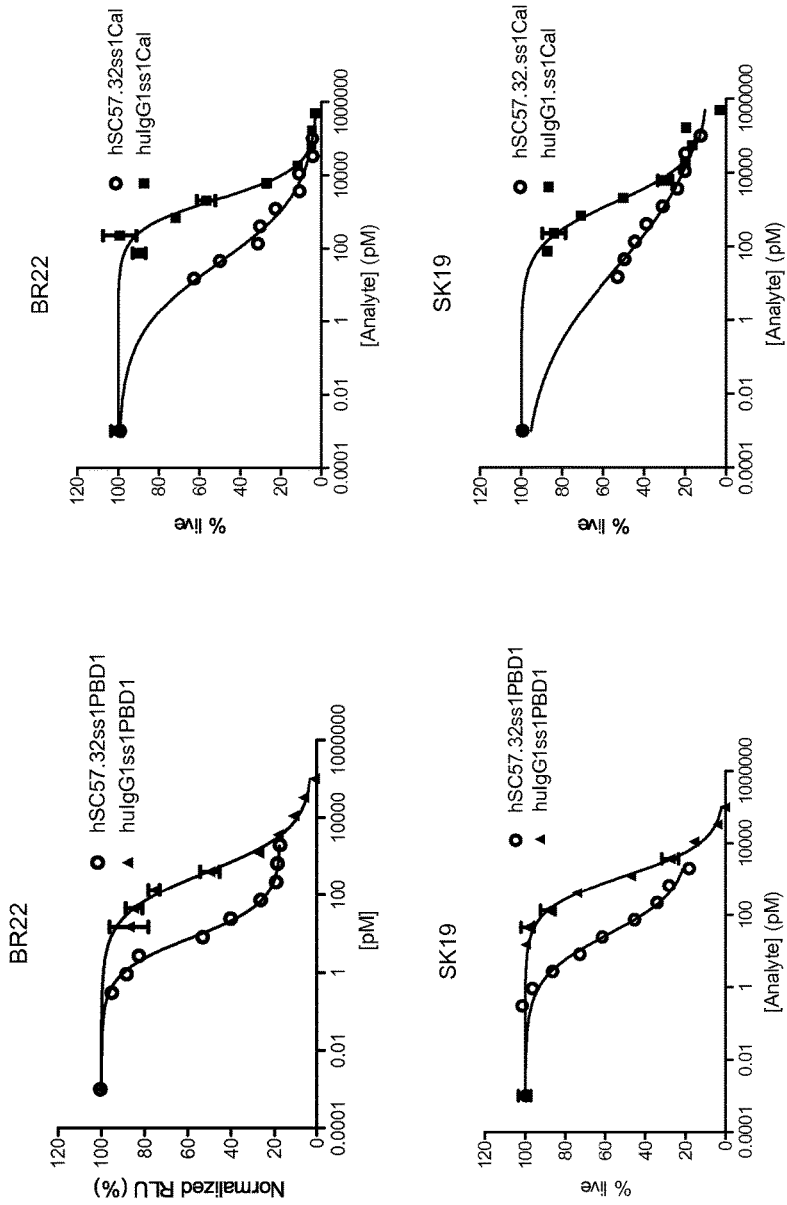

Single cell suspensions of HEK293T cells overexpressing hMFI2, SK-MEL-28, cells endogenously expressing MFI2 or naïve HEK293T cells were plated at 500 cells per well into BD Tissue Culture plates (BD Biosciences). Single cell suspensions of BR22 and SK19 cells derived from PDX tumors were plated at 2500 cells per well into Primeria plates. One day later, various concentrations of purified ADC or human IgG1 control antibody conjugated to PBD1 or Calicheamicin were added to the cultures. The cells were incubated for 96 hours or 7 days in the case of the PDX derived tumor lines. After the incubation viable cells were enumerated using CellTiter-Glo® (Promega) as per the manufacturer's instructions. Raw luminescence counts using cultures containing non-treated cells were set as 100% reference values and all other counts were calculated as a percentage of the reference value. FIGS. 11A and 11B show that all cells treated were much more sensitive to the anti-MFI2 ADCs compared to the human IgG1 control antibody. Furthermore, the ADCs had very little effect on naïve HEK293T cells that did not overexpress MFI2 compared to the HEK293T cells overexpressing MFI2, demonstrating the specificity of the ADCs to the MFI2 antigen (FIG. 11A). FIG. 11B shows the ability of anti-MFI2 ADCs comprising various toxins (PBDs and Calicheamicin) to effectively kill BR and SK tumors.

The above results demonstrate the ability of anti-MFI2 ADCs to specifically mediate internalization and delivery of cytotoxic payloads to cells expressing MFI2, including melanoma and breast tumor cells.

Example 21

Anti-MFI2 Antibody Drug Conjugates Suppress Tumor Growth in Vivo

The anti-MFI2 ADCs, generated as described in Example 18 above, were tested to demonstrate their ability to suppress BR, LU and SK tumor growth in immunodeficient mice.

PDX tumor lines expressing MFI2 (e.g. SK44, LU92, BR22 and BR86) and tumor lines exhibiting lower levels of MFI2 expression (e.g. LU134), were grown subcutaneously in the flanks of female NOD/SCID mice using art-recognized techniques. Tumor volumes and mouse weights were monitored once or twice per week. When tumor volumes reached 150-250 mm$^3$, mice were randomly assigned to treatment groups.

Figure 12A:
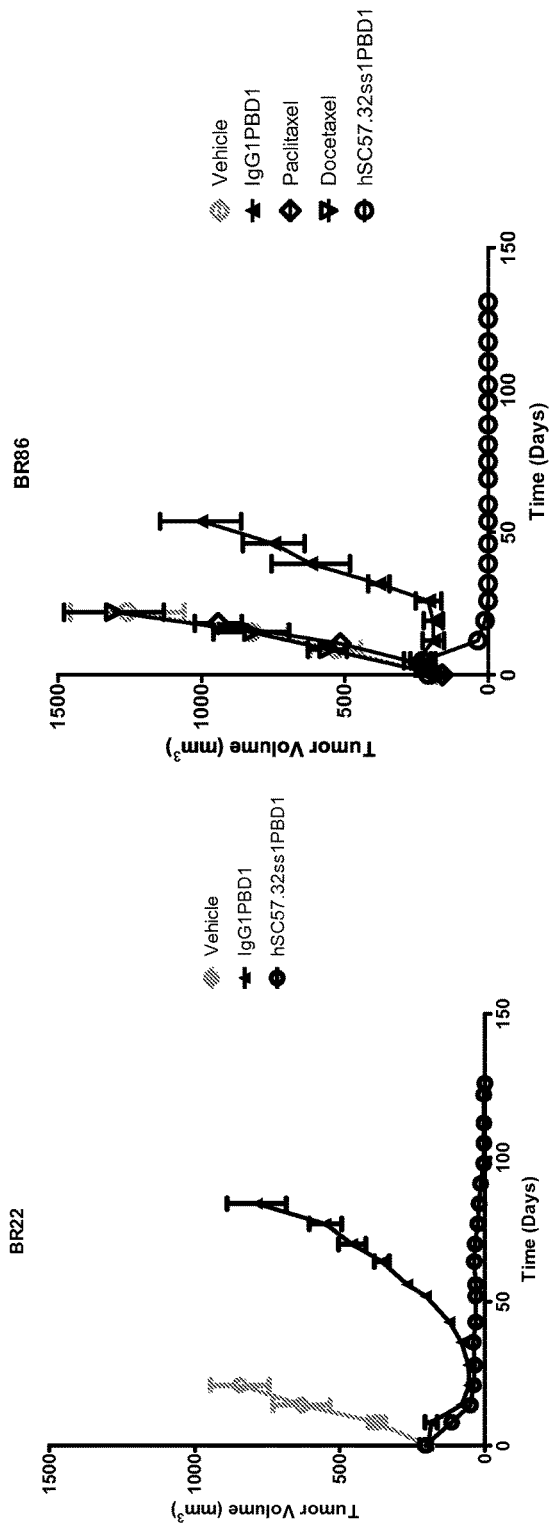
FIGS. 12A and 12B show that anti-MFI2 ADCs are able to internalize into BR (FIG. 12A) and LU and MEL (FIG. 12B) tumors in vivo and cause a significant and prolonged reduction in tumor volume.
Figure 12B:
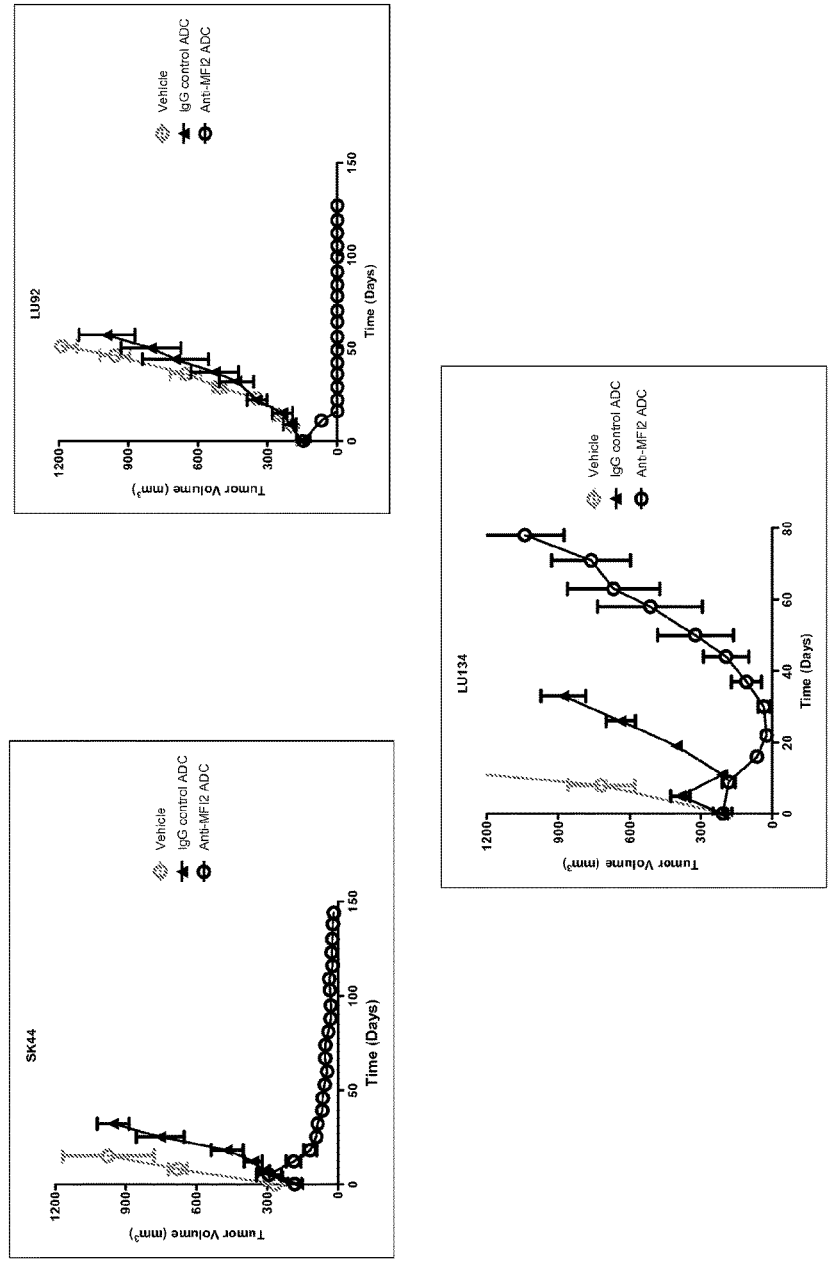

In the studies conducted on mice with BR tumors, the mice were injected intraperitoneally with either a single dose of 20 mg/kg Docetaxel or Paclitaxel (the standard of care), a single dose of 0.8 mg/kg hSC57.32ss1PBD1 or anti-hapten control human IgG1PBD1, or a single dose of vehicle control (FIG. 12A). In the studies conducted on mice with melanoma or lung tumors, the mice were injected intraperitoneally with either a single dose of 2 mg/kg hSC57.43PBD1 (denoted as anti-MFI2 ADC in FIG. 12B) or anti-hapten control human IgG1PBD1, or a single dose of vehicle control (FIG. 12B).

Following treatment, tumor volumes and mouse weights were monitored until tumors exceeded 800 mm$^3$ or mice became sick. Mice treated with anti-MFI2 ADCs did not exhibit any adverse health effects beyond those typically seen in immunodeficient, tumor-bearing NOD/SCID mice. The administration of the anti-MFI2 ADC, resulted in significant tumor suppression lasting over 100 days in SK44, LU92, BR22 and BR86 tumors, whereas the administration of the control ADC IgG1 PBD1 (and in the case of BR86, the standard of care, paclitaxel and docetaxel), did not result in tumor volume reduction. Conversely, the anti-MFI2 ADC exhibited very little effect on tumor volume reduction in LU134 tumors that had much lower expression levels of MFI2 as measured by a chemiluminescent assay (Example 14) and flow cytometry (Example 11).

The ability of anti-MFI2 ADCs to specifically kill MFI2-expressing tumor cells and dramatically suppress tumor growth in vivo for extended periods further validates the use of anti-MFI2 ADCs in the therapeutic treatment of cancer and in particular in TNBR subtypes of breast cancer. Of further interest, as shown in FIG. 12A with two standard of care drugs, BR86 is a drug-resistant tumor cell line and thus the results also show that anti-MFI2 ADCs are efficacious in reducing the tumor volume of drug resistant tumors.

Example 22

Enrichment of MFI2 Expression in Cancer Stem Cell Populations

Tumor cells can be divided broadly into two types of cell subpopulations: non-tumorigenic cells (NTG) and tumor initiating cells or tumorigenic cells. Tumorigenic cells have the ability to form tumors when implanted into immunocompromised mice, whereas non-tumorigenic cells do not. Cancer stem cells (CSCs) are a subset of tumorigenic cells and are able to self-replicate indefinitely while maintaining the capacity for multilineage differentiation.

To determine whether MFI2 expression in tumors could be correlated with enhanced tumorigenicity, the following study was conducted. Human SK-MEL PDX tumor samples were grown in immunocompromised mice and were resected after the tumor reached 800-2,000 mm$^3$. The tumors were dissociated into single cell suspensions using art-recognized enzymatic digestion techniques (see, for example, U.S.P.N. 2007/0292414). Human SK-MEL PDX tumor cells were stained with mouse anti-CD45 or anti-H2kD antibodies to differentiate between human tumor cells and mouse cells. The tumors were also stained with anti-MFI2 antibody (SC57.43) and then sorted using a FAC-SAria™ Flow Cytometer (BD Biosciences). The human TNBR PDX tumor cells were separated into cell populations expressing MFI2 (MFI2-hi) and cell populations that did not express MFI2 (MFI2-neg), as defined with a parallel isotype-stained control sample. Five female NOD/SCID immunocompromised mice were injected subcutaneously with 50 MFI2-hi SK-MEL tumor cells; and five mice were injected with 200 MFI2-neg SK-MEL tumor cells. Tumor volumes were measured on a weekly basis for four months.

Figure 13:
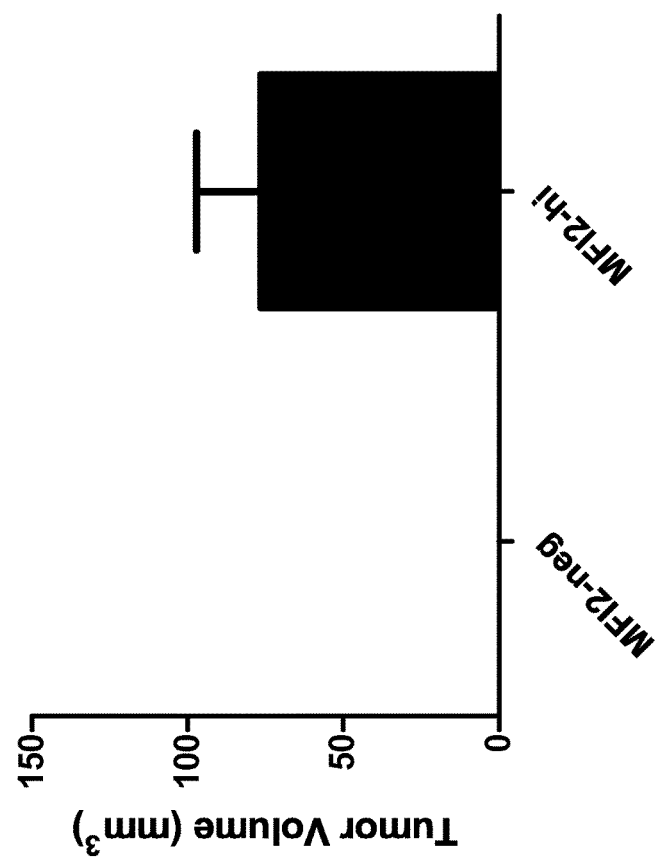
FIG. 13 shows that MFI2 is associated with tumor initiating cells; tumor cells expressing MFI2 are able to functionally reconstitute tumors in vivo whereas tumor cells that do not express MFI2 are not able to reconstitute tumors in vivo.

FIG. 13 shows that MFI2-hi tumor cells were able to functionally reconstitute tumors in vivo, whereas MFI2-neg tumors were not. Thus, tumor cells expressing MFI2 were much more tumorigenic than those tumor cells that did not express MFI2, suggesting that the MFI2 protein can functionally define a tumorigenic subpopulation within human tumors, and supporting the concept that selected anti-MFI2 ADCs can be used to target a tumorigenic subpopulation of tumor cells, which could result in significant tumor regression and prevention of tumor recurrence.

Example 23

Reduction of Tumor Initiating Cell Frequency by Anti-MFI2 Antibody-Drug Conjugates As demonstrated in Examples 1, 2 and 16 MFI2 expression is associated with tumorigenic cells. Accordingly, to demonstrate that treatment with anti-MFI2 ADCs reduces the frequency of TICs that are known to be drug resistant and to fuel tumor recurrence and metastasis, in vivo limiting dilution assays (LDA) are performed, for example, essentially as described below.

PDX tumors (e.g. breast, lung or melanoma) are grown subcutaneously in immunodeficient mice. When tumor volumes average 150 mm$^3$-250 mm$^3$ in size, the mice are randomly segregated into two groups. One group is injected intraperitoneally with a human IgG1 conjugated to a drug as a negative control; and the other group is injected intraperitoneally with an anti-MFI2 ADC (e.g., as prepared in Example 18). One week following dosing, representative mice from each group are euthanized and their tumors are harvested and dispersed to single-cell suspensions. The tumor cells from each treatment group are then harvested, pooled and disaggregated as previously described in Example 1. The cells are labeled with FITC conjugated anti-mouse H2kD and anti-mouse CD45 antibodies to detect mouse cells; EpCAM to detect human cells; and DAPI to detect dead cells. The resulting suspension is then sorted by FACS using a BD FACS Canto II flow cytometer and live human tumor cells are isolated and collected.

A number of cohorts of mice are injected with either 1250, 375, 115 or 35 sorted live, human cells from tumors treated with anti-MFI2 ADC. As a negative control the same number of mice per cohort are transplanted with either 1000, 300, 100 or 30 sorted live, human cells from tumors treated with the control IgG1 ADC. Tumors in recipient mice are measured weekly, and individual mice are euthanized before tumors reach 1500 mm$^3$. Recipient mice are scored as having positive or negative tumor growth. Positive tumor growth is defined as growth of a tumor exceeding 100 mm$^3$. Poisson distribution statistics (L-Calc software, Stemcell Technologies) are used to calculate the frequency of TICs in each population.

The invention claimed is:

1. A humanized antibody that binds to a human MFI2 protein and comprises a light chain variable region and a heavy chain variable region, wherein the antibody comprises:
   (a) three complementarity determining regions of a light chain variable region comprising an amino acid sequence set forth as SEQ ID NO: 99 and three complementarity determining regions of a heavy chain variable region comprising an amino acid sequence set forth as SEQ ID NO: 101;
   (b) three complementarity determining regions of a light chain variable region comprising an amino acid sequence set forth as SEQ ID NO: 105 and three complementarity determining regions of a heavy chain variable region comprising an amino acid sequence set forth as SEQ ID NO: 107;
   (c) three complementarity determining regions of a light chain variable region comprising an amino acid sequence set forth as SEQ ID NO: 93 and three complementarity determining regions of a heavy chain variable region comprising an amino acid sequence set forth as SEQ ID NO: 95; or
   (d) three complementarity determining regions of a light chain variable region comprising an amino acid sequence set forth as SEQ ID NO: 93 and three complementarity determining regions of a heavy chain variable region comprising an amino acid sequence set forth as SEQ ID NO: 97.

2. The humanized antibody of claim 1, wherein the antibody comprises three complementarity determining regions of a light chain variable region comprising an amino acid sequence set forth as SEQ ID NO: 99 and three complementarity determining regions of a heavy chain variable region comprising an amino acid sequence set forth as SEQ ID NO: 101.

3. The humanized antibody of claim 2, wherein the antibody comprises:
   (a) residues 24-34 of SEQ ID NO: 99 for CDR-L1, residues 50-56 of SEQ ID NO: 99 for CDR-L2, residues 89-97 of SEQ ID NO: 99 for CDR-L3, residues 31-35 of SEQ ID NO: 101 for CDR-H1, residues 50-65 of SEQ ID NO: 101 for CDR-H2 and residues 95-102 of SEQ ID NO: 101 for CDR-H3, wherein the CDR residues are numbered according to Kabat;
   (b) residues 24-34 of SEQ ID NO: 99 for CDR-L1, residues 50-56 of SEQ ID NO: 99 for CDR-L2, residues 89-97 of SEQ ID NO: 99 for CDR-L3, residues 26-32 of SEQ ID NO: 101 for CDR-H1, residues 52-56 of SEQ ID NO: 101 for CDR-H2 and residues 95-102 of SEQ ID NO: 101 for CDR-H3, wherein the CDR residues are numbered according to Chothia; or
   (c) residues 30-36 of SEQ ID NO: 99 for CDR-L1, residues 46-55 of SEQ ID NO: 99 for CDR-L2, residues 89-96 of SEQ ID NO: 99 for CDR-L3, residues 30-35 of SEQ ID NO: 101 for CDR-H1, residues 47-58 of SEQ ID NO: 101 for CDR-H2 and residues 93-101 of SEQ ID NO: 101 for CDR-H3, wherein the CDR residues are numbered according to MacCallum.

4. The humanized antibody of claim 1, wherein the antibody comprises three complementarity determining regions of a light chain variable region comprising an amino acid sequence set forth as SEQ ID NO: 105 and three complementarity determining regions of a heavy chain variable region comprising an amino acid sequence set forth as SEQ ID NO: 107.

5. The humanized antibody of claim 4, wherein the antibody comprises:
   (a) residues 24-34 of SEQ ID NO: 105 for CDR-L1, residues 50-56 of SEQ ID NO: 105 for CDR-L2, residues 89-97 of SEQ ID NO: 105 for CDR-L3, residues 31-35 of SEQ ID NO: 107 for CDR-H1, residues 50-65 of SEQ ID NO: 107 for CDR-H2 and residues 95-102 of SEQ ID NO: 107 for CDR-H3, wherein the CDR residues are numbered according to Kabat;
   (b) residues 24-34 of SEQ ID NO: 105 for CDR-L1, residues 50-56 of SEQ ID NO: 105 for CDR-L2, residues 89-97 of SEQ ID NO: 105 for CDR-L3, residues 26-32 of SEQ ID NO: 107 for CDR-H1, residues 52-56 of SEQ ID NO: 107 for CDR-H2 and residues 95-102 of SEQ ID NO: 107 for CDR-H3, wherein the CDR residues are numbered according to Chothia; or
   (c) residues 30-36 of SEQ ID NO: 105 for CDR-L1, residues 46-55 of SEQ ID NO: 105 for CDR-L2, residues 89-96 of SEQ ID NO: 105 for CDR-L3, residues 30-35 of SEQ ID NO: 107 for CDR-H1, residues 47-58 of SEQ ID NO: 107 for CDR-H2 and residues 93-101 of SEQ ID NO: 107 for CDR-H3, wherein the CDR residues are numbered according to MacCallum.

6. The humanized antibody of claim 1, wherein the antibody comprises
   (a) a light chain variable region comprising an amino acid sequence set forth as SEQ ID NO: 99 and a heavy chain variable region comprising an amino acid sequence set forth as SEQ ID NO: 101;
   (b) a light chain variable region comprising an amino acid sequence set forth as SEQ ID NO: 93 and a heavy chain variable region comprising an amino acid sequence set forth as SEQ ID NO: 95;

(c) a light chain variable region comprising an amino acid sequence set forth as SEQ ID NO: 93 and a heavy chain variable region comprising an amino acid sequence set forth as SEQ ID NO: 97;

(d) a light chain variable region comprising an amino acid sequence set forth as SEQ ID NO: 99 and a heavy chain variable region comprising an amino acid sequence set forth as SEQ ID NO: 103; or (e) a light chain variable region comprising an amino acid sequence set forth as SEQ ID NO: 105 and a heavy chain variable region comprising an amino acid sequence set forth as SEQ ID NO: 107.

7. The humanized antibody of claim 1, wherein the antibody comprises a light chain variable region comprising an amino acid sequence set forth as SEQ ID NO: 99 and a heavy chain variable region comprising an amino acid sequence set forth as SEQ ID NO: 101.

8. The humanized antibody of claim 1, wherein the antibody comprises a light chain variable region comprising an amino acid sequence set forth as SEQ ID NO: 105 and a heavy chain variable region comprising an amino acid sequence set forth as SEQ ID NO: 107.

9. The humanized antibody of claim 1, wherein the antibody comprises:
(a) a light chain comprising an amino acid sequence set forth as SEQ ID NO: 112 and a heavy chain comprising an amino acid sequence set forth as SEQ ID NO: 114;
(b) a light chain comprising an amino acid sequence set forth as SEQ ID NO: 112 and a heavy chain comprising an amino acid sequence set forth as SEQ ID NO: 113;
(c) a light chain comprising an amino acid sequence set forth as SEQ ID NO: 112 and a heavy chain comprising an amino acid sequence set forth as SEQ ID NO: 115;
(d) a light chain comprising an amino acid sequence set forth as SEQ ID NO: 116 and a heavy chain comprising an amino acid sequence set forth as SEQ ID NO: 117; or
(e) a light chain set comprising an amino acid sequence forth as SEQ ID NO: 116 and a heavy chain comprising an amino acid sequence set forth as SEQ ID NO: 118.

10. The humanized antibody of claim 1, wherein the antibody comprises a light chain comprising an amino acid sequence set forth as SEQ ID NO: 112 and a heavy chain comprising an amino acid sequence set forth as SEQ ID NO: 114.

11. The humanized antibody of claim 1, wherein the antibody comprises a light chain comprising an amino acid sequence set forth as SEQ ID NO: 116 and a heavy chain comprising an amino acid sequence set forth as SEQ ID NO: 118.

12. The humanized antibody of claim 1, wherein the antibody is conjugated to a cytotoxic agent.

13. The humanized antibody of claim 12, wherein the cytotoxic agent is a dolastatin, a duocarmycin, a pyrrolobenzodiazepine (PBD), an auristatin, an aminitin, a maytansinoid, a calichearmicin, or a radioisotope.

14. An antibody drug conjugate comprising a humanized antibody conjugated to a cytotoxic agent, wherein the humanized antibody is the antibody of claim 1.

15. The antibody drug conjugate of claim 14, wherein the antibody comprises three complementarity determining regions of a light chain variable region comprising an amino acid sequence set forth as SEQ ID NO: 99 and three complementarity determining regions of a heavy chain variable region comprising an amino acid sequence set forth as SEQ ID NO: 101.

16. The antibody drug conjugate of claim 15, wherein the antibody comprises:
(a) residues 24-34 of SEQ ID NO: 99 for CDR-L1, residues 50-56 of SEQ ID NO: 99 for CDR-L2, residues 89-97 of SEQ ID NO: 99 for CDR-L3, residues 31-35 of SEQ ID NO: 101 for CDR-H1, residues 50-65 of SEQ ID NO: 101 for CDR-H2 and residues 95-102 of SEQ ID NO: 101 for CDR-H3, wherein the CDR residues are numbered according to Kabat;
(b) residues 24-34 of SEQ ID NO: 99 for CDR-L1, residues 50-56 of SEQ ID NO: 99 for CDR-L2, residues 89-97 of SEQ ID NO: 99 for CDR-L3, residues 26-32 of SEQ ID NO: 101 for CDR-H1, residues 52-56 of SEQ ID NO: 101 for CDR-H2 and residues 95-102 of SEQ ID NO: 101 for CDR-H3, wherein the CDR residues are numbered according to Chothia; or
(c) residues 30-36 of SEQ ID NO: 99 for CDR-L1, residues 46-55 of SEQ ID NO: 99 for CDR-L2, residues 89-96 of SEQ ID NO: 99 for CDR-L3, residues 30-35 of SEQ ID NO: 101 for CDR-H1, residues 47-58 of SEQ ID NO: 101 for CDR-H2 and residues 93-101 of SEQ ID NO: 101 for CDR-H3, wherein the CDR residues are numbered according to MacCallum.

17. The antibody drug conjugate of claim 16, wherein the antibody comprises three complementarity determining regions of a light chain variable region comprising an amino acid sequence set forth as SEQ ID NO: 105 and three complementarity determining regions of a heavy chain variable region comprising an amino acid sequence set forth as SEQ ID NO: 107.

18. The antibody drug conjugate of claim 17, wherein the antibody comprises:
(a) residues 24-34 of SEQ ID NO: 105 for CDR-L1, residues 50-56 of SEQ ID NO: 105 for CDR-L2, residues 89-97 of SEQ ID NO: 105 for CDR-L3, residues 31-35 of SEQ ID NO: 107 for CDR-H1, residues 50-65 of SEQ ID NO: 107 for CDR-H2 and residues 95-102 of SEQ ID NO: 107 for CDR-H3, wherein the CDR residues are numbered according to Kabat;
(b) residues 24-34 of SEQ ID NO: 105 for CDR-L1, residues 50-56 of SEQ ID NO: 105 for CDR-L2, residues 89-97 of SEQ ID NO: 105 for CDR-L3, residues 26-32 of SEQ ID NO: 107 for CDR-H1, residues 52-56 of SEQ ID NO: 107 for CDR-H2 and residues 95-102 of SEQ ID NO: 107 for CDR-H3, wherein the CDR residues are numbered according to Chothia; or
(c) residues 30-36 of SEQ ID NO: 105 for CDR-L1, residues 46-55 of SEQ ID NO: 105 for CDR-L2, residues 89-96 of SEQ ID NO: 105 for CDR-L3, residues 30-35 of SEQ ID NO: 107 for CDR-H1, residues 47-58 of SEQ ID NO: 107 for CDR-H2 and residues 93-101 of SEQ ID NO: 107 for CDR-H3, wherein the CDR residues are numbered according to MacCallum.

19. The antibody drug conjugate of claim 14, wherein the antibody comprises:
(a) a light chain variable region comprising an amino acid sequence set forth as SEQ ID NO: 99 and a heavy chain variable region comprising an amino acid sequence set forth as SEQ ID NO: 101;
(b) a light chain variable region comprising an amino acid sequence set forth as SEQ ID NO: 93 and a heavy chain variable region comprising an amino acid sequence set forth as SEQ ID NO: 95;

(c) a light chain variable region comprising an amino acid sequence set forth as SEQ ID NO: 93 and a heavy chain variable region comprising an amino acid sequence set forth as SEQ ID NO: 97;

(d) a light chain variable region comprising an amino acid sequence set forth as SEQ ID NO: 99 and a heavy chain variable region comprising an amino acid sequence set forth as SEQ ID NO: 103; or (e) a light chain variable region comprising an amino acid sequence set forth as SEQ ID NO: 105 and a heavy chain variable region comprising an amino acid sequence set forth as SEQ ID NO: 107.

20. The antibody drug conjugate of claim 14, wherein the antibody comprises a light chain variable region comprising an amino acid sequence set forth as SEQ ID NO: 99 and a heavy chain variable region comprising an amino acid sequence set forth as SEQ ID NO: 101.

21. The antibody drug conjugate of claim 14, wherein the antibody comprises a light chain variable region comprising an amino acid sequence set forth as SEQ ID NO: 105 and a heavy chain variable region comprising an amino acid sequence set forth as SEQ ID NO: 107.

22. The antibody drug conjugate of claim 14, wherein the antibody comprises:

(a) a light chain comprising an amino acid sequence set forth as SEQ ID NO: 112 and a heavy chain comprising an amino acid sequence set forth as SEQ ID NO: 114;

(b) a light chain comprising an amino acid sequence set forth as SEQ ID NO: 112 and a heavy chain comprising an amino acid sequence set forth as SEQ ID NO: 113;

(c) a light chain comprising an amino acid sequence set forth as SEQ ID NO: 112 and a heavy chain comprising an amino acid sequence set forth as SEQ ID NO: 115;

(d) a light chain comprising an amino acid sequence set forth as SEQ ID NO: 116 and a heavy chain comprising an amino acid sequence set forth as SEQ ID NO: 117; or (e) a light chain set comprising an amino acid sequence forth as SEQ ID NO: 116 and a heavy chain comprising an amino acid sequence set forth as SEQ ID NO: 118.

23. The antibody drug conjugate of claim 14, wherein the antibody comprises a light chain comprising an amino acid sequence set forth as SEQ ID NO: 112 and a heavy chain comprising an amino acid sequence set forth as SEQ ID NO: 114.

24. The antibody drug conjugate of claim 14, wherein the antibody comprises a light chain set comprising an amino acid sequence forth as SEQ ID NO: 116 and a heavy chain comprising an amino acid sequence set forth as SEQ ID NO: 118.

25. The antibody drug conjugate of claim 14, wherein the cytotoxic agent is a dolastatin, a duocarmycin, a pyrrolobenzodiazepine (PBD), an auristatin, an aminitin, a maytansinoid, a calicheamicin, or a radioisotope.

26. A pharmaceutical composition comprising (a) the antibody drug conjugate of claim 14 and (b) a pharmaceutically acceptable carrier.

27. The pharmaceutical composition of claim 26, wherein the antibody comprises three complementarity determining regions of a light chain variable region comprising an amino acid sequence set forth as SEQ ID NO: 99 and three complementarity determining regions of a heavy chain variable region comprising an amino acid sequence set forth as SEQ ID NO: 101.

28. The pharmaceutical composition of claim 26, wherein the antibody comprises three complementarity determining regions of a light chain variable region comprising an amino acid sequence set forth as SEQ ID NO: 105 and three complementarity determining regions of a heavy chain variable region comprising an amino acid sequence set forth as SEQ ID NO: 107.

29. The pharmaceutical composition of claim 26, wherein the antibody comprises (a) a light chain variable region comprising an amino acid sequence set forth as SEQ ID NO: 99 and a heavy chain variable region comprising an amino acid sequence set forth as SEQ ID NO: 101;

(b) a light chain variable region comprising an amino acid sequence set forth as SEQ ID NO: 93 and a heavy chain variable region comprising an amino acid sequence set forth as SEQ ID NO: 95;

(c) a light chain variable region comprising an amino acid sequence set forth as SEQ ID NO: 93 and a heavy chain variable region comprising an amino acid sequence set forth as SEQ ID NO: 97;

(d) a light chain variable region comprising an amino acid sequence set forth as SEQ ID NO: 99 and a heavy chain variable region comprising an amino acid sequence set forth as SEQ ID NO: 103; or (e) a light chain variable region comprising an amino acid sequence set forth as SEQ ID NO: 105 and a heavy chain variable region comprising an amino acid sequence set forth as SEQ ID NO: 107.

30. The pharmaceutical composition of claim 26, wherein the antibody comprises:

(a) a light chain comprising an amino acid sequence set forth as SEQ ID NO: 112 and a heavy chain comprising an amino acid sequence set forth as SEQ ID NO: 114;

(b) a light chain comprising an amino acid sequence set forth as SEQ ID NO: 112 and a heavy chain comprising an amino acid sequence set forth as SEQ ID NO: 113;

(c) a light chain comprising an amino acid sequence set forth as SEQ ID NO: 112 and a heavy chain comprising an amino acid sequence set forth as SEQ ID NO: 115;

(d) a light chain comprising an amino acid sequence set forth as SEQ ID NO: 116 and a heavy chain comprising an amino acid sequence set forth as SEQ ID NO: 117; or (e) a light chain set comprising an amino acid sequence forth as SEQ ID NO: 116 and a heavy chain comprising an amino acid sequence set forth as SEQ ID NO: 118.

31. The pharmaceutical composition of claim 26, wherein the antibody comprises a light chain comprising an amino acid sequence set forth as SEQ ID NO: 112 and a heavy chain comprising an amino acid sequence set forth as SEQ ID NO: 114.

32. The pharmaceutical composition of claim 26, wherein the cytotoxic agent is a dolastatin, a duocarmycin, a pyrrolobenzodiazepine (PBD), an auristatin, an aminitin, a maytansinoid, a calicheamicin, or a radioisotope.

* * * * *

SEQUENCE LISTING

<160> NUMBER OF SEQ ID NOS: 137

<210> SEQ ID NO 1
<211> LENGTH: 107
<212> TYPE: PRT
<213> ORGANISM: Homo sapiens
<220> FEATURE:
<221> NAME/KEY: MISC_FEATURE
<223> OTHER INFORMATION: Kappa light chain constant region protein
<220> FEATURE:
<221> NAME/KEY: MISC_FEATURE
<223> OTHER INFORMATION: Kappa light chain (LC) constant region protein

<400> SEQUENCE: 1

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 2
<211> LENGTH: 329
<212> TYPE: PRT
<213> ORGANISM: Homo sapiens
<220> FEATURE:
<221> NAME/KEY: MISC_FEATURE
<223> OTHER INFORMATION: IgG1 heavy chain (hc) constant region protein

<400> SEQUENCE: 2

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu

```
                165                 170                 175
Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```

<210> SEQ ID NO 3
<211> LENGTH: 737
<212> TYPE: PRT
<213> ORGANISM: Homo sapiens
<220> FEATURE:
<221> NAME/KEY: MISC_FEATURE
<223> OTHER INFORMATION: MFI2 protein

<400> SEQUENCE: 3

```
Met Arg Gly Pro Ser Gly Ala Leu Trp Leu Leu Leu Ala Leu Arg Thr
1               5                   10                  15

Val Leu Gly Gly Met Glu Val Arg Trp Cys Ala Thr Ser Asp Pro Glu
            20                  25                  30

Gln His Lys Cys Gly Asn Met Ser Glu Ala Phe Arg Glu Ala Gly Ile
        35                  40                  45

Gln Pro Ser Leu Leu Cys Val Arg Gly Thr Ser Ala Asp His Cys Val
    50                  55                  60

Gln Leu Ile Ala Ala Gln Glu Ala Asp Ala Ile Thr Leu Asp Gly Gly
65                  70                  75                  80

Ala Ile Tyr Glu Ala Gly Lys Glu His Gly Leu Lys Pro Val Val Gly
                85                  90                  95

Glu Val Tyr Asp Gln Glu Val Gly Thr Ser Tyr Tyr Ala Val Ala Val
            100                 105                 110

Val Arg Arg Ser Ser His Val Thr Ile Asp Thr Leu Lys Gly Val Lys
        115                 120                 125

Ser Cys His Thr Gly Ile Asn Arg Thr Val Gly Trp Asn Val Pro Val
    130                 135                 140

Gly Tyr Leu Val Glu Ser Gly Arg Leu Ser Val Met Gly Cys Asp Val
145                 150                 155                 160

Leu Lys Ala Val Ser Asp Tyr Phe Gly Gly Ser Cys Val Pro Gly Ala
                165                 170                 175

Gly Glu Thr Ser Tyr Ser Glu Ser Leu Cys Arg Leu Cys Arg Gly Asp
            180                 185                 190
```

```
Ser Ser Gly Glu Gly Val Cys Asp Lys Ser Pro Leu Glu Arg Tyr Tyr
        195                 200                 205

Asp Tyr Ser Gly Ala Phe Arg Cys Leu Ala Glu Gly Ala Gly Asp Val
        210                 215                 220

Ala Phe Val Lys His Ser Thr Val Leu Glu Asn Thr Asp Gly Lys Thr
225                 230                 235                 240

Leu Pro Ser Trp Gly Gln Ala Leu Leu Ser Gln Asp Phe Glu Leu Leu
                245                 250                 255

Cys Arg Asp Gly Ser Arg Ala Asp Val Thr Glu Trp Arg Gln Cys His
            260                 265                 270

Leu Ala Arg Val Pro Ala His Ala Val Val Arg Ala Asp Thr Asp
        275                 280                 285

Gly Gly Leu Ile Phe Arg Leu Leu Asn Glu Gly Gln Arg Leu Phe Ser
        290                 295                 300

His Glu Gly Ser Ser Phe Gln Met Phe Ser Ser Glu Ala Tyr Gly Gln
305                 310                 315                 320

Lys Asp Leu Leu Phe Lys Asp Ser Thr Ser Glu Leu Val Pro Ile Ala
                325                 330                 335

Thr Gln Thr Tyr Glu Ala Trp Leu Gly His Glu Tyr Leu His Ala Met
            340                 345                 350

Lys Gly Leu Leu Cys Asp Pro Asn Arg Leu Pro Pro Tyr Leu Arg Trp
        355                 360                 365

Cys Val Leu Ser Thr Pro Glu Ile Gln Lys Cys Gly Asp Met Ala Val
        370                 375                 380

Ala Phe Arg Arg Gln Arg Leu Lys Pro Glu Ile Gln Cys Val Ser Ala
385                 390                 395                 400

Lys Ser Pro Gln His Cys Met Glu Arg Ile Gln Ala Glu Gln Val Asp
                405                 410                 415

Ala Val Thr Leu Ser Gly Glu Asp Ile Tyr Thr Ala Gly Lys Thr Tyr
            420                 425                 430

Gly Leu Val Pro Ala Ala Gly Glu His Tyr Ala Pro Glu Asp Ser Ser
        435                 440                 445

Asn Ser Tyr Tyr Val Val Ala Val Val Arg Arg Asp Ser Ser His Ala
450                 455                 460

Phe Thr Leu Asp Glu Leu Arg Gly Lys Arg Ser Cys His Ala Gly Phe
465                 470                 475                 480

Gly Ser Pro Ala Gly Trp Asp Val Pro Val Gly Ala Leu Ile Gln Arg
                485                 490                 495

Gly Phe Ile Arg Pro Lys Asp Cys Asp Val Leu Thr Ala Val Ser Glu
            500                 505                 510

Phe Phe Asn Ala Ser Cys Val Pro Val Asn Asn Pro Lys Asn Tyr Pro
        515                 520                 525

Ser Ser Leu Cys Ala Leu Cys Val Gly Asp Glu Gln Gly Arg Asn Lys
530                 535                 540

Cys Val Gly Asn Ser Gln Glu Arg Tyr Tyr Gly Tyr Arg Gly Ala Phe
545                 550                 555                 560

Arg Cys Leu Val Glu Asn Ala Gly Asp Val Ala Phe Val Arg His Thr
                565                 570                 575

Thr Val Phe Asp Asn Thr Asn Gly His Asn Ser Glu Pro Trp Ala Ala
            580                 585                 590

Glu Leu Arg Ser Glu Asp Tyr Glu Leu Leu Cys Pro Asn Gly Ala Arg
        595                 600                 605

Ala Glu Val Ser Gln Phe Ala Ala Cys Asn Leu Ala Gln Ile Pro His
```

```
                610                 615                 620
Ala Val Met Val Arg Pro Asp Thr Asn Ile Phe Thr Val Tyr Gly Leu
625                 630                 635                 640

Leu Asp Lys Ala Gln Asp Leu Phe Gly Asp Asp His Asn Lys Asn Gly
            645                 650                 655

Phe Lys Met Phe Asp Ser Ser Asn Tyr His Gly Gln Asp Leu Leu Phe
            660                 665                 670

Lys Asp Ala Thr Val Arg Ala Val Pro Val Gly Glu Lys Thr Thr Tyr
            675                 680                 685

Arg Gly Trp Leu Gly Leu Asp Tyr Val Ala Ala Leu Glu Gly Met Ser
        690                 695                 700

Ser Gln Gln Cys Ser Gly Ala Ala Ala Pro Ala Pro Gly Ala Pro Leu
705                 710                 715                 720

Leu Pro Leu Leu Leu Pro Ala Leu Ala Ala Arg Leu Leu Pro Pro Ala
                725                 730                 735

Leu

<210> SEQ ID NO 4

<400> SEQUENCE: 4

000

<210> SEQ ID NO 5

<400> SEQUENCE: 5

000

<210> SEQ ID NO 6

<400> SEQUENCE: 6

000

<210> SEQ ID NO 7

<400> SEQUENCE: 7

000

<210> SEQ ID NO 8

<400> SEQUENCE: 8

000

<210> SEQ ID NO 9

<400> SEQUENCE: 9

000

<210> SEQ ID NO 10

<400> SEQUENCE: 10

000

<210> SEQ ID NO 11

<400> SEQUENCE: 11
```

<210> SEQ ID NO 12
<400> SEQUENCE: 12
000

<210> SEQ ID NO 13
<400> SEQUENCE: 13
000

<210> SEQ ID NO 14
<400> SEQUENCE: 14
000

<210> SEQ ID NO 15
<400> SEQUENCE: 15
000

<210> SEQ ID NO 16
<400> SEQUENCE: 16
000

<210> SEQ ID NO 17
<400> SEQUENCE: 17
000

<210> SEQ ID NO 18
<400> SEQUENCE: 18
000

<210> SEQ ID NO 19
<400> SEQUENCE: 19
000

<210> SEQ ID NO 20
<211> LENGTH: 318
<212> TYPE: DNA
<213> ORGANISM: Mus musculus
<220> FEATURE:
<221> NAME/KEY: MISC_FEATURE
<223> OTHER INFORMATION: SC57.1 VL DNA

<400> SEQUENCE: 20

```
caaattgttc tcacccagtc tccagcaatc atgtctgcat ctccagggga gaaggtcacc      60
atgacctgca gtgccagctc aagtgtaagt tacatgcact ggtaccagca gaagtcaggc     120
acctccccca aaagatggat ttatgacaca tccaaactgg cttctggagt cccagttcgc     180
ttcagtggca gtgggtctgg gacctcttac tctctcacaa tcagcagcat tgaggctgac     240
gatgctgcca cttattactg ccagcagtgg agtagaaccc cacccacgtt cggagggggg     300
```
accaagctgg aaataaaa                                                    318

<210> SEQ ID NO 21
<211> LENGTH: 106
<212> TYPE: PRT
<213> ORGANISM: Mus musculus
<220> FEATURE:
<221> NAME/KEY: MISC_FEATURE
<223> OTHER INFORMATION: SC57.1 VL protein

<400> SEQUENCE: 21

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Val Arg Phe Ser Gly Ser
    50                  55                  60

Gly Ser Gly Thr Ser Tyr Ser Leu Thr Ile Ser Ser Ile Glu Ala Asp
65                  70                  75                  80

Asp Ala Ala Thr Tyr Tyr Cys Gln Gln Trp Ser Arg Thr Pro Pro Thr
                85                  90                  95

Phe Gly Gly Gly Thr Lys Leu Glu Ile Lys
            100                 105

<210> SEQ ID NO 22
<211> LENGTH: 354
<212> TYPE: DNA
<213> ORGANISM: Mus musculus
<220> FEATURE:
<221> NAME/KEY: MISC_FEATURE
<223> OTHER INFORMATION: SC57.1 VH DNA

<400> SEQUENCE: 22
caggtgcaac tgaagcagtc aggacctggc ctagtgcagc cctcacagag cctgtccatc     60
acctgcacag tctctggttt ctcattaact gactatggtg tacactgggt tcgccagtct    120
ccaggaaagg gtctggactg gctgggagtg atatggagtg gtggaaacac agactataat    180
gcagctttca tatccagact gagcatcagc aaggacaatt ccaagagcca aattttcttt    240
gaaatgaaca gtctacaaga tactgacaca gccatatatt actgtgccag acaacttcat    300
tactacggcc ctttgcttta ctggggccaa gggactctgg tcactgtctc tgca          354

<210> SEQ ID NO 23
<211> LENGTH: 118
<212> TYPE: PRT
<213> ORGANISM: Mus musculus
<220> FEATURE:
<221> NAME/KEY: MISC_FEATURE
<223> OTHER INFORMATION: SC57.1 VH protein

<400> SEQUENCE: 23

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asp Tyr
            20                  25                  30

Gly Val His Trp Val Arg Gln Ser Pro Gly Lys Gly Leu Asp Trp Leu
        35                  40                  45

Gly Val Ile Trp Ser Gly Gly Asn Thr Asp Tyr Asn Ala Ala Phe Ile
    50                  55                  60

```
Ser Arg Leu Ser Ile Ser Lys Asp Asn Ser Lys Ser Gln Ile Phe Phe
 65                  70                  75                  80

Glu Met Asn Ser Leu Gln Asp Thr Asp Thr Ala Ile Tyr Tyr Cys Ala
                 85                  90                  95

Arg Gln Leu His Tyr Tyr Gly Pro Phe Ala Tyr Trp Gly Gln Gly Thr
            100                 105                 110

Leu Val Thr Val Ser Ala
        115

<210> SEQ ID NO 24
<211> LENGTH: 321
<212> TYPE: DNA
<213> ORGANISM: Mus musculus
<220> FEATURE:
<221> NAME/KEY: MISC_FEATURE
<223> OTHER INFORMATION: SC57.3 VL DNA

<400> SEQUENCE: 24
gatattgtgc taactcagtc tccagccacc ctgtctgtga ctccaggaga tagcgtcagt     60
ctttcctgca gggccagcca aggtattagc aacaacctac actggtatca acaaaaatca    120
catgagtctc caaggcttct catcaagtat gcttcccagt ccatctctgg gatcccctcc    180
aggttcagcg gcagtggatc agggacagat ttcgctctca gtatcaacag tgtggagact    240
gaagattttg gaatgttttt ctgtcaacag agtaacagct ggccgctcac gttcggtgct    300
gggaccaagc tggagctgaa a                                              321

<210> SEQ ID NO 25
<211> LENGTH: 107
<212> TYPE: PRT
<213> ORGANISM: Mus musculus
<220> FEATURE:
<221> NAME/KEY: MISC_FEATURE
<223> OTHER INFORMATION: SC57.3 VL protein

<400> SEQUENCE: 25

Asp Ile Val Leu Thr Gln Ser Pro Ala Thr Leu Ser Val Thr Pro Gly
  1               5                  10                  15

Asp Ser Val Ser Leu Ser Cys Arg Ala Ser Gln Gly Ile Ser Asn Asn
                 20                  25                  30

Leu His Trp Tyr Gln Gln Lys Ser His Glu Ser Pro Arg Leu Leu Ile
             35                  40                  45

Lys Tyr Ala Ser Gln Ser Ile Ser Gly Ile Pro Ser Arg Phe Ser Gly
 50                  55                  60

Ser Gly Ser Gly Thr Asp Phe Ala Leu Ser Ile Asn Ser Val Glu Thr
 65                  70                  75                  80

Glu Asp Phe Gly Met Phe Phe Cys Gln Gln Ser Asn Ser Trp Pro Leu
                 85                  90                  95

Thr Phe Gly Ala Gly Thr Lys Leu Glu Leu Lys
            100                 105

<210> SEQ ID NO 26
<211> LENGTH: 351
<212> TYPE: DNA
<213> ORGANISM: Mus musculus
<220> FEATURE:
<221> NAME/KEY: MISC_FEATURE
<223> OTHER INFORMATION: SC57.3 VH DNA

<400> SEQUENCE: 26
```

| | |
|---|---|
| caggtgcagc tgaagcagtc aggacctggc ctagtgcagc cctcacagag cctgtccatc | 60 |
| acctgcacag tctctggttt ctcattaagt agttatggtg tacactgggt tcgccagtct | 120 |
| ccaggaaagg gtctggaatg gctgggagtg atatggagtg gtggaaacac agactataat | 180 |
| gcagctttca tatccagact gagcatcagc aaggacaact ccaagagcca agttttcttt | 240 |
| aaaatgaaca gtctgcaagc tgatgacaca gccatatatt actgtgccag aaggaataac | 300 |
| tcggcctggt ttgcttactg gggccaaggg actctggtca ctgtctctgc a | 351 |

<210> SEQ ID NO 27
<211> LENGTH: 117
<212> TYPE: PRT
<213> ORGANISM: Mus musculus
<220> FEATURE:
<221> NAME/KEY: MISC_FEATURE
<223> OTHER INFORMATION: SC57.3 VH protein

<400> SEQUENCE: 27

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Ser Ser Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Ala Ala Phe Ile
    50                  55                  60

Ser Arg Leu Ser Ile Ser Lys Asp Asn Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

Arg Arg Asn Asn Ser Ala Trp Phe Ala Tyr Trp Gly Gln Gly Thr Leu
            100                 105                 110

Val Thr Val Ser Ala
        115

<210> SEQ ID NO 28
<211> LENGTH: 336
<212> TYPE: DNA
<213> ORGANISM: Mus musculus
<220> FEATURE:
<221> NAME/KEY: MISC_FEATURE
<223> OTHER INFORMATION: SC57.4 VL DNA

<400> SEQUENCE: 28

| | |
|---|---|
| gatgttgtga tgacccaaac tccactctcc ctgcctgtca gtcttggaga tcaagcctcc | 60 |
| atctcttgca gatctagtca gagccttgta cacagtaatg aaacaccta tttacattgg | 120 |
| taccttcaga agccaggcca gtctccaaag ctcctgatct acagagtttc caatcgattt | 180 |
| tctggggtcc cagacaggtt cagtggcagt ggatcaggga cagatttcac actcaagatc | 240 |
| agcagagtgg aggctgagga tctgggagtt tatctctgct ctcaaagtac acatgttccg | 300 |
| ctcacgttcg gtgctgggac caagctggag ctgaaa | 336 |

<210> SEQ ID NO 29
<211> LENGTH: 112
<212> TYPE: PRT
<213> ORGANISM: Mus musculus
<220> FEATURE:
<221> NAME/KEY: MISC_FEATURE
<223> OTHER INFORMATION: SC57.4 VL protein

<400> SEQUENCE: 29

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Leu Cys Ser Gln Ser
                85                  90                  95

Thr His Val Pro Leu Thr Phe Gly Ala Gly Thr Lys Leu Glu Leu Lys
                100                 105                 110

<210> SEQ ID NO 30
<211> LENGTH: 366
<212> TYPE: DNA
<213> ORGANISM: Mus musculus
<220> FEATURE:
<221> NAME/KEY: MISC_FEATURE
<223> OTHER INFORMATION: SC57.4 VH DNA

<400> SEQUENCE: 30
gagatccagc tgcagcagtc tggacctgag atggtgaagc ctggggcttc agtgaaggta      60
acctgcaagg cttctggcta ctcattcact gacttcaaca tgcactggat gaaacagagc     120
catggaaaga gccttgagtg gattggatat attgatcctt acaaggtgg tattagctac      180 aaccagaagt tcaagggcag ggccacattg actgttgaca gtcctccag cacagccttc      240 atgcatctca atagtctgac atctgacgac tctgcagtct attactgtgc aagagattac     300
tacggtagta gattccctta ctattttgat tactggggcc aaggcaccac tctcacagtc     360
tcctca                                                                366

<210> SEQ ID NO 31
<211> LENGTH: 122
<212> TYPE: PRT
<213> ORGANISM: Mus musculus
<220> FEATURE:
<221> NAME/KEY: MISC_FEATURE
<223> OTHER INFORMATION: SC57.4 VH protein

<400> SEQUENCE: 31

Glu Ile Gln Leu Gln Gln Ser Gly Pro Glu Met Val Lys Pro Gly Ala
1               5                   10                  15

Ser Val Lys Val Thr Cys Lys Ala Ser Gly Tyr Ser Phe Thr Asp Phe
            20                  25                  30

Asn Met His Trp Met Lys Gln Ser His Gly Lys Ser Leu Glu Trp Ile
        35                  40                  45

Gly Tyr Ile Asp Pro Tyr Lys Gly Gly Ile Ser Tyr Asn Gln Lys Phe
    50                  55                  60

Lys Gly Arg Ala Thr Leu Thr Val Asp Lys Ser Ser Thr Ala Phe
65                  70                  75                  80

Met His Leu Asn Ser Leu Thr Ser Asp Asp Ser Ala Val Tyr Tyr Cys
                85                  90                  95

Ala Arg Asp Tyr Tyr Gly Ser Arg Phe Pro Tyr Tyr Phe Asp Tyr Trp
                100                 105                 110

```
Gly Gln Gly Thr Thr Leu Thr Val Ser Ser
        115                 120
```

```
<210> SEQ ID NO 32
<211> LENGTH: 321
<212> TYPE: DNA
<213> ORGANISM: Mus musculus
<220> FEATURE:
<221> NAME/KEY: MISC_FEATURE
<223> OTHER INFORMATION: SC57.5 VL DNA

<400> SEQUENCE: 32
gacattgtga tgacccagtc tcacaaattc atgtccacat cagtaggaga cagggtcagc     60
atcacctgta aggccagtca ggatgtgtat gctgctgtag cctggtatca tcaaaaacca    120
gggcaatctc ctaaactact gatttactgg gcatccaccc ggcacgctgg agtccctgat    180
cgcttcacag gcagtggatc tgggacagat tatactctca ccatcagcag tgtgcaggct    240
gaagacctgg cactttatta ctgtcagcaa cattatcgca ctccgtggac gttcggtgga    300
ggcaccaagc tggaaatcaa a                                              321
```

```
<210> SEQ ID NO 33
<211> LENGTH: 107
<212> TYPE: PRT
<213> ORGANISM: Mus musculus
<220> FEATURE:
<221> NAME/KEY: MISC_FEATURE
<223> OTHER INFORMATION: SC57.5 VL protein

<400> SEQUENCE: 33

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Tyr Ala Ala
            20                  25                  30

Val Ala Trp Tyr His Gln Lys Pro Gly Gln Ser Pro Lys Leu Leu Ile
        35                  40                  45

Tyr Trp Ala Ser Thr Arg His Ala Gly Val Pro Asp Arg Phe Thr Gly
    50                  55                  60

Ser Gly Ser Gly Thr Asp Tyr Thr Leu Thr Ile Ser Ser Val Gln Ala
65                  70                  75                  80

Glu Asp Leu Ala Leu Tyr Tyr Cys Gln Gln His Tyr Arg Thr Pro Trp
                85                  90                  95

Thr Phe Gly Gly Gly Thr Lys Leu Glu Ile Lys
            100                 105
```

```
<210> SEQ ID NO 34
<211> LENGTH: 354
<212> TYPE: DNA
<213> ORGANISM: Mus musculus
<220> FEATURE:
<221> NAME/KEY: MISC_FEATURE
<223> OTHER INFORMATION: SC57.5 VH DNA

<400> SEQUENCE: 34
gaggtccagc tgcaacagtc tggacctgag ctggtgaagc ctggggcctc agtgaagata     60
tcctgcaagg cttctggtta ctcattcact gactactact gcactgggt gaagcaaagc    120 catgtaaaga gccttgagtg gattggacgg attaatcctt acaatggtgc tactagttac    180
aaccagattt tcaaggacaa ggccagcttg actgtagata gtcctccag cacagcctac    240 atggacctcc acagcctgac atctgaggac tctgcagtct attactgtgc aagaggggg     300
```

```
gactatgatt tccsctggta ctggggccaa ggcaccactc tcacagtctc ccca          354
```

<210> SEQ ID NO 35
<211> LENGTH: 118
<212> TYPE: PRT
<213> ORGANISM: Mus musculus
<220> FEATURE:
<221> NAME/KEY: MISC_FEATURE
<223> OTHER INFORMATION: SC57.5 VH protein

<400> SEQUENCE: 35

```
Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Asp Tyr
            20                  25                  30

Tyr Leu His Trp Val Lys Gln Ser His Val Lys Ser Leu Glu Trp Ile
        35                  40                  45

Gly Arg Ile Asn Pro Tyr Asn Gly Ala Thr Ser Tyr Asn Gln Ile Phe
    50                  55                  60

Lys Asp Lys Ala Ser Leu Thr Val Asp Lys Ser Ser Thr Ala Tyr
65                  70                  75                  80

Met Asp Leu His Ser Leu Thr Ser Glu Asp Ser Ala Val Tyr Tyr Cys
                85                  90                  95

Ala Arg Gly Gly Asp Tyr Asp Phe Pro Trp Tyr Trp Gly Gln Gly Thr
            100                 105                 110

Thr Leu Thr Val Ser Pro
        115
```

<210> SEQ ID NO 36
<211> LENGTH: 336
<212> TYPE: DNA
<213> ORGANISM: Mus musculus
<220> FEATURE:
<221> NAME/KEY: MISC_FEATURE
<223> OTHER INFORMATION: SC57.6 VL DNA

<400> SEQUENCE: 36

```
gacattgtga tgtcccagtc tccgtcctcc ctggctgtgt cagcagggga gaaggtcact    60
atgagctgca atccagtca gagtctgctc acacagtagaa tccgaaagaa ctacttggct   120
tggtaccagc agaaaccagg gcagtctcct aaactgctga tctactgggc atccactagg   180
gaatctgggg tccctgatcg cttcacaggc agtggatctg ggacagattt cactctcacc   240
atcagcagtg tgcaggctga agacctggca gtttattact gcaagcaatc ttataatctg   300
ttcacgttcg gagggggac caaactggaa ataaaa                              336
```

<210> SEQ ID NO 37
<211> LENGTH: 112
<212> TYPE: PRT
<213> ORGANISM: Mus musculus
<220> FEATURE:
<221> NAME/KEY: MISC_FEATURE
<223> OTHER INFORMATION: SC57.6 VL protein

<400> SEQUENCE: 37

```
Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu His Ser
            20                  25                  30

Arg Ile Arg Lys Asn Tyr Leu Ala Trp Tyr Gln Gln Lys Pro Gly Gln
```

```
                35                  40                  45
Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Phe Thr Phe Gly Gly Gly Thr Lys Leu Glu Ile Lys
            100                 105                 110

<210> SEQ ID NO 38
<211> LENGTH: 357
<212> TYPE: DNA
<213> ORGANISM: Mus musculus
<220> FEATURE:
<221> NAME/KEY: MISC_FEATURE
<223> OTHER INFORMATION: SC57.6 VH DNA

<400> SEQUENCE: 38
ggagtgcagg tggtggagtc tgggggaggt gtagtgcagc ctggagggtc cctgaaactc      60
tcctgtgcag cctctggatt cactttcagt agctatgcca tgtcttgggt tcgccagact     120
ccagagaaga ggctggagtg gtcgcatac cttagtaggg gtggtggtag cacctattat     180
ctagacactg taaagggccg attcaccatc tccagagaca tgccaagaa caccctgtac     240
ctacaaatga acagtctgaa gtctgaggac acggccatgt attactgtgc aagactggat     300
ggttacaact ggtacttcga tgtctggggc gcagggaccc cggtcaccgt ctcctca        357

<210> SEQ ID NO 39
<211> LENGTH: 119
<212> TYPE: PRT
<213> ORGANISM: Mus musculus
<220> FEATURE:
<221> NAME/KEY: MISC_FEATURE
<223> OTHER INFORMATION: SC57.6 VH protein

<400> SEQUENCE: 39

Gly Val Gln Val Val Glu Ser Gly Gly Gly Val Val Gln Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Glu Trp Val
        35                  40                  45

Ala Tyr Leu Ser Arg Gly Gly Gly Ser Thr Tyr Tyr Leu Asp Thr Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Met Tyr Tyr Cys
                85                  90                  95

Ala Arg Leu Asp Gly Tyr Asn Trp Tyr Phe Asp Val Trp Gly Ala Gly
            100                 105                 110

Thr Pro Val Thr Val Ser Ser
        115

<210> SEQ ID NO 40
<211> LENGTH: 321
<212> TYPE: DNA
<213> ORGANISM: Mus musculus
<220> FEATURE:
<221> NAME/KEY: MISC_FEATURE
```

<223> OTHER INFORMATION: SC57.8 VL DNA

<400> SEQUENCE: 40

```
gacattgtga tgacccagtc tcacaaattc atgtccacat cagtaggaga cagggtcaac    60
atcacctgca aggccagtca ggatgtgggt acgactgtag cctggtatca acagaaacca   120
gggcaatctc ctaaactact tatttactgg gcatccaccc ggcacactgg agtccctgat   180
cgcttcacag gcagtggatc tgggacagat ttcactctca ttattagcaa tgtgcagtct   240
gaagacttgg cagattattt ctgtcagcaa tatagcagct atcctctcac gttcggtgct   300
gggaccaagc tggagctgaa a                                             321
```

<210> SEQ ID NO 41
<211> LENGTH: 107
<212> TYPE: PRT
<213> ORGANISM: Mus musculus
<220> FEATURE:
<221> NAME/KEY: MISC_FEATURE
<223> OTHER INFORMATION: SC57.8 VL protein

<400> SEQUENCE: 41

Asp Ile Val Met Thr Gln Ser His Lys Phe Met Ser Thr Ser Val Gly
1               5                   10                  15

Asp Arg Val Asn Ile Thr Cys Lys Ala Ser Gln Asp Val Gly Thr Thr
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Ile Ile Ser Asn Val Gln Ser
65                  70                  75                  80

Glu Asp Leu Ala Asp Tyr Phe Cys Gln Gln Tyr Ser Ser Tyr Pro Leu
                85                  90                  95

Thr Phe Gly Ala Gly Thr Lys Leu Glu Leu Lys
            100                 105

<210> SEQ ID NO 42
<211> LENGTH: 351
<212> TYPE: DNA
<213> ORGANISM: Mus musculus
<220> FEATURE:
<221> NAME/KEY: MISC_FEATURE
<223> OTHER INFORMATION: SC57.8 VH DNA

<400> SEQUENCE: 42

```
caggtgcagc tgaagcagtc aggacctggc ctagtgcagc cctcacagag cctgtccatc    60
tcctgcacag tctctggttt ctcattaact acctatggtg tatactgggt tcgccagtct   120
ccaggaaagg gtctggagtg gctgggagtg atatggagtg gtggaagcac agactataat   180
gcagctttca tatccagact gatcatcagc aaggacaatt ccaagagcca gttttctttt   240
aaaatgaaca gtctgcaagc taatgacaca gccatatatt actgtgccag aatctcctat   300
gattacgacg gggcttactg gggccaaggg actctggtca ctgtctctgc a             351
```

<210> SEQ ID NO 43
<211> LENGTH: 117
<212> TYPE: PRT
<213> ORGANISM: Mus musculus
<220> FEATURE:
<221> NAME/KEY: MISC_FEATURE
<223> OTHER INFORMATION: SC57.8 VH protein

<400> SEQUENCE: 43

Gln Val Gln Leu Lys Gln Ser Gly Pro Gly Leu Val Gln Pro Ser Gln
1               5                   10                  15

Ser Leu Ser Ile Ser Cys Thr Val Ser Gly Phe Ser Leu Thr Thr Tyr
            20                  25                  30

Gly Val Tyr Trp Val Arg Gln Ser Pro Gly Lys Gly Leu Glu Trp Leu
        35                  40                  45

Gly Val Ile Trp Ser Gly Gly Ser Thr Asp Tyr Asn Ala Ala Phe Ile
    50                  55                  60

Ser Arg Leu Ile Ile Ser Lys Asp Asn Ser Lys Ser Gln Val Phe Phe
65              70                  75                  80

Lys Met Asn Ser Leu Gln Ala Asn Asp Thr Ala Ile Tyr Tyr Cys Ala
                85                  90                  95

Arg Ile Ser Tyr Asp Tyr Asp Gly Ala Tyr Trp Gly Gln Gly Thr Leu
            100                 105                 110

Val Thr Val Ser Ala
        115

<210> SEQ ID NO 44
<211> LENGTH: 318
<212> TYPE: DNA
<213> ORGANISM: Mus musculus
<220> FEATURE:
<221> NAME/KEY: MISC_FEATURE
<223> OTHER INFORMATION: SC57.9 VL DNA

<400> SEQUENCE: 44
caaattgttc tcacccagtc tccagcaatc atgtctgcat ctccagggga gaaggtcacc      60
ataacctgca gtgccagctc aagtgtaagt tacatgcact ggttccagca gaagccaggc     120
acttctccca aactctggat ttataccaca tccaacctgg cttctggagt ccctgctcgc     180
ttcagtggca gtggatctgg aacctcttac tctctcacaa tcagccgaat ggaggctgaa     240
gatgctgcca cttattactg ccagcaaagg agtagtttcc cacccacgtt cggctcgggg     300
acaaagttgg aaataaaa                                                   318

<210> SEQ ID NO 45
<211> LENGTH: 106
<212> TYPE: PRT
<213> ORGANISM: Mus musculus
<220> FEATURE:
<221> NAME/KEY: MISC_FEATURE
<223> OTHER INFORMATION: SC57.9 VL protein

<400> SEQUENCE: 45

Gln Ile Val Leu Thr Gln Ser Pro Ala Ile Met Ser Ala Ser Pro Gly
1               5                   10                  15

Glu Lys Val Thr Ile Thr Cys Ser Ala Ser Ser Val Ser Tyr Met
            20                  25                  30

His Trp Phe Gln Gln Lys Pro Gly Thr Ser Pro Lys Leu Trp Ile Tyr
        35                  40                  45

Thr Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65              70                  75                  80

Asp Ala Ala Thr Tyr Tyr Cys Gln Gln Arg Ser Ser Phe Pro Pro Thr
                85                  90                  95

```
Phe Gly Ser Gly Thr Lys Leu Glu Ile Lys
            100                 105
```

```
<210> SEQ ID NO 46
<211> LENGTH: 351
<212> TYPE: DNA
<213> ORGANISM: Mus musculus
<220> FEATURE:
<221> NAME/KEY: MISC_FEATURE
<223> OTHER INFORMATION: SC57.9  VH DNA

<400> SEQUENCE: 46
caggttcagc tgcagcagtc tggacctgag ctgatgaagc ctggggcctc agtgaagata      60
tcctgcaagg ctactggcta cacattcagt agctactgga tagagtgggt aaagcagagg     120
cctggacatg gccttgagtg gattggagag attttacctg gaagtggtag tactgagtat     180
aatgagaagt tcaagggcaa ggccacattc accgcagata catcttccaa cacagcctac     240
atgcaactca gcagcctgac atctgaggac tctgacgtct attactgtgc aagaaagagg     300
tacgggacta tggactactg gggtcaagga acctcagtca ccgtctcctc a              351
```

```
<210> SEQ ID NO 47
<211> LENGTH: 117
<212> TYPE: PRT
<213> ORGANISM: Mus musculus
<220> FEATURE:
<221> NAME/KEY: MISC_FEATURE
<223> OTHER INFORMATION: SC57.9 VH protein

<400> SEQUENCE: 47

Gln Val Gln Leu Gln Gln Ser Gly Pro Glu Leu Met Lys Pro Gly Ala
1               5                   10                  15

Ser Val Lys Ile Ser Cys Lys Ala Thr Gly Tyr Thr Phe Ser Ser Tyr
            20                  25                  30

Trp Ile Glu Trp Val Lys Gln Arg Pro Gly His Gly Leu Glu Trp Ile
        35                  40                  45

Gly Glu Ile Leu Pro Gly Ser Gly Ser Thr Glu Tyr Asn Glu Lys Phe
    50                  55                  60

Lys Gly Lys Ala Thr Phe Thr Ala Asp Thr Ser Ser Asn Thr Ala Tyr
65                  70                  75                  80

Met Gln Leu Ser Ser Leu Thr Ser Glu Asp Ser Asp Val Tyr Tyr Cys
                85                  90                  95

Ala Arg Lys Arg Tyr Gly Thr Met Asp Tyr Trp Gly Gln Gly Thr Ser
            100                 105                 110

Val Thr Val Ser Ser
        115
```

```
<210> SEQ ID NO 48
<211> LENGTH: 321
<212> TYPE: DNA
<213> ORGANISM: Mus musculus
<220> FEATURE:
<221> NAME/KEY: MISC_FEATURE
<223> OTHER INFORMATION: SC57.10 (SC57.32) VL DNA

<400> SEQUENCE: 48
gatatccaga tgacacagac tacatcctcc ctgtctgcct ctctgggaga cagagtcacc      60
atcagttgca gggcaagtca ggacattagc aattatttaa actggtatca gcagaaacca     120
gatggaactg ttaaactcct gatctttttac acatcaagat tacactcagg agtcccatcc    180
aggttcagtg gtagtgggtc tggaacagat tattctctca ccattagcaa cctggaacaa    240
```

```
gaagattttg ccacttactt ttgccaacag ggtaatacgc ttcctccgac gttcggtgga      300
ggcaccaagc tggaaatcaa a                                                321
```

<210> SEQ ID NO 49
<211> LENGTH: 107
<212> TYPE: PRT
<213> ORGANISM: Mus musculus
<220> FEATURE:
<221> NAME/KEY: MISC_FEATURE
<223> OTHER INFORMATION: SC57.10 (SC57.32) VL protein

<400> SEQUENCE: 49

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Phe Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Phe Ala Thr Tyr Phe Cys Gln Gln Gly Asn Thr Leu Pro Pro
                85                  90                  95

Thr Phe Gly Gly Gly Thr Lys Leu Glu Ile Lys
            100                 105
```

<210> SEQ ID NO 50
<211> LENGTH: 357
<212> TYPE: DNA
<213> ORGANISM: Mus musculus
<220> FEATURE:
<221> NAME/KEY: MISC_FEATURE
<223> OTHER INFORMATION: SC57.10 (SC57.32) VH DNA

<400> SEQUENCE: 50

```
caggttcagc tgcagcagtc tggagctgag ctgatgaagc ctggggcctc agtgaagata      60
tcctgcaagg ctactggcta cacattcagt aactacagga tagagtggat aaaacagagg     120
cctggacatg gccttgagtg gattggagag attttaccta gaggtggtaa tactaactac     180
aatgagaagt tcaagggcaa ggccacattc actgcagata catcctccaa cacagcctac     240
atgcaactca ccagcctgac atctgaggac tctgccgtct attactgtgc aagggatgat     300
ggttactacg ggaggtttgc ttactggggc caagggactc tggtcactgt ctctgca        357
```

<210> SEQ ID NO 51
<211> LENGTH: 119
<212> TYPE: PRT
<213> ORGANISM: Mus musculus
<220> FEATURE:
<221> NAME/KEY: MISC_FEATURE
<223> OTHER INFORMATION: SC57.10 (SC57.32) VH protein

<400> SEQUENCE: 51

```
Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Asn Tyr
            20                  25                  30

Arg Ile Glu Trp Ile Lys Gln Arg Pro Gly His Gly Leu Glu Trp Ile
        35                  40                  45
```

Gly Glu Ile Leu Pro Arg Gly Gly Asn Thr Asn Tyr Asn Glu Lys Phe
 50                  55                  60

Lys Gly Lys Ala Thr Phe Thr Ala Asp Thr Ser Ser Asn Thr Ala Tyr
 65                  70                  75                  80

Met Gln Leu Thr Ser Leu Thr Ser Glu Asp Ser Ala Val Tyr Tyr Cys
                 85                  90                  95

Ala Arg Asp Asp Gly Tyr Tyr Gly Arg Phe Ala Tyr Trp Gly Gln Gly
                100                 105                 110

Thr Leu Val Thr Val Ser Ala
        115

<210> SEQ ID NO 52
<211> LENGTH: 321
<212> TYPE: DNA
<213> ORGANISM: Mus musculus
<220> FEATURE:
<221> NAME/KEY: MISC_FEATURE
<223> OTHER INFORMATION: SC57.11 VL DNA

<400> SEQUENCE: 52
gatatccaga tgacacagac tacatcctcc ctctctgcct ctctgggaga cagagtcacc    60
atcagttgca gggcaagtca ggacattagc agttatttaa actggtatca gcagaaacca   120
gatggaactg ttaaactcct gatctattac acatcaagat tacactcagg agtcccatca   180
aggttcagtg gcagtgggtc tggaacagat tattctctca ccattaacaa cctggagcaa   240
gaagatattg ccacttactt ttgccaacag ggtaatacgc ttcctccgac gttcggtgga   300
ggcaccaagc tggaaatcaa a                                              321

<210> SEQ ID NO 53
<211> LENGTH: 107
<212> TYPE: PRT
<213> ORGANISM: Mus musculus
<220> FEATURE:
<221> NAME/KEY: MISC_FEATURE
<223> OTHER INFORMATION: SC57.11 VL protein

<400> SEQUENCE: 53

Asp Ile Gln Met Thr Gln Thr Thr Ser Ser Leu Ser Ala Ser Leu Gly
 1               5                  10                  15

Asp Arg Val Thr Ile Ser Cys Arg Ala Ser Gln Asp Ile Ser Ser Tyr
                20                  25                  30

Leu Asn Trp Tyr Gln Gln Lys Pro Asp Gly Thr Val Lys Leu Leu Ile
            35                  40                  45

Tyr Tyr Thr Ser Arg Leu His Ser Gly Val Pro Ser Arg Phe Ser Gly
 50                  55                  60

Ser Gly Ser Gly Thr Asp Tyr Ser Leu Thr Ile Asn Asn Leu Glu Gln
 65                  70                  75                  80

Glu Asp Ile Ala Thr Tyr Phe Cys Gln Gln Gly Asn Thr Leu Pro Pro
                 85                  90                  95

Thr Phe Gly Gly Gly Thr Lys Leu Glu Ile Lys
                100                 105

<210> SEQ ID NO 54
<211> LENGTH: 357
<212> TYPE: DNA
<213> ORGANISM: Mus musculus
<220> FEATURE:
<221> NAME/KEY: MISC_FEATURE
<223> OTHER INFORMATION: SC57.11 VH DNA

<400> SEQUENCE: 54

```
caggttcagc tgcagcagtc tggagctgag ctgatgaagc tggggcctc agtgaagata      60
tcctgcaagg ctactggcta cacattcagt aactacagga tagagtggat gaaacagagg    120
cctggacatg gccttgagtg gattggagag attttaccta gaactggtaa tactaactac    180
aatgagaact tcaagggcaa ggccacattc actgcagata tcctccaa cacagcctac      240
atacaactca gcagcctgac atctgaggac tctgccgtct attactgtgc aagggatgat    300
ggttactacg ggaggtttgc ttactggggc caagggactc tggtcactgt ctctgca       357
```

<210> SEQ ID NO 55
<211> LENGTH: 119
<212> TYPE: PRT
<213> ORGANISM: Mus musculus
<220> FEATURE:
<221> NAME/KEY: MISC_FEATURE
<223> OTHER INFORMATION: SC57.11 VH protein

<400> SEQUENCE: 55

```
Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Asn Tyr
            20                  25                  30

Arg Ile Glu Trp Met Lys Gln Arg Pro Gly His Gly Leu Glu Trp Ile
        35                  40                  45

Gly Glu Ile Leu Pro Arg Thr Gly Asn Thr Asn Tyr Asn Glu Asn Phe
    50                  55                  60

Lys Gly Lys Ala Thr Phe Thr Ala Asp Thr Ser Ser Asn Thr Ala Tyr
65                  70                  75                  80

Ile Gln Leu Ser Ser Leu Thr Ser Glu Asp Ser Ala Val Tyr Tyr Cys
                85                  90                  95

Ala Arg Asp Asp Gly Tyr Tyr Gly Arg Phe Ala Tyr Trp Gly Gln Gly
            100                 105                 110

Thr Leu Val Thr Val Ser Ala
        115
```

<210> SEQ ID NO 56
<211> LENGTH: 321
<212> TYPE: DNA
<213> ORGANISM: Mus musculus
<220> FEATURE:
<221> NAME/KEY: MISC_FEATURE
<223> OTHER INFORMATION: SC57.12 VL DNA

<400> SEQUENCE: 56

```
gacatccaga tgactcagtc tccacccctcc ctatctgcat ctgtgggaga aactgtcacc    60
atcacatgtc gaacaagtga gaatatttac agttatttaa catggtatca gcagaaacag   120
ggaaaatctc ctcagctcct ggtctataat gcaaaaacct agcagagggg tgtgccatca   180
aggttcagtg gcagtggatc aggcacacag ttttctctga gatcaacag cctgcagcct    240
gaggattttg ggagttatta ctgtcaacat cattatggta ctccgctcac gttcggtgct   300
gggaccaagc tggagctgaa a                                             321
```

<210> SEQ ID NO 57
<211> LENGTH: 107
<212> TYPE: PRT
<213> ORGANISM: Mus musculus
<220> FEATURE:

```
<221> NAME/KEY: MISC_FEATURE
<223> OTHER INFORMATION: SC57.12 VL protein

<400> SEQUENCE: 57

Asp Ile Gln Met Thr Gln Ser Pro Ser Leu Ser Ala Ser Val Gly
1               5                   10                  15

Glu Thr Val Thr Ile Thr Cys Arg Thr Ser Glu Asn Ile Tyr Ser Tyr
            20                  25                  30

Leu Thr Trp Tyr Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Gly Thr Pro Leu
                85                  90                  95

Thr Phe Gly Ala Gly Thr Lys Leu Glu Leu Lys
            100                 105

<210> SEQ ID NO 58
<211> LENGTH: 366
<212> TYPE: DNA
<213> ORGANISM: Mus musculus
<220> FEATURE:
<221> NAME/KEY: MISC_FEATURE
<223> OTHER INFORMATION: SC57.12 VH DNA

<400> SEQUENCE: 58
caggtgcagc tgaaggagtc aggacctggc ctggtggcgc cctcacagag cctgtccatc      60
acttgcactg tctctgggtt ttcattaacc agttatggtg tacactgggt tcgccagcct    120
ccaggaaagg gtctggagtg gctgggaatt atatgggctg gtggaaccac aaattataat    180
tcggctctca gtccagact gagcatcaga aagacaact ccaagagcca agttttctta    240
aaaatgaaca gtctgcaaac tgatgacaca gccatgtact actgtgccag agatagggc    300 tatgatggtt acttcgacta tgctgtggac tactggggtc aaggaacctc agtcaccgtc    360
tcctca                                                                366

<210> SEQ ID NO 59
<211> LENGTH: 122
<212> TYPE: PRT
<213> ORGANISM: Mus musculus
<220> FEATURE:
<221> NAME/KEY: MISC_FEATURE
<223> OTHER INFORMATION: SC57.12 VH protein

<400> SEQUENCE: 59

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Gly Val His Trp Val Arg Gln Pro Pro Gly Lys Gly Leu Glu Trp Leu
        35                  40                  45

Gly Ile Ile Trp Ala Gly Gly Thr Thr Asn Tyr Asn Ser Ala Leu Met
    50                  55                  60

Ser Arg Leu Ser Ile Arg Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95
```

Arg Asp Arg Gly Tyr Asp Gly Tyr Phe Asp Tyr Ala Val Asp Tyr Trp
                100                 105                 110

Gly Gln Gly Thr Ser Val Thr Val Ser Ser
        115                 120

<210> SEQ ID NO 60
<211> LENGTH: 336
<212> TYPE: DNA
<213> ORGANISM: Mus musculus
<220> FEATURE:
<221> NAME/KEY: MISC_FEATURE
<223> OTHER INFORMATION: SC57.14 VL DNA

<400> SEQUENCE: 60
gacattgtga tgtcacagtc tccatcctcc ctggctgtgt cagcaggaga gaaggtcact    60
atgagctgca atccagtca gagtctgctc aacagtagaa cccgaaagaa ctacttggct   120
tggtaccagc agaaaccagg gcagtctcct aaactgctga tctactgggc atccactagg   180
gaatctgggg tccctgatcg cttcacaggc agtggatctg ggacagattt cactctcacc   240
atcagcagtg tgcaggctga agacctggca gtttattact gcaagcaatc ttataatctg   300
tggacgttcg gtggaggcac caagctggaa atcaaa                              336

<210> SEQ ID NO 61
<211> LENGTH: 112
<212> TYPE: PRT
<213> ORGANISM: Mus musculus
<220> FEATURE:
<221> NAME/KEY: MISC_FEATURE
<223> OTHER INFORMATION: SC57.14 VL protein

<400> SEQUENCE: 61

Asp Ile Val Met Ser Gln Ser Pro Ser Ser Leu Ala Val Ser Ala Gly
1               5                   10                  15

Glu Lys Val Thr Met Ser Cys Lys Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Trp Thr Phe Gly Gly Gly Thr Lys Leu Glu Ile Lys
            100                 105                 110

<210> SEQ ID NO 62
<211> LENGTH: 357
<212> TYPE: DNA
<213> ORGANISM: Mus musculus
<220> FEATURE:
<221> NAME/KEY: MISC_FEATURE
<223> OTHER INFORMATION: SC57.14 VH DNA

<400> SEQUENCE: 62
gatgtacagc ttcaggagtc aggacctggc ctcgtgaaac cttctcagtc tctgtctctc    60
acctgctctg tcactggcta ctccatcacc agtggttatt actggaactg gatccggcag   120
tttccaggaa acaaactgga atggatgggc tacataagct acgacggtta caataactac   180

```
gacccatctc tcaaaaatcg aatctccatc actcgtgaca catctaagaa ccagttttc      240 ctgaagttga attctgtgac tactgaggac acagctacat attactgtgc aagcaactat      300
tggtacgacg cttactttga ctactggggc caaggcacca ctctcacagt ctcctca        357
```

<210> SEQ ID NO 63
<211> LENGTH: 119
<212> TYPE: PRT
<213> ORGANISM: Mus musculus
<220> FEATURE:
<221> NAME/KEY: MISC_FEATURE
<223> OTHER INFORMATION: SC57.14 VH protein

<400> SEQUENCE: 63

```
Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
            20                  25                  30

Tyr Tyr Trp Asn Trp Ile Arg Gln Phe Pro Gly Asn Lys Leu Glu Trp
        35                  40                  45

Met Gly Tyr Ile Ser Tyr Asp Gly Tyr Asn Asn Tyr Asp Pro Ser Leu
    50                  55                  60

Lys Asn Arg Ile Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

Ala Ser Asn Tyr Trp Tyr Asp Ala Tyr Phe Asp Tyr Trp Gly Gln Gly
            100                 105                 110

Thr Thr Leu Thr Val Ser Ser
        115
```

<210> SEQ ID NO 64
<211> LENGTH: 321
<212> TYPE: DNA
<213> ORGANISM: Mus musculus
<220> FEATURE:
<221> NAME/KEY: MISC_FEATURE
<223> OTHER INFORMATION: SC57.15 VL DNA

<400> SEQUENCE: 64

```
gacatccaga tgactcagtc tccagcttca ctgtctgcat ctgtgggaga aactgtcacc      60
atcacatgtg gagcaagtga gaatatttac ggtgctttaa attggtatca gcggaaacag      120
ggaaaatctc ctcagctcct gatctatggt gcaaccaact ggcagatgg catgtcatcg       180 aggttcagtg gcagtggatc tggtggacag tattctctca agatcagtgg cctgcatcct      240
gccgatgttg caacgtatta ctgtcaaaat gtattaaata ctccgtggac gttcggtgga      300
ggcaccaagc tggaaatcaa a                                                321
```

<210> SEQ ID NO 65
<211> LENGTH: 107
<212> TYPE: PRT
<213> ORGANISM: Mus musculus
<220> FEATURE:
<221> NAME/KEY: MISC_FEATURE
<223> OTHER INFORMATION: SC57.15 VL protein

<400> SEQUENCE: 65

```
Asp Ile Gln Met Thr Gln Ser Pro Ala Ser Leu Ser Ala Ser Val Gly
1               5                   10                  15

Glu Thr Val Thr Ile Thr Cys Gly Ala Ser Glu Asn Ile Tyr Gly Ala
```

```
                  20                  25                  30

Leu Asn Trp Tyr Gln Arg Lys Gln Gly Lys Ser Pro Gln Leu Leu Ile
            35                  40                  45

Tyr Gly Ala Thr Asn Leu Ala Asp Gly Met Ser Ser Arg Phe Ser Gly
        50                  55                  60

Ser Gly Ser Gly Gly Gln Tyr Ser Leu Lys Ile Ser Gly Leu His Pro
65                  70                  75                  80

Ala Asp Val Ala Thr Tyr Tyr Cys Gln Asn Val Leu Asn Thr Pro Trp
                85                  90                  95

Thr Phe Gly Gly Gly Thr Lys Leu Glu Ile Lys
            100                 105

<210> SEQ ID NO 66
<211> LENGTH: 372
<212> TYPE: DNA
<213> ORGANISM: Mus musculus
<220> FEATURE:
<221> NAME/KEY: MISC_FEATURE
<223> OTHER INFORMATION: SC57.15 VH DNA

<400> SEQUENCE: 66
gatgtgcagc ttcaggagtc aggacctgac ctggtgaaac cttctcagtc actttcactc      60
acctgcgctg tcactggcta ctccatcacc agtgcttata cctggcactg gatccggcag     120
tttccaggaa acaaactgga atggatgggc tacatgcact acagtggtag cactagctac     180
aacccatctc tcaaaagtcg aatctctatc actcgagaca catccaagaa ccagttcttc     240
ctgcagttga attctgtgac tactgaggac acagccacat attactgtgc aaattcccte     300 ctttactacg gctacgggtt gtactggtac ttcgatgtct ggggcgcagg gaccacggtc     360
accgtctcct ca                                                         372

<210> SEQ ID NO 67
<211> LENGTH: 124
<212> TYPE: PRT
<213> ORGANISM: Mus musculus
<220> FEATURE:
<221> NAME/KEY: MISC_FEATURE
<223> OTHER INFORMATION: SC57.15 VH protein

<400> SEQUENCE: 67

Asp Val Gln Leu Gln Glu Ser Gly Pro Asp Leu Val Lys Pro Ser Gln
1               5                   10                  15

Ser Leu Ser Leu Thr Cys Ala Val Thr Gly Tyr Ser Ile Thr Ser Ala
            20                  25                  30

Tyr Thr Trp His Trp Ile Arg Gln Phe Pro Gly Asn Lys Leu Glu Trp
        35                  40                  45

Met Gly Tyr Met His Tyr Ser Gly Ser Thr Ser Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Asn Ser Leu Leu Tyr Tyr Gly Tyr Gly Leu Tyr Trp Tyr Phe Asp
            100                 105                 110

Val Trp Gly Ala Gly Thr Thr Val Thr Val Ser Ser
        115                 120

<210> SEQ ID NO 68
```

<211> LENGTH: 321
<212> TYPE: DNA
<213> ORGANISM: Mus musculus
<220> FEATURE:
<221> NAME/KEY: MISC_FEATURE
<223> OTHER INFORMATION: SC57.17 VL DNA

<400> SEQUENCE: 68

```
gatatccaga tgacacagac tacatcctcc ctgtctgcct ctctgggaga cagagtcacc    60
atcagttgca gtgcaagtca ggacataaac aattatttaa actggtatca acagaaacca   120
gatggaactg ttaaactcct gatccattac acatcaagtt tacactcagg agtcccatca   180
aggttcagtg gcagtgggtc tgggacagat tattctctca ccatcagcaa cctggaacct   240
gaagatattg ccacttacta ttgtcagcag tatagtaagg ttccgtggac gttcggtgga   300
ggcaccaagc tggaaatcaa a                                              321
```

<210> SEQ ID NO 69
<211> LENGTH: 107
<212> TYPE: PRT
<213> ORGANISM: Mus musculus
<220> FEATURE:
<221> NAME/KEY: MISC_FEATURE
<223> OTHER INFORMATION: SC57.17 VL protein

<400> SEQUENCE: 69

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Asp Ile Asn Asn Tyr
            20                  25                  30

Leu Asn Trp Tyr Gln Gln Lys Pro Asp Gly Thr Val Lys Leu Leu Ile
        35                  40                  45

His Tyr Thr Ser Ser Leu His Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ser Lys Val Pro Trp
                85                  90                  95

Thr Phe Gly Gly Gly Thr Lys Leu Glu Ile Lys
            100                 105

<210> SEQ ID NO 70
<211> LENGTH: 366
<212> TYPE: DNA
<213> ORGANISM: Mus musculus
<220> FEATURE:
<221> NAME/KEY: MISC_FEATURE
<223> OTHER INFORMATION: SC57.17 VH DNA

<400> SEQUENCE: 70

```
gaagttcagc tgcagcagtc tggggcagag cttgtgaagc caggggcctc agtcaagttg    60
tcctgcacag cttctggctt caacattaaa gacacctata tgcactgggt gaagcagagg   120
cctgaacagg gcctggagtg gattggaagg attgatccag cgaatgtaaa tactagcgat   180
gacccgaagt tccagggcaa ggccactata gcagcagaca catcctccaa cacagtttac   240
ctgcagctca gcagcctgac atctgaggac actgccgtct attattgtgc tagagactat   300
aggtacgacg gatattacta tgcaatggac tactggggtc aaggaaccct agtcaccgtc   360
tcctca                                                               366
```

```
<210> SEQ ID NO 71
<211> LENGTH: 122
<212> TYPE: PRT
<213> ORGANISM: Mus musculus
<220> FEATURE:
<221> NAME/KEY: MISC_FEATURE
<223> OTHER INFORMATION: SC57.17 VH protein

<400> SEQUENCE: 71
```

| Glu | Val | Gln | Leu | Gln | Gln | Ser | Gly | Ala | Glu | Leu | Val | Lys | Pro | Gly | Ala |
|---|---|---|---|---|---|---|---|---|---|---|---|---|---|---|---|
| 1 | | | | 5 | | | | | 10 | | | | | 15 | |

| Ser | Val | Lys | Leu | Ser | Cys | Thr | Ala | Ser | Gly | Phe | Asn | Ile | Lys | Asp | Thr |
|---|---|---|---|---|---|---|---|---|---|---|---|---|---|---|---|
| | | | 20 | | | | | 25 | | | | | 30 | | |

| Tyr | Met | His | Trp | Val | Lys | Gln | Arg | Pro | Glu | Gln | Gly | Leu | Glu | Trp | Ile |
|---|---|---|---|---|---|---|---|---|---|---|---|---|---|---|---|
| | | 35 | | | | | 40 | | | | | 45 | | | |

| Gly | Arg | Ile | Asp | Pro | Ala | Asn | Val | Asn | Thr | Ser | Asp | Asp | Pro | Lys | Phe |
|---|---|---|---|---|---|---|---|---|---|---|---|---|---|---|---|
| | 50 | | | | | 55 | | | | | 60 | | | | |

| Gln | Gly | Lys | Ala | Thr | Ile | Ala | Ala | Asp | Thr | Ser | Ser | Asn | Thr | Val | Tyr |
|---|---|---|---|---|---|---|---|---|---|---|---|---|---|---|---|
| 65 | | | | | 70 | | | | | 75 | | | | | 80 |

| Leu | Gln | Leu | Ser | Ser | Leu | Thr | Ser | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Arg | Asp | Tyr | Arg | Tyr | Asp | Gly | Tyr | Tyr | Tyr | Ala | Met | Asp | Tyr | Trp |
|---|---|---|---|---|---|---|---|---|---|---|---|---|---|---|---|
| | | | 100 | | | | | 105 | | | | | 110 | | |

| Gly | Gln | Gly | Thr | Ser | Val | Thr | Val | Ser | Ser |
|---|---|---|---|---|---|---|---|---|---|
| | | | 115 | | | | | 120 | |

```
<210> SEQ ID NO 72
<211> LENGTH: 321
<212> TYPE: DNA
<213> ORGANISM: Mus musculus
<220> FEATURE:
<221> NAME/KEY: MISC_FEATURE
<223> OTHER INFORMATION: SC57.20 VL DNA

<400> SEQUENCE: 72
gacattgtga tgacccagtc tcacaaattc atgtccacat cagtaggaga cagggtcagc      60
atcacctgca aggccagtca agatgtgggt tctgctgttg cctggtctca acagaaacca     120
ggacaatctc ctaaactact gatttactgg gcatcctccc ggcacactgg agtccctgat     180
cgcttcacag gcagtggatc tgggacagat ttcactctca ccattagcaa tgtgcagtct     240
gaagacttgg cagattattt ctgtcagcaa tatagcaact atcctctcac gttcggtgct     300
gggaccaagc tggagctgaa a                                                321

<210> SEQ ID NO 73
<211> LENGTH: 107
<212> TYPE: PRT
<213> ORGANISM: Mus musculus
<220> FEATURE:
<221> NAME/KEY: MISC_FEATURE
<223> OTHER INFORMATION: SC57.20 VL protein

<400> SEQUENCE: 73
```

| Asp | Ile | Val | Met | Thr | Gln | Ser | His | Lys | Phe | Met | Ser | Thr | Ser | Val | Gly |
|---|---|---|---|---|---|---|---|---|---|---|---|---|---|---|---|
| 1 | | | | 5 | | | | | 10 | | | | | 15 | |

| Asp | Arg | Val | Ser | Ile | Thr | Cys | Lys | Ala | Ser | Gln | Asp | Val | Gly | Ser | Ala |
|---|---|---|---|---|---|---|---|---|---|---|---|---|---|---|---|
| | | | 20 | | | | | 25 | | | | | 30 | | |

| Val | Ala | Trp | Ser | Gln | Gln | Lys | Pro | Gly | Gln | Ser | Pro | Lys | Leu | Leu | Ile |
|---|---|---|---|---|---|---|---|---|---|---|---|---|---|---|---|
| | | 35 | | | | | 40 | | | | | 45 | | | |

| Tyr | Trp | Ala | Ser | Ser | Arg | His | Thr | Gly | Val | Pro | Asp | Arg | Phe | Thr | Gly |
|---|---|---|---|---|---|---|---|---|---|---|---|---|---|---|---|
| | 50 | | | | | 55 | | | | | 60 | | | | |

```
Ser Gly Ser Gly Thr Asp Phe Thr Leu Thr Ile Ser Asn Val Gln Ser
 65                  70                  75                  80

Glu Asp Leu Ala Asp Tyr Phe Cys Gln Gln Tyr Ser Asn Tyr Pro Leu
                 85                  90                  95

Thr Phe Gly Ala Gly Thr Lys Leu Glu Leu Lys
            100                 105
```

<210> SEQ ID NO 74
<211> LENGTH: 354
<212> TYPE: DNA
<213> ORGANISM: Mus musculus
<220> FEATURE:
<221> NAME/KEY: MISC_FEATURE
<223> OTHER INFORMATION: SC57.20 VH DNA

<400> SEQUENCE: 74

```
gatgtgcagc tacaggagtc aggacctgac ctggtgaaac cttctcagtc actttcactc      60
acctgcactg tcactggcta ctccatcacc agtggttata gctggcactg gatccggcag     120
tttccaggaa acaaactgga atggatgggc ttcatacact acagtggtag ctctaactac     180
aacccatttc tcaaaagtcg aatctctatc actcgagaca catccaagaa ccagttcttc     240
ctgcagatga attctgtgaa tacagaggac acagccacat attactgttc aagaaaaggc     300
tccttctatc ctatggacta ctggggtcaa ggaacctcag tcaccgtctc ctca          354
```

<210> SEQ ID NO 75
<211> LENGTH: 118
<212> TYPE: PRT
<213> ORGANISM: Mus musculus
<220> FEATURE:
<221> NAME/KEY: MISC_FEATURE
<223> OTHER INFORMATION: SC57.20 VH protein

<400> SEQUENCE: 75

```
Asp Val Gln Leu Gln Glu Ser Gly Pro Asp Leu Val Lys Pro Ser Gln
  1               5                  10                  15

Ser Leu Ser Leu Thr Cys Thr Val Thr Gly Tyr Ser Ile Thr Ser Gly
             20                  25                  30

Tyr Ser Trp His Trp Ile Arg Gln Phe Pro Gly Asn Lys Leu Glu Trp
         35                  40                  45

Met Gly Phe Ile His Tyr Ser Gly Ser Ser Asn Tyr Asn Pro Phe Leu
     50                  55                  60

Lys Ser Arg Ile Ser Ile Thr Arg Asp Thr Ser Lys Asn Gln Phe Phe
 65                  70                  75                  80

Leu Gln Met Asn Ser Val Asn Thr Glu Asp Thr Ala Thr Tyr Tyr Cys
                 85                  90                  95

Ser Arg Lys Gly Ser Phe Tyr Pro Met Asp Tyr Trp Gly Gln Gly Thr
            100                 105                 110

Ser Val Thr Val Ser Ser
        115
```

<210> SEQ ID NO 76
<211> LENGTH: 321
<212> TYPE: DNA
<213> ORGANISM: Mus musculus
<220> FEATURE:
<221> NAME/KEY: MISC_FEATURE
<223> OTHER INFORMATION: SC57.27 VL DNA

<400> SEQUENCE: 76

```
gacatccaga tgactcagtc tccagtctcc ctatctgcat ctgtgggaga aactgtcacc    60
atcacatgtc gagcaagtga gattatttac agttatttag catggtatca gcagaaacag   120
ggaaaatctc ctcagctcct ggtctataat gcaaaaacct agcagaagg tgtgccatca    180 aggttcagtg gcagtggatc aggcacacag ttttctctga agatcaacag cctgcagcct   240
gaagattttg ggacttatta ctgtcaacat cattatggtg ttcctgtcac gttcggtgct   300
gggaccaagc tggagctgaa a                                             321
```

<210> SEQ ID NO 77
<211> LENGTH: 107
<212> TYPE: PRT
<213> ORGANISM: Mus musculus
<220> FEATURE:
<221> NAME/KEY: MISC_FEATURE
<223> OTHER INFORMATION: SC57.27 VL protein

<400> SEQUENCE: 77

```
Asp Ile Gln Met Thr Gln Ser Pro Val Ser Leu Ser Ala Ser Val Gly
1               5                   10                  15

Glu Thr Val Thr Ile Thr Cys Arg Ala Ser Glu Ile Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Thr Tyr Tyr Cys Gln His His Tyr Gly Val Pro Val
                85                  90                  95

Thr Phe Gly Ala Gly Thr Lys Leu Glu Leu Lys
            100                 105
```

<210> SEQ ID NO 78
<211> LENGTH: 357
<212> TYPE: DNA
<213> ORGANISM: Mus musculus
<220> FEATURE:
<221> NAME/KEY: MISC_FEATURE
<223> OTHER INFORMATION: SC57.27 VH DNA

<400> SEQUENCE: 78

```
gaactgaaac tggtggagtc tggggggagac ttagtgaagc ctggagggtc cctgaaactc    60
tcctgtgcag cctctggatt ctctttcaat aactatgcca tgtcttgggt tcgtcagact   120
ccagagaaga ggctggagtg ggtcgcatcc attagtagtg gtggaactac gttctatcca   180
gacagtgtga aggccgatt taccatgtcc agagatcatg ccaggaacat cctgtacctg   240
caaatgaaca gtctgaggtc tgaggacacg gccatgtatt actgtgtaag aggccaatgg   300
ttatcactct attctatgga ctactgggggt caaggaacct cagtcaccgt ctcctca     357
```

<210> SEQ ID NO 79
<211> LENGTH: 119
<212> TYPE: PRT
<213> ORGANISM: Mus musculus
<220> FEATURE:
<221> NAME/KEY: MISC_FEATURE
<223> OTHER INFORMATION: SC57.27 VH protein

<400> SEQUENCE: 79

```
Glu Leu Lys Leu Val Glu Ser Gly Gly Asp Leu Val Lys Pro Gly Gly
```

```
1               5                   10                  15
Ser Leu Lys Leu Ser Cys Ala Ala Ser Gly Phe Ser Phe Asn Asn Tyr
                20                  25                  30

Ala Met Ser Trp Val Arg Gln Thr Pro Glu Lys Arg Leu Glu Trp Val
            35                  40                  45

Ala Ser Ile Ser Ser Gly Gly Thr Thr Phe Tyr Pro Asp Ser Val Lys
        50                  55                  60

Gly Arg Phe Thr Met Ser Arg Asp His Ala Arg Asn Ile Leu Tyr Leu
65                  70                  75                  80

Gln Met Asn Ser Leu Arg Ser Glu Asp Thr Ala Met Tyr Tyr Cys Val
                85                  90                  95

Arg Gly Gln Trp Leu Ser Leu Tyr Ser Met Asp Tyr Trp Gly Gln Gly
            100                 105                 110

Thr Ser Val Thr Val Ser Ser
        115
```

<210> SEQ ID NO 80
<211> LENGTH: 321
<212> TYPE: DNA
<213> ORGANISM: Mus musculus
<220> FEATURE:
<221> NAME/KEY: MISC_FEATURE
<223> OTHER INFORMATION: SC57.31 VL DNA

<400> SEQUENCE: 80

```
gatattgtgc taactcagtc tccagccacc ctgtctgtga ctccaggaga tagcgtcagt    60
ctttcctgca gggccagcca aagtgttggc aacagcctac actggtatca acaaaaatca   120
catgagctct caaggcttct catcaagtat gcttcccagt ccatctctgg atcccctcc   180
aggttcagtg gcagtggatc agggacagat ttcactctca gtatcaacag tgtggagact   240
gaagattttg gaatgtattt ctgtcaacag agtgacagct ggccgctcac gttcggtact   300
gggaccaagc tggagctgaa a                                              321
```

<210> SEQ ID NO 81
<211> LENGTH: 107
<212> TYPE: PRT
<213> ORGANISM: Mus musculus
<220> FEATURE:
<221> NAME/KEY: MISC_FEATURE
<223> OTHER INFORMATION: SC57.31 VL protein

<400> SEQUENCE: 81

```
Asp Ile Val Leu Thr Gln Ser Pro Ala Thr Leu Ser Val Thr Pro Gly
1               5                   10                  15

Asp Ser Val Ser Leu Ser Cys Arg Ala Ser Gln Ser Val Gly Asn Ser
                20                  25                  30

Leu His Trp Tyr Gln Gln Lys Ser His Glu Ser Pro Arg Leu Leu Ile
            35                  40                  45

Lys Tyr Ala Ser Gln Ser Ile Ser Gly Ile Pro Ser Arg Phe Ser Gly
        50                  55                  60

Ser Gly Ser Gly Thr Asp Phe Thr Leu Ser Ile Asn Ser Val Glu Thr
65                  70                  75                  80

Glu Asp Phe Gly Met Tyr Phe Cys Gln Gln Ser Asp Ser Trp Pro Leu
                85                  90                  95

Thr Phe Gly Thr Gly Thr Lys Leu Glu Leu Lys
            100                 105
```

```
<210> SEQ ID NO 82
<211> LENGTH: 360
<212> TYPE: DNA
<213> ORGANISM: Mus musculus
<220> FEATURE:
<221> NAME/KEY: MISC_FEATURE
<223> OTHER INFORMATION: SC57.31 VH DNA

<400> SEQUENCE: 82
caggtgcacc tgaaggagtc aggacctggc ctggtggcgc cctcacagag cctgtccatc      60
acttgcactg tctctgggtt ttcattaacc acctatggtg tacactgggt tcgccagcct    120
ccaggaaagg gtctggagtg gctgggagta atatgggctg gtggaagcac aaaatataat    180
tcggctttca tgtccagact gagcatcagc aaagacaact ccaagaccca agttctctta    240
aaaatgaaca gtctgcaaac tgatgacaca gccatgtact actgtgccag agtggcctcc    300
cacggtagta gctcctggtt tgcttactgg ggccaaggga ctctggtcac tgtctctgca    360

<210> SEQ ID NO 83
<211> LENGTH: 120
<212> TYPE: PRT
<213> ORGANISM: Mus musculus
<220> FEATURE:
<221> NAME/KEY: MISC_FEATURE
<223> OTHER INFORMATION: SC57.31 VH protein

<400> SEQUENCE: 83

Gln Val His Leu Lys Glu Ser Gly Pro Gly Leu Val Ala Pro Ser Gln
 1               5                  10                  15

Ser Leu Ser Ile Thr Cys Thr Val Ser Gly Phe Ser Leu Thr Thr Tyr
             20                  25                  30

Gly Val His Trp Val Arg Gln Pro Pro Gly Lys Gly Leu Glu Trp Leu
         35                  40                  45

Gly Val Ile Trp Ala Gly Gly Ser Thr Lys Tyr Asn Ser Ala Phe Met
     50                  55                  60

Ser Arg Leu Ser Ile Ser Lys Asp Asn Ser Lys Thr Gln Val Leu Leu
 65                  70                  75                  80

Lys Met Asn Ser Leu Gln Thr Asp Asp Thr Ala Met Tyr Tyr Cys Ala
                 85                  90                  95

Arg Val Ala Ser His Gly Ser Ser Ser Trp Phe Ala Tyr Trp Gly Gln
            100                 105                 110

Gly Thr Leu Val Thr Val Ser Ala
        115                 120

<210> SEQ ID NO 84
<211> LENGTH: 339
<212> TYPE: DNA
<213> ORGANISM: Mus musculus
<220> FEATURE:
<221> NAME/KEY: MISC_FEATURE
<223> OTHER INFORMATION: SC57.43 VL DNA

<400> SEQUENCE: 84
gatgttgtga tgacccaaac tccactctcc ctgcctgtca gtcttggaga tcaagcctcc     60
atctcttgca gatctagtca gagccttgta cacagtaatg aaacaccta  tttacattgg   120 tacctgcaga agccaggcca gtctccaaag ctcctgatct acaaagtttc caaccgattt   180
tctggggtcc cagacaggtt cagtggcagt ggatcaggga cagatttcac actcaagatc   240
agcagagtgg aggctgagga tctgggagtt tatttctgct ctcaaagtac acatgttcct   300
ctgtacacgt tcggaggggg gaccaagctg gaaataaaa                          339
```

```
<210> SEQ ID NO 85
<211> LENGTH: 113
<212> TYPE: PRT
<213> ORGANISM: Mus musculus
<220> FEATURE:
<221> NAME/KEY: MISC_FEATURE
<223> OTHER INFORMATION: SC57.43 VL protein

<400> SEQUENCE: 85

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Leu Tyr Thr Phe Gly Gly Gly Thr Lys Leu Glu Ile
            100                 105                 110

Lys

<210> SEQ ID NO 86
<211> LENGTH: 351
<212> TYPE: DNA
<213> ORGANISM: Mus musculus
<220> FEATURE:
<221> NAME/KEY: MISC_FEATURE
<223> OTHER INFORMATION: SC57.43 VH DNA

<400> SEQUENCE: 86
gaagtgaagc tggtggagtc tgggggaggt ttagtgcagc ctggagggtc cctgaaactc      60
tcctgtgcag cctctggatt cactttcggt agctatacca tgtcttgggt tcgccagact     120
ccagagaaga ggctggagtg ggtcgcatac attagtaatg gtggttatgt cacctactac     180
ccagacactg taaagggccg attcaccatc tccagagaca tgccaagaa taccctgtac      240 ctgcaaatga gcagtctgaa gtctgaggac acggccatgt attactgtgc aagaggatac     300
gactggtact cgatgtctg gggcgcaggg accacggtca ccgtctcctc a               351

<210> SEQ ID NO 87
<211> LENGTH: 117
<212> TYPE: PRT
<213> ORGANISM: Mus musculus
<220> FEATURE:
<221> NAME/KEY: MISC_FEATURE
<223> OTHER INFORMATION: SC57.43 VH protein

<400> SEQUENCE: 87

Glu Val Lys Leu Val Glu Ser Gly Gly Gly Leu Val Gln Pro Gly Gly
1               5                   10                  15

Ser Leu Lys Leu Ser Cys Ala Ala Ser Gly Phe Thr Phe Gly Ser Tyr
            20                  25                  30

Thr Met Ser Trp Val Arg Gln Thr Pro Glu Lys Arg Leu Glu Trp Val
        35                  40                  45

Ala Tyr Ile Ser Asn Gly Gly Tyr Val Thr Tyr Tyr Pro Asp Thr Val
```

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Gly Tyr Asp Trp Tyr Phe Asp Val Trp Gly Ala Gly Thr Thr
            100                 105                 110

Val Thr Val Ser Ser
        115

<210> SEQ ID NO 88
<211> LENGTH: 321
<212> TYPE: DNA
<213> ORGANISM: Mus musculus
<220> FEATURE:
<221> NAME/KEY: MISC_FEATURE
<223> OTHER INFORMATION: SC57.60 VL DNA

<400> SEQUENCE: 88
gacatccaga tgactcagtc tccagcctcc ctatctgcat ctgtgggaga aactgtcacc     60
atcacatgtc gagcaagtga gaatatttac agttatttag catggtctca gcagaagcag    120
ggaaaatctc ctcacctcct ggtctataat gcaaaaacct tagcagaagg tgtgccatca    180
aggttcagtg gcagtggatc aggcacacag ttttctctga agatcaacag cctgcagcct    240
gaagattttg ggagttatta ctgtcaacat cattatggta ttccgctcac gttcggtgct    300
gggaccaagc tggagctgaa a                                               321

<210> SEQ ID NO 89
<211> LENGTH: 107
<212> TYPE: PRT
<213> ORGANISM: Mus musculus
<220> FEATURE:
<221> NAME/KEY: MISC_FEATURE
<223> OTHER INFORMATION: SC57.60 VL protein

<400> SEQUENCE: 89

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Ser Gln Gln Lys Gln Gly Lys Ser Pro His Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Gly Ile Pro Leu
                85                  90                  95

Thr Phe Gly Ala Gly Thr Lys Leu Glu Leu Lys
            100                 105

<210> SEQ ID NO 90
<211> LENGTH: 360
<212> TYPE: DNA
<213> ORGANISM: Mus musculus
<220> FEATURE:
<221> NAME/KEY: MISC_FEATURE
<223> OTHER INFORMATION: SC57.60 VH DNA

<400> SEQUENCE: 90

```
caggttcagc tgcagcagtc tggggctgag ctggtgaggc ctgggtcctc agtgaagatt    60
tcctgcaagg cttctggcta tgcattcagt agctactgga tgaactgggt gaagcagagg   120
cctggacagg gtcttgagtg gattggacag atttatcctg agatggtga tactaactac    180 aatgaaaagt tcaagggtaa agccacattg actgcagaca atcctccag cacagcctac    240 atgcagctca gcagtctaac atctgaggac tctgcggtct acttctgtgc aagagcttac    300
tacggaaacc tctatgttat ggactactgg ggtcaaggaa cctcagtcac cgtctcctca   360

<210> SEQ ID NO 91
<211> LENGTH: 120
<212> TYPE: PRT
<213> ORGANISM: Mus musculus
<220> FEATURE:
<221> NAME/KEY: MISC_FEATURE
<223> OTHER INFORMATION: SC57.60 VH protein

<400> SEQUENCE: 91

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Tyr Pro Gly Asp Gly Asp Thr Asn Tyr Asn Gly Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Ala Tyr Tyr Gly Asn Leu Tyr Val Met Asp Tyr Trp Gly Gln
            100                 105                 110

Gly Thr Ser Val Thr Val Ser Ser
        115                 120

<210> SEQ ID NO 92
<211> LENGTH: 321
<212> TYPE: DNA
<213> ORGANISM: Artificial
<220> FEATURE:
<223> OTHER INFORMATION: Humanized antibody sequence
<220> FEATURE:
<221> NAME/KEY: MISC_FEATURE
<223> OTHER INFORMATION: hSC57.5 VL DNA

<400> SEQUENCE: 92
gacatccaga tgacacagtc accttcaagt ctgagtgcct ccgtaggtga tagagtcacc    60
attacatgca aagcatctca agacgtttac gctgccgtgg cttggtacca gcagaaaccc   120
ggcaaggctc caaagttgct gatttactgg gcaagcactc gccacgctgg cgttccttca   180 cgttttcag gcagtggaag cgggaccgac ttcaccctga ccatctctag tctccagccc   240
gaggactttg ctacctacta ctgccagcag cattaccgta caccttggac tttcggccaa   300
ggcaccaagg tcgagattaa a                                             321

<210> SEQ ID NO 93
<211> LENGTH: 107
<212> TYPE: PRT
<213> ORGANISM: Artificial
<220> FEATURE:
```

<223> OTHER INFORMATION: Humanized antibody sequence
<220> FEATURE:
<221> NAME/KEY: MISC_FEATURE
<223> OTHER INFORMATION: hSC57.5 VL protein

<400> SEQUENCE: 93

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Tyr Ala Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Ala Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Arg Thr Pro Trp
                85                  90                  95

Thr Phe Gly Gln Gly Thr Lys Val Glu Ile Lys
            100                 105

<210> SEQ ID NO 94
<211> LENGTH: 354
<212> TYPE: DNA
<213> ORGANISM: Artificial
<220> FEATURE:
<223> OTHER INFORMATION: Humanized antibody sequence
<220> FEATURE:
<221> NAME/KEY: MISC_FEATURE
<223> OTHER INFORMATION: hSC57.5 VH DNA

<400> SEQUENCE: 94
gaagtgcaac tcgtgcagag cggggccgaa gtaaaaaaac caggcgagag cttgaaaatt      60
tcttgcaagg gatccggcta ctccttcaca gactactatc tccactgggt ccgccagatg     120
cccggcaaag gccttgaatg gatgggcaga ataaatccct acaacggcgc tacctcctat     180
aatcagatct tcaaggatca agtgaccatc tccgccgata gtccatctc cacagcttat      240 cttcagtgga gctcactgaa ggctagcgat actgccatgt attactgtgc aaggggcggc     300
gactacgatt tcccttggta ttggggccag ggaactaccg tcactgttag cagc            354

<210> SEQ ID NO 95
<211> LENGTH: 118
<212> TYPE: PRT
<213> ORGANISM: Artificial
<220> FEATURE:
<223> OTHER INFORMATION: Humanized antibody sequence
<220> FEATURE:
<221> NAME/KEY: MISC_FEATURE
<223> OTHER INFORMATION: hSC57.5 VH protein

<400> SEQUENCE: 95

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asp Tyr
            20                  25                  30

Tyr Leu His Trp Val Arg Gln Met Pro Gly Lys Gly Leu Glu Trp Met
        35                  40                  45

Gly Arg Ile Asn Pro Tyr Asn Gly Ala Thr Ser Tyr Asn Gln Ile Phe
    50                  55                  60

Lys Asp Gln Val Thr Ile Ser Ala Asp Lys Ser Ile Ser Thr Ala Tyr

```
                    65                  70                  75                  80
Leu Gln Trp Ser Ser Leu Lys Ala Ser Asp Thr Ala Met Tyr Tyr Cys
                85                  90                  95

Ala Arg Gly Gly Asp Tyr Asp Phe Pro Trp Tyr Trp Gly Gln Gly Thr
            100                 105                 110

Thr Val Thr Val Ser Ser
        115

<210> SEQ ID NO 96
<211> LENGTH: 354
<212> TYPE: DNA
<213> ORGANISM: Artificial
<220> FEATURE:
<223> OTHER INFORMATION: Humanized antibody sequence
<220> FEATURE:
<221> NAME/KEY: MISC_FEATURE
<223> OTHER INFORMATION: hSC57.5v1 VH DNA

<400> SEQUENCE: 96
gaagtgcaac tcgtgcagag cggggccgaa gtaaaaaaac caggcgagag cttgaaaatt    60
tcttgcaagg gatccggcta ctccttcaca gactactatc tccactgggt ccgccagatg   120
cccggcaaag gccttgaatg gatgggcaga ataaatccct acaacgccgc tacctcctat   180
aatcagatct tcaaggatca agtgaccatc tccgccgata gtccatctc cacagcttat   240 cttcagtgga gctcactgaa ggctagcgat actgccatgt attactgtgc aaggggcggc   300
gactacgatt tcccttggta ttggggccag ggaactaccg tcactgttag cagc          354

<210> SEQ ID NO 97
<211> LENGTH: 118
<212> TYPE: PRT
<213> ORGANISM: Artificial
<220> FEATURE:
<223> OTHER INFORMATION: Humanized antibody sequence
<220> FEATURE:
<221> NAME/KEY: MISC_FEATURE
<223> OTHER INFORMATION: hSC57.5v1 VH protein

<400> SEQUENCE: 97

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asp Tyr
            20                  25                  30

Tyr Leu His Trp Val Arg Gln Met Pro Gly Lys Gly Leu Glu Trp Met
        35                  40                  45

Gly Arg Ile Asn Pro Tyr Asn Ala Ala Thr Ser Tyr Asn Gln Ile Phe
    50                  55                  60

Lys Asp Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Gly Asp Tyr Asp Phe Pro Trp Tyr Trp Gly Gln Gly Thr
            100                 105                 110

Thr Val Thr Val Ser Ser
        115

<210> SEQ ID NO 98
<211> LENGTH: 321
<212> TYPE: DNA
<213> ORGANISM: Artificial
<220> FEATURE:
```

<223> OTHER INFORMATION: Humanized antibody sequence
<220> FEATURE:
<221> NAME/KEY: MISC_FEATURE
<223> OTHER INFORMATION: hSC57.32 VL DNA

<400> SEQUENCE: 98

```
gatattcaga tgactcagtc tcccagcagc cttagcgcat ctgtgggaga tcgtgtcacc    60
attacctgcc gcgcttcaca ggacatttct aactacctca actggtatca gcagaagcca   120
ggtaaggcac caaagctcct gatctactat acttctagac tgcacagcgg tgtgccatct   180
agattctctg gaagtgggag cggcacagac tacacactga caatcagctc cttgcagcct   240
gaagattttg caacttatta ttgccagcag ggaaacacac tgccaccaac cttcggcggt   300
gggaccaagg tggagatcaa g                                             321
```

<210> SEQ ID NO 99
<211> LENGTH: 107
<212> TYPE: PRT
<213> ORGANISM: Artificial
<220> FEATURE:
<223> OTHER INFORMATION: Humanized antibody sequence
<220> FEATURE:
<221> NAME/KEY: MISC_FEATURE
<223> OTHER INFORMATION: hSC57.32 VL protein

<400> SEQUENCE: 99

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Pro
                85                  90                  95

Thr Phe Gly Gly Gly Thr Lys Val Glu Ile Lys
            100                 105

<210> SEQ ID NO 100
<211> LENGTH: 357
<212> TYPE: DNA
<213> ORGANISM: Artificial
<220> FEATURE:
<223> OTHER INFORMATION: Humanized antibody sequence
<220> FEATURE:
<221> NAME/KEY: MISC_FEATURE
<223> OTHER INFORMATION: hSC57.32 VH DNA

<400> SEQUENCE: 100

```
caagtgcagt tggtacagtc tggcgcagag gtcaaaaaac ccggagcttc agtgaaagtg    60
tcctgcaaag ccagtggata cattcact aactaccgta ttgagtgggt ccgtcaggct    120
ccaggccagg gctggagtg gatgggtgaa atactgcctc gcggcggcaa tactaactac   180
aatgagaagt ttaaggggag agttacattc accgccgata ctagtacttc caccgcctat   240
atggagctcc gttccctccg gagcgatgac actgccgtgt actattgcgc ccgtgacgac   300
ggttattacg ggaggtttgc ttactgggga caggtacat tggtgacagt atcatct     357
```

```
<210> SEQ ID NO 101
<211> LENGTH: 119
<212> TYPE: PRT
<213> ORGANISM: Artificial
<220> FEATURE:
<223> OTHER INFORMATION: Humanized antibody sequence
<220> FEATURE:
<221> NAME/KEY: MISC_FEATURE
<223> OTHER INFORMATION: hSC57.32 VH protein

<400> SEQUENCE: 101

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Arg Ile Glu Trp Val Arg Gln Ala Pro Gly Gln Gly Leu Glu Trp Met
            35                  40                  45

Gly Glu Ile Leu Pro Arg Gly Gly Asn Thr Asn Tyr Asn Glu Lys Phe
        50                  55                  60

Lys Gly Arg Val Thr Phe Thr Ala Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Asp Gly Tyr Tyr Gly Arg Phe Ala Tyr Trp Gly Gln Gly
            100                 105                 110

Thr Leu Val Thr Val Ser Ser
        115

<210> SEQ ID NO 102
<211> LENGTH: 357
<212> TYPE: DNA
<213> ORGANISM: Artificial
<220> FEATURE:
<223> OTHER INFORMATION: Humanized antibody sequence
<220> FEATURE:
<221> NAME/KEY: MISC_FEATURE
<223> OTHER INFORMATION: hSC57.32v1 VH DNA

<400> SEQUENCE: 102
caagtgcagt tggtacagtc tggcgcagag gtcaaaaaac ccggagcttc agtgaaagtg      60
tcctgcaaag ccagtggata cattcact aactaccgta ttgagtgggt ccgtcaggct      120
ccaggccagg ggctggagtg gatgggtgaa atactgcctc gcggcggcaa tactaactac      180
aatgagaagt ttaaggggag agttacaatg accgccgata ctagtacttc caccgcctat      240
atggagctcc gttccctccg gagcgatgac actgccgtgt actattgcgc ccgtgacgac      300
ggttattacg ggaggtttgc ttactgggga caggtacat tggtgacagt atcatct          357

<210> SEQ ID NO 103
<211> LENGTH: 119
<212> TYPE: PRT
<213> ORGANISM: Artificial
<220> FEATURE:
<223> OTHER INFORMATION: Humanized antibody sequence
<220> FEATURE:
<221> NAME/KEY: MISC_FEATURE
<223> OTHER INFORMATION: hSC57.32v1 VH protein

<400> SEQUENCE: 103

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30
```

Arg Ile Glu Trp Val Arg Gln Ala Pro Gly Gln Gly Leu Glu Trp Met
            35                  40                  45

Gly Glu Ile Leu Pro Arg Gly Gly Asn Thr Asn Tyr Asn Glu Lys Phe
        50                  55                  60

Lys Gly Arg Val Thr Met Thr Ala Asp Thr Ser Thr Ser Thr Ala Tyr
65                  70                  75                  80

Met Glu Leu Arg Ser Leu Arg Ser Asp Thr Ala Val Tyr Tyr Cys
                85                  90                  95

Ala Arg Asp Asp Gly Tyr Tyr Gly Arg Phe Ala Tyr Trp Gly Gln Gly
            100                 105                 110

Thr Leu Val Thr Val Ser Ser
        115

<210> SEQ ID NO 104
<211> LENGTH: 339
<212> TYPE: DNA
<213> ORGANISM: Artificial
<220> FEATURE:
<223> OTHER INFORMATION: Humanized antibody sequence
<220> FEATURE:
<221> NAME/KEY: MISC_FEATURE
<223> OTHER INFORMATION: hSC57.43 VL DNA

<400> SEQUENCE: 104
gacatcgtaa tgacacagtc tccagatagt ctcgccgtga gtctgggaga gcgtgctact    60
atcaactgtc ggtcttctca gtccctcgtc cattctaatg gaaacactta cctccattgg   120
tatcagcaga aacccggtca gccaccaaag ttgctgatat acaaggtctc caaccgcttt   180
agcggggtgc ctgatcgttt cagcgggtca ggaagcggga cagacttcac cttgacaata   240
tcatctctgc aggcagaaga tgtagccgtg tattactgct cccagtctac acacgtacct   300
ctgtacacat tcggggggcgg caccaaggtg gagattaag                         339

<210> SEQ ID NO 105
<211> LENGTH: 113
<212> TYPE: PRT
<213> ORGANISM: Artificial
<220> FEATURE:
<223> OTHER INFORMATION: Humanized antibody sequence
<220> FEATURE:
<221> NAME/KEY: MISC_FEATURE
<223> OTHER INFORMATION: hSC57.43 VL protein

<400> SEQUENCE: 105

Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Ser Leu Val His Ser
            20                  25                  30

Asn Gly Asn Thr Tyr Leu His Trp Tyr Gln Gln Lys Pro Gly Gln Pro
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Ser Gln Ser
                85                  90                  95

Thr His Val Pro Leu Tyr Thr Phe Gly Gly Gly Thr Lys Val Glu Ile
            100                 105                 110

Lys

<210> SEQ ID NO 106
<211> LENGTH: 351
<212> TYPE: DNA
<213> ORGANISM: Artificial
<220> FEATURE:
<223> OTHER INFORMATION: Humanized antibody sequence
<220> FEATURE:
<221> NAME/KEY: MISC_FEATURE
<223> OTHER INFORMATION: hSC57.43 VH DNA

<400> SEQUENCE: 106
caggtgcagc tggtggaatc tggtggcgga gtggtgcagc ctggcagatc cctgagactg      60
tcttgtgccg cctccggctt caccttcggc tcctacacca tgtcctgggt gcgacaggct     120
cctggcaagg gcctggaatg ggtggcctac atctccaacg gcggctacgt gacctactac     180
cccgacaccg tgaagggccg gttcaccatc tctcgggaca actccaagaa caccctgtac     240
ctgcagatga actccctgcg ggccgaggac accgccgtgt actattgtgc cagaggctac     300
gactggtact tcgacgtgtg gggccagggc accaccgtga cagtgtcatc t              351

<210> SEQ ID NO 107
<211> LENGTH: 117
<212> TYPE: PRT
<213> ORGANISM: Artificial
<220> FEATURE:
<223> OTHER INFORMATION: Humanized antibody sequence
<220> FEATURE:
<221> NAME/KEY: MISC_FEATURE
<223> OTHER INFORMATION: hSC57.43 VH protein

<400> SEQUENCE: 107

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Gly Ser Tyr
            20                  25                  30

Thr Met Ser Trp Val Arg Gln Ala Pro Gly Lys Gly Leu Glu Trp Val
        35                  40                  45

Ala Tyr Ile Ser Asn Gly Gly Tyr Val Thr Tyr Tyr Pro Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Asp Trp Tyr Phe Asp Val Trp Gly Gln Gly Thr Thr
            100                 105                 110

Val Thr Val Ser Ser
        115

<210> SEQ ID NO 108
<211> LENGTH: 214
<212> TYPE: PRT
<213> ORGANISM: Artificial
<220> FEATURE:
<223> OTHER INFORMATION: Humanized antibody sequence
<220> FEATURE:
<221> NAME/KEY: MISC_FEATURE
<223> OTHER INFORMATION: hSC57.5 full length light chain protein

<400> SEQUENCE: 108

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Tyr Ala Ala
            20                  25                  30

Val Ala Trp Tyr Gln Gln Lys Pro Gly Lys Ala Pro Lys Leu Leu Ile
            35                  40                  45

Tyr Trp Ala Ser Thr Arg His Ala Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Arg Thr Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 109
<211> LENGTH: 447
<212> TYPE: PRT
<213> ORGANISM: Artificial
<220> FEATURE:
<223> OTHER INFORMATION: Humanized antibody sequence
<220> FEATURE:
<221> NAME/KEY: MISC_FEATURE
<223> OTHER INFORMATION: hSC57.5 full length heavy chain protein

<400> SEQUENCE: 109

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asp Tyr
            20                  25                  30

Tyr Leu His Trp Val Arg Gln Met Pro Gly Lys Gly Leu Glu Trp Met
            35                  40                  45

Gly Arg Ile Asn Pro Tyr Asn Gly Ala Thr Ser Tyr Asn Gln Ile Phe
50                  55                  60

Lys Asp Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Gly Asp Tyr Asp Phe Pro Trp Tyr Trp Gly Gln Gly Thr
            100                 105                 110

Thr Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly
            435                 440                 445

<210> SEQ ID NO 110
<211> LENGTH: 447
<212> TYPE: PRT
<213> ORGANISM: Artificial
<220> FEATURE:
<223> OTHER INFORMATION: Humanized antibody sequence
<220> FEATURE:
<221> NAME/KEY: MISC_FEATURE
<223> OTHER INFORMATION: hSC57.5v1ss1 full length heavy chain protein

<400> SEQUENCE: 110

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asp Tyr
            20                  25                  30

Tyr Leu His Trp Val Arg Gln Met Pro Gly Lys Gly Leu Glu Trp Met
        35                  40                  45

Gly Arg Ile Asn Pro Tyr Asn Ala Ala Thr Ser Tyr Asn Gln Ile Phe
 50                  55                  60

Lys Asp Gln Val Thr Ile Ser Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Gly Gly Asp Tyr Asp Phe Pro Trp Tyr Trp Gly Gln Gly Thr
            100                 105                 110

Thr Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Ser Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 111
<211> LENGTH: 447
<212> TYPE: PRT

```
<213> ORGANISM: Artificial
<220> FEATURE:
<223> OTHER INFORMATION: Humanized antibody sequence
<220> FEATURE:
<221> NAME/KEY: MISC_FEATURE
<223> OTHER INFORMATION: hSC57.5v1 full length heavy chain protein

<400> SEQUENCE: 111
```

| | | | | | | | | | | | | | | |
|---|---|---|---|---|---|---|---|---|---|---|---|---|---|---|
| Glu | Val | Gln | Leu | Val | Gln | Ser | Gly | Ala | Glu | Val | Lys | Pro | Gly | Glu |
| 1 | | | | 5 | | | | | 10 | | | | | 15 |
| Ser | Leu | Lys | Ile | Ser | Cys | Lys | Gly | Ser | Gly | Tyr | Ser | Phe | Thr | Asp | Tyr |
| | | | 20 | | | | | 25 | | | | | 30 | | |
| Tyr | Leu | His | Trp | Val | Arg | Gln | Met | Pro | Gly | Lys | Gly | Leu | Glu | Trp | Met |
| | | 35 | | | | | 40 | | | | | 45 | | | |
| Gly | Arg | Ile | Asn | Pro | Tyr | Asn | Ala | Ala | Thr | Ser | Tyr | Asn | Gln | Ile | Phe |
| 50 | | | | | 55 | | | | | 60 | | | | | |
| Lys | Asp | Gln | Val | Thr | Ile | Ser | Ala | Asp | Lys | Ser | Ile | Ser | Thr | Ala | Tyr |
| 65 | | | | 70 | | | | | 75 | | | | | 80 | |
| Leu | Gln | Trp | Ser | Ser | Leu | Lys | Ala | Ser | Asp | Thr | Ala | Met | Tyr | Tyr | Cys |
| | | | | 85 | | | | | 90 | | | | | 95 | |
| Ala | Arg | Gly | Gly | Asp | Tyr | Asp | Phe | Pro | Trp | Tyr | Trp | Gly | Gln | Gly | Thr |
| | | | 100 | | | | | 105 | | | | | 110 | | |
| Thr | Val | Thr | Val | Ser | Ser | Ala | Ser | Thr | Lys | Gly | Pro | Ser | Val | Phe | Pro |
| | | 115 | | | | | 120 | | | | | 125 | | | |
| Leu | Ala | Pro | Ser | Ser | Lys | Ser | Thr | Ser | Gly | Gly | Thr | Ala | Ala | Leu | Gly |
| | | 130 | | | | | 135 | | | | | 140 | | | |
| Cys | Leu | Val | Lys | Asp | Tyr | Phe | Pro | Glu | Pro | Val | Thr | Val | Ser | Trp | Asn |
| 145 | | | | | 150 | | | | | 155 | | | | | 160 |
| Ser | Gly | Ala | Leu | Thr | Ser | Gly | Val | His | Thr | Phe | Pro | Ala | Val | Leu | Gln |
| | | | | 165 | | | | | 170 | | | | | 175 | |
| Ser | Ser | Gly | Leu | Tyr | Ser | Leu | Ser | Ser | Val | Val | Thr | Val | Pro | Ser | Ser |
| | | | 180 | | | | | 185 | | | | | 190 | | |
| Ser | Leu | Gly | Thr | Gln | Thr | Tyr | Ile | Cys | Asn | Val | Asn | His | Lys | Pro | Ser |
| | | | 195 | | | | | 200 | | | | | 205 | | |
| Asn | Thr | Lys | Val | Asp | Lys | Lys | Val | Glu | Pro | Lys | Ser | Cys | Asp | Lys | Thr |
| | 210 | | | | | 215 | | | | | 220 | | | | |
| His | Thr | Cys | Pro | Pro | Cys | Pro | Ala | Pro | Glu | Leu | Leu | Gly | Gly | Pro | Ser |
| 225 | | | | | 230 | | | | | 235 | | | | | 240 |
| Val | Phe | Leu | Phe | Pro | Pro | Lys | Pro | Lys | Asp | Thr | Leu | Met | Ile | Ser | Arg |
| | | | | 245 | | | | | 250 | | | | | 255 | |
| Thr | Pro | Glu | Val | Thr | Cys | Val | Val | Val | Asp | Val | Ser | His | Glu | Asp | Pro |
| | | | 260 | | | | | 265 | | | | | 270 | | |
| Glu | Val | Lys | Phe | Asn | Trp | Tyr | Val | Asp | Gly | Val | Glu | Val | His | Asn | Ala |
| | | 275 | | | | | 280 | | | | | 285 | | | |
| Lys | Thr | Lys | Pro | Arg | Glu | Glu | Gln | Tyr | Asn | Ser | Thr | Tyr | Arg | Val | Val |
| | 290 | | | | | 295 | | | | | 300 | | | | |
| Ser | Val | Leu | Thr | Val | Leu | His | Gln | Asp | Trp | Leu | Asn | Gly | Lys | Glu | Tyr |
| 305 | | | | | 310 | | | | | 315 | | | | | 320 |
| Lys | Cys | Lys | Val | Ser | Asn | Lys | Ala | Leu | Pro | Ala | Pro | Ile | Glu | Lys | Thr |
| | | | | 325 | | | | | 330 | | | | | 335 | |
| Ile | Ser | Lys | Ala | Lys | Gly | Gln | Pro | Arg | Glu | Pro | Gln | Val | Tyr | Thr | Leu |
| | | | 340 | | | | | 345 | | | | | 350 | | |
| Pro | Pro | Ser | Arg | Asp | Glu | Leu | Thr | Lys | Asn | Gln | Val | Ser | Leu | Thr | Cys |
| | | 355 | | | | | 360 | | | | | 365 | | | |
| Leu | Val | Lys | Gly | Phe | Tyr | Pro | Ser | Asp | Ile | Ala | Val | Glu | Trp | Glu | Ser |

```
                    370                 375                 380
Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly
                435                 440                 445

<210> SEQ ID NO 112
<211> LENGTH: 214
<212> TYPE: PRT
<213> ORGANISM: Artificial
<220> FEATURE:
<223> OTHER INFORMATION: Humanized antibody sequence
<220> FEATURE:
<221> NAME/KEY: MISC_FEATURE
<223> OTHER INFORMATION: hSC57.32 full length light chain protein

<400> SEQUENCE: 112

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Pro
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 113
<211> LENGTH: 448
<212> TYPE: PRT
<213> ORGANISM: Artificial
<220> FEATURE:
<223> OTHER INFORMATION: Humanized antibody sequence
<220> FEATURE:
<221> NAME/KEY: MISC_FEATURE
<223> OTHER INFORMATION: hSC57.32  full length heavy chain protein
```

<400> SEQUENCE: 113

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Arg Ile Glu Trp Val Arg Gln Ala Pro Gly Gln Gly Leu Glu Trp Met
        35                  40                  45

Gly Glu Ile Leu Pro Arg Gly Gly Asn Thr Asn Tyr Asn Glu Lys Phe
    50                  55                  60

Lys Gly Arg Val Thr Phe Thr Ala Asp Thr Ser Thr Ser Thr Ala Tyr
65                  70                  75                  80

Met Glu Leu Arg Ser Leu Arg Ser Asp Thr Ala Val Tyr Tyr Cys
                85                  90                  95

Ala Arg Asp Asp Gly Tyr Tyr Gly Arg Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys

```
                    405                 410                 415
Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

<210> SEQ ID NO 114
<211> LENGTH: 448
<212> TYPE: PRT
<213> ORGANISM: Artificial
<220> FEATURE:
<223> OTHER INFORMATION: Humanized antibody sequence
<220> FEATURE:
<221> NAME/KEY: MISC_FEATURE
<223> OTHER INFORMATION: hSC57.32ss1 full length heavy chain protein

<400> SEQUENCE: 114

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Arg Ile Glu Trp Val Arg Gln Ala Pro Gly Gln Gly Leu Glu Trp Met
        35                  40                  45

Gly Glu Ile Leu Pro Arg Gly Gly Asn Thr Asn Tyr Asn Glu Lys Phe
    50                  55                  60

Lys Gly Arg Val Thr Phe Thr Ala Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Asp Gly Tyr Tyr Gly Arg Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Ser Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
```

```
                305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

<210> SEQ ID NO 115
<211> LENGTH: 448
<212> TYPE: PRT
<213> ORGANISM: Artificial
<220> FEATURE:
<223> OTHER INFORMATION: Humanized antibody sequence
<220> FEATURE:
<221> NAME/KEY: MISC_FEATURE
<223> OTHER INFORMATION: hSC57.32v1 full length heavy chain protein

<400> SEQUENCE: 115

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Arg Ile Glu Trp Val Arg Gln Ala Pro Gly Gln Gly Leu Glu Trp Met
            35                  40                  45

Gly Glu Ile Leu Pro Arg Gly Gly Asn Thr Asn Tyr Asn Glu Lys Phe
        50                  55                  60

Lys Gly Arg Val Thr Met Thr Ala Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Asp Gly Tyr Tyr Gly Arg Phe Ala Tyr Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
```

```
                    210                 215                 220
Thr His Thr Cys Pro Pro Cys Pro Ala Pro Glu Leu Gly Gly Pro
225                 230                 235                 240

Ser Val Phe Leu Phe Pro Pro Lys Pro Lys Asp Thr Leu Met Ile Ser
                    245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                    325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                    405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

<210> SEQ ID NO 116
<211> LENGTH: 220
<212> TYPE: PRT
<213> ORGANISM: Artificial
<220> FEATURE:
<223> OTHER INFORMATION: Humanized antibody sequence
<220> FEATURE:
<221> NAME/KEY: MISC_FEATURE
<223> OTHER INFORMATION: hSC57.43 full length light chain protein

<400> SEQUENCE: 116

Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Ser Leu Val His Ser
                20                  25                  30

Asn Gly Asn Thr Tyr Leu His Trp Tyr Gln Gln Lys Pro Gly Gln Pro
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Ser Gln Ser
                85                  90                  95

Thr His Val Pro Leu Tyr Thr Phe Gly Gly Gly Thr Lys Val Glu Ile
                100                 105                 110

Lys Arg Thr Val Ala Ala Pro Ser Val Phe Ile Phe Pro Pro Ser Asp
```

```
            115                 120                 125
Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
                195                 200                 205

Ser Pro Val Thr Lys Ser Phe Asn Arg Gly Glu Cys
                210                 215                 220

<210> SEQ ID NO 117
<211> LENGTH: 446
<212> TYPE: PRT
<213> ORGANISM: Artificial
<220> FEATURE:
<223> OTHER INFORMATION: Humanized antibody sequence
<220> FEATURE:
<221> NAME/KEY: MISC_FEATURE
<223> OTHER INFORMATION: hSC57.43 full length heavy chain protein

<400> SEQUENCE: 117

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Gly Ser Tyr
                20                  25                  30

Thr Met Ser Trp Val Arg Gln Ala Pro Gly Lys Gly Leu Glu Trp Val
            35                  40                  45

Ala Tyr Ile Ser Asn Gly Gly Tyr Val Thr Tyr Tyr Pro Asp Thr Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Asp Trp Tyr Phe Asp Val Trp Gly Gln Gly Thr Thr
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
                195                 200                 205

Thr Lys Val Asp Lys Lys Val Glu Pro Lys Ser Cys Asp Lys Thr His
            210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
```

```
                245                 250                 255
Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 118
<211> LENGTH: 446
<212> TYPE: PRT
<213> ORGANISM: Artificial
<220> FEATURE:
<223> OTHER INFORMATION: Humanized antibody sequence
<220> FEATURE:
<221> NAME/KEY: MISC_FEATURE
<223> OTHER INFORMATION: hSC57.43ss1 full length heavy chain protein

<400> SEQUENCE: 118

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Gly Ser Tyr
            20                  25                  30

Thr Met Ser Trp Val Arg Gln Ala Pro Gly Lys Gly Leu Glu Trp Val
        35                  40                  45

Ala Tyr Ile Ser Asn Gly Gly Tyr Val Thr Tyr Tyr Pro Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Asp Trp Tyr Phe Asp Val Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
```

```
                145                 150                 155                 160
        Gly Ala Leu Thr Ser Gly Val His Thr Phe Pro Ala Val Leu Gln Ser
                         165                 170                 175

Ser Gly Leu Tyr Ser Leu Ser Ser Val Val Thr Val Pro Ser Ser Ser
                         180                 185                 190

Leu Gly Thr Gln Thr Tyr Ile Cys Asn Val Asn His Lys Pro Ser Asn
                         195                 200                 205

Thr Lys Val Asp Lys Lys Val Glu Pro Lys Ser Ser Asp Lys Thr His
                 210                 215                 220

Thr Cys Pro Pro Cys Pro Ala Pro Glu Leu Leu Gly Gly Pro Ser Val
        225                 230                 235                 240

Phe Leu Phe Pro Pro Lys Pro Lys Asp Thr Leu Met Ile Ser Arg Thr
                         245                 250                 255

Pro Glu Val Thr Cys Val Val Val Asp Val Ser His Glu Asp Pro Glu
                         260                 265                 270

Val Lys Phe Asn Trp Tyr Val Asp Gly Val Glu Val His Asn Ala Lys
                         275                 280                 285

Thr Lys Pro Arg Glu Glu Gln Tyr Asn Ser Thr Tyr Arg Val Val Ser
                 290                 295                 300

Val Leu Thr Val Leu His Gln Asp Trp Leu Asn Gly Lys Glu Tyr Lys
        305                 310                 315                 320

Cys Lys Val Ser Asn Lys Ala Leu Pro Ala Pro Ile Glu Lys Thr Ile
                         325                 330                 335

Ser Lys Ala Lys Gly Gln Pro Arg Glu Pro Gln Val Tyr Thr Leu Pro
                         340                 345                 350

Pro Ser Arg Asp Glu Leu Thr Lys Asn Gln Val Ser Leu Thr Cys Leu
                         355                 360                 365

Val Lys Gly Phe Tyr Pro Ser Asp Ile Ala Val Glu Trp Glu Ser Asn
                 370                 375                 380

Gly Gln Pro Glu Asn Asn Tyr Lys Thr Thr Pro Pro Val Leu Asp Ser
        385                 390                 395                 400

Asp Gly Ser Phe Phe Leu Tyr Ser Lys Leu Thr Val Asp Lys Ser Arg
                         405                 410                 415

Trp Gln Gln Gly Asn Val Phe Ser Cys Ser Val Met His Glu Ala Leu
                         420                 425                 430

His Asn His Tyr Thr Gln Lys Ser Leu Ser Leu Ser Pro Gly
                         435                 440                 445

<210> SEQ ID NO 119
<211> LENGTH: 11
<212> TYPE: PRT
<213> ORGANISM: Mus musculus
<220> FEATURE:
<221> NAME/KEY: MISC_FEATURE
<223> OTHER INFORMATION: hSC57.5 CDRL1 protein

<400> SEQUENCE: 119

Lys Ala Ser Gln Asp Val Tyr Ala Ala Val Ala
1               5                   10

<210> SEQ ID NO 120
<211> LENGTH: 7
<212> TYPE: PRT
<213> ORGANISM: Mus musculus
<220> FEATURE:
<221> NAME/KEY: MISC_FEATURE
<223> OTHER INFORMATION: hSC57.5 CDRL2 protein
```

```
<400> SEQUENCE: 120

Trp Ala Ser Thr Arg His Ala
1               5

<210> SEQ ID NO 121
<211> LENGTH: 9
<212> TYPE: PRT
<213> ORGANISM: Mus musculus
<220> FEATURE:
<221> NAME/KEY: MISC_FEATURE
<223> OTHER INFORMATION: hSC57.5 CDRL3 protein

<400> SEQUENCE: 121

Gln Gln His Tyr Arg Thr Pro Trp Thr
1               5

<210> SEQ ID NO 122
<211> LENGTH: 5
<212> TYPE: PRT
<213> ORGANISM: Mus musculus
<220> FEATURE:
<221> NAME/KEY: MISC_FEATURE
<223> OTHER INFORMATION: hSC57.5 CDRH1 protein

<400> SEQUENCE: 122

Asp Tyr Tyr Leu His
1               5

<210> SEQ ID NO 123
<211> LENGTH: 17
<212> TYPE: PRT
<213> ORGANISM: Mus musculus
<220> FEATURE:
<221> NAME/KEY: MISC_FEATURE
<223> OTHER INFORMATION: hSC57.5 CDRH2 protein

<400> SEQUENCE: 123

Arg Ile Asn Pro Tyr Asn Gly Ala Thr Ser Tyr Asn Gln Ile Phe Lys
1               5                   10                  15

Asp

<210> SEQ ID NO 124
<211> LENGTH: 17
<212> TYPE: PRT
<213> ORGANISM: Mus musculus
<220> FEATURE:
<221> NAME/KEY: MISC_FEATURE
<223> OTHER INFORMATION: hSC57.5v1 CDRH2 protein

<400> SEQUENCE: 124

Arg Ile Asn Pro Tyr Asn Ala Ala Thr Ser Tyr Asn Gln Ile Phe Lys
1               5                   10                  15

Asp

<210> SEQ ID NO 125
<211> LENGTH: 9
<212> TYPE: PRT
<213> ORGANISM: Mus musculus
<220> FEATURE:
<221> NAME/KEY: MISC_FEATURE
<223> OTHER INFORMATION: hSC57.5 CDRH3 protein

<400> SEQUENCE: 125

Gly Gly Asp Tyr Asp Phe Pro Trp Tyr
1               5
```

```
<210> SEQ ID NO 126
<211> LENGTH: 11
<212> TYPE: PRT
<213> ORGANISM: Mus musculus
<220> FEATURE:
<221> NAME/KEY: MISC_FEATURE
<223> OTHER INFORMATION: hSC57.32 CDRL1 protein

<400> SEQUENCE: 126

Arg Ala Ser Gln Asp Ile Ser Asn Tyr Leu Asn
1               5                   10

<210> SEQ ID NO 127
<211> LENGTH: 7
<212> TYPE: PRT
<213> ORGANISM: Mus musculus
<220> FEATURE:
<221> NAME/KEY: MISC_FEATURE
<223> OTHER INFORMATION: hSC57.32 CDRL2 protein

<400> SEQUENCE: 127

Tyr Thr Ser Arg Leu His Ser
1               5

<210> SEQ ID NO 128
<211> LENGTH: 9
<212> TYPE: PRT
<213> ORGANISM: Mus musculus
<220> FEATURE:
<221> NAME/KEY: MISC_FEATURE
<223> OTHER INFORMATION: hSC57.32 CDRL3 protein

<400> SEQUENCE: 128

Gln Gln Gly Asn Thr Leu Pro Pro Thr
1               5

<210> SEQ ID NO 129
<211> LENGTH: 5
<212> TYPE: PRT
<213> ORGANISM: Mus musculus
<220> FEATURE:
<221> NAME/KEY: MISC_FEATURE
<223> OTHER INFORMATION: hSC57.32 CDRH1 protein

<400> SEQUENCE: 129

Asn Tyr Arg Ile Glu
1               5

<210> SEQ ID NO 130
<211> LENGTH: 17
<212> TYPE: PRT
<213> ORGANISM: Mus musculus
<220> FEATURE:
<221> NAME/KEY: MISC_FEATURE
<223> OTHER INFORMATION: hSC57.32 CDRH2 protein

<400> SEQUENCE: 130

Glu Ile Leu Pro Arg Gly Gly Asn Thr Asn Tyr Asn Glu Lys Phe Lys
1               5                   10                  15

Gly

<210> SEQ ID NO 131
<211> LENGTH: 10
<212> TYPE: PRT
<213> ORGANISM: Mus musculus
<220> FEATURE:
<221> NAME/KEY: MISC_FEATURE
```

<223> OTHER INFORMATION: hSC57.32 CDRH3 protein

<400> SEQUENCE: 131

Asp Asp Gly Tyr Tyr Gly Arg Phe Ala Tyr
1               5                   10

<210> SEQ ID NO 132
<211> LENGTH: 16
<212> TYPE: PRT
<213> ORGANISM: Mus musculus
<220> FEATURE:
<221> NAME/KEY: MISC_FEATURE
<223> OTHER INFORMATION: hSC57.43 CDRL1 protein

<400> SEQUENCE: 132

Arg Ser Ser Gln Ser Leu Val His Ser Asn Gly Asn Thr Tyr Leu His
1               5                   10                  15

<210> SEQ ID NO 133
<211> LENGTH: 7
<212> TYPE: PRT
<213> ORGANISM: Mus musculus
<220> FEATURE:
<221> NAME/KEY: MISC_FEATURE
<223> OTHER INFORMATION: hSC57.43 CDRL2 protein

<400> SEQUENCE: 133

Lys Val Ser Asn Arg Phe Ser
1               5

<210> SEQ ID NO 134
<211> LENGTH: 10
<212> TYPE: PRT
<213> ORGANISM: Mus musculus
<220> FEATURE:
<221> NAME/KEY: MISC_FEATURE
<223> OTHER INFORMATION: hSC57.43 CDRL3 protein

<400> SEQUENCE: 134

Phe Gly Gly Gly Thr Lys Val Glu Ile Lys
1               5                   10

<210> SEQ ID NO 135
<211> LENGTH: 5
<212> TYPE: PRT
<213> ORGANISM: Mus musculus
<220> FEATURE:
<221> NAME/KEY: MISC_FEATURE
<223> OTHER INFORMATION: hSC57.43 CDRH1 protein

<400> SEQUENCE: 135

Ser Tyr Thr Met Ser
1               5

<210> SEQ ID NO 136
<211> LENGTH: 17
<212> TYPE: PRT
<213> ORGANISM: Mus musculus
<220> FEATURE:
<221> NAME/KEY: MISC_FEATURE
<223> OTHER INFORMATION: hSC57.43 CDRH2 protein

<400> SEQUENCE: 136

Tyr Ile Ser Asn Gly Gly Tyr Val Thr Tyr Tyr Pro Asp Thr Val Lys
1               5                   10                  15
Gly

```
<210> SEQ ID NO 137
<211> LENGTH: 8
<212> TYPE: PRT
<213> ORGANISM: Mus musculus
<220> FEATURE:
<221> NAME/KEY: MISC_FEATURE
<223> OTHER INFORMATION: hSC57.43 CDRH3 protein

<400> SEQUENCE: 137

Gly Tyr Asp Trp Tyr Phe Asp Val
1               5
```

UNITED STATES PATENT AND TRADEMARK OFFICE
CERTIFICATE OF CORRECTION

PATENT NO.        : 10,428,156 B2
APPLICATION NO.   : 15/508836
DATED             : October 1, 2019
INVENTOR(S)       : Samuel Williams et al.

Page 1 of 1

It is certified that error appears in the above-identified patent and that said Letters Patent is hereby corrected as shown below:

In the Claims

At Claim 13, Column 209, Line 57, the text "noid, a calichearmicin, or a radioisotope." should be changed to --noid, a calicheamicin, or a radioisotope.--

At Claim 17, Column 210, Line 25, the text "17. The antibody drug conjugate of claim 16, wherein the" should be changed to --17. The antibody drug conjugate of claim 14, wherein the--

Signed and Sealed this
Second Day of June, 2020

Andrei Iancu
*Director of the United States Patent and Trademark Office*